(12) United States Patent
Moisa et al.

(10) Patent No.: US 11,026,637 B2
(45) Date of Patent: Jun. 8, 2021

(54) SYSTEMS AND METHODS FOR SELECTING, ACTIVATING, OR SELECTING AND ACTIVATING TRANSDUCERS

(71) Applicant: Kardium Inc., Burnaby (CA)

(72) Inventors: Saar Moisa, Vancouver (CA); Michael Hermann Weber, Sointula (CA)

(73) Assignee: KARDIUM INC., Burnaby (CA)

( * ) Notice: Subject to any disclaimer, the term of this patent is extended or adjusted under 35 U.S.C. 154(b) by 0 days.

(21) Appl. No.: 16/388,063

(22) Filed: Apr. 18, 2019

(65) Prior Publication Data

US 2019/0239822 A1 Aug. 8, 2019

Related U.S. Application Data

(63) Continuation of application No. 15/827,499, filed on Nov. 30, 2017, now Pat. No. 10,722,184, which is a
(Continued)

(51) Int. Cl.
*A61B 5/00* (2006.01)
*A61B 5/01* (2006.01)
(Continued)

(52) U.S. Cl.
CPC .............. *A61B 5/743* (2013.01); *A61B 5/015* (2013.01); *A61B 5/02* (2013.01); *A61B 5/283* (2021.01);
(Continued)

(58) Field of Classification Search
CPC ............................ A61B 18/1206; A61B 5/015
(Continued)

(56) References Cited

U.S. PATENT DOCUMENTS

| 4,114,202 A | 9/1978 | Roy et al. |
| 4,164,046 A | 8/1979 | Cooley |

(Continued)

FOREIGN PATENT DOCUMENTS

| EP | 1169976 A1 | 1/2002 |
| EP | 0723467 B1 | 4/2002 |

(Continued)

OTHER PUBLICATIONS

Office Action response filed in copending U.S. Appl. No. 15/827,499 dated Jan. 13, 2020.
(Continued)

*Primary Examiner* — Nadia A Mahmood
(74) *Attorney, Agent, or Firm* — Rossi, Kimms & McDowell LLP

(57) ABSTRACT

A graphical representation may be displayed including at least a plurality of transducer graphical elements, each transducer graphical element of the plurality of transducer graphical elements representative of a respective transducer of a plurality of transducers of a transducer-based device. A set of user input may be received including an instruction set to reposition a first transducer graphical element in a state in which the first transducer graphical element is located at a first location in the graphical representation and a second transducer graphical element is located at a second location in the graphical representation, the second location closer to a predetermined location in the graphical representation than the first location. In response to conclusion of receipt of the set of user input, the first transducer graphical element may be repositioned from the first location in the graphical representation to the predetermined location in the graphical representation.

26 Claims, 37 Drawing Sheets

Related U.S. Application Data continuation-in-part of application No. 14/942,459, filed on Nov. 16, 2015, now Pat. No. 10,368,936.

(60) Provisional application No. 62/080,750, filed on Nov. 17, 2014.

(51) Int. Cl.

| | | |
|---|---|---|
| *G06F 3/0484* | (2013.01) | |
| *A61B 5/02* | (2006.01) | |
| *G06F 3/0482* | (2013.01) | |
| *G06F 3/0481* | (2013.01) | |
| *A61B 5/283* | (2021.01) | |
| *A61B 5/287* | (2021.01) | |
| *A61B 18/00* | (2006.01) | |
| *A61B 5/15* | (2006.01) | |
| *A61B 5/157* | (2006.01) | |
| *A61B 18/14* | (2006.01) | |
| *A61B 34/10* | (2016.01) | |
| *G16H 40/63* | (2018.01) | |

(52) U.S. Cl.
CPC .......... *A61B 5/287* (2021.01); *A61B 5/6859* (2013.01); *A61B 5/6869* (2013.01); *A61B 5/72* (2013.01); *A61B 5/748* (2013.01); *A61B 5/7435* (2013.01); *G06F 3/0482* (2013.01); *G06F 3/04815* (2013.01); *G06F 3/04842* (2013.01); *G06F 3/04847* (2013.01); *A61B 5/157* (2013.01); *A61B 5/150022* (2013.01); *A61B 5/150969* (2013.01); *A61B 18/1492* (2013.01); *A61B 2018/00214* (2013.01); *A61B 2018/00267* (2013.01); *A61B 2018/00357* (2013.01); *A61B 2018/00577* (2013.01); *A61B 2018/00642* (2013.01); *A61B 2018/00702* (2013.01); *A61B 2018/00791* (2013.01); *A61B 2018/00839* (2013.01); *A61B 2018/00875* (2013.01); *A61B 2018/1467* (2013.01); *A61B 2034/107* (2016.02); *A61B 2560/0475* (2013.01); *G16H 40/63* (2018.01)

(58) Field of Classification Search
USPC ........................................................ 600/508
See application file for complete search history.

(56) References Cited

U.S. PATENT DOCUMENTS

| | | |
|---|---|---|
| 4,225,148 A | 9/1980 | Andersson |
| 4,240,441 A | 12/1980 | Khalil |
| 4,263,680 A | 4/1981 | Reul et al. |
| 4,273,128 A | 6/1981 | Lary |
| 4,411,266 A | 10/1983 | Cosman |
| 4,490,859 A | 1/1985 | Black et al. |
| 4,543,090 A | 9/1985 | McCoy |
| 4,699,147 A | 10/1987 | Chilson et al. |
| 4,770,187 A | 9/1988 | Lash et al. |
| 4,794,912 A | 1/1989 | Lia |
| 4,850,957 A | 7/1989 | Summers |
| 4,887,613 A | 12/1989 | Farr et al. |
| 4,890,602 A | 1/1990 | Hake |
| 4,890,612 A | 1/1990 | Kensey |
| 4,893,613 A | 1/1990 | Hake |
| 4,895,166 A | 1/1990 | Farr et al. |
| 4,921,499 A | 5/1990 | Hoffman et al. |
| 4,940,064 A | 7/1990 | Desai |
| 4,942,788 A | 7/1990 | Farr et al. |
| 4,979,514 A | 12/1990 | Sekii et al. |
| 4,998,933 A | 3/1991 | Eggers et al. |
| 5,026,384 A | 6/1991 | Farr et al. |
| 5,047,047 A | 9/1991 | Yoon |
| 5,122,137 A | 6/1992 | Lennox |
| 5,127,902 A | 7/1992 | Fischell |
| 5,146,926 A | 9/1992 | Cohen |
| 5,156,151 A | 10/1992 | Imran |
| 5,174,299 A | 12/1992 | Nelson |
| 5,176,693 A | 1/1993 | Pannek, Jr. |
| 5,178,620 A | 1/1993 | Eggers et al. |
| 5,192,291 A | 3/1993 | Pannek, Jr. |
| 5,201,316 A | 4/1993 | Pomeranz et al. |
| 5,228,442 A | 7/1993 | Imran |
| 5,242,386 A | 9/1993 | Holzer |
| 5,255,679 A | 10/1993 | Imran |
| 5,279,299 A | 1/1994 | Imran |
| 5,293,869 A | 3/1994 | Edwards et al. |
| 5,312,435 A | 5/1994 | Nash et al. |
| 5,317,952 A | 6/1994 | Immega |
| 5,327,889 A | 7/1994 | Imran |
| 5,341,807 A | 8/1994 | Nardella |
| 5,366,443 A | 11/1994 | Eggers et al. |
| 5,379,773 A | 1/1995 | Hornsby |
| 5,419,767 A | 5/1995 | Eggers et al. |
| 5,450,860 A | 9/1995 | O'Conner |
| 5,478,353 A | 12/1995 | Yoon |
| 5,496,267 A | 3/1996 | Drasler et al. |
| 5,531,760 A | 7/1996 | Alwafaie |
| 5,545,193 A | 8/1996 | Fleischman et al. |
| 5,557,967 A | 9/1996 | Renger |
| 5,588,432 A | 12/1996 | Crowley |
| 5,593,424 A | 1/1997 | Northrup, III |
| 5,598,848 A | 2/1997 | Swanson et al. |
| 5,599,345 A | 2/1997 | Edwards et al. |
| 5,620,481 A | 4/1997 | Desai et al. |
| 5,662,587 A | 9/1997 | Grundfest et al. |
| 5,681,308 A | 10/1997 | Edward et al. |
| 5,681,336 A | 10/1997 | Clement et al. |
| 5,687,723 A | 11/1997 | Avitall |
| 5,687,737 A | 11/1997 | Branham et al. |
| 5,697,285 A | 12/1997 | Nappi et al. |
| 5,713,896 A | 2/1998 | Marcella |
| 5,713,942 A | 2/1998 | Sten et al. |
| 5,716,397 A | 2/1998 | Myers |
| 5,720,726 A | 2/1998 | Marcadis et al. |
| 5,728,114 A | 3/1998 | Evans et al. |
| 5,730,127 A | 3/1998 | Avitall |
| 5,762,066 A | 6/1998 | Law et al. |
| 5,769,846 A | 6/1998 | Edwards et al. |
| 5,782,239 A | 7/1998 | Webster, Jr. |
| 5,782,879 A | 7/1998 | Rosborough et al. |
| 5,800,495 A | 9/1998 | Machek et al. |
| 5,810,802 A | 9/1998 | Panescu et al. |
| 5,824,066 A | 10/1998 | Gross |
| 5,836,990 A | 11/1998 | Li |
| 5,848,972 A | 12/1998 | Triedman et al. |
| 5,876,343 A | 3/1999 | Teo |
| 5,881,727 A | 3/1999 | Edwards |
| 5,891,136 A | 4/1999 | McGee et al. |
| 5,904,711 A | 5/1999 | Flom et al. |
| 5,916,163 A | 6/1999 | Panescu et al. |
| 5,919,207 A | 7/1999 | Taheri |
| 5,921,924 A | 7/1999 | Avitall |
| 5,935,075 A | 8/1999 | Casscells et al. |
| 5,935,079 A | 8/1999 | Swanson et al. |
| 5,941,251 A | 8/1999 | Panescu et al. |
| 5,961,440 A | 10/1999 | Schweich, Jr. et al. |
| 5,968,040 A | 10/1999 | Swanson et al. |
| 5,984,950 A | 11/1999 | Cragg et al. |
| 6,001,069 A | 12/1999 | Tachibana et al. |
| 6,014,581 A | 1/2000 | Whayne et al. |
| 6,104,944 A | 8/2000 | Martinelli |
| 6,138,043 A | 10/2000 | Avitall |
| 6,142,993 A | 11/2000 | Whayne et al. |
| 6,156,046 A | 12/2000 | Passafaro et al. |
| 6,183,468 B1 | 2/2001 | Swanson |
| 6,210,432 B1 | 4/2001 | Solem et al. |
| 6,216,043 B1 | 4/2001 | Swanson et al. |
| 6,217,573 B1 | 4/2001 | Webster |
| 6,241,747 B1 | 6/2001 | Ruff |
| 6,245,064 B1 | 6/2001 | Lesh et al. |
| 6,248,124 B1 | 6/2001 | Pedros et al. |
| 6,258,258 B1 | 7/2001 | Sartori |

(56) References Cited

U.S. PATENT DOCUMENTS

| | | |
|---|---|---|
| 6,266,550 B1 | 7/2001 | Selmon et al. |
| 6,304,769 B1 | 10/2001 | Arenson et al. |
| 6,306,135 B1 | 10/2001 | Ellmam et al. |
| 6,308,091 B1 | 10/2001 | Avitall |
| 6,319,249 B1 | 11/2001 | Töllner |
| 6,346,105 B1 | 2/2002 | Tu et al. |
| 6,350,263 B1 | 2/2002 | Wetzig et al. |
| 6,358,258 B1 | 3/2002 | Arcia et al. |
| 6,383,151 B1 | 5/2002 | Diederich et al. |
| 6,389,311 B1 | 5/2002 | Whayne et al. |
| 6,391,024 B1 | 5/2002 | Sun et al. |
| 6,391,048 B1 | 5/2002 | Ginn et al. |
| 6,391,054 B2 | 5/2002 | Carpentier et al. |
| 6,402,781 B1 | 6/2002 | Langberg et al. |
| 6,436,052 B1 | 8/2002 | Nikolic et al. |
| 6,475,223 B1 | 11/2002 | Werp et al. |
| 6,485,409 B1 | 11/2002 | Voloshin et al. |
| 6,485,489 B2 | 11/2002 | Teirstein et al. |
| 6,506,210 B1 | 1/2003 | Kanner |
| 6,514,249 B1 | 2/2003 | Maguire et al. |
| 6,529,756 B1 | 3/2003 | Phan et al. |
| 6,537,198 B1 | 3/2003 | Vidlund et al. |
| 6,537,314 B2 | 3/2003 | Langberg et al. |
| 6,540,670 B1 | 4/2003 | Hirata et al. |
| 6,551,312 B2 | 4/2003 | Zhang et al. |
| 6,569,160 B1 | 5/2003 | Goldin et al. |
| 6,569,198 B1 | 5/2003 | Wilson et al. |
| 6,575,971 B2 | 6/2003 | Hauck et al. |
| 6,589,208 B2 | 7/2003 | Ewers et al. |
| 6,626,930 B1 | 9/2003 | Allen et al. |
| 6,632,238 B2 | 10/2003 | Ginn et al. |
| 6,635,056 B2 | 10/2003 | Kadhiresan et al. |
| 6,640,119 B1 | 10/2003 | Budd et al. |
| 6,652,515 B1 | 11/2003 | Maguire et al. |
| 6,652,517 B1 | 11/2003 | Hall et al. |
| 6,662,034 B2 | 12/2003 | Segner et al. |
| 6,666,862 B2 | 12/2003 | Jain et al. |
| 6,704,590 B2 | 3/2004 | Haldeman |
| 6,723,038 B1 | 4/2004 | Schroeder et al. |
| 6,725,085 B2 | 4/2004 | Schwartzman et al. |
| 6,726,716 B2 | 4/2004 | Marquez |
| 6,733,499 B2 | 5/2004 | Scheib |
| 6,735,465 B2 | 5/2004 | Panescu |
| 6,760,616 B2 | 7/2004 | Hoey et al. |
| 6,780,197 B2 | 8/2004 | Roe et al. |
| 6,788,969 B2 | 9/2004 | Dupree et al. |
| 6,795,721 B2 | 9/2004 | Coleman et al. |
| 6,797,001 B2 | 9/2004 | Mathis et al. |
| 6,800,090 B2 | 10/2004 | Alferness et al. |
| 6,837,886 B2 | 1/2005 | Collins et al. |
| 6,852,076 B2 | 2/2005 | Nikolic et al. |
| 6,855,143 B2 | 2/2005 | Davison et al. |
| 6,890,353 B2 | 5/2005 | Cohn et al. |
| 6,892,091 B1 | 5/2005 | Ben-Haim et al. |
| 6,899,674 B2 | 5/2005 | Viebach et al. |
| 6,907,297 B2 | 6/2005 | Wellman et al. |
| 6,908,478 B2 | 6/2005 | Alferness et al. |
| 6,913,576 B2 | 7/2005 | Bowman |
| 6,918,903 B2 | 7/2005 | Bass |
| 6,926,669 B1 | 8/2005 | Stewart et al. |
| 6,936,047 B2 | 8/2005 | Nasab et al. |
| 6,942,657 B2 | 9/2005 | Sinofsky et al. |
| 6,949,122 B2 | 9/2005 | Adams et al. |
| 6,955,640 B2 | 10/2005 | Sanders et al. |
| 6,960,229 B2 | 11/2005 | Mathis et al. |
| 6,966,908 B2 | 11/2005 | Maguire et al. |
| 6,986,775 B2 | 1/2006 | Morales et al. |
| 6,989,010 B2 | 1/2006 | Francischelli et al. |
| 6,989,028 B2 | 1/2006 | Lashinski et al. |
| 6,994,093 B2 | 2/2006 | Murphy et al. |
| 6,997,925 B2 | 2/2006 | Maguire et al. |
| 6,997,951 B2 | 2/2006 | Solem et al. |
| 7,001,383 B2 | 2/2006 | Keidar |
| 7,003,342 B2 | 2/2006 | Plaza |
| 7,025,776 B1 | 4/2006 | Houser et al. |
| 7,044,135 B2 | 5/2006 | Lesh |
| 7,048,734 B1 | 5/2006 | Fleischman et al. |
| 7,050,848 B2 | 5/2006 | Hoey et al. |
| 7,052,487 B2 | 5/2006 | Cohn et al. |
| 7,068,867 B2 | 6/2006 | Adoram et al. |
| 7,141,019 B2 | 11/2006 | Pearlman |
| 7,144,363 B2 | 12/2006 | Pai et al. |
| 7,177,677 B2 | 2/2007 | Kaula et al. |
| 7,186,210 B2 | 3/2007 | Feld et al. |
| 7,187,964 B2 | 3/2007 | Khoury |
| 7,189,202 B2 | 3/2007 | Lau et al. |
| 7,194,294 B2 | 3/2007 | Panescu et al. |
| 7,252,664 B2 | 8/2007 | Nasab et al. |
| 7,279,007 B2 | 10/2007 | Nikolic et al. |
| 7,282,030 B2 | 10/2007 | Frei et al. |
| 7,300,435 B2 | 11/2007 | Wham et al. |
| 7,303,526 B2 | 12/2007 | Sharkey et al. |
| 7,335,196 B2 | 2/2008 | Swanson et al. |
| 7,340,307 B2 | 3/2008 | Maguire et al. |
| 7,507,252 B2 | 3/2009 | Lashinski et al. |
| 7,530,980 B2 | 5/2009 | Hooven |
| 7,575,566 B2 | 8/2009 | Scheib |
| 7,593,760 B2 | 9/2009 | Rodriguez et al. |
| 7,610,078 B2 | 10/2009 | Willis |
| 7,633,502 B2 | 12/2009 | Willis et al. |
| 7,738,967 B2 | 6/2010 | Salo |
| 8,103,338 B2 | 1/2012 | Harlev et al. |
| 8,150,499 B2 | 4/2012 | Gelbart et al. |
| 8,200,308 B2 | 6/2012 | Zhang et al. |
| 8,216,216 B2 | 7/2012 | Warnking et al. |
| 8,221,411 B2 | 7/2012 | Francischelli et al. |
| 8,224,432 B2 | 7/2012 | MacAdam et al. |
| 8,326,419 B2 | 12/2012 | Rosenberg et al. |
| 8,352,019 B2 | 1/2013 | Starks |
| 8,398,626 B2 | 3/2013 | Buysse et al. |
| 8,401,645 B2 | 3/2013 | Rosenberg et al. |
| 8,414,508 B2 | 4/2013 | Thapliyal et al. |
| 8,442,613 B2 | 5/2013 | Kim et al. |
| 8,442,625 B2 | 5/2013 | Markowitz et al. |
| 8,457,371 B2 | 6/2013 | Markowitz et al. |
| 8,463,368 B2 | 6/2013 | Harlev et al. |
| 8,478,393 B2 | 7/2013 | Ramanathan et al. |
| 8,532,734 B2 | 9/2013 | Markowitz et al. |
| 8,571,647 B2 | 10/2013 | Harlev et al. |
| 8,615,287 B2 | 12/2013 | Harlev et al. |
| 8,657,814 B2 | 2/2014 | Werneth et al. |
| 8,663,120 B2 | 3/2014 | Markowitz et al. |
| 8,706,260 B2 | 4/2014 | Stewart et al. |
| 8,725,240 B2 | 5/2014 | Harlev et al. |
| 8,831,701 B2 | 9/2014 | Markowitz et al. |
| 8,834,461 B2 | 9/2014 | Werneth et al. |
| 8,838,216 B2 | 9/2014 | Francis et al. |
| 8,849,384 B2 | 9/2014 | Greenspan |
| 8,897,516 B2 | 11/2014 | Turgeman |
| 8,920,411 B2 | 12/2014 | Gelbart et al. |
| 8,926,605 B2 | 1/2015 | McCarthy et al. |
| 8,932,284 B2 | 1/2015 | McCarthy et al. |
| 8,961,506 B2 | 2/2015 | McCarthy et al. |
| 9,011,423 B2 | 4/2015 | Brewster et al. |
| 9,033,893 B2 | 5/2015 | Spector |
| 9,044,245 B2 | 6/2015 | Condie et al. |
| 9,095,350 B2 | 8/2015 | Condie et al. |
| 9,101,333 B2 | 8/2015 | Schwartz |
| 9,107,599 B2 | 8/2015 | Harlev et al. |
| 9,119,633 B2 | 9/2015 | Gelbart et al. |
| 9,119,634 B2 | 9/2015 | Gelbart et al. |
| 9,179,860 B2 | 11/2015 | Markowitz et al. |
| 9,179,972 B2 | 11/2015 | Olson |
| 9,204,935 B2 | 12/2015 | Hauck et al. |
| 9,265,434 B2 | 2/2016 | Merschon et al. |
| 9,277,872 B2 | 3/2016 | Harlev et al. |
| 9,277,960 B2 | 3/2016 | Weinkam et al. |
| 9,282,910 B2 | 3/2016 | Narayan et al. |
| 9,332,920 B2 | 5/2016 | Thakur et al. |
| 9,398,862 B2 | 7/2016 | Harlev et al. |
| 9,408,544 B2 | 8/2016 | Laughner et al. |
| 9,433,465 B2 | 9/2016 | Gliner et al. |
| 9,439,578 B2 | 9/2016 | Thakur et al. |
| 9,456,759 B2 | 10/2016 | Lian et al. |

(56) References Cited

U.S. PATENT DOCUMENTS

| | | |
|---|---|---|
| 9,474,491 B2 | 10/2016 | Li et al. |
| 9,486,272 B2 | 11/2016 | Bonyak et al. |
| 9,504,518 B2 | 11/2016 | Condie et al. |
| 9,532,725 B2 | 1/2017 | Laughner et al. |
| 9,532,828 B2 | 1/2017 | Condie et al. |
| 9,554,718 B2 | 1/2017 | Bar-Tal et al. |
| 9,554,847 B2 | 1/2017 | Govari et al. |
| 9,572,620 B2 | 2/2017 | Ryu et al. |
| 9,579,064 B2 | 2/2017 | Kovtun et al. |
| 9,603,651 B2 | 3/2017 | Ghosh |
| 9,603,661 B2 | 3/2017 | Gelbart et al. |
| 9,610,045 B2 | 4/2017 | Du et al. |
| 9,622,806 B2 | 4/2017 | Mihalik |
| 9,629,567 B2 | 4/2017 | Porath et al. |
| 9,636,032 B2 | 5/2017 | Thakur et al. |
| 9,655,535 B2 | 5/2017 | Narayan et al. |
| 9,662,033 B2 | 5/2017 | Severino |
| 9,693,699 B2 | 7/2017 | Spector et al. |
| 9,730,603 B2 | 8/2017 | Laughner et al. |
| 9,737,267 B2 | 8/2017 | Strom et al. |
| 9,743,854 B2 | 8/2017 | Stewart et al. |
| 9,763,587 B2 | 9/2017 | Altmann |
| 9,763,625 B2 | 9/2017 | Laughner et al. |
| 9,782,094 B2 | 10/2017 | Du et al. |
| 9,795,314 B2 | 10/2017 | Laughner et al. |
| 9,814,523 B2 | 11/2017 | Condie et al. |
| 9,848,833 B2 | 12/2017 | Govari et al. |
| 9,861,802 B2 | 1/2018 | Mickelsen |
| 9,875,578 B2 | 1/2018 | Zar et al. |
| 9,888,972 B2 | 2/2018 | Brewster et al. |
| 9,895,079 B2 | 2/2018 | Massarwa et al. |
| 9,913,589 B2 | 3/2018 | Scharf et al. |
| 9,918,649 B2 | 3/2018 | Thakur et al. |
| 9,918,788 B2 | 3/2018 | Paul et al. |
| 9,940,747 B2 | 4/2018 | Katz et al. |
| 9,949,657 B2 | 4/2018 | Ravuna et al. |
| 9,955,889 B2 | 5/2018 | Urman et al. |
| 9,980,653 B2 | 5/2018 | Lichtenstein et al. |
| 9,980,679 B2 | 5/2018 | Reinders et al. |
| 9,987,083 B2 | 6/2018 | Gelbart et al. |
| 9,987,084 B2 | 6/2018 | Gelbart et al. |
| 10,004,413 B2 | 6/2018 | Bokan et al. |
| 10,010,368 B2 | 7/2018 | Laske et al. |
| 10,016,145 B2 | 7/2018 | Thakur et al. |
| 10,028,783 B2 | 7/2018 | Gelbart et al. |
| 10,064,678 B2 | 9/2018 | Corvi et al. |
| 10,085,659 B2 | 10/2018 | Laughner et al. |
| 2001/0003158 A1 | 6/2001 | Kensey et al. |
| 2001/0005787 A1 | 6/2001 | Oz et al. |
| 2001/0018611 A1 | 8/2001 | Solem et al. |
| 2001/0020126 A1 | 9/2001 | Swanson et al. |
| 2002/0002329 A1 | 1/2002 | Avitall |
| 2002/0016628 A1 | 2/2002 | Langberg et al. |
| 2002/0087156 A1 | 7/2002 | Maguire et al. |
| 2002/0087173 A1 | 7/2002 | Alferness et al. |
| 2002/0099415 A1 | 7/2002 | Panescu et al. |
| 2002/0107478 A1 | 8/2002 | Wendlandt |
| 2002/0107511 A1 | 8/2002 | Collins et al. |
| 2002/0115941 A1 | 8/2002 | Whayne et al. |
| 2002/0115944 A1 | 8/2002 | Mendes et al. |
| 2002/0165535 A1 | 11/2002 | Lesh et al. |
| 2002/0169445 A1 | 11/2002 | Jain et al. |
| 2002/0169504 A1 | 11/2002 | Alferness et al. |
| 2002/0177782 A1 | 11/2002 | Penner |
| 2002/0183836 A1 | 12/2002 | Liddicoat et al. |
| 2002/0183841 A1 | 12/2002 | Cohn et al. |
| 2002/0188170 A1 | 12/2002 | Santamore et al. |
| 2003/0023130 A1 | 1/2003 | Ciaccio et al. |
| 2003/0028118 A1 | 2/2003 | Dupree et al. |
| 2003/0028183 A1 | 2/2003 | Sanchez et al. |
| 2003/0050637 A1 | 3/2003 | Maguire et al. |
| 2003/0050685 A1 | 3/2003 | Nikolic et al. |
| 2003/0055420 A1 | 3/2003 | Kadhiresan et al. |
| 2003/0060820 A1 | 3/2003 | Maguire et al. |
| 2003/0069570 A1 | 4/2003 | Witzel et al. |
| 2003/0069573 A1 | 4/2003 | Kadhiresan et al. |
| 2003/0069636 A1 | 4/2003 | Solem et al. |
| 2003/0078465 A1 | 4/2003 | Pai et al. |
| 2003/0078494 A1 | 4/2003 | Panescu et al. |
| 2003/0078509 A1 | 4/2003 | Panescu |
| 2003/0078671 A1 | 4/2003 | Lesniak et al. |
| 2003/0105384 A1 | 6/2003 | Sharkey et al. |
| 2003/0105520 A1 | 6/2003 | Alferness et al. |
| 2003/0109770 A1 | 6/2003 | Sharkey et al. |
| 2003/0125726 A1 | 7/2003 | Maguire et al. |
| 2003/0181819 A1 | 9/2003 | Desai |
| 2003/0212395 A1 | 11/2003 | Woloszko et al. |
| 2003/0229395 A1 | 12/2003 | Cox |
| 2004/0002626 A1 | 1/2004 | Feld et al. |
| 2004/0006337 A1 | 1/2004 | Nasab et al. |
| 2004/0054279 A1 | 3/2004 | Hanley |
| 2004/0133273 A1 | 7/2004 | Cox |
| 2004/0138744 A1 | 7/2004 | Lashinski et al. |
| 2004/0153146 A1 | 8/2004 | Lashinski et al. |
| 2004/0158321 A1 | 8/2004 | Reuter et al. |
| 2004/0176797 A1 | 9/2004 | Opolski |
| 2004/0186566 A1 | 9/2004 | Hindrichs et al. |
| 2004/0215232 A1 | 10/2004 | Belhe et al. |
| 2004/0243170 A1 | 12/2004 | Suresh et al. |
| 2004/0249408 A1 | 12/2004 | Murphy et al. |
| 2004/0249453 A1 | 12/2004 | Cartledge et al. |
| 2004/0267358 A1 | 12/2004 | Reitan |
| 2005/0004668 A1 | 1/2005 | Aklog et al. |
| 2005/0010206 A1 | 1/2005 | Nasab et al. |
| 2005/0015109 A1 | 1/2005 | Lichtenstein |
| 2005/0043604 A1 | 2/2005 | Beatty et al. |
| 2005/0054938 A1 | 3/2005 | Wehman et al. |
| 2005/0055089 A1 | 3/2005 | Macoviak et al. |
| 2005/0060030 A1 | 3/2005 | Lashinski et al. |
| 2005/0064665 A1 | 3/2005 | Han |
| 2005/0065420 A1 | 3/2005 | Collins et al. |
| 2005/0065504 A1 | 3/2005 | Melsky et al. |
| 2005/0080402 A1 | 4/2005 | Santamore et al. |
| 2005/0096047 A1 | 5/2005 | Haberman et al. |
| 2005/0096647 A1 | 5/2005 | Steinke et al. |
| 2005/0107723 A1 | 5/2005 | Wehman et al. |
| 2005/0107871 A1 | 5/2005 | Realyvasques et al. |
| 2005/0125030 A1 | 6/2005 | Forsberg et al. |
| 2005/0148892 A1 | 7/2005 | Desai |
| 2005/0149014 A1 | 7/2005 | Hauck et al. |
| 2005/0154252 A1 | 7/2005 | Sharkey et al. |
| 2005/0165388 A1 | 7/2005 | Bhola |
| 2005/0182365 A1 | 8/2005 | Hennemann |
| 2005/0187620 A1 | 8/2005 | Pai et al. |
| 2005/0197692 A1 | 9/2005 | Pai et al. |
| 2005/0197693 A1 | 9/2005 | Pai et al. |
| 2005/0197694 A1 | 9/2005 | Pai et al. |
| 2005/0203558 A1 | 9/2005 | Maschke |
| 2005/0209525 A1 | 9/2005 | Bojovic et al. |
| 2005/0209636 A1 | 9/2005 | Widomski et al. |
| 2005/0216054 A1 | 9/2005 | Widomski et al. |
| 2005/0240249 A1 | 10/2005 | Tu et al. |
| 2005/0251116 A1 | 11/2005 | Steinke et al. |
| 2005/0251132 A1 | 11/2005 | Oral et al. |
| 2005/0256521 A1 | 11/2005 | Kozel |
| 2005/0261580 A1 | 11/2005 | Willis et al. |
| 2005/0267574 A1 | 12/2005 | Cohn et al. |
| 2006/0009755 A1 | 1/2006 | Sra |
| 2006/0009756 A1 | 1/2006 | Francischelli et al. |
| 2006/0014998 A1 | 1/2006 | Sharkey et al. |
| 2006/0015002 A1 | 1/2006 | Moaddeb et al. |
| 2006/0015003 A1 | 1/2006 | Moaddes et al. |
| 2006/0015038 A1 | 1/2006 | Weymarn-Scharli |
| 2006/0015096 A1 | 1/2006 | Hauck et al. |
| 2006/0025800 A1 | 2/2006 | Suresh |
| 2006/0030881 A1 | 2/2006 | Sharkey et al. |
| 2006/0064006 A1 | 3/2006 | Strommer et al. |
| 2006/0084966 A1 | 4/2006 | Maguire et al. |
| 2006/0085049 A1 | 4/2006 | Cory et al. |
| 2006/0089637 A1 | 4/2006 | Werneth et al. |
| 2006/0135968 A1 | 6/2006 | Schaller |
| 2006/0135970 A1 | 6/2006 | Schaller |
| 2006/0173251 A1 | 8/2006 | Govari et al. |
| 2006/0184242 A1 | 8/2006 | Lichtenstein |

(56) References Cited

U.S. PATENT DOCUMENTS

| | | |
|---|---|---|
| 2006/0199995 A1 | 9/2006 | Vijay |
| 2006/0229491 A1 | 10/2006 | Sharkey et al. |
| 2006/0235286 A1 | 10/2006 | Stone et al. |
| 2006/0235314 A1 | 10/2006 | Migliuolo et al. |
| 2006/0264980 A1 | 11/2006 | Khairkhahan et al. |
| 2006/0281965 A1 | 12/2006 | Khairkhahan et al. |
| 2006/0293698 A1 | 12/2006 | Douk |
| 2006/0293725 A1 | 12/2006 | Rubinsky et al. |
| 2007/0016068 A1 | 1/2007 | Grunwald et al. |
| 2007/0038208 A1 | 2/2007 | Kefer |
| 2007/0083193 A1 | 4/2007 | Werneth et al. |
| 2007/0083195 A1 | 4/2007 | Werneth et al. |
| 2007/0088362 A1 | 4/2007 | Bonutti et al. |
| 2007/0115390 A1 | 5/2007 | Makara et al. |
| 2007/0118215 A1 | 5/2007 | Moaddeb |
| 2007/0129717 A1 | 6/2007 | Brown, III et al. |
| 2007/0161846 A1 | 7/2007 | Nikolic et al. |
| 2007/0198058 A1 | 8/2007 | Gelbart et al. |
| 2007/0213578 A1 | 9/2007 | Khairkhahan et al. |
| 2007/0213815 A1 | 9/2007 | Khairkhahan et al. |
| 2007/0232949 A1 | 10/2007 | Saksena |
| 2007/0236491 A1 | 10/2007 | Hundley et al. |
| 2007/0239062 A1 | 10/2007 | Chopra |
| 2007/0249999 A1 | 10/2007 | Sklar et al. |
| 2007/0270688 A1 | 11/2007 | Gelbart et al. |
| 2007/0299343 A1 | 12/2007 | Waters |
| 2008/0004534 A1 | 1/2008 | Gelbart et al. |
| 2008/0004643 A1 | 1/2008 | To et al. |
| 2008/0004697 A1 | 1/2008 | Lichtenstein et al. |
| 2008/0045778 A1 | 2/2008 | Lichtenstein et al. |
| 2008/0071298 A1 | 3/2008 | Khairkhahan et al. |
| 2008/0091990 A1 | 4/2008 | Berenfeld et al. |
| 2008/0172048 A1 | 7/2008 | Martin et al. |
| 2008/0194979 A1 | 8/2008 | Madry et al. |
| 2008/0281322 A1 | 11/2008 | Sherman et al. |
| 2008/0312713 A1 | 12/2008 | Wilfley et al. |
| 2009/0018617 A1 | 1/2009 | Skelton et al. |
| 2009/0069704 A1 | 3/2009 | MacAdam et al. |
| 2009/0131930 A1 | 5/2009 | Gelbart et al. |
| 2009/0148012 A1 | 6/2009 | Altmann et al. |
| 2009/0157058 A1 | 6/2009 | Ferren et al. |
| 2009/0163801 A1 | 6/2009 | Sliwa |
| 2009/0182325 A1 | 7/2009 | Werneth et al. |
| 2009/0192441 A1 | 7/2009 | Gelbart et al. |
| 2009/0253976 A1 | 10/2009 | Harlev et al. |
| 2009/0264781 A1 | 10/2009 | Scharf |
| 2009/0287271 A1 | 11/2009 | Blum et al. |
| 2009/0287304 A1 | 11/2009 | Dahlgren et al. |
| 2010/0016762 A1 | 1/2010 | Thapliyal et al. |
| 2010/0023004 A1 | 1/2010 | Francischelli et al. |
| 2010/0113928 A1 | 5/2010 | Thapliyal et al. |
| 2010/0113985 A1 | 5/2010 | Thapliyal et al. |
| 2010/0114094 A1 | 5/2010 | Thapliyal |
| 2010/0204694 A1 | 8/2010 | Mehta et al. |
| 2010/0249771 A1 | 9/2010 | Pearson et al. |
| 2010/0268059 A1 | 10/2010 | Ryu et al. |
| 2010/0286551 A1 | 11/2010 | Harlev et al. |
| 2011/0034912 A1 | 2/2011 | De Graff et al. |
| 2011/0125172 A1 | 5/2011 | Gelbart et al. |
| 2012/0078076 A1 | 3/2012 | Stewart et al. |
| 2012/0136346 A1 | 5/2012 | Condie et al. |
| 2012/0136348 A1 | 5/2012 | Condie et al. |
| 2012/0172859 A1 | 7/2012 | Condie et al. |
| 2012/0172867 A1 | 7/2012 | Ryu et al. |
| 2012/0277567 A1 | 11/2012 | Harlev et al. |
| 2013/0066220 A1 | 3/2013 | Weinkam et al. |
| 2013/0172884 A1 | 7/2013 | Schoenbach et al. |
| 2013/0274562 A1 | 10/2013 | Ghaffari et al. |
| 2013/0296679 A1 | 11/2013 | Condie et al. |
| 2013/0296850 A1 | 11/2013 | Olson |
| 2013/0310702 A1 | 11/2013 | Reinders et al. |
| 2013/0310826 A1 | 11/2013 | Goertzen et al. |
| 2013/0310827 A1 | 11/2013 | Brewster et al. |
| 2013/0310828 A1 | 11/2013 | Reinders et al. |
| 2013/0345538 A1 | 12/2013 | Harlev et al. |
| 2014/0121659 A1 | 5/2014 | Paul et al. |
| 2014/0213894 A1 | 7/2014 | Gelbart et al. |
| 2014/0296850 A1 | 10/2014 | Condie et al. |
| 2014/0303610 A1 | 10/2014 | McCarthy et al. |
| 2014/0303614 A1 | 10/2014 | McCarthy et al. |
| 2014/0364848 A1 | 12/2014 | Heimbecher et al. |
| 2015/0105701 A1 | 4/2015 | Mayer et al. |
| 2015/0182740 A1 | 7/2015 | Mickelsen |
| 2015/0366508 A1 | 12/2015 | Chou et al. |
| 2016/0008061 A1 | 1/2016 | Fung et al. |
| 2016/0058505 A1 | 3/2016 | Condie et al. |
| 2016/0106498 A1 | 4/2016 | Highsmith |
| 2016/0287137 A1 | 10/2016 | Condie et al. |
| 2016/0346030 A1 | 12/2016 | Thapliyal et al. |
| 2016/0367325 A1 | 12/2016 | Brewster et al. |
| 2017/0035499 A1 | 2/2017 | Stewart et al. |
| 2017/0065339 A1 | 3/2017 | Mickelsen |
| 2017/0065340 A1 | 3/2017 | Long |
| 2017/0079712 A1 | 3/2017 | Levin et al. |
| 2017/0092013 A1 | 3/2017 | Perlman et al. |
| 2017/0103570 A1 | 4/2017 | Zar et al. |
| 2017/0105627 A1 | 4/2017 | Katz et al. |
| 2017/0119453 A1 | 5/2017 | Ryu et al. |
| 2017/0128013 A1 | 5/2017 | Reinders et al. |
| 2017/0143414 A1 | 5/2017 | Sliwa et al. |
| 2017/0156792 A1 | 6/2017 | Ziv-Ari et al. |
| 2017/0202470 A1 | 7/2017 | Urman et al. |
| 2017/0202516 A1 | 7/2017 | Bar-Tal et al. |
| 2017/0202521 A1 | 7/2017 | Urman et al. |
| 2017/0312012 A1 | 11/2017 | Harlev et al. |
| 2018/0042674 A1 | 2/2018 | Mickelsen |
| 2018/0042675 A1 | 2/2018 | Long |
| 2018/0056074 A1 | 3/2018 | Clark et al. |
| 2018/0064488 A1 | 3/2018 | Long |
| 2018/0068439 A1 | 3/2018 | Hareland |
| 2018/0093088 A1 | 4/2018 | Mickelsen |
| 2018/0110561 A1 | 4/2018 | Levin et al. |
| 2018/0125575 A1 | 5/2018 | Schwartz et al. |
| 2018/0140363 A1 | 5/2018 | Brewster et al. |
| 2018/0158238 A1 | 6/2018 | Cohen et al. |
| 2018/0160978 A1 | 6/2018 | Cohen et al. |
| 2018/0161097 A1 | 6/2018 | Zoabi et al. |
| 2018/0177467 A1 | 6/2018 | Katz et al. |
| 2018/0177552 A1 | 6/2018 | Zoabi et al. |
| 2018/0182157 A1 | 6/2018 | Zar et al. |
| 2018/0182159 A1 | 6/2018 | Cohen et al. |
| 2018/0190009 A1 | 7/2018 | Cohen et al. |
| 2018/0199976 A1 | 7/2018 | Fischer |
| 2018/0199990 A1 | 7/2018 | Monir et al. |
| 2018/0200497 A1 | 7/2018 | Mickelsen |
| 2018/0206920 A1 | 7/2018 | Pappone et al. |
| 2018/0214202 A1 | 8/2018 | Howard et al. |
| 2018/0242868 A1 | 8/2018 | Cohen et al. |
| 2018/0242914 A1 | 8/2018 | Reinders et al. |
| 2018/0256055 A1 | 9/2018 | Zigelman et al. |
| 2018/0296114 A1 | 10/2018 | Welsh et al. |
| 2018/0325597 A1 | 11/2018 | Schwartz et al. |
| 2019/0029608 A1 | 1/2019 | Moisa et al. |
| 2019/0029609 A1 | 1/2019 | Moisa et al. |

FOREIGN PATENT DOCUMENTS

| | | |
|---|---|---|
| EP | 1240868 A1 | 9/2002 |
| EP | 1645234 A1 | 4/2006 |
| EP | 1182980 B1 | 6/2006 |
| EP | 1280467 B1 | 11/2008 |
| EP | 1451595 B1 | 7/2009 |
| EP | 2499968 A1 | 9/2012 |
| EP | 1909679 B1 | 11/2013 |
| EP | 2307098 B1 | 3/2015 |
| EP | 2848191 A1 | 3/2015 |
| EP | 2873365 A1 | 5/2015 |
| EP | 2984986 A2 | 2/2016 |
| EP | 2645953 B1 | 8/2016 |
| EP | 2661236 B1 | 8/2016 |
| EP | 2749213 B1 | 9/2016 |
| EP | 2604211 B1 | 10/2016 |
| EP | 3130285 A1 | 2/2017 |
| EP | 3141185 A1 | 3/2017 |

(56) References Cited

FOREIGN PATENT DOCUMENTS

| | | | |
|---|---|---|---|
| EP | 2689722 | B1 | 6/2017 |
| EP | 2613723 | B1 | 10/2017 |
| EP | 3225161 | A1 | 10/2017 |
| EP | 2892454 | B1 | 1/2018 |
| EP | 3318211 | A2 | 5/2018 |
| EP | 3321890 | A1 | 5/2018 |
| EP | 3139997 | B1 | 9/2018 |
| EP | 3375365 | A2 | 9/2018 |
| WO | 9313708 | A1 | 7/1993 |
| WO | 95/10320 | A1 | 4/1995 |
| WO | 95/20349 | A1 | 8/1995 |
| WO | 97/17892 | A2 | 5/1997 |
| WO | 0134026 | A1 | 5/2001 |
| WO | 0228303 | A1 | 4/2002 |
| WO | 03/015611 | A2 | 2/2003 |
| WO | 03022148 | A1 | 3/2003 |
| WO | 03/077800 | A1 | 9/2003 |
| WO | 2004/012629 | A1 | 2/2004 |
| WO | 2004/047679 | A1 | 6/2004 |
| WO | 2004/084746 | A2 | 10/2004 |
| WO | 2004/100803 | A1 | 11/2004 |
| WO | 2005/070330 | A1 | 8/2005 |
| WO | 2005/102181 | A1 | 11/2005 |
| WO | 2006/017809 | A2 | 2/2006 |
| WO | 2006/105121 | A2 | 10/2006 |
| WO | 2006/135747 | A2 | 12/2006 |
| WO | 2006/135749 | A2 | 12/2006 |
| WO | 2007/021647 | A2 | 2/2007 |
| WO | 2007/024983 | A2 | 3/2007 |
| WO | 2007/115390 | A1 | 10/2007 |
| WO | 2008/002606 | A2 | 1/2008 |
| WO | 2008135731 | A1 | 11/2008 |
| WO | 2009/065042 | A2 | 5/2009 |
| WO | 2010031830 | A1 | 3/2010 |
| WO | 2010054409 | A1 | 5/2010 |
| WO | 2012/033984 | A1 | 3/2012 |
| WO | 2012/100184 | A2 | 7/2012 |
| WO | 2012/100185 | A2 | 7/2012 |
| WO | 2012151301 | A1 | 11/2012 |
| WO | 2013/176880 | A1 | 11/2013 |
| WO | 2013/0176881 | A1 | 11/2013 |
| WO | 2016181317 | A2 | 11/2016 |
| WO | 2016181318 | A1 | 11/2016 |
| WO | 2016183468 | A1 | 11/2016 |
| WO | 2017009165 | A1 | 1/2017 |
| WO | 2017024123 | A1 | 2/2017 |
| WO | 2017087740 | A1 | 5/2017 |
| WO | 2017120169 | A1 | 7/2017 |
| WO | 2017192480 | A2 | 11/2017 |
| WO | 2017192495 | A1 | 11/2017 |
| WO | 2017192510 | A2 | 11/2017 |
| WO | 2017192542 | A2 | 11/2017 |
| WO | 2018023132 | A1 | 2/2018 |
| WO | 2018165425 | A1 | 9/2018 |

OTHER PUBLICATIONS

International Search Report and Written Opinion issued in PCT/CA2013/050350 dated Aug. 2, 2013.
International Search Report and Written Opinion issued in PCT/US2013/039982 dated Sep. 17, 2013.
International Search Report and Written Opinion issued in PCT/US2013/039977 dated Sep. 27, 2013.
Brewster et al., "Systems and Methods for Selecting, Activating, or Selecting and Activating Transducers", Response to Restriction Requirement filed Dec. 23, 2014 for U.S. Appl. No. 13/792,670, 15 pages.
Reinders et al., "Systems and Methods for Activating Transducers", Response to Restriction Requirement filed Dec. 23, 2014 for U.S. Appl. No. 13/792,945, 16 pages.
Reinders et al., "Systems and Methods for Activating Transducers", Notice of Allowance for U.S. Appl. No. 13/792,945 dated Jan. 27, 2015, 49 pages.
Reinders et al., "Systems and Methods for Activating Transducers", Response to Restriction Requirement filed Dec. 23, 2014 for U.S. Appl. No. 13/792,781, 15 pages.
Reinders et al., "Systems and Methods for Activating Transducers", Notice of Allowance dated Feb. 3, 2015 for U.S. Appl. No. 13/792,781, 52 pages.
Brewster et al., "Systems and Methods for Selecting, Activating, or Selecting and Activating Transducers", Notice of Allowance dated Feb. 4, 2015 for U.S. Appl. No. 13/792,670, 47 pages.
Partial Supplementary European Search Report issued in EP13794418.7, dated Jun. 1, 2015.
Extended European Search Report issued in EP137936902, dated May 22, 2015.
Extended European Search Report issued in EP13794418.7, dated Sep. 16, 2015, 12 pages.
Reinders et al., "Systems and Methods for Activating Transducers", Non-Final Office Action dated Sep. 30, 2015 for U.S. Appl. No. 14/686,457, 54 pages.
Brewster et al., "Systems and Methods for Selecting, Activating, or Selecting and Activating Transducers", Non-Final Office Action dated Oct. 2, 2015 for U.S. Appl. No. 14/686,408, 53 pages.
Goertzen et al., "Systems and Methods for Selecting, Activating, or Selecting and Activating Transducers", Office Action for U.S. Appl. No. 13/792,596 dated Nov. 24, 2015, 64 pages.
Reinders et al., "Systems and Methods for Activating Transducers", Office Action for U.S. Appl. No. 14/948,924 dated Dec. 31, 2015, 55 pages.
Office Action issued in European Application No. 13794418.7 dated Jun. 7, 2017.
Office Action issued in U.S. Appl. No. 15/254,207 dated Jun. 1, 2017.
Notice of Allowance issued in U.S. Appl. No. 13/792,596 dated May 5, 2017.
Response to Restriction Requirement and Amendment filed in U.S. Appl. No. 15/254,207 dated Apr. 5, 2017.
Amendment filed in U.S. Appl. No. 15/254,207 dated Aug. 23, 2017.
Notice of Allowance issued in U.S. Appl. No. 15/254,207 dated Oct. 4, 2017.
Kottkamp et al. "Global multielectrode contact mapping plus ablation with a single catheter: Preclinical and preliminary experience in humans with atrial fibrillation." Journal of Cardiovascular Electrophysiology. 2017: 1-10. vol. 28, Issue 11.
Mounsey. "A novel multielectrode combined mapping and ablation basket catheter: A future player in the atrial fibrillation ablation space?" Journal of Cardiovascular Electrophysiology. 2017: 1-2. vol. 28, Issue 11.
Office Action issued in copending U.S. Appl. No. 14/942,459 dated Jan. 18, 2019.
Office Action issued in European Appln. No. 13793690.2 dated Oct. 19, 2018.
Amendment filed in U.S. Appl. No. 14/942,459 dated Feb. 26, 2019.
Notice of Allowance issued in U.S. Appl. No. 14/942,459 dated Apr. 4, 2019.
Copending U.S. Appl. No. 16/388,093, filed Apr. 18, 2019.
Copending U.S. Appl. No. 16/599,305, filed Oct. 11, 2019.
Extended European Search Report issued in European Appln. No. 19188918.7 dated Nov. 4, 2019.
Notice of Allowance issued in copending U.S. Appl. No. 15/860,921 dated Sep. 18, 2019.
Preliminary Amendment filed in copending U.S. Appl. No. 16/599,305 dated Oct. 29, 2019.
Notice of Allowance issued in copending U.S. Appl. No. 15/964,951 dated Nov. 7, 2019.
Office Action issued in copending U.S. Appl. No. 15/827,499 dated Nov. 7, 2019.
Amendment filed in copending U.S. Appl. No. 15/827,499 dated Jul. 26, 2019.
Becker, et al., "Ablation of Atrial Fibrillation: Energy Sources and Navigation Tools: A Review", Journal of Electrocardiology, Supplement 2004, pp. 55-62, vol. 37.

(56) References Cited

OTHER PUBLICATIONS

Buchbinder, Maurice, "Dynamic Mitral Valve Annuloplasty: A Reshapable Ring for Residual and Recurring MR", Foundation for Cardiovascular Medicine, May 24, 2007.
Calkins, Hugh, "Electrophysiology: Radiofrequency Catheter Ablation of Supraventricular Arrhythmias", Education in Heart, 2001; pp. 594-600, vol. 85.
De Ponti, et al., "Non-Fluoroscopic Mapping Systems for Electrophysiology: the Tool or Toy Dilemma After 10 Years", European Heart Journal, 2006; pp. 1134-1136, vol. 27.
Gabriel, et al., "The Dielectric Properties of Biological Tissues: I. Literature Survey", Phys. Med. Biol.; 1996, pp. 2231-2249, vol. 41.
Konings, et al., "Development of an Intravascular Impedance Catheter for Detection of Fatty Lesions in Arteries", IEEE Transactions on Medical Imaging, Aug. 1997, pp. 439-446, vol. 16, No. 4.
Mack, Michael J., "New Techniques for Percutaneous Repair of the Mitral Valve", Heart Fail Rev, 2006; pp. 259-268, vol. 11.
Otasevic, et al., "First-in-Man Implantation of Left Ventricular Partitioning Device in a Patient With Chronic Heart Failure: Twelve-Month Follow-Up", Journal of Cardiac Failure, 2007, pp. 517-520, vol. 13, No. 7.
Sharkey, et al., "Left Ventricular Apex Occluder. Description of a Ventricular Partitioning Device", EuroIntervention, 2006, pp. 125-127.
Stiles, et al., "Simulated Characterization of Atherosclerotic Lesions in the Coronary Arteries by Measurement of Bioimpedance", IEEE Transactions on Biomedical Engineering, Jul. 2003, pp. 916-921, vol. 50, No. 7.
Tanaka, et al., "Artificial SMA Valve for Treatment of Urinary Incontinence: Upgrading of Valve and Introduction of Transcutaneous Transformer", Bio-Medical Materials and Engineering; 1999, pp. 97-112, vol. 9.
Timek, et al., "Septal-Lateral Annular Cinching Abolishes Acute Ischemic Mitral Regurgitation", Journal of Thoracic and Cardiovascular Surgery, May 2002, pp. 881-888, vol. 123, No. 5.
Timek, et al., "Septal-Lateral Annular Cinching (SLAC) Reduces Mitral Annular Size Without Perturbing Normal Annular Dynamics", Journal of Heart Valve Disease, Jan. 2002, vol. 11, No. 1, pp. 1-9.
Valvano, et al., "Thermal Conductivity and Diffusivity of Biomaterials Measured with Self-Heated Thermistors", International Journal of Thermophysics, 1985, pp. 301-311, vol. 6, No. 3.
Prosecution Documents for U.S. Appl. No. 11/436,584, now abandoned.
Prosecution Documents for U.S. Appl. No. 11/941,819, now published as US 2009-0131930 A1.
Prosecution Documents for U.S. Appl. No. 12/010,458, now published as US 2009-0192441 A1.
Prosecution Documents for U.S. Appl. No. 12/950,871, now patented as U.S. Pat. No. 8,150,499.
Specification and Drawings of U.S. Appl. No. 10/690,131.
International Search Report issued in PCT/US2007/014902 dated Dec. 5, 2007, 5 pages.
International Search Report issued in PCT/US2008/083644 dated Dec. 2, 2009, 5 pages.
International Preliminary Report on Patentability issued in PCT/US2007/014902 dated Jan. 6, 2009, 8 pages.
Written Opinion issued in PCT/US2007/014902 dated Dec. 5, 2007, 7 pages.
Written Opinion issued in PCT/US2008/083644 dated Dec. 2, 2009, 9 pages.
"Waveforms and Segments", Ensile System Instructions for use, 54-06154-001 Rev02, Chapter 7 , pp. 85-90 © 2007 St. Jude Medical.
Office Action issued in U.S. Appl. No. 14/948,924 dated Aug. 8, 2016.
Notice of Allowance issued in U.S. Appl. No. 14/686,457 dated May 11, 2016.
Goertzen et al., "Systems and Methods for Selecting, Activating, or Selecting and Activating Transducers", Amendment filed on May 17, 2016 for U.S. Appl. No. 13/792,596. 20 pages.
Reinders et al., "Systems and Methods for Activating Transducers" Amendment filed Jun. 20, 2016 for U.S. Appl. No. 14/948,924. 8 pages.
Brewster et al., "Systems and Methods for Selecting, Activating, or Selecting and Activating Transducers", Response to NFOA and Terminal Disclaimer filed Mar. 31, 2016 for U.S. Appl. No. 14/686,408. 5 pages.
Notice of Allowance issued in U.S. Appl. No. 14/686,408 dated May 11, 2016.
Office Action issued in U.S. Appl. No. 13/792,596 dated Aug. 26, 2016.
Notice of Allowance issued in U.S. Appl. No. 15/000,491 dated Sep. 2, 2016.
Examination Report issued in European Application No. 13793690.2 dated Nov. 17, 2016.
Notice of Allowance issued in U.S. Appl. No. 14/948,924 dated Dec. 21, 2016.
Reinders et al., "Systems and Methods for Activating Transducers" Response to FOA and Terminal Disclaimer filed in U.S. Appl. No. 14/948,924 dated Dec. 12, 2016.
Reinders et al., "Systems and Methods for Activating Transducers", Amendment After Allowance filed Feb. 13, 2015 for U.S. Appl. No. 13/792,945, 14 pages.
Reinders et al., "Systems and Methods for Activating Transducers", Amendment After Allowance filed Feb. 13, 2015 for U.S. Appl. No. 13/792,781, 14 pages.
Brewster et al. "Systems and Methods for Selecting, Activating, or Selecting and Activating Transducers", Preliminary Amendment filed in Sep. 21, 2016 for U.S. Appl. No. 15/254,207, 11 pages.
Brewster et al. "Systems and Methods for Selecting, Activating, or Selecting and Activating Transducers", Preliminary Amendment filed in May 15, 2015 for U.S. Appl. No. 14/686,408, 8 pages.
Brewster et al., "Systems and Methods for Selecting, Activating, or Selecting and Activating Transducers", Amendment After Allowance filed in Feb. 13, 2015 for U.S. Appl. No. 13/792,670, 11 pages.
Goertzen et al. "Systems and Methods for Selecting, Activating, or Selecting and Activating Transducers", Preliminary Amendment filed in Feb. 13, 2015 for U.S. Appl. No. 13/792,596, 11 pages.
Goertzen et al., "Systems and Methods for Selecting, Activating, or Selecting and Activating Transducers", Response to Restriction Requirement filed Jun. 29, 2015 for U.S. Appl. No. 13/792,596, 6 pages.
Goertzen et al., "Systems and Methods for Selecting, Activating, or Selecting and Activating Transducers", Amendment filed Jan. 10, 2017 for U.S. Appl. No. 13/792,596, 21 pages.
Intention to Grant issued in European Application No. 13794418.7 dated Apr. 9, 2019.
Copending U.S. Appl. No. 16/415,016, filed May 17, 2019.
Copending U.S. Appl. No. 16/426,091, filed May 30, 2019.
Office Action issued in copending U.S. Appl. No. 15/827,499 dated Jun. 17, 2019.
Intention to Grant issued in European Application No. 13793690.2 dated May 27, 2019.
Preliminary Amendment filed in copending U.S. Appl. No. 16/426,091 dated Jun. 25, 2019.
Preliminary Amendment filed in copending U.S. Appl. No. 16/415,016 dated Jun. 25, 2019.
Notice of Allowance issued in U.S. Appl. No. 15/414,834 dated Jan. 29, 2018.
Preliminary Amendment filed in U.S. Appl. No. 15/964,951 dated Jun. 6, 2018.
Desjardins. "Infarct Architecture and Characteristics on Delayed Enhanced Magnetic Resonance Imaging and Electroanatomic Mapping in Patients with Post-Infarction Ventricular Arrhythmia." Heart Rhythm. May 2009: 644-651. vol. 6, No. 5.
Yamada. "Pulmonary Vein Isolation with a Multielectrode Basket Catheter." Indian Pacing and Electrophysiology Journal. 2006: 97-109. vol. 7, No. 2.

(56) References Cited

OTHER PUBLICATIONS

Harada et al. "Computerized Potential Distribution Mapping: A New Intraoperative Mapping Technique for Ventricular Tachycardia Surgery." The Society of Thoracic Surgeons. 1990: 649-655. vol. 49.
Yamada et al. "Computerized Three-Dimensional Potential Mapping with a Multielectrode Basket Catheter Can be Useful for Pulmonary Vein Electrical Disconnection." Journal of Interventional Cardiac Electrophysiology. 2005: 23-33. vol. 12.
Laxer. "A Graphical Display System for Animating Mapped Cardiac Potentials." Third Annual IEEE Symposium on Computer-Based Medical Systems. 1990: 197-204.
Keck et al. "Electromechanical Mapping for Determination of Myocardial Contractility and Viability." Journal of the American College of Cardiology. Sep. 18, 2002: 1067-1074. vol. 40, No. 6.
Linton et al. "Cardiac ripple mapping: A novel three-dimensional visualization method for use with electroanatomic mapping of cardiac arrhythmias." Heart Rhythm Society. Dec. 2009: 1754-1762. vol. 6. No. 12.
Bhakta et al. "Principles of Electroanatomic Mapping." Indian Pacing and Electrophysiology Journal. 2008: 32-50. vol. 8, No. 1.
EnSite System. "EnSite v.8.0. Chapter 1." St. Jude Medical. 2008: 3.
Ideker et al. "A Computerized Method for the Rapid Display of Ventricular Activation During the Intraoperative Study of Arrhythmias." Circulation. 1979: 449-458. vol. 59, No. 3.
Gupta et al. "Cardiac Mapping: Utility or Futility?" Indian Pacing and Electrophysiology Journal. 2002: 20-32. vol. 2, No. 1.
De Groot et al. "Voltage and Activation Mapping." Circulation. 2003: 2099-2106. vol. 108.
Schmitt et al. "Clinical Experience With a Novel Multielectrode Basket Catheter in Right Atrial Tachycardias." Circulation. 1999: 2414-2422. vol. 99.
Response to Office Action filed in copending U.S. Appl. No. 15/827,499 dated Jan. 13, 2020.
Notice of Allowance issued in copending U.S. Appl. No. 15/827,499 dated Apr. 9, 2020.
Response to Office Action filed in copending U.S. Appl. No. 16/139,772 dated Apr. 3, 2020.
Response to Office Action filed in copending U.S. Appl. No. 16/139,860 dated Apr. 3, 2020.
Notice of Allowance issued in copending U.S. Appl. No. 16/139,860 dated May 11, 2020.
Extended European Search Report issued in European Application No. 19202799.3 dated Jan. 29, 2020.
Office Action issued in copending U.S. Appl. No. 16/139,860 dated Feb. 10, 2020.
Office Action issued in copending U.S. Appl. No. 16/139,772 dated Feb. 10, 2020.
Notice of Allowance issued in U.S. Appl. No. 16/415,016 dated Sep. 10, 2020.
Notice of Allowance issued in copending U.S. Appl. No. 16/426,091 dated Oct. 19, 2020.
Copending U.S. Appl. No. 17/075,104, filed Oct. 20, 2020.
Response filed in copending U.S. Appl. No. 16/388,093 dated Nov. 10, 2020.
Preliminary Amendment filed in copending U.S. Appl. No. 17/075,104 dated Nov. 19, 2020.
Office Action issued in copending U.S. Appl. No. 16/599,305 dated Dec. 23, 2020.
Copending U.S. Appl. No. 17/148,054, filed Jan. 13, 2021.
Notice of Allowance issued in U.S. Appl. No. 16/139,772 dated Jul. 2, 2020.
Office Action issued in U.S. Appl. No. 16/388,093 dated Aug. 11, 2020.
Preliminary Amendment filed in copending U.S. Appl. No. 17/148,054 dated Jan. 29, 2021.
Notice of Allowance issued in copending U.S. Appl. No. 16/388,093 dated Feb. 22, 2021.
Response filed in copending U.S. Appl. No. 16/599,305 dated Mar. 23, 2021.
Extended European Search Report issued in European Application No. 20208810.0 dated Mar. 22, 2021.

SYSTEMS AND METHODS FOR SELECTING, ACTIVATING, OR SELECTING AND ACTIVATING TRANSDUCERS

CROSS-REFERENCE TO RELATED APPLICATIONS

This application is a continuation of U.S. patent application Ser. No. 15/827,499, filed Nov. 30, 2017, now U.S. Pat. No. 10,722,184, issued on Jul. 28, 2020, which is a continuation-in-part of U.S. patent application Ser. No. 14/942,459, filed Nov. 16, 2015, now U.S. Pat. No. 10,368,936, issued on Aug. 6, 2019, which claims the benefit of U.S. Provisional Application No. 62/080,750, filed Nov. 17, 2014, the entire disclosure of each of the applications cited in this sentence is hereby incorporated herein by reference.

TECHNICAL FIELD

Aspects of this disclosure generally are related to systems and methods for selecting, activating, or selecting and activating transducers, such systems and methods applicable to, among other things, medical systems.

BACKGROUND

Cardiac surgery was initially undertaken using highly invasive open procedures. A sternotomy, which is a type of incision in the center of the chest that separates the sternum was typically employed to allow access to the heart. In the past several decades, more and more cardiac operations are performed using intravascular or percutaneous techniques, where access to inner organs or other tissue is gained via a catheter.

Intravascular or percutaneous surgeries benefit patients by reducing surgery risk, complications and recovery time. However, the use of intravascular or percutaneous technologies also raises some particular challenges. Medical devices used in intravascular or percutaneous surgery need to be deployed via catheter systems which significantly increase the complexity of the device structure. As well, doctors do not have direct visual contact with the medical devices once the devices are positioned within the body.

One example of where intravascular or percutaneous medical techniques have been employed is in the treatment of a heart disorder called atrial fibrillation. Atrial fibrillation is a disorder in which spurious electrical signals cause an irregular heartbeat. Atrial fibrillation has been treated with open heart methods using a technique known as the "Cox-Maze procedure". During this procedure, physicians create specific patterns of lesions in the left or right atria to block various paths taken by the spurious electrical signals. Such lesions were originally created using incisions, but are now typically created by ablating the tissue with various techniques including radio-frequency (RF) energy, microwave energy, laser energy and cryogenic techniques. The procedure is performed with a high success rate under the direct vision that is provided in open procedures, but is relatively complex to perform intravascularly or percutaneously because of the difficulty in creating the lesions in the correct locations. Various problems, potentially leading to severe adverse results, may occur if the lesions are placed incorrectly. It is particularly important to know the position of the various transducers which will be creating the lesions relative to cardiac features such as the pulmonary veins and mitral valve. The continuity, transmurality and placement of the lesion patterns that are formed can impact the ability to block paths taken within the heart by spurious electrical signals. Other requirements for various ones of the transducers to perform additional functions such as, but not limited to, mapping various anatomical features, mapping electrophysiological activity, sensing tissue characteristics such as impedance and temperature and tissue stimulation can also complicate the operation of the employed medical device.

In this regard, there is a need for improved intra-bodily-cavity transducer-based device systems or control mechanisms thereof with improved performance and reduced complexity as compared to conventional device systems.

In this regard, there is a need for improved intra-bodily-cavity transducer-based device systems or control mechanisms thereof with enhanced graphical path generation capabilities, the graphical path forming an accurate basis for a tissue ablation path.

In this regard, there is a need for improved intra-bodily-cavity transducer-based device systems or control mechanisms thereof with enhanced transducer selection capabilities.

SUMMARY

At least the above-discussed need is addressed and technical solutions are achieved by various embodiments of the present invention. In some embodiments, device systems and methods executed by such systems exhibit enhanced capabilities for the selection or selection and activation of various transducers, which may be located within a bodily cavity, such as an intra-cardiac cavity. In some embodiments, the systems or a portion thereof may be percutaneously or intravascularly delivered to position the various transducers within the bodily cavity. Various ones of the transducers may be activated to distinguish tissue from blood and may be used to deliver positional information of the device relative to various anatomical features in the bodily cavity, such as the pulmonary veins and mitral valve in an atrium. Various ones of the transducers may employ characteristics such as blood flow detection, impedance change detection or deflection force detection to discriminate between blood and tissue. Various ones of the transducers may be used to treat tissue within a bodily cavity. Treatment may include tissue ablation by way of non-limiting example. Various ones of the transducers may be used to stimulate tissue within the bodily cavity. Stimulation can include pacing by way of non-limiting example. Other advantages will become apparent from the teaching herein to those of skill in the art.

In some embodiments, a system may be summarized as including a data processing device system, an input-output device system communicatively connected to the data processing device system, and a memory device system communicatively connected to the data processing device system and storing a program executable by the data processing device system. The program may include display instructions, input-processing instructions, and graphical representation modification instructions.

The display instructions may be configured to cause the input-output device system to display a graphical representation including at least a plurality of transducer graphical elements, each transducer graphical element of the plurality of transducer graphical elements representative of a respective transducer of a plurality of transducers of a transducer-based device. The graphical representation may include a first spatial relationship between the plurality of transducer graphical elements that is consistent with a second spatial relationship between the plurality of transducers of the transducer-based device.

The input-processing instructions may be configured to cause reception of a set of user input via the input-output device system. The set of user input may include an instruction set to reposition a first transducer graphical element of the plurality of transducer graphical elements in a state in which the first transducer graphical element is located at a first location in the graphical representation and a second transducer graphical element of the plurality of transducer graphical elements is located at a second location in the graphical representation. The second location may be closer to a predetermined location in the graphical representation than the first location.

The graphical representation modification instructions may be configured to cause, in response to conclusion of receipt of the set of user input including the instruction set to reposition the first transducer graphical element, the input-output device system to reposition the first transducer graphical element from the first location in the graphical representation to the predetermined location in the graphical representation. According to some embodiments, the second location and the predetermined location are different locations.

In some embodiments, the predetermined location is more centrally located in the graphical representation than the first location, and the repositioning of the first transducer graphical element centralizes the first transducer graphical element in the graphical representation. In some embodiments, the graphical representation modification instructions are configured to cause, in response to the conclusion of receipt of the set of user input including the instruction set to reposition the first transducer graphical element, the input-output device system to reposition the second transducer graphical element from the second location in the graphical representation to a third location in the graphical representation, and the predetermined location is more centrally located in the graphical representation than the third location. In some embodiments, the predetermined location is in a first direction extending from the first location and in a second direction extending from the third location, with the first direction and the second direction being non-parallel directions. In some embodiments, the first location is spaced in the graphical representation from the predetermined location by a first distance and the third location is spaced from the second location by a second distance, with the first distance and the second distance being different distances.

According to some embodiments, the system includes the transducer-based device, with the input-output device system including the transducer-based device. In some embodiments, the transducers of the plurality of transducers are circumferentially arranged about a pole of a structure of the transducer-based device, and a first particular location in the graphical representation corresponds to the pole of the structure. The first particular location in the graphical representation may be closer to the predetermined location than to the first location at least in a state in which the first transducer graphical element is located at the first location. In some embodiments, the first particular location in the graphical representation is located centrally in the graphical representation at least in the state in which the first transducer graphical element is located at the first location. In some embodiments, the graphical representation modification instructions are configured to cause, in response to the conclusion of receipt of the set of user input including the instruction set to reposition the first transducer graphical element, the input-output device system to reconfigure the graphical representation to cause a second particular location in the graphical representation to correspond to the pole of the structure instead of the first particular location. The second particular location may be located farther from the predetermined location than the first particular location. In some embodiments, at least the second transducer graphical element appears rotated in the graphical representation about a graphical region corresponding to a pole location of the pole of the structure between a transition from the state in which the first transducer graphical element is located at the first location and a state in which the first transducer graphical element is located at the predetermined location upon conclusion of the repositioning of the first transducer graphical element from the first location in the graphical representation to the predetermined location in the graphical representation. In some embodiments, at least the second transducer graphical element appears rotated in the graphical representation about a graphical region corresponding to a pole location of the pole of the structure upon conclusion of the repositioning of the first transducer graphical element from the first location in the graphical representation to the predetermined location in the graphical representation. In some embodiments, the program includes sampling instructions configured to cause sampling of data by each of one or more transducers of the plurality of transducers of the transducer-based device, and generation instructions configured to cause generation of intra-cardiac information based at least in part on the sampled data. In some embodiments, the one or more transducers include the first transducer, the second transducer, or both the first transducer and the second transducer. The graphical representation may represent the intra-cardiac information among the plurality of transducer graphical elements. The graphical representation modification instructions may be configured to cause, in response to the conclusion of receipt of the set of user input including the instruction set to reposition the first transducer graphical element, the input-output device system to reposition the representation of the intra-cardiac information among the plurality of transducer graphical elements in accordance with the repositioning of the first transducer graphical element from the first location in the graphical representation to the predetermined location in the graphical representation.

According to some embodiments, the plurality of transducers are arranged in a three-dimensional distribution, and the plurality of transducer graphical elements are arranged in the graphical representation in a particular spatial distribution representing the three-dimensional distribution distorted onto a two-dimensional plane.

According to some embodiments, the plurality of transducers are arranged in a three-dimensional distribution, and the plurality of transducer graphical elements are arranged in the graphical representation according to a conformal map of the three-dimensional distribution. The conformal map of the three-dimensional distribution may be a transverse Mercator map of the three-dimensional distribution.

According to some embodiments, the program includes storage instructions configured to cause the memory device system to store particular information prior to the reception of the set of user input via the input-output device system. The particular information may be indicative of a location of the predetermined location in the graphical representation.

According to some embodiments, the input-output device system is communicatively connected to the transducer-based device, and the set of user input is a first set of user input. The program may include selection instructions configured to cause reception of a second set of user input via the input-output device system. The second set of user input may include a second instruction set to select, in a state in which the input-output device system has repositioned the first transducer graphical element from the first location in the graphical representation to the predetermined location in the graphical representation, a set of transducer graphical elements of the plurality of transducer graphical elements. The program may include activation instructions configured to cause activation, via the input-output device system, of a set of transducers of the plurality of transducers of the transducer-based device in response to reception of the second set of user input including the second instruction set to select the set of transducer graphical elements, the set of transducers corresponding to the set of transducer graphical elements.

In some embodiments, a transducer activation system may be summarized as including a data processing device system, an input-output device system communicatively connected to the data processing device system, and a memory device system communicatively connected to the data processing device system and storing a program executable by the data processing device system. The program may include display instructions configured to cause the input-output device system to display a graphical representation of at least intra-cardiac information. The program may include input-processing instructions configured to: cause reception of first user input via the input-output device system and, in response to receiving the first user input, place a first user input element in an activated state; cause reception of second user input via the input-output device system and, in response to receiving the second user input, place the first user input element in a deactivated state; and cause reception of motion-based user input via the input-output device system. The program may include path definition instructions configured to cause definition of a graphical path including a first location on the graphical path defined according to a first parameter set associated with the first user input, a second location on the graphical path defined according to a second parameter set associated with the second user input, and an elongate path portion of the graphical path defined according to a path traced by the motion-based user input. The program may include activation instructions configured to cause activation of a transducer-based device system, initiated during or after completion of the definition of the graphical path, to transmit energy sufficient for tissue ablation along an ablation path corresponding to the graphical path. The display instructions may be configured to the cause the input-output device system to display the graphical path including each of the first location, the second location, and the elongate path portion among the graphical representation of the intra-cardiac information.

In some embodiments, the program may include sampling instructions configured to cause sampling of data by each of one or more transducers of the transducer-based device system, a portion of the transducer-based device system including the one or more transducers positionable in a cardiac chamber during the sampling. The program may include generation instructions configured to cause generation of the intra-cardiac information based at least in part on the sampled data. The sampled data may be sampled from each of a plurality of locations in the cardiac chamber, and the generation instructions may be configured to cause mapping of each of a plurality of parts of the intra-cardiac information to a respective one of the plurality of locations in the cardiac chamber. The display instructions may be configured to cause the input-output device system to display the plurality of parts of the intra-cardiac information with a first spatial relationship that is consistent with a second spatial relationship between the plurality of locations in the cardiac chamber. The one or more transducers may include a plurality of transducers and the sampling instructions may be configured to cause the sampled data to be sampled concurrently from the plurality of locations in the cardiac chamber.

In some embodiments, the sampled data includes temperature data and the graphical representation of the intra-cardiac information includes a graphical representation of at least some of the temperature data or a derivation thereof. In some embodiments, the sampled data includes impedance data or conductivity data and the graphical representation of the intra-cardiac information includes a graphical representation of at least some of the impedance data or conductivity data or a derivation thereof. In some embodiments, the sampled data includes pressure data and the graphical representation of the intra-cardiac information includes a graphical representation of at least some of the pressure data or a derivation thereof. In some embodiments, the sampled data includes flow data associated with blood flow in the cardiac chamber and the graphical representation of the intra-cardiac information includes a graphical representation of at least some of the flow data or a derivation thereof. In some embodiments, the sampled data comprises intra-cardiac electrogram voltage data and the graphical representation of the intra-cardiac information includes a graphical representation of at least some of the intra-cardiac electrogram voltage data or a derivation thereof.

In some embodiments, the graphical representation of the intra-cardiac information may include a map of an interior tissue surface region of a cardiac chamber.

In some embodiments, a portion of the transducer-based device system includes a plurality of transducers positionable in a cardiac chamber, and the display instructions may be configured to cause the input-output device system to display a plurality of transducer graphical elements concurrently with the graphical path and the graphical representation of the intra-cardiac information, each of the transducer graphical elements corresponding to at least part of a respective one of the plurality of transducers, a first spatial relationship between the displayed transducer graphical elements consistent with a second spatial relationship between the transducers. In some embodiments, the graphical representation of the intra-cardiac information may include a map of an interior tissue surface region of the cardiac chamber displayed concurrently with the plurality of transducer graphical elements. In some embodiments, the first user input indicates a selection of a first transducer graphical element set including at least a first transducer graphical element of the plurality of transducer graphical elements, and the second user input indicates a selection of a second transducer graphical element set including at least a second transducer graphical element of the plurality of transducer graphical elements other than the first transducer graphical element.

In some embodiments, the first user input indicates a selection of a first transducer graphical element set including at least a first transducer graphical element of the plurality of transducer graphical elements, and the motion-based user input indicates a selection of a second transducer graphical element set including at least a second transducer graphical element of the plurality of transducer graphical elements other than the first transducer graphical element. In some embodiments, the first transducer graphical element set, the second transducer graphical element set, or each of the first and the second transducer graphical element sets includes a group of transducer graphical elements, each group of transducer graphical elements corresponding to a respective one of a plurality of groups of adjacent ones of the transducers. In some embodiments, the activation instructions may be configured to cause transmission, initiated during or after completion of the definition of the graphical path, of energy sufficient for tissue ablation from at least each respective transducer corresponding to each transducer graphical element in each of the first transducer graphical element set and the second transducer graphical element set. In some embodiments, the displayed graphical path is represented at least in part by the first transducer graphical element, the second transducer graphical element, and a third transducer graphical element other than the first and the second transducer graphical elements, the third transducer graphical element part of the first transducer graphical element set or the second transducer graphical element set, and the activation instructions may be configured to cause transmission, initiated during or after completion of the definition of the graphical path, of energy sufficient for tissue ablation from at least each respective transducer corresponding to the first transducer graphical element, the second transducer graphical element, and the third transducer graphical element.

In some embodiments, the second user input indicates a termination of the definition of the graphical path.

In some embodiments, a portion of the transducer-based device system includes a plurality of transducers positionable in a cardiac chamber. The display instructions may be configured to cause the input-output device system to display a plurality of transducer graphical elements concurrently with the graphical path and the graphical representation of the intra-cardiac information, each of the transducer graphical elements corresponding to at least part of a respective one of the plurality of transducers, a first spatial relationship between the displayed transducer graphical elements consistent with a second spatial relationship between the transducers. The display instructions may be configured to cause the input-output device system to display a plurality of between graphical elements concurrently with the transducer graphical elements, the graphical path, and the graphical representation of the intra-cardiac information, each of the plurality of between graphical element associated with a region of space between transducers of a respective one of a plurality of groups of adjacent ones of the transducers, each region of space not including any transducer. The first user input may indicate a selection of a first between graphical element of the plurality of between graphical elements, and the second user input may indicate a selection of a second between graphical element of the plurality of between graphical elements other than the first between graphical element. The first between graphical element, the second between graphical element, or each of the first and the second between graphical elements may be associated with a region of space that is not associated with any physical part of the transducer-based device system. The first parameter set may include a first display-screen-location associated with the first user input, and the second parameter set may include a second display-screen-location associated with the second user input. The path definition instructions may be configured to cause definition of the first location based at least on an analysis of the first display-screen-location in relation to one or more of the transducer graphical elements, and the path definition instructions may be configured to cause definition of the second location based at least on an analysis of the second display-screen-location in relation to one or more of the transducer graphical elements. In some embodiments, the first location may be a location of a first one of the transducer graphical elements, and the second location may be a location of a second one of the transducer graphical elements.

In some embodiments, a portion of the transducer-based device system includes a plurality of transducers positionable in a cardiac chamber. The display instructions may be configured to cause the input-output device system to display a plurality of transducer graphical elements concurrently with the graphical path and the graphical representation of the intra-cardiac information, each of the transducer graphical elements corresponding to at least part of a respective one of the plurality of transducers, a first spatial relationship between the displayed transducer graphical elements consistent with a second spatial relationship between the transducers. The display instructions may be configured to cause the input-output device system to display a plurality of between graphical elements concurrently with the transducer graphical elements, the graphical path, and the graphical representation of the intra-cardiac information, each of the plurality of between graphical elements associated with a region of space between transducers of a respective one of a plurality of groups of adjacent ones of the transducers, each region of space not including any transducer. The path traced by the motion-based user input may indicate at least a selection of at least one of the between graphical elements. The selected at least one of the between graphical elements may be associated with a region of space that is not associated with any physical part of the transducer-based device system. The selected at least one of the between graphical elements may include an elongated portion extending between two respective ends, each of the respective ends located at least proximate a respective one of two of the transducer graphical elements, and the elongate path portion of the graphical path may be provided at least in part by the elongated portion of the selected at least one of the between graphical elements. In some embodiments, the activation instructions may be configured to cause transmission, initiated during or after completion of the definition of the graphical path, of energy sufficient for tissue ablation from at least each transducer of the respective one of the plurality of groups of adjacent ones of the transducers corresponding to the selected at least one of the between graphical elements. The activation instructions may be configured to cause concurrent monopolar activation, initiated during or after completion of the definition of the graphical path, of the transducers of the respective one of the plurality of groups of adjacent ones of the transducers corresponding to the selected at least one of the between graphical elements.

In some embodiments, a portion of the transducer-based device system includes a plurality of transducers positionable in a cardiac chamber. The display instructions may be configured to cause the input-output device system to display a plurality of transducer graphical elements concurrently with the graphical path and the graphical representation of the intra-cardiac information, each of the transducer graphical elements corresponding to at least part of a respective one of the plurality of transducers, a first spatial relationship between the displayed transducer graphical elements consistent with a second spatial relationship between the transducers. The first user input may indicate a selection of a first transducer graphical element set including at least a first transducer graphical element of the plurality of transducer graphical elements, and the motion-based user input may indicate a selection of a second transducer graphical element set including at least a second transducer graphical element of the plurality of transducer graphical elements other than the first transducer graphical element. In some embodiments, the path definition instructions may be configured to cause the path traced by the motion-based user input or a portion thereof to snap to the second transducer graphical element or a portion thereof in response to the path traced by the motion-based user input or the portion thereof being away from the second transducer graphical element but within a predetermined distance from the second transducer graphical element or a part thereof. In some embodiments, the path definition instructions may be configured to cause the elongate path portion of the graphical path to include the second transducer graphical element or a portion thereof in response to the path traced by the motion-based user input or a portion thereof being away from the second transducer graphical element but within a predetermined display region associated with the second transducer graphical element. In some embodiments, the path definition instructions may be configured to cause the elongate path portion of the graphical path to include the second transducer graphical element or a portion thereof in response to the path traced by the motion-based user input or a portion thereof passing through a predetermined display region associated with the second transducer graphical element, the predetermined display region including at least a part of the second transducer graphical element, and the second transducer graphical element not occupying all of the predetermined display region. In some embodiments, the path definition instructions may be configured to cause the elongate path portion of the graphical path to include the second transducer graphical element or a portion thereof in response to the path traced by the motion-based user input or a portion thereof being away from the second transducer graphical element but within a predetermined distance from the second transducer graphical element or a part thereof. In some embodiments, the path definition instructions may be configured to cause the path traced by the motion-based user input or a portion thereof to snap to a particular between graphical element of the at least one of the between graphical elements or a portion of the particular between graphical element in response to the path traced by the motion-based user input or the portion thereof being away from the particular between graphical element but within a predetermined distance from the particular between graphical element or a part thereof. In some embodiments, the path definition instructions may be configured to cause the elongate path portion of the graphical path to include a particular between graphical element of the at least one of the between graphical elements or a portion of the particular between graphical element in response to the path traced by the motion-based user input or a portion thereof being away from the particular between graphical element but within a predetermined display region associated with the particular between graphical element. In some embodiments, the path definition instructions may be configured to cause the elongate path portion of the graphical path to include a particular between graphical element of the at least one of the between graphical elements or a portion of the particular between graphical element in response to the path traced by the motion-based user input or a portion thereof passing through a predetermined display region associated with the particular between graphical element, the predetermined display region including at least a part of the particular between graphical element, and the particular between graphical element not occupying all of the predetermined display region. In some embodiments, the path definition instructions may be configured to cause the elongate path portion of the graphical path to include a particular between graphical element of the at least one of the between graphical elements or a portion of the particular between graphical element in response to the path traced by the motion-based user input or a portion thereof being away from the particular between graphical element but within a predetermined distance from the particular between graphical element or a part thereof.

In some embodiments, the path definition instructions may further include graphical path adjustment instructions configured to reduce a size of the elongate path portion in response to a user-based retracing of a portion of the path traced by the motion-based user input.

In some embodiments, a portion of the transducer-based device system includes a plurality of transducers positionable in a cardiac chamber. The display instructions may be configured to cause the input-output device system to display a plurality of transducer graphical elements concurrently with the graphical path and the graphical representation of the intra-cardiac information, each of the transducer graphical elements corresponding to at least part of a respective one of the plurality of transducers, a first spatial relationship between the displayed transducer graphical elements consistent with a second spatial relationship between the transducers. In some embodiments, the motion-based user input may indicate a selection of a group of the transducer graphical elements, and the program may further include de-selection instructions configured to deselect at least one transducer graphical element in the group of the transducer graphical elements in response to a user-based retracing of a portion of the path traced by the motion-based user input. In some embodiments, the display instructions may be configured to cause the input-output device system to display a plurality of between graphical elements concurrently with the transducer graphical elements, the graphical path, and the graphical representation of the intra-cardiac information, each of the plurality of between graphical elements associated with a region of space between transducers of a respective one of a plurality of groups of adjacent ones of the transducers, each region of space not including any transducer, and wherein the path traced by the motion-based user input indicates at least a selection of a group of the between graphical elements, and the program may further include de-selection instructions configured deselect at least one between graphical element in the group of the transducer graphical elements in response to a user-based retracing of a portion of the path traced by the motion-based user input.

In some embodiments, the first user input may include at least engaging the first user input element and the second user input may include at least disengaging the first user input element. In some embodiments, the first user input element may include a keyboard key, a mouse button, or a touch screen. In some embodiments, the first user input element includes a touch screen, and the engaging of the first user input element may include a registering of an initiation of user-contact with the touch screen, and the disengaging the first user input element may include a registering of a cessation of the user-contact with the touch screen.

In some embodiments, the first user input may include at least engaging each of at least two user input elements of the input-output device system and the second user input may include at least disengaging at least one but not all of the at least two user input elements.

In some embodiments, the input-processing instructions may be configured to cause reception of a third user input other than the first and the second user inputs and the motion-based user input, and the path definition instructions may be configured to require reception of the third user input in order to at least enable definition of the elongate path portion of the graphical path according to the path traced by the motion-based user input. In some embodiments, the input-processing instructions may be configured to cause a second user input element to be placed in a respective activated state in response to receiving the third user input, and the path definition instructions may be configured to require that the first user input element and the second user input element be in the respective activated states in order to at least enable definition of the elongate path portion of the graphical path according to the path traced by the motion-based user input. In some embodiments, the input-processing instructions may be configured to cause reception of a fourth user input other than the first, second, and third user inputs. The input-processing instructions may be configured to cause the second user input element to be placed in a respective deactivated state in response to receiving the fourth user input, and the path definition instructions may be configured to cause further definition of the elongate path portion of the graphical path according to the path traced by the motion-based user input even though the fourth user input has been received and the second user input element has, consequently, been placed in the respective deactivated state.

In some embodiments, the first user input precedes the motion-based user input.

In some embodiments, wherein a portion of the transducer-based device system includes a plurality of transducers positionable in a cardiac chamber, and the display instructions are configured to cause the input-output device system to display a plurality of transducer graphical elements concurrently with the graphical path and the graphical representation of the intra-cardiac information, each of the transducer graphical elements corresponding to at least part of a respective one of the plurality of transducers, a first spatial relationship between the displayed transducer graphical elements consistent with a second spatial relationship between the transducers. In some embodiments, the display instructions may be configured to cause a change in a visual characteristic of at least one of the transducer graphical elements when the display instructions cause the input-output device system to display the graphical path. The display instructions may be configured to cause a change in a visual characteristic of the at least one of the between graphical elements in response to the reception of the motion-based user input. In some embodiments, each of two or more of the plurality of transducers may include a respective electrode, and the transducer graphical elements corresponding to the two or more of the plurality of transducers each may include a shape that is consistent with a shape of the respective electrode of a corresponding one of the two or more of the plurality of transducers, wherein at least two of the transducer graphical elements corresponding to the two or more of the plurality of transducers comprise different shapes.

In some embodiments, the graphical path may be displayed as including an interrupted form. In some embodiments, the graphical path may be displayed as including a circumferential path that surrounds a region of the graphical representation of the intra-cardiac information. In some embodiments, the graphical representation of the intra-cardiac information may include a graphical representation of at least a map indicating a spatial relationship between various anatomical features in a cardiac chamber. In some embodiments, the graphical representation of the intra-cardiac information may include a graphical representation of at least a map of values of at least one tissue electrical characteristic sensed by the transducer-based device system in a cardiac chamber. In some embodiments, the graphical representation of the intra-cardiac information may include a graphical representation of at least a map of intra-cardiac electrogram values originating from information provided by the transducer-based device system. In some embodiments, the graphical representation of the intra-cardiac information may include a graphical representation of at least a map of temperature distribution in a cardiac chamber.

In some embodiments, the input-output device system may include the transducer-based device system. The transducer-based device system may include a catheter-based device. A portion of the catheter-based device may include a structure selectively moveable between a delivery configuration in which the structure is sized to be percutaneously deliverable to a cardiac chamber and a deployed configuration in which the structure has a size too large to be percutaneously deliverable to the cardiac chamber. In some embodiments, the display instructions may be configured to cause the input-output device system to graphically display changes in the intra-cardiac information at least during: a) reception of the first user input, b) reception of the second user input, c) reception of the motion-based user input, or any combination of a), b) and c).

Various systems may include combinations and subsets of all the systems summarized above.

In some embodiments, a transducer activation system may be summarized as including a data processing device system, an input-output device system communicatively connected to the data processing device system, and a memory device system communicatively connected to the data processing device system and storing a program executable by the data processing device system. The data processing device system may be configured by the program at least to: (a) cause the input-output device system to display a graphical representation of at least intra-cardiac information; (b) cause reception of first user input via the input-output device system and, in response to receiving the first user input, place a first user input element in an activated state; (c) cause reception of second user input via the input-output device system and, in response to receiving the second user input, place the first user input element in a deactivated state; and (d) cause reception of motion-based user input via the input-output device system. The data processing device system may be further configured by the program at least to cause definition of a graphical path including a first location on the graphical path defined according to a first parameter set associated with the first user input, a second location on the graphical path defined according to a second parameter set associated with the second user input, and an elongate path portion of the graphical path defined according to a path traced by the motion-based user input. The data processing device system may be further configured by the program at least to cause activation of a transducer-based device system, initiated during or after completion of the definition of the graphical path, to transmit energy sufficient for tissue ablation along an ablation path corresponding to the graphical path. The data processing device system may be further configured by the program at least to cause the input-output device system to display the graphical path including each of the first location, the second location, and the elongate path portion among the graphical representation of the intra-cardiac information.

In some embodiments, a method may be executed by a data processing device system according to a program stored by a memory device system communicatively connected to the data processing device system, the data processing device system further communicatively connected to an input-output device system. The method may include the data processing device system (a) causing display, via the input-output device system, of a graphical representation including at least a plurality of transducer graphical elements, each transducer graphical element of the plurality of transducer graphical elements representative of a respective transducer of a plurality of transducers of a transducer-based device, and the graphical representation including a first spatial relationship between the plurality of transducer graphical elements that is consistent with a second spatial relationship between the plurality of transducers of the transducer-based device; (b) receiving, via the input-output device system, a set of user input, including an instruction set to reposition a first transducer graphical element of the plurality of transducer graphical elements in a state in which the first transducer graphical element is located at a first location in the graphical representation and a second transducer graphical element of the plurality of transducer graphical elements is located at a second location in the graphical representation, the second location closer to a predetermined location in the graphical representation than the first location; and (c) repositioning, in response to conclusion of receipt of the set of user input including the instruction set to reposition the first transducer graphical element, and via the input-output device system, the first transducer graphical element from the first location in the graphical representation to the predetermined location in the graphical representation.

In some embodiments, a transducer activation method may be executed by a data processing device system according to a program stored by a memory device system communicatively connected to the data processing device system, the data processing device system further communicatively connected to an input-output device system. The method may include the data processing device system (a) causing the input-output device system to display a graphical representation of at least intra-cardiac information; (b) causing reception of first user input via the input-output device system and, in response to receiving the first user input, placing a first user input element in an activated state; (c) causing reception of second user input via the input-output device system and, in response to receiving the second user input, placing the first user input element in a deactivated state; and (d) causing reception of motion-based user input via the input-output device system. The method may further include the data processing device system causing definition of a graphical path including a first location on the graphical path defined according to a first parameter set associated with the first user input, a second location on the graphical path defined according to a second parameter set associated with the second user input, and an elongate path portion of the graphical path defined according to a path traced by the motion-based user input. The method may further include the data processing device system causing activation of a transducer-based device system, initiated during or after completion of the definition of the graphical path, to transmit energy sufficient for tissue ablation along an ablation path corresponding to the graphical path. The method may further include the data processing device system causing the input-output device system to display the graphical path including each of the first location, the second location, and the elongate path portion among the graphical representation of the intra-cardiac information.

In some embodiments, a computer-readable storage medium system may include one or more computer-readable storage mediums storing a program executable by one or more data processing devices of a data processing device system communicatively connected to an input-output device system. The program may include a display module configured to cause the input-output device system to display a graphical representation including at least a plurality of transducer graphical elements, each transducer graphical element of the plurality of transducer graphical elements representative of a respective transducer of a plurality of transducers of a transducer-based device, and the graphical representation including a first spatial relationship between the plurality of transducer graphical elements that is consistent with a second spatial relationship between the plurality of transducers of the transducer-based device. The program may also include an input-processing module configured to cause reception of a set of user input via the input-output device system, the set of user input including an instruction set to reposition a first transducer graphical element of the plurality of transducer graphical elements in a state in which the first transducer graphical element is located at a first location in the graphical representation and a second transducer graphical element of the plurality of transducer graphical elements is located at a second location in the graphical representation, the second location closer to a predetermined location in the graphical representation than the first location. The program may also include a graphical representation modification module configured to cause, in response to conclusion of receipt of the set of user input including the instruction set to reposition the first transducer graphical element, the input-output device system to reposition the first transducer graphical element from the first location in the graphical representation to the predetermined location in the graphical representation.

In some embodiments, a computer-readable storage medium system may include one or more computer-readable storage mediums storing a program executable by one or more data processing devices of a data processing device system communicatively connected to an input-output device system. The program may include a display module configured to cause the input-output device system to display a graphical representation of at least intra-cardiac information. The program may include an input-processing module configured to: cause reception of first user input via the input-output device system and, in response to receiving the first user input, place a first user input element in an activated state; cause reception of second user input via the input-output device system and, in response to receiving the second user input, place the first user input element in a deactivated state; and cause reception of motion-based user input via the input-output device system. The program may include a path definition module configured to cause definition of a graphical path including a first location on the graphical path defined according to a first parameter set associated with the first user input, a second location on the graphical path defined according to a second parameter set associated with the second user input, and an elongate path portion of the graphical path defined according to a path traced by the motion-based user input. The program may include an activation module configured to cause activation of a transducer-based device system, initiated during or after completion of the definition of the graphical path, to transmit energy sufficient for tissue ablation along an ablation path corresponding to the graphical path. The display module may be configured to the cause the input-output device system to display the graphical path including each of the first location, the second location, and the elongate path portion among the graphical representation of the intra-cardiac information.

In some embodiments, a transducer activation system may be summarized as including a data processing device system, an input-output device system communicatively connected to the data processing device system, and a memory device system communicatively connected to the data processing device system and storing a program executable by the data processing device system. The program may include display instructions configured to cause the input-output device system to display a graphical representation of at least intra-cardiac information. The program may include input-processing instructions configured to: cause reception of first user input via the input-output device system and, in response to receiving the first user input, place a first user input element in an activated state; cause reception of second user input via the input-output device system and, in response to receiving the second user input, place the first user input element in a deactivated state; and cause reception of motion-based user input via the input-output device system. The program may include path definition instructions configured to cause definition of a graphical path including a first location on the graphical path defined according to a first parameter set associated with the first user input, a second location on the graphical path defined according to a second parameter set associated with the second user input, and at least a third location on the graphical path other than the first location and the second location defined according to a path traced by the motion-based user input. The program may include activation instructions configured to cause activation of a transducer-based device system, initiated during or after completion of the definition of the graphical path, to transmit energy sufficient for tissue ablation along an ablation path corresponding to the graphical path. The display instructions may be configured to the cause the input-output device system to display the graphical path including the first location, the second location, and the at least the third location among the graphical representation of the intra-cardiac information.

In some embodiments, the program may further include sampling instructions configured to cause sampling of data by each of one or more transducers of the transducer-based device system, a portion of the transducer-based device system including the one or more transducers positionable in a cardiac chamber during the sampling. The program may include generation instructions configured to cause generation of the intra-cardiac information based at least in part on the sampled data. The sampled data may be sampled from each of a plurality of locations in the cardiac chamber, and the generation instructions may be configured to cause mapping of each of a plurality of parts of the intra-cardiac information to a respective one of the plurality of locations in the cardiac chamber, and the display instructions may be configured to cause the input-output device system to display the plurality of parts of the intra-cardiac information with a first spatial relationship that is consistent with a second spatial relationship between the plurality of locations in the cardiac chamber. The one or more transducers may include a plurality of transducers and the sampling instructions may be configured to cause the sampled data to be sampled concurrently from the plurality of locations in the cardiac chamber. In some embodiments, the sampled data may include temperature data and the graphical representation of the intra-cardiac information includes a graphical representation of at least some of the temperature data or a derivation thereof. In some embodiments, the sampled data may include impedance data or conductivity data and the graphical representation of the intra-cardiac information includes a graphical representation of at least some of the impedance data or conductivity data or a derivation thereof. In some embodiments, the sampled data may include pressure data and the graphical representation of the intra-cardiac information includes a graphical representation of at least some of the pressure data or a derivation thereof. In some embodiments, the sampled data may include flow data associated with blood flow in the cardiac chamber and the graphical representation of the intra-cardiac information includes a graphical representation of at least some of the flow data or a derivation thereof. In some embodiments, the sampled data may include intra-cardiac electrogram voltage data and the graphical representation of the intra-cardiac information includes a graphical representation of at least some of the intra-cardiac electrogram voltage data or a derivation thereof.

In some embodiments, the graphical representation of the intra-cardiac information may include a map of an interior tissue surface region of a cardiac chamber.

In some embodiments, a portion of the transducer-based device system may include a plurality of transducers positionable in a cardiac chamber, and the display instructions may be configured to cause the input-output device system to display a plurality of transducer graphical elements concurrently with the graphical path and the graphical representation of the intra-cardiac information, each of the transducer graphical elements corresponding to at least part of a respective one of the plurality of transducers, a first spatial relationship between the displayed transducer graphical elements consistent with a second spatial relationship between the transducers. In some embodiments, the graphical representation of the intra-cardiac information may include a map of an interior tissue surface region of the cardiac chamber displayed concurrently with the plurality of transducer graphical elements. In some embodiments, the first user input may indicate a selection of a first transducer graphical element set that includes at least a first transducer graphical element of the plurality of transducer graphical elements, and the second user input may indicate a selection of a second transducer graphical element set that includes at least a second transducer graphical element of the plurality of transducer graphical elements other than the first transducer graphical element. In some embodiments, the first user input may indicate a selection of a first transducer graphical element set that includes at least a first transducer graphical element of the plurality of transducer graphical elements, and the motion-based user input may indicate a selection of a second transducer graphical element set that includes at least a second transducer graphical element of the plurality of transducer graphical elements other than the first transducer graphical element. In the first transducer graphical element set, the second transducer graphical element set, or each of the first and the second transducer graphical element sets comprises a group of transducer graphical elements, each group of transducer graphical elements corresponding to a respective one of a plurality of groups of adjacent ones of the transducers. In some embodiments, the activation instructions may be configured to cause transmission, initiated during or after completion of the definition of the graphical path, of energy sufficient for tissue ablation from at least each respective transducer corresponding to each transducer graphical element in each of the first transducer graphical element set and the second transducer graphical element set. In some embodiments, the displayed graphical path is represented at least in part by the first transducer graphical element, the second transducer graphical element, and a third transducer graphical element other than the first and the second transducer graphical elements, the third transducer graphical element part of the first transducer graphical element set or the second transducer graphical element set, and the activation instructions may be configured to cause transmission, initiated during or after completion of the definition of the graphical path, of energy sufficient for tissue ablation from at least each respective transducer corresponding to the first transducer graphical element, the second transducer graphical element, and the third transducer graphical element.

In some embodiments, the second user input indicates a termination of the definition of the graphical path.

In some embodiments, a portion of the transducer-based device system may include a plurality of transducers positionable in a cardiac chamber, and the display instructions may be configured to cause the input-output device system to display a plurality of transducer graphical elements concurrently with the graphical path and the graphical representation of the intra-cardiac information, each of the transducer graphical elements corresponding to at least part of a respective one of the plurality of transducers, a first spatial relationship between the displayed transducer graphical elements consistent with a second spatial relationship between the transducers. In some embodiments, the display instructions may be configured to cause the input-output device system to display a plurality of between graphical elements concurrently with the transducer graphical elements, the graphical path, and the graphical representation of the intra-cardiac information, each of the plurality of between graphical element associated with a region of space between transducers of a respective one of a plurality of groups of adjacent ones of the transducers, each region of space not including any transducer, and the first user input may indicate a selection of a first between graphical element of the plurality of between graphical elements, and the second user input may indicate a selection of a second between graphical element of the plurality of between graphical elements other than the first between graphical element. The first between graphical element, the second between graphical element, or each of the first and the second between graphical elements may be associated with a region of space that is not associated with any physical part of the transducer-based device system. In some embodiments, the first parameter set includes a first display-screen-location associated with the first user input, and the second parameter set includes a second display-screen-location associated with the second user input. The path definition instructions may be configured to cause definition of the first location based at least on an analysis of the first display-screen-location in relation to one or more of the transducer graphical elements, and the path definition instructions may be configured to cause definition of the second location based at least on an analysis of the second display-screen-location in relation to one or more of the transducer graphical elements. The first location may be a location of a first one of the transducer graphical elements, and the second location may be a location of a second one of the transducer graphical elements.

In some embodiments, a portion of the transducer-based device system may include a plurality of transducers positionable in a cardiac chamber, and the display instructions may be configured to cause the input-output device system to display a plurality of transducer graphical elements concurrently with the graphical path and the graphical representation of the intra-cardiac information, each of the transducer graphical elements corresponding to at least part of a respective one of the plurality of transducers, a first spatial relationship between the displayed transducer graphical elements consistent with a second spatial relationship between the transducers. The display instructions may be configured to cause the input-output device system to display a plurality of between graphical elements concurrently with the transducer graphical elements, the graphical path, and the graphical representation of the intra-cardiac information, each of the plurality of between graphical elements associated with a region of space between transducers of a respective one of a plurality of groups of adjacent ones of the transducers, each region of space not including any transducer, and the path traced by the motion-based user input may indicate at least a selection of at least one of the between graphical elements. In some embodiments, the selected at least one of the between graphical elements may be associated with a region of space that is not associated with any physical part of the transducer-based device system. In some embodiments, the at least the third location may be indicated at least in part by the selected at least one of the between graphical elements. In some embodiments, the activation instructions may be configured to cause transmission, initiated during or after completion of the definition of the graphical path, of energy sufficient for tissue ablation from at least each transducer of the respective one of the plurality of groups of adjacent ones of the transducers corresponding to the selected at least one of the between graphical elements. The activation instructions may be configured to cause concurrent monopolar activation, initiated during or after completion of the definition of the graphical path, of the transducers of the respective one of the plurality of groups of adjacent ones of the transducers corresponding to the selected at least one of the between graphical elements.

In some embodiments, a portion of the transducer-based device system includes a plurality of transducers positionable in a cardiac chamber, and the display instructions may be configured to cause the input-output device system to display a plurality of transducer graphical elements concurrently with the graphical path and the graphical representation of the intra-cardiac information, each of the transducer graphical elements corresponding to at least part of a respective one of the plurality of transducers, a first spatial relationship between the displayed transducer graphical elements consistent with a second spatial relationship between the transducers. The first user input may indicate a selection of a first transducer graphical element set that includes at least a first transducer graphical element of the plurality of transducer graphical elements, and the motion-based user input may indicate a selection of a second transducer graphical element set that includes at least a second transducer graphical element of the plurality of transducer graphical elements other than the first transducer graphical element. In some embodiments, the path definition instructions may be configured to cause the path traced by the motion-based user input or a portion thereof to snap to the second transducer graphical element or a portion thereof in response to the path traced by the motion-based user input or the portion thereof being away from the second transducer graphical element but within a predetermined distance from the second transducer graphical element or a part thereof, and the second transducer graphical element includes the third location. In some embodiments, the path definition instructions may be configured to cause the graphical path to include the second transducer graphical element or a portion thereof in response to the path traced by the motion-based user input or a portion thereof being away from the second transducer graphical element but within a predetermined display region associated with the second transducer graphical element, and the second transducer graphical element includes the third location. In some embodiments, the path definition instructions may be configured to cause the graphical path to include the second transducer graphical element or a portion thereof in response to the path traced by the motion-based user input or a portion thereof passing through a predetermined display region associated with the second transducer graphical element, the predetermined display region including at least a part of the second transducer graphical element, and the second transducer graphical element not occupying all of the predetermined display region, and the second transducer graphical element includes the third location. In some embodiments, the path definition instructions may be configured to cause the graphical path to include the second transducer graphical element or a portion thereof in response to the path traced by the motion-based user input or a portion thereof being away from the second transducer graphical element but within a predetermined distance from the second transducer graphical element or a part thereof, and the second transducer graphical element includes the third location. In some embodiments, the path definition instructions may be configured to cause the path traced by the motion-based user input or a portion thereof to snap to a particular between graphical element of the at least one of the between graphical elements or a portion of the particular between graphical element in response to the path traced by the motion-based user input or the portion thereof being away from the particular between graphical element but within a predetermined distance from the particular between graphical element or a part thereof, and the particular between graphical element includes the third location. In some embodiments, the path definition instructions may be configured to cause the graphical path to include a particular between graphical element of the at least one of the between graphical elements or a portion of the particular between graphical element in response to the path traced by the motion-based user input or a portion thereof being away from the particular between graphical element but within a predetermined display region associated with the particular between graphical element, and the particular between graphical element includes the third location. In some embodiments, the path definition instructions may be configured to cause the graphical path to include a particular between graphical element of the at least one of the between graphical elements or a portion of the particular between graphical element in response to the path traced by the motion-based user input or a portion thereof passing through a predetermined display region associated with the particular between graphical element, the predetermined display region including at least a part of the particular between graphical element, and the particular between graphical element not occupying all of the predetermined display region, and the particular between graphical element includes the third location. In some embodiments, the path definition instructions may be configured to cause the graphical path to include a particular between graphical element of the at least one of the between graphical elements or a portion of the particular between graphical element in response to the path traced by the motion-based user input or a portion thereof being away from the particular between graphical element but within a predetermined distance from the particular between graphical element or a part thereof, and the particular between graphical element includes the third location.

In some embodiments, a portion of the transducer-based device system includes a plurality of transducers positionable in a cardiac chamber, and the display instructions may be configured to cause the input-output device system to display a plurality of transducer graphical elements concurrently with the graphical path and the graphical representation of the intra-cardiac information, each of the transducer graphical elements corresponding to at least part of a respective one of the plurality of transducers, a first spatial relationship between the displayed transducer graphical elements consistent with a second spatial relationship between the transducers. In some embodiments, the motion-based user input may indicate a selection of a group of the transducer graphical elements, and the program further includes de-selection instructions configured deselect at least one transducer graphical element in the group of the transducer graphical elements in response to a user-based retracing of a portion of the path traced by the motion-based user input. In some embodiments, the display instructions may be configured to cause the input-output device system to display a plurality of between graphical elements concurrently with the transducer graphical elements, the graphical path, and the graphical representation of the intra-cardiac information, each of the plurality of between graphical elements associated with a region of space between transducers of a respective one of a plurality of groups of adjacent ones of the transducers, each region of space not including any transducer. The path traced by the motion-based user input may indicate at least a selection of a group of the between graphical elements, and the program may further include de-selection instructions configured deselect at least one between graphical element in the group of the between graphical elements in response to a user-based retracing of a portion of the path traced by the motion-based user input.

In some embodiments, the first user input may include at least engaging the first user input element and the second user input may include at least disengaging the first user input element. In some embodiments, the first user input element may include a keyboard key, a mouse button, or a touch screen. In some embodiments, the first user input element may include a touch screen, and the engaging of the first user input element includes a registering of an initiation of user-contact with the touch screen, and the disengaging the first user input element includes a registering of a cessation of the user-contact with the touch screen. In some embodiments, the first user input may include at least engaging each of at least two user input elements of the input-output device system and the second user input may include at least disengaging at least one but not all of the at least two user input elements.

In some embodiments, the input-processing instructions may be configured to cause reception of a third user input other than the first and the second user input and the motion-based user input, and the path definition instructions may be configured to require reception of the third user input in order to at least enable definition of an elongate path portion of the graphical path according to the path traced by the motion-based user input, the elongate path portion including the third location. The input-processing instructions may be configured to cause a second user input element to be placed in a respective activated state in response to receiving the third user input, and the path definition instructions may be configured to require that the first user input element and the second user input element be in the respective activated states in order to at least enable definition of the elongate path portion of the graphical path according to the path traced by the motion-based user input. In some embodiments, the input-processing instructions may be configured to cause reception of a fourth user input other than the first, second, and third user inputs. The input-processing instructions may be configured to cause the second user input element to be placed in a respective deactivated state in response to receiving the fourth user input, and the path definition instructions may be configured to cause further definition of the elongate path portion of the graphical path according to the path traced by the motion-based user input even though the fourth user input has been received and the second user input element has, consequently, been placed in the respective deactivated state.

In some embodiments, the first user input precedes the motion-based user input.

In some embodiments, a portion of the transducer-based device system includes a plurality of transducers positionable in a cardiac chamber, and the display instructions may be configured to cause the input-output device system to display a plurality of transducer graphical elements concurrently with the graphical path and the graphical representation of the intra-cardiac information, each of the transducer graphical elements corresponding to at least part of a respective one of the plurality of transducers, a first spatial relationship between the displayed transducer graphical elements consistent with a second spatial relationship between the transducers. In some embodiments, the display instructions may be configured to cause a change in a visual characteristic of at least one of the transducer graphical elements when the display instructions cause the input-output device system to display the graphical path. The display instructions may be configured to cause a change in a visual characteristic of the at least one of the between graphical elements in response to the reception of the motion-based user input. In some embodiments, each of two or more of the plurality of transducers may include a respective electrode, and the transducer graphical elements corresponding to the two or more of the plurality of transducers each include a shape that is consistent with a shape of the respective electrode of a corresponding one of the two or more of the plurality of transducers. At least two of the transducer graphical elements corresponding to the two or more of the plurality of transducers may include different shapes.

In some embodiments, the graphical path may be displayed as including an interrupted form. In some embodiments, the graphical path may be displayed as including a circumferential path that surrounds a region of the graphical representation of the intra-cardiac information. In some embodiments, the graphical representation of the intra-cardiac information may include a graphical representation of at least a map indicating a spatial relationship between various anatomical features in a cardiac chamber. In some embodiments, the graphical representation of the intra-cardiac information may include a graphical representation of at least a map of values of at least one tissue electrical characteristic sensed by the transducer-based device system in a cardiac chamber. In some embodiments, the graphical representation of the intra-cardiac information may include a graphical representation of at least a map of intra-cardiac electrogram values originating from information provided by the transducer-based device system. In some embodiments, the graphical representation of the intra-cardiac information may include a graphical representation of at least a map of temperature distribution in a cardiac chamber.

In some embodiments, the input-output device system may include the transducer-based device system. The transducer-based device system may include a catheter-based device. A portion of the catheter-based device may include a structure selectively moveable between a delivery configuration in which the structure is sized to be percutaneously deliverable to a cardiac chamber and a deployed configuration in which the structure has a size too large to be percutaneously deliverable to the cardiac chamber.

In some embodiments, an elongate path portion of the graphical path is defined according to a path traced by the motion-based user input, the at least the third location located on the elongated path portion of the path. In some embodiments, the first location and the second location are the same location. In some embodiments, the display instructions may be configured to cause the input-output device system to graphically display changes in the intra-cardiac information at least during: a) reception of the first user input, b) reception of the second user input, c) reception of the motion-based user input, or any combination of a), b) and c).

In some embodiments, a transducer activation system may be summarized as including a data processing device system, an input-output device system communicatively connected to the data processing device system, and a memory device system communicatively connected to the data processing device system and storing a program executable by the data processing device system. The data processing device system may be configured by the program at least to: (a) cause the input-output device system to display a graphical representation of at least intra-cardiac information; (b) cause reception of first user input via the input-output device system and, in response to receiving the first user input, place a first user input element in an activated state; (c) cause reception of second user input via the input-output device system and, in response to receiving the second user input, place the first user input element in a deactivated state; and (d) cause reception of motion-based user input via the input-output device system. The data processing device system may be further configured by the program at least to cause definition of a graphical path including a first location on the graphical path defined according to a first parameter set associated with the first user input, a second location on the graphical path defined according to a second parameter set associated with the second user input, and at least a third location on the graphical path other than the first location and the second location defined according to a path traced by the motion-based user input. The data processing device system may be further configured by the program at least to cause activation of a transducer-based device system, initiated during or after completion of the definition of the graphical path, to transmit energy sufficient for tissue ablation along an ablation path corresponding to the graphical path. The data processing device system may be further configured by the program at least to cause the input-output device system to display the graphical path including the first location, the second location, and the at least the third location among the graphical representation of the intra-cardiac information.

In some embodiments, a transducer activation method may be executed by a data processing device system according to a program stored by a memory device system communicatively connected to the data processing device system, the data processing device system further communicatively connected to an input-output device system. The method may include the data processing device system (a) causing the input-output device system to display a graphical representation of at least intra-cardiac information; (b) causing reception of first user input via the input-output device system and, in response to receiving the first user input, placing a first user input element in an activated state; (c) causing reception of second user input via the input-output device system and, in response to receiving the second user input, placing the first user input element in a deactivated state; and (d) causing reception of motion-based user input via the input-output device system. The method may include the data processing device system causing definition of a graphical path including a first location on the graphical path defined according to a first parameter set associated with the first user input, a second location on the graphical path defined according to a second parameter set associated with the second user input, and at least a third location on the graphical path other than the first location and the second location defined according to a path traced by the motion-based user input. The method may include the data processing device system causing activation of a transducer-based device system, initiated during or after completion of the definition of the graphical path, to transmit energy sufficient for tissue ablation along an ablation path corresponding to the graphical path. The method may include the data processing device system causing the input-output device system to display the graphical path including the first location, the second location, and the at least the third location among the graphical representation of the intra-cardiac information.

In some embodiments, a computer-readable storage medium system may include one or more computer-readable storage mediums storing a program executable by one or more data processing devices of a data processing device system communicatively connected to an input-output device system. The program may include a display module configured to cause the input-output device system to display a graphical representation of at least intra-cardiac information. The program may include an input-processing module configured to: cause reception of first user input via the input-output device system and, in response to receiving the first user input, place a first user input element in an activated state; cause reception of second user input via the input-output device system and, in response to receiving the second user input, place the first user input element in a deactivated state; and cause reception of motion-based user input via the input-output device system. The program may include a path definition module configured to cause definition of a graphical path including a first location on the graphical path defined according to a first parameter set associated with the first user input, a second location on the graphical path defined according to a second parameter set associated with the second user input, and at least a third location on the graphical path other than the first location and the second location defined according to a path traced by the motion-based user input. The program may include an activation module configured to cause activation of a transducer-based device system, initiated during or after completion of the definition of the graphical path, to transmit energy sufficient for tissue ablation along an ablation path corresponding to the graphical path. The display module may be configured to the cause the input-output device system to display the graphical path including the first location, the second location, and the at least the third location among the graphical representation of the intra-cardiac information.

In some embodiments, a graphical path display device system may be summarized as including a data processing device system, an input-output device system communicatively connected to the data processing device system, and a memory device system communicatively connected to the data processing device system and storing a program executable by the data processing device system. The program may include input-processing instructions configured to: cause reception of first user input via the input-output device system and, in response to receiving the first user input, place a first user input element in an activated state; cause reception of motion-based user input via the input-output device system; and cause reception of second user input via the input-output device system and, in response to receiving the second user input, place the first user input element in a deactivated state. The program may include path definition instructions configured to cause definition of a graphical path including a plurality of graphical-path-elements, the path definition instructions configured to cause initiation of the definition of the graphical path in response to receiving the first user input, to cause generation of an interim-definition of the graphical path according to a path traced by the motion-based user input, and to cause conclusion of the definition of the graphical path in response to receiving the second user input, each of the respective graphical-path-elements associated with a respective display region including at least a portion of the respective graphical-path-element, but the respective graphical-path-element not occupying all of the respective display region. The path definition instructions may be configured to cause the interim-definition of the graphical path to be generated to identify the plurality of graphical-path-elements as those whose display regions have been passed through by at least some of the path traced by the motion-based user input. The program may include display instructions configured to cause the input-output device system to display, prior to the conclusion of the definition of the graphical path, a graphical representation of the graphical path including the identified plurality of graphical-path-elements consistent with the interim-definition of the graphical path. The path definition instructions may be configured to cause generation of a modified-interim-definition of the graphical path prior to the conclusion of the definition of the graphical path to exclude at least one of the identified plurality of graphical-path-elements in response to a user-based retracing of a portion of the path traced by the motion-based user input, the excluded at least one of the identified plurality of graphical-path-elements being those whose display regions have been passed through by the retracing of the portion of the path traced by the motion-based user input. The display instructions may be configured to cause the input-output device system to change the display of the graphical representation of the graphical path to account for the excluded at least one of the identified plurality of graphical-path-elements consistent with the modified-interim-definition of the graphical path prior to the conclusion of the definition of the graphical path.

In some embodiments, the portion of the path traced by the motion-based user input and the portion of the path retraced by the motion-based user input pass through the same ones of the display regions. In some embodiments, the portion of the path traced by the motion-based user input and the portion of the path retraced by the motion-based user input pass through the same ones of the display regions in a reverse order that the same ones of the display regions were passed through during the interim-definition of the graphical path.

In some embodiments, a graphical path display device system may be summarized as including a data processing device system, an input-output device system communicatively connected to the data processing device system, and a memory device system communicatively connected to the data processing device system and storing a program executable by the data processing device system. The data processing device system may be configured by the program at least to: cause reception of first user input via the input-output device system and, in response to receiving the first user input, place a first user input element in an activated state; cause reception of motion-based user input via the input-output device system; and cause reception of second user input via the input-output device system and, in response to receiving the second user input, place the first user input element in a deactivated state. The data processing device system may be further configured by the program at least to: cause definition of a graphical path including a plurality of graphical-path-elements; cause initiation of the definition of the graphical path in response to receiving the first user input, to cause generation of an interim-definition of the graphical path according to a path traced by the motion-based user input; and cause conclusion of the definition of the graphical path in response to receiving the second user input. Each of the respective graphical-path-elements may be associated with a respective display region including at least a portion of the respective graphical-path-element, but the respective graphical-path-element not occupying all of the respective display region. The data processing device system may be further configured by the program at least to cause the interim-definition of the graphical path to be generated to identify the plurality of graphical-path-elements as those whose display regions have been passed through by at least some of the path traced by the motion-based user input. The data processing device system may be further configured by the program at least to cause the input-output device system to display, prior to the conclusion of the definition of the graphical path, a graphical representation of the graphical path including the identified plurality of graphical-path-elements consistent with the interim-definition of the graphical path. The data processing device system may be further configured by the program at least to cause generation of a modified-interim-definition of the graphical path prior to the conclusion of the definition of the graphical path to exclude at least one of the identified plurality of graphical-path-elements in response to a user-based retracing of a portion of the path traced by the motion-based user input. The excluded at least one of the identified plurality of graphical-path-elements may be those whose display regions have been passed through by the retracing of the portion of the path traced by the motion-based user input. The data processing device system may be further configured by the program at least to cause the input-output device system to change the display of the graphical representation of the graphical path to account for the excluded at least one of the identified plurality of graphical-path-elements consistent with the modified-interim-definition of the graphical path prior to the conclusion of the definition of the graphical path.

In some embodiments, a graphical path display method may be executed by a data processing device system according to a program stored by a memory device system communicatively connected to the data processing device system, the data processing device system further communicatively connected to an input-output device system. The method may include the data processing device system receiving first user input via the input-output device system and, in response to receiving the first user input, placing a first user input element in an activated state; receiving motion-based user input via the input-output device system; and receiving second user input via the input-output device system and, in response to receiving the second user input, placing the first user input element in a deactivated state. The method may further include the data processing device system causing definition of a graphical path including a plurality of graphical-path-elements; causing initiation of the definition of the graphical path in response to receiving the first user input, to cause generation of an interim-definition of the graphical path according to a path traced by the motion-based user input; and causing conclusion of the definition of the graphical path in response to receiving the second user input. Each of the respective graphical-path-elements may be associated with a respective display region including at least a portion of the respective graphical-path-element, but the respective graphical-path-element not occupying all of the respective display region. The method may further include the data processing device system causing the interim-definition of the graphical path to be generated to identify the plurality of graphical-path-elements as those whose display regions have been passed through by at least some of the path traced by the motion-based user input. The method may further include the data processing device system causing the input-output device system to display, prior to the conclusion of the definition of the graphical path, a graphical representation of the graphical path including the identified plurality of graphical-path-elements consistent with the interim-definition of the graphical path. The method may further include the data processing device system causing generation of a modified-interim-definition of the graphical path prior to the conclusion of the definition of the graphical path to exclude at least one of the identified plurality of graphical-path-elements in response to a user-based retracing of a portion of the path traced by the motion-based user input. The excluded at least one of the identified plurality of graphical-path-elements may be those whose display regions have been passed through by the retracing of the portion of the path traced by the motion-based user input. The method may further include the data processing device system causing the input-output device system to change the display of the graphical representation of the graphical path to account for the excluded at least one of the identified plurality of graphical-path-elements consistent with the modified-interim-definition of the graphical path prior to the conclusion of the definition of the graphical path.

In some embodiments, a computer-readable storage medium system may include one or more computer-readable storage mediums storing a program executable by one or more data processing devices of a data processing device system communicatively connected to an input-output device system. The program may include an input-processing module configured to: cause reception of first user input via the input-output device system and, in response to receiving the first user input, place a first user input element in an activated state; cause reception of motion-based user input via the input-output device system; and cause reception of second user input via the input-output device system and, in response to receiving the second user input, place the first user input element in a deactivated state. The program may include a path definition module configured to cause definition of a graphical path including a plurality of graphical-path-elements, the path definition module configured to cause initiation of the definition of the graphical path in response to receiving the first user input, to cause generation of an interim-definition of the graphical path according to a path traced by the motion-based user input, and to cause conclusion of the definition of the graphical path in response to receiving the second user input, each of the respective graphical-path-elements associated with a respective display region including at least a portion of the respective graphical-path-element, but the respective graphical-path-element not occupying all of the respective display region. The path definition module may be configured to cause the interim-definition of the graphical path to be generated to identify the plurality of graphical-path-elements as those whose display regions have been passed through by at least some of the path traced by the motion-based user input. The program may include a display module configured to cause the input-output device system to display, prior to the conclusion of the definition of the graphical path, a graphical representation of the graphical path including the identified plurality of graphical-path-elements consistent with the interim-definition of the graphical path. The path definition module may be configured to cause generation of a modified-interim-definition of the graphical path prior to the conclusion of the definition of the graphical path to exclude at least one of the identified plurality of graphical-path-elements in response to a user-based retracing of a portion of the path traced by the motion-based user input, the excluded at least one of the identified plurality of graphical-path-elements being those whose display regions have been passed through by the retracing of the portion of the path traced by the motion-based user input. The display module may be configured to cause the input-output device system to change the display of the graphical representation of the graphical path to account for the excluded at least one of the identified plurality of graphical-path-elements consistent with the modified-interim-definition of the graphical path prior to the conclusion of the definition of the graphical path.

Various systems may include combinations and subsets of all the systems summarized above or otherwise described herein.

Any of the features of any of the methods discussed herein may be combined with any of the other features of any of the methods discussed herein. In addition, a computer program product may be provided that comprises program code portions for performing some or all of any of the methods and associated features thereof described herein, when the computer program product is executed by a computer or other computing device or device system. Such a computer program product may be stored on one or more computer-readable storage mediums.

In some embodiments, each of any or all of the computer-readable storage mediums or medium systems described herein is a non-transitory computer-readable storage medium or medium system including one or more non-transitory computer-readable storage mediums storing the respective program(s).

Further, any or all of the methods and associated features thereof discussed herein may be implemented by all or part of a device system or apparatus, such as any of those described herein.

BRIEF DESCRIPTION OF THE DRAWINGS

It is to be understood that the attached drawings are for purposes of illustrating aspects of various embodiments and may include elements that are not to scale.

DETAILED DESCRIPTION

Figure 1:
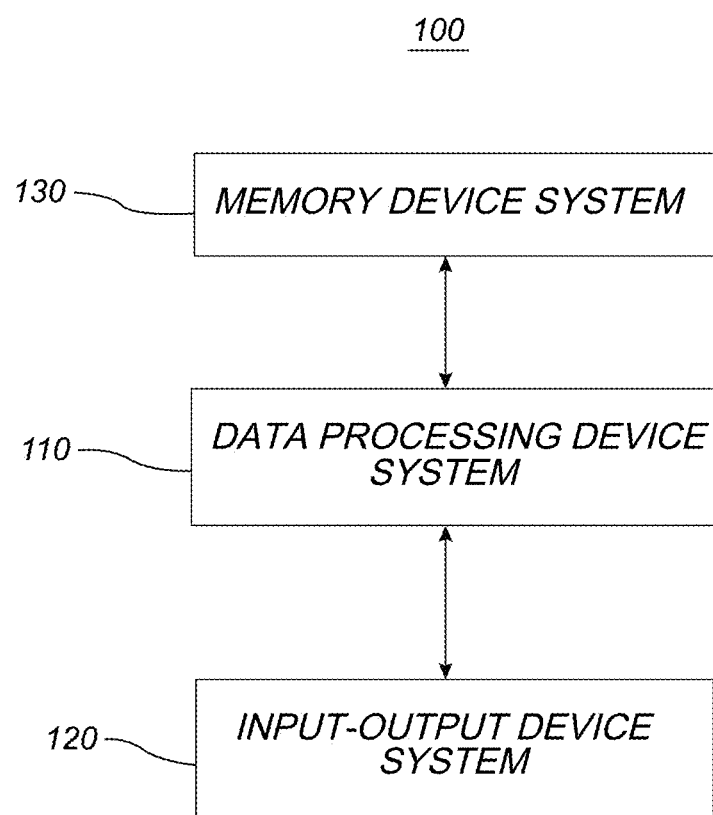
FIG. 1 includes a schematic representation of a transducer-activation system according to various example embodiments, the transducer-activation system including a data processing device system, an input-output device system, and a memory device system.

In the following description, certain specific details are set forth in order to provide a thorough understanding of various embodiments of the invention. However, one skilled in the art will understand that the invention may be practiced at a more general level without these details. In other instances, well-known structures have not been shown or described in detail to avoid unnecessarily obscuring descriptions of various embodiments of the invention.

Any reference throughout this specification to "one embodiment" or "an embodiment" or "an example embodiment" or "an illustrated embodiment" or "a particular embodiment" and the like means that a particular feature, structure or characteristic described in connection with the embodiment is included in at least one embodiment. Thus, any appearance of the phrase "in one embodiment" or "in an embodiment" or "in an example embodiment" or "in this illustrated embodiment" or "in this particular embodiment" or the like in this specification is not necessarily all referring to one embodiment or a same embodiment. Furthermore, the particular features, structures or characteristics of different embodiments may be combined in any suitable manner to form one or more other embodiments.

It is noted that, unless otherwise explicitly noted or required by context, the word "or" is used in this disclosure in a non-exclusive sense. In addition, unless otherwise explicitly noted or required by context, the word "set" is intended to mean one or more, and the word "subset" is intended to mean a set having the same or fewer elements of those present in the subset's parent or superset.

Further, the phrase "at least" is used herein at times to emphasize the possibility that other elements can exist besides those explicitly listed. However, unless otherwise explicitly noted (such as by the use of the term "only") or required by context, non-usage herein of the phrase "at least" does not exclude the possibility that other elements can exist besides those explicitly listed. For example, the phrase, "activation of at least transducer A" includes activation of transducer A by itself, as well as activation of transducer A and activation of one or more other additional elements besides transducer A. In the same manner, the phrase, "activation of transducer A" includes activation of transducer A by itself, as well as activation of transducer A and activation of one or more other additional elements besides transducer A. However, the phrase, "activation of only transducer A" includes only activation of transducer A, and excludes activation of any other transducers besides transducer A.

The word "ablation" as used in this disclosure should be understood to include any disruption to certain properties of tissue. Most commonly, the disruption is to the electrical conductivity and is achieved by transferring thermal energy, which can be generated with resistive or radio-frequency (RF) techniques for example. Other properties, such as mechanical or chemical, and other means of disruption, such as optical, are included when the term "ablation" is used.

The word "fluid" as used in this disclosure should be understood to include any fluid that can be contained within a bodily cavity or can flow into or out of, or both into and out of a bodily cavity via one or more bodily openings positioned in fluid communication with the bodily cavity. In the case of cardiac applications, fluid such as blood will flow into and out of various intra-cardiac cavities (e.g., a left atrium or right atrium).

The words "bodily opening" as used in this disclosure should be understood to include a naturally occurring bodily opening or channel or lumen; a bodily opening or channel or lumen formed by an instrument or tool using techniques that can include, but are not limited to, mechanical, thermal, electrical, chemical, and exposure or illumination techniques; a bodily opening or channel or lumen formed by trauma to a body; or various combinations of one or more of the above. Various elements having respective openings, lumens or channels and positioned within the bodily opening (e.g., a catheter sheath) may be present in various embodiments. These elements may provide a passageway through a bodily opening for various devices employed in various embodiments.

The words "bodily cavity" as used in this disclosure should be understood to mean a cavity in a body. The bodily cavity may be a cavity or chamber provided in a bodily organ (e.g., an intra-cardiac cavity of a heart).

The word "tissue" as used in some embodiments in this disclosure should be understood to include any surface-forming tissue that is used to form a surface of a body or a surface within a bodily cavity, a surface of an anatomical feature or a surface of a feature associated with a bodily opening positioned in fluid communication with the bodily cavity. The tissue can include part or all of a tissue wall or membrane that defines a surface of the bodily cavity. In this regard, the tissue can form an interior surface of the cavity that surrounds a fluid within the cavity. In the case of cardiac applications, tissue can include tissue used to form an interior surface of an intra-cardiac cavity such as a left atrium or right atrium. In some embodiments, the word tissue can refer to a tissue having fluidic properties (e.g., blood) and may be referred to as fluidic tissue.

The term "transducer" as used in this disclosure should be interpreted broadly as any device capable of distinguishing between fluid and tissue, sensing temperature, creating heat, ablating tissue, sensing, sampling or measuring electrical activity of a tissue surface (e.g., sensing, sampling or measuring intra-cardiac electrograms, or sensing, sampling or measuring intra-cardiac voltage data), stimulating tissue, or any combination thereof. A transducer can convert input energy of one form into output energy of another form. Without limitation, a transducer can include an electrode that functions as, or as part of, a sensing device included in the transducer, an energy delivery device included in the transducer, or both a sensing device and an energy delivery device included in the transducer. A transducer may be constructed from several parts, which may be discrete components or may be integrally formed. In this regard, although transducers, electrodes, or both transducers and electrodes are referenced with respect to various embodiments, it is understood that other transducers or transducer elements may be employed in other embodiments. It is understood that a reference to a particular transducer in various embodiments may also imply a reference to an electrode, as an electrode may be part of the transducer as shown, e.g., with FIG. 4 discussed below.

The term "activation" as used in this disclosure should be interpreted broadly as making active a particular function as related to various transducers disclosed in this disclosure. Particular functions may include, but are not limited to, tissue ablation, sensing, sampling or measuring electrophysiological activity (e.g., sensing, sampling or measuring intra-cardiac electrogram information or sensing, sampling or measuring intra-cardiac voltage data), sensing, sampling or measuring temperature and sensing, sampling or measuring electrical characteristics (e.g., tissue impedance or tissue conductivity). For example, in some embodiments, activation of a tissue ablation function of a particular transducer is initiated by causing energy sufficient for tissue ablation from an energy source device system to be delivered to the particular transducer. Alternatively, in this example, the activation can be deemed to be initiated when the particular transducer causes a temperature sufficient for the tissue ablation due to the energy provided by the energy source device system. Also in this example, the activation can last for a duration of time concluding when the ablation function is no longer active, such as when energy sufficient for the tissue ablation is no longer provided to the particular transducer. Alternatively, in this example, the activation period can be deemed to be concluded when the temperature caused by the particular transducer is below the temperature sufficient for the tissue ablation. In some contexts, however, the word "activation" can merely refer to the initiation of the activating of a particular function, as opposed to referring to both the initiation of the activating of the particular function and the subsequent duration in which the particular function is active. In these contexts, the phrase or a phrase similar to "activation initiation" may be used.

The term "program" in this disclosure should be interpreted as a set of instructions or modules that can be executed by one or more components in a system, such a controller system or data processing device system, in order to cause the system to perform one or more operations. The set of instructions or modules can be stored by any kind of memory device, such as those described subsequently with respect to the memory device system 130 or 330 shown in FIGS. 1 and 3, respectively. In addition, this disclosure sometimes describes that the instructions or modules of a program are configured to cause the performance of a function. The phrase "configured to" in this context is intended to include at least (a) instructions or modules that are presently in a form executable by one or more data processing devices to cause performance of the function (e.g., in the case where the instructions or modules are in a compiled and unencrypted form ready for execution), and (b) instructions or modules that are presently in a form not executable by the one or more data processing devices, but could be translated into the form executable by the one or more data processing devices to cause performance of the function (e.g., in the case where the instructions or modules are encrypted in a non-executable manner, but through performance of a decryption process, would be translated into a form ready for execution). The word "module" can be defined as a set of instructions. In some instances, this disclosure describes that the instructions or modules of a program perform a function. Such descriptions should be deemed to be equivalent to describing that the instructions or modules are configured to cause the performance of the function.

Each of the phrases "derived from" or "derivation of" or "derivation thereof" or the like is intended to mean to come from at least some part of a source, be created from at least some part of a source, or be developed as a result of a process in which at least some part of a source forms an input. For example, a data set derived from some particular portion of data may include at least some part of the particular portion of data, or may be created from at least part of the particular portion of data, or may be developed in response to a data manipulation process in which at least part of the particular portion of data forms an input. In some embodiments, a data set may be derived from a subset of the particular portion of data. In some embodiments, the particular portion of data is analyzed to identify a particular subset of the particular portion of data, and a data set is derived from the subset. In various ones of these embodiments, the subset may include some, but not all, of the particular portion of data. In some embodiments, changes in at least one part of a particular portion of data may result in changes in a data set derived at least in part from the particular portion of data.

In this regard, each of the phrases "derived from" or "derivation of" or "derivation thereof" or the like is used herein at times merely to emphasize the possibility that such data or information may be modified or subject to one or more operations. For example, if a device generates first data for display, the process of converting the generated first data into a format capable of being displayed may alter the first data. This altered form of the first data may be considered a derivative or derivation of the first data. For instance, the first data may be a one-dimensional array of numbers, but the display of the first data may be a color-coded bar chart representing the numbers in the array. For another example, if the above-mentioned first data is transmitted over a network, the process of converting the first data into a format acceptable for network transmission or understanding by a receiving device may alter the first data. As before, this altered form of the first data may be considered a derivative or derivation of the first data. For yet another example, generated first data may undergo a mathematical operation, a scaling, or a combining with other data to generate other data that may be considered derived from the first data. In this regard, it can be seen that data is commonly changing in form or being combined with other data throughout its movement through one or more data processing device systems, and any reference to information or data herein is intended to include these and like changes, regardless of whether or not the phrase "derived from" or "derivation of" or "derivation thereof" or the like is used in reference to the information or data. As indicated above, usage of the phrase "derived from" or "derivation of" or "derivation thereof" or the like merely emphasizes the possibility of such changes. Accordingly, the addition of or deletion of the phrase "derived from" or "derivation of" or "derivation thereof" or the like should have no impact on the interpretation of the respective data or information. For example, the above-discussed color-coded bar chart may be considered a derivative of the respective first data or may be considered the respective first data itself.

The word "device" and the phrase "device system" both are intended to include one or more physical devices or sub-devices (e.g., pieces of equipment) that interact to perform one or more functions, regardless of whether such devices or sub-devices are located within a same housing or different housings. In this regard, for example, this disclosure sometimes refers to a "catheter device", but such catheter device could equivalently be referred to as a "catheter device system". The word "device" may equivalently be referred to as a "device system".

In some contexts, the term "adjacent" is used in this disclosure to refer to objects that do not have another substantially similar object between them. For example, object A and object B could be considered adjacent if they contact each other (and, thus, it could be considered that no other object is between them), or if they do not contact each other, but no other object that is substantially similar to object A, object B, or both objects A and B, depending on context, is between them.

Further, the phrase "in response to" may be is used in this disclosure. For example, this phrase might be used in the following context, where an event A occurs in response to the occurrence of an event B. In this regard, such phrase can include, for example, that at least the occurrence of the event B causes or triggers the event A.

Further, the phrase "graphical representation" used herein is intended to include a visual representation presented via a display device and may include computer-generated text, graphics, animations, or one or more combinations thereof, which may include one or more visual representations originally generated, at least in part, by an image-capture device, such as fluoroscopy images, CT scan images, MM images, etc.

Further still, example methods are described herein with respect to FIG. 6. Such figures are described to include blocks associated with computer-executable instructions. It should be noted that the respective instructions associated with any such blocks herein need not be separate instructions and may be combined with other instructions to form a combined instruction set. The same set of instructions may be associated with more than one block. In this regard, the block arrangement shown in each of the method figures herein is not limited to an actual structure of any program or set of instructions or required ordering of method tasks, and such method figures, according to some embodiments, merely illustrate the tasks that instructions are configured to perform, for example, upon execution by a data processing device system in conjunction with interactions with one or more other devices or device systems.

FIG. 1 schematically illustrates a special purpose transducer selection, activation, or selection and activation system 100 that may be employed to at least select, control, activate, or monitor a function or activation of one or more transducers, according to some embodiments. The system 100 includes a data processing device system 110, an input-output device system 120, and a processor-accessible memory device system 130. The processor-accessible memory device system 130 and the input-output device system 120 are communicatively connected to the data processing device system 110.

The data processing device system 110 includes one or more data processing devices that implement or execute, in conjunction with other devices, such as those in the system 100, the methods of various embodiments, including the example methods of FIG. 6 described herein. Each of the phrases "data processing device", "data processor", "processor", and "computer" is intended to include any data processing device, such as a central processing unit (CPU), a desktop computer, a laptop computer, a mainframe computer, a tablet computer, a personal digital assistant, a cellular phone, and any other device for processing data, managing data, or handling data, whether implemented with electrical, magnetic, optical, biological components, or otherwise.

The memory device system 130 includes one or more processor-accessible memory devices configured to store information, including the information needed to execute the methods of various embodiments, including the example methods of FIGS. 6A-6F and 7 described herein. The memory device system 130 may be a distributed processor-accessible memory device system including multiple processor-accessible memory devices communicatively connected to the data processing device system 110 via a plurality of computers and/or devices. On the other hand, the memory device system 130 need not be a distributed processor-accessible memory system and, consequently, may include one or more processor-accessible memory devices located within a single data processing device.

Each of the phrases "processor-accessible memory" and "processor-accessible memory device" is intended to include any processor-accessible data storage device, whether volatile or nonvolatile, electronic, magnetic, optical, or otherwise, including but not limited to, registers, floppy disks, hard disks, Compact Discs, DVDs, flash memories, ROMs, and RAMs. In some embodiments, each of the phrases "processor-accessible memory" and "processor-accessible memory device" is intended to include a non-transitory computer-readable storage medium. And in some embodiments, the memory device system 130 can be considered a non-transitory computer-readable storage medium system.

The phrase "communicatively connected" is intended to include any type of connection, whether wired or wireless, between devices, data processors, or programs between which data may be communicated. Further, the phrase "communicatively connected" is intended to include a connection between devices or programs within a single data processor, a connection between devices or programs located in different data processors, and a connection between devices not located in data processors at all. In this regard, although the memory device system 130 is shown separately from the data processing device system 110 and the input-output device system 120, one skilled in the art will appreciate that the memory device system 130 may be located completely or partially within the data processing device system 110 or the input-output device system 120. Further in this regard, although the input-output device system 120 is shown separately from the data processing device system 110 and the memory device system 130, one skilled in the art will appreciate that such system may be located completely or partially within the data processing system 110 or the memory device system 130, depending upon the contents of the input-output device system 120. Further still, the data processing device system 110, the input-output device system 120, and the memory device system 130 may be located entirely within the same device or housing or may be separately located, but communicatively connected, among different devices or housings. In the case where the data processing device system 110, the input-output device system 120, and the memory device system 130 are located within the same device, the system 100 of FIG. 1 can be implemented by a single application-specific integrated circuit (ASIC) in some embodiments.

The input-output device system 120 may include a mouse, a keyboard, a touch screen, another computer, or any device or combination of devices from which a desired selection, desired information, instructions, or any other data is input to the data processing device system 110. The input-output device system 120 may include a user-activatable control system that is responsive to a user action. The user-activatable control system may include at least one user input element, such as, for example, a mouse button, a keyboard key, a touch screen, or any other user input element that may be placed into an activated or deactivated state on the basis of a particular user action, such as, for example, the clicking/releasing of a mouse button, the pressing/releasing of a keyboard key, or the contacting of/separating from a touch screen. Such user input elements are described in more detail below. The input-output device system 120 may include any suitable interface for receiving information, instructions or any data from other devices and systems described in various ones of the embodiments. In this regard, the input-output device system 120 may include various ones of other systems described in various embodiments. For example, the input-output device system 120 may include at least a portion a transducer-based device system or catheter-based device. The phrase "transducer-based device system" is intended to include one or more physical systems that include various transducers. The phrase "transducer-based device" is intended to include one or more physical devices that include various transducers.

The input-output device system 120 also may include an image generating device system, a display device system, a processor-accessible memory device, or any device or combination of devices to which information, instructions, or any other data is output by the data processing device system 110. In this regard, if the input-output device system 120 includes a processor-accessible memory device, such memory device may or may not form part or all of the memory device system 130. The input-output device system 120 may include any suitable interface for outputting information, instructions or data to other devices and systems described in various ones of the embodiments. In this regard, the input-output device system 120 may include various other devices or systems described in various embodiments. In some embodiments, the input-output device system 120 may include one or more display devices that display one or more of the graphical interfaces of FIG. 5, described below.

Various embodiments of transducer-based devices are described herein. Some of the described devices are medical devices that are percutaneously or intravascularly deployed. Some of the described devices are moveable between a delivery or unexpanded configuration (e.g., FIGS. 3A, 3B discussed below) in which a portion of the device is sized for passage through a bodily opening leading to a bodily cavity, and an expanded or deployed configuration (e.g., FIGS. 3C, 3D discussed below) in which the portion of the device has a size too large for passage through the bodily opening leading to the bodily cavity. An example of an expanded or deployed configuration is when the portion of the transducer-based device is in its intended-deployed-operational state inside the bodily cavity. Another example of the expanded or deployed configuration is when the portion of the transducer-based device is being changed from the delivery configuration to the intended-deployed-operational state to a point where the portion of the device now has a size too large for passage through the bodily opening leading to the bodily cavity.

In some example embodiments, the device includes transducers that sense characteristics (e.g., convective cooling, permittivity, force) that distinguish between fluid, such as a fluidic tissue (e.g., blood), and tissue forming an interior surface of the bodily cavity. Such sensed characteristics can allow a medical system to map the cavity, for example, using positions of openings or ports into and out of the cavity to determine a position or orientation (e.g., pose), or both of the portion of the device in the bodily cavity. In some example embodiments, the described devices are capable of ablating tissue in a desired pattern within the bodily cavity.

In some example embodiments, the devices are capable of sensing various cardiac functions (e.g., electrophysiological activity including intra-cardiac voltages). In some example embodiments, the devices are capable of providing stimulation (e.g., electrical stimulation) to tissue within the bodily cavity. Electrical stimulation may include pacing.

Figure 2:
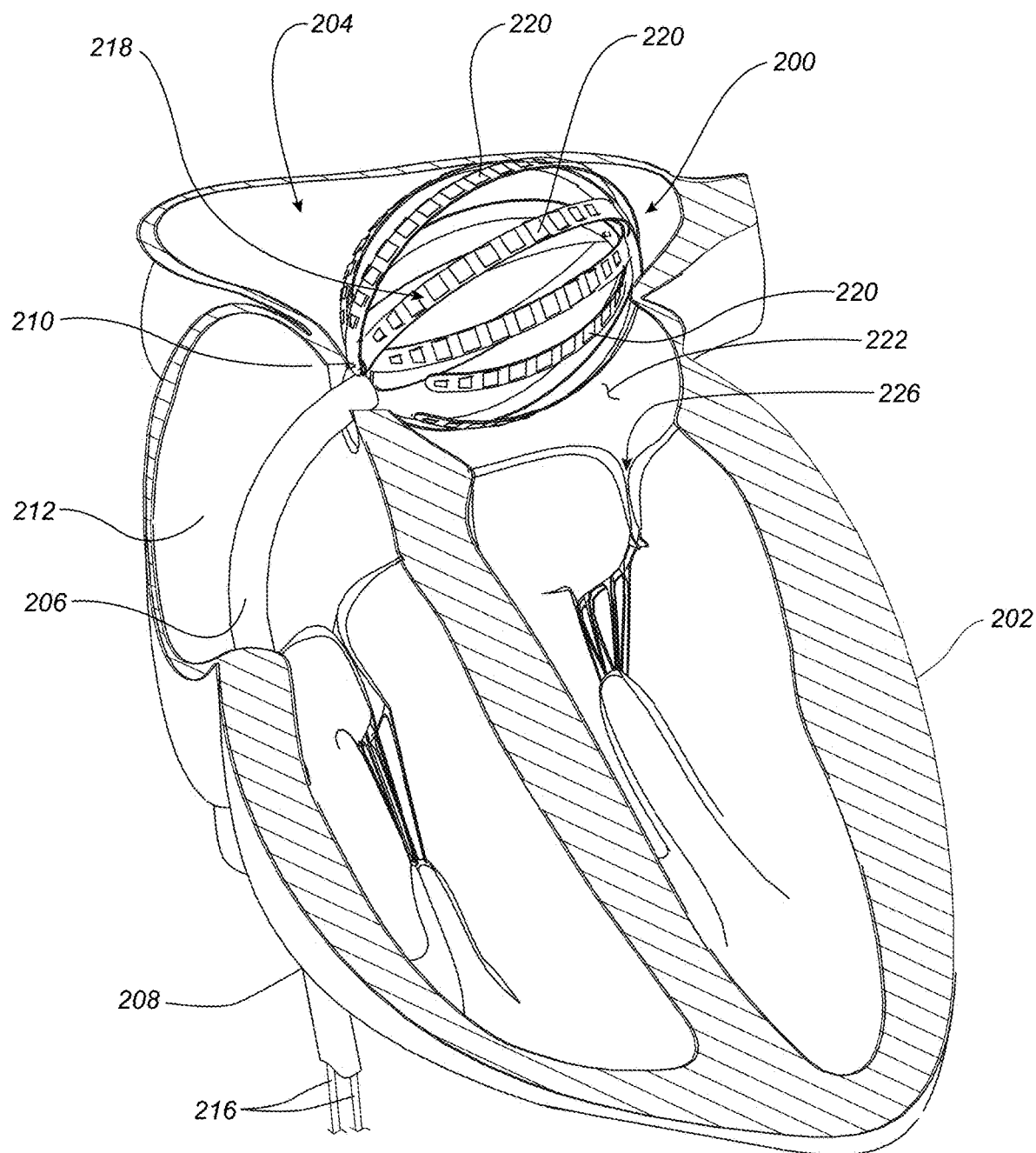
FIG. 2 includes a cutaway diagram of a heart showing a transducer-based device percutaneously placed in a left atrium of the heart according to various example embodiments.

FIG. 2 is a representation of a transducer-based device 200 useful in investigating or treating a bodily organ, for example, a heart 202, according to one example embodiment.

Transducer-based device 200 can be percutaneously or intravascularly inserted into a portion of the heart 202, such as an intra-cardiac cavity like left atrium 204. In this example, the transducer-based device 200 is part of a catheter 206 inserted via the inferior vena cava 208 and penetrating through a bodily opening in transatrial septum 210 from right atrium 212. (In this regard, transducer-based devices or device systems described herein that include a catheter may also be referred to as catheter devices or catheter-based devices, in some embodiments.) In other embodiments, other paths may be taken.

Catheter 206 includes an elongated flexible rod or shaft member appropriately sized to be delivered percutaneously or intravascularly. Various portions of catheter 206 may be steerable. Catheter 206 may include one or more lumens. The lumen(s) may carry one or more communications or power paths, or both. For example, the lumens(s) may carry one or more electrical conductors 216 (two shown). Electrical conductors 216 provide electrical connections to transducer-based device 200 that are accessible externally from a patient in which the transducer-based device 200 is inserted.

Transducer-based device 200 includes a frame or structure 218 which assumes an unexpanded configuration for delivery to left atrium 204. Structure 218 is expanded (e.g., shown in a deployed or expanded configuration in FIG. 2) upon delivery to left atrium 204 to position a plurality of transducers 220 (three called out in FIG. 2) proximate the interior surface formed by tissue 222 of left atrium 204. In some embodiments, at least some of the transducers 220 are used to sense a physical characteristic of a fluid (e.g., blood) or tissue 222, or both, that may be used to determine a position or orientation (e.g., pose), or both, of a portion of a device 200 within, or with respect to left atrium 204. For example, transducers 220 may be used to determine a location of pulmonary vein ostia or a mitral valve 226, or both. In some embodiments, at least some of the transducers 220 may be used to selectively ablate portions of the tissue 222. For example, some of the transducers 220 may be used to ablate a pattern around the bodily openings, ports or pulmonary vein ostia, for instance to reduce or eliminate the occurrence of atrial fibrillation. In some embodiments, at least some of the transducers 220 are used to ablate cardiac tissue. In some embodiments, at least some of the transducers 220 are used to sense or sample intra-cardiac voltage data or sense or sample intra-cardiac electrogram data. In some embodiments, at least some of the transducers 220 are used to sense or sample intra-cardiac voltage data or sense or sample intra-cardiac electrogram data while at least some of the transducers 220 are concurrently ablating cardiac tissue. In some embodiments, at least one of the sensing or sampling transducers 220 is provided by at least one of the ablating transducers 220. In some embodiments, at least a first one of the transducers 220 senses or samples intra-cardiac voltage data or intra-cardiac electrogram data at a location at least proximate to a tissue location ablated by at least a second one of the transducers 220. In some embodiments, the first one of the transducers 220 is other than the second one of the transducers 220.

Figure 3A:
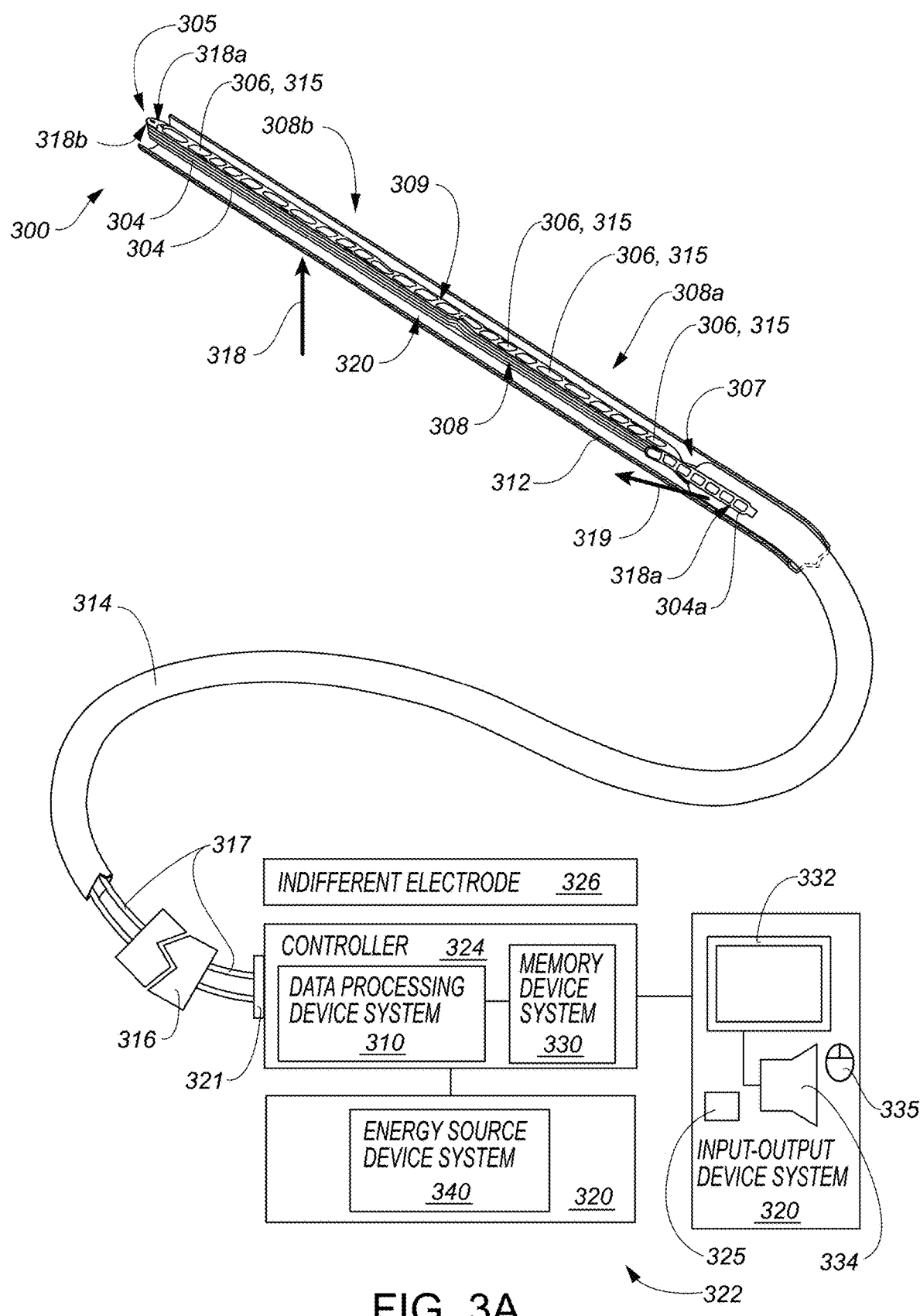
FIG. 3A includes a partially schematic representation of a medical system according to various example embodiments, the medical system including a data processing device system, an input-output device system, a memory device system, and a transducer-based device having a plurality of transducers and an expandable structure shown in a delivery or unexpanded configuration.
Figure 3B:
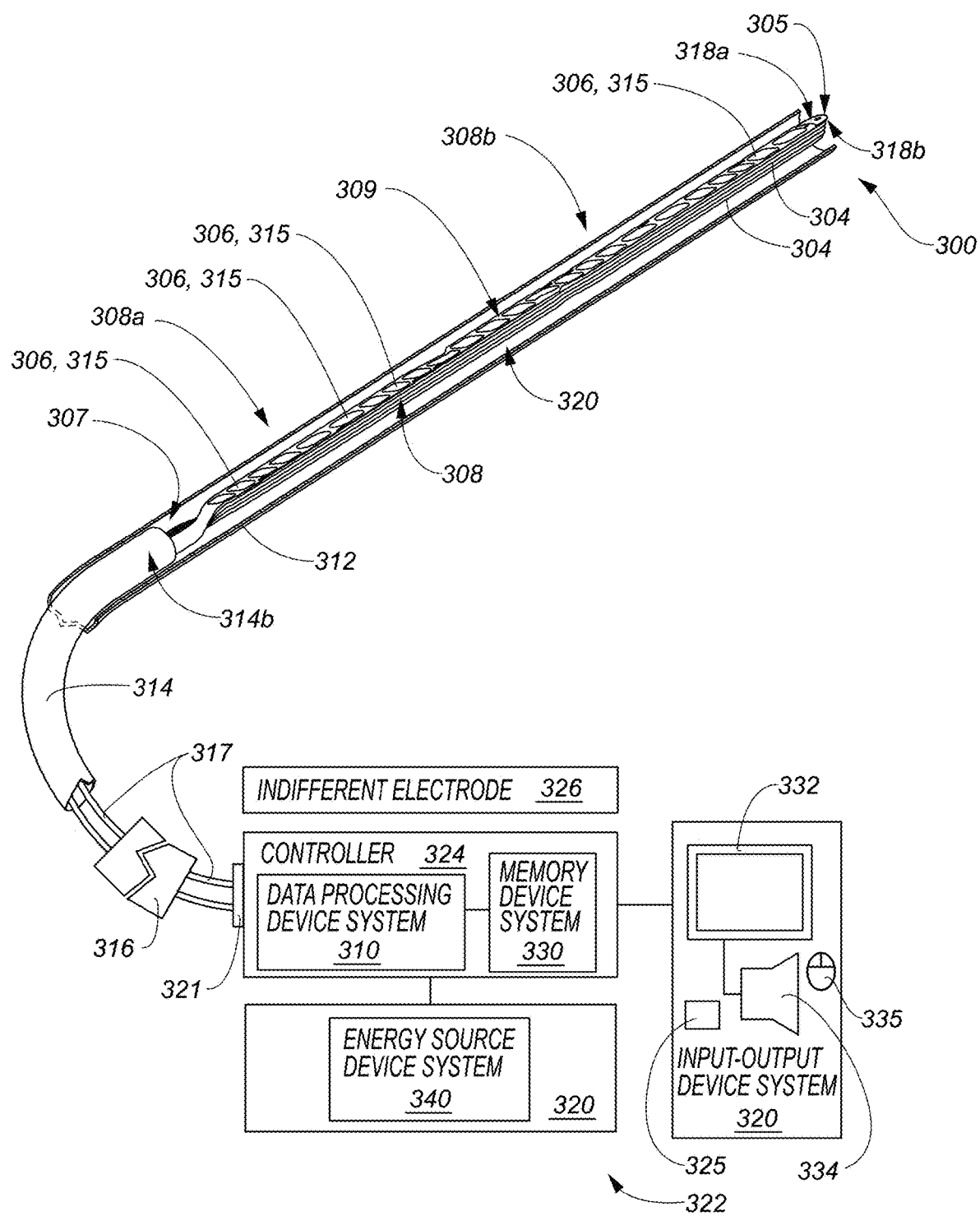
FIG. 3B includes a portion of the medical system of FIG. 3A as viewed from a different viewing direction.
Figure 3C:
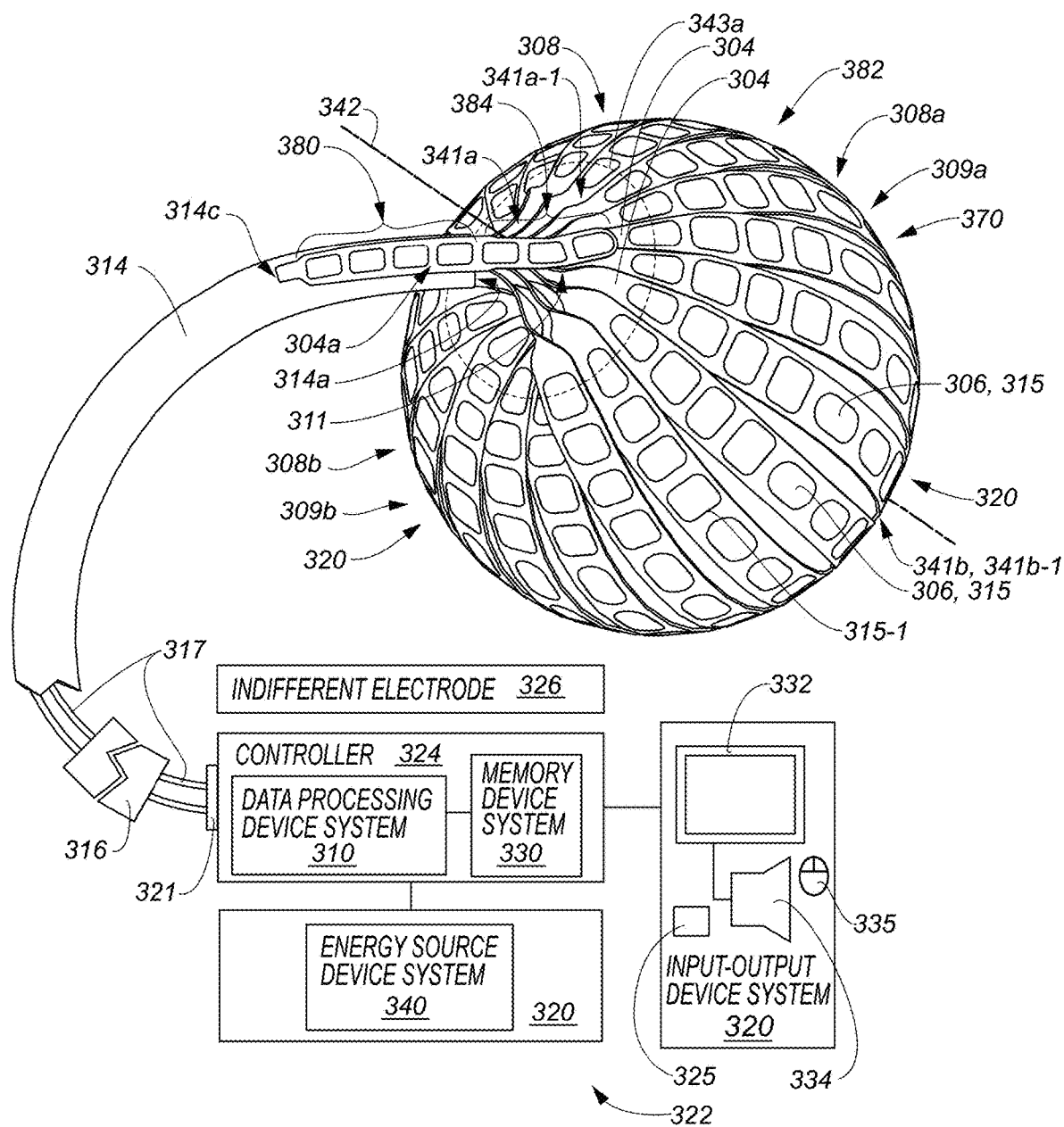
FIG. 3C includes the representation of the medical system of FIGS. 3A and 3B with the expandable structure shown in a deployed or expanded configuration.
Figure 3D:
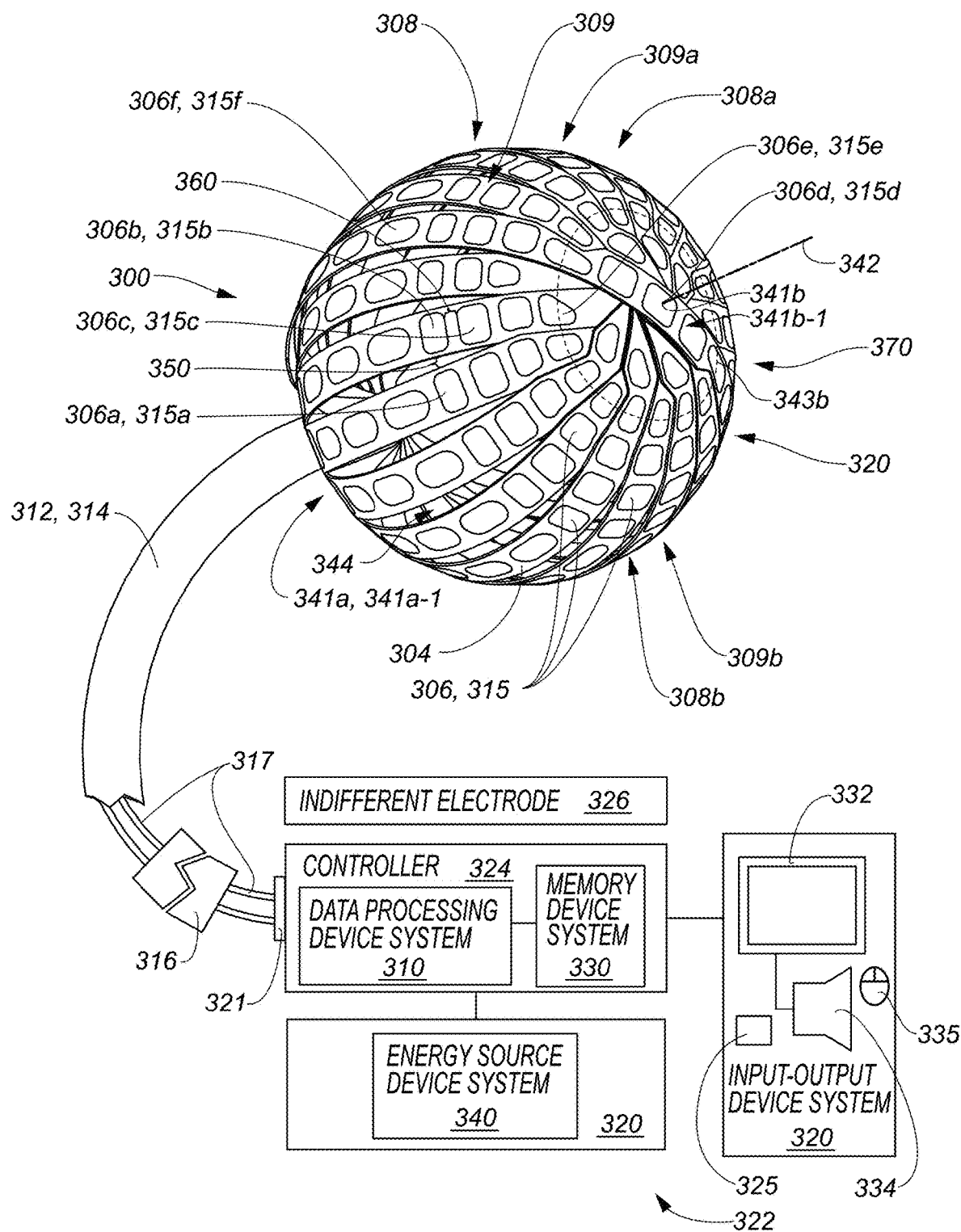
FIG. 3D includes a portion of the medical system of FIG. 3C as viewed from a different viewing direction.

FIGS. 3A, 3B, 3C and 3D (collectively, FIG. 3) include a transducer-based device system (e.g., a portion thereof shown schematically) that includes a transducer-based device 300 according to some embodiments. Transducer-based device 300 includes a plurality of elongate members 304 (not all of the elongate members called out in each of FIGS. 3A, 3B, 3C and 3D) and a plurality of transducers 306 (not all of the transducers called out in FIG. 3) (some of the transducers 306 called out in FIG. 3D as 306a, 306b, 306c, 306d, 306e and 306f). FIG. 3B includes a representation of a portion of the transducer-based device 300 shown in FIG. 3A but as viewed from a different viewing direction. FIG. 3D includes a representation of a portion of the transducer-based device 300 shown in FIG. 3C but as viewed from a different viewing direction. It is noted that for clarity of illustration, all the elongate members shown in FIGS. 3C and 3D are not represented in FIGS. 3A and 3B. As will become apparent, the plurality of transducers 306 is positionable within a bodily cavity. For example, in some embodiments, the transducers 306 are able to be positioned in a bodily cavity by movement into, within, or into and within the bodily cavity, with or without a change in a configuration of the plurality of transducers 306. In some embodiments, the plurality of transducers 306 are arranged to form a two- or three-dimensional distribution, grid or array of the transducers capable of mapping, ablating or stimulating an inside surface of a bodily cavity or lumen without requiring mechanical scanning. As shown, for example, in FIGS. 3A and 3B, the plurality of transducers 306 are arranged in a distribution receivable in a bodily cavity. In various ones of the FIG. 3, each of at least some of transducers 306 includes a respective electrode 315 (not all of the electrode 315 called out in each of the FIG. 3, some of the electrodes in FIG. 3D called out as 315a, 315b, 315c, 315d, 315e and 315f).

The elongate members 304 are arranged in a frame or structure 308 that is selectively movable between an unexpanded or delivery configuration (e.g., as shown in FIGS. 3A, 3B) and an expanded or deployed configuration (e.g., as shown in FIGS. 3C, 3D) that may be used to position elongate members 304 against a tissue surface within the bodily cavity or position the elongate members 304 in the vicinity of the tissue surface. At least the expanded or deployed configuration shown in FIGS. 3C and 3D is an example of a three-dimensional distribution of the transducers 306. In some embodiments, structure 308 has a size in the unexpanded or delivery configuration suitable for delivery through a bodily opening (e.g., via catheter sheath 312 (shown in FIGS. 3A and 3B, but removed from FIGS. 3C and 3D for clarity)) to the bodily cavity. At least in a state in which the structure 308 is in the expanded or deployed configuration, the structure 308 may be considered to have two opposing poles 341a and 341b, marked by the intersection with axis 342 extending through the structure 308 as shown in FIGS. 3C and 3D. At least some of the plurality of transducers 306 are circumferentially arranged, e.g., in successive ring-like arrangements, about each of the poles 341a and 341b according to some embodiments. Two such ring-like arrangements are illustrated, for example, as broken-line rings 343a and 343b in FIG. 3C and FIG. 3D, respectively. At least some of the plurality of transducers 306 are arranged in a plurality of groups of the transducers 306, the groups of transducers 306 arranged like lines of longitude (e.g., along respective elongate members 304) about the structure 308 between each of the poles 341a and 341b, according to some embodiments. At least some of the plurality of transducers 306 are arranged in a plurality of groups of the transducers 306, the transducers in each group of transducers 306 arrayed along a path (e.g., along at least a respective portion of a respective elongate member 304) that extends toward the pole 341a, the pole 341b, or both poles 341a and 341b, according to some embodiments. In some embodiments, each path extends like a line of longitude between the poles 341a and 341b.

In various embodiments, catheter sheath 312 typically includes a length sufficient to allow the catheter sheath to extend between a location at least proximate a bodily cavity into which the structure 308 is to be delivered and a location outside a body comprising the bodily cavity. In some embodiments, structure 308 has a size in the expanded or deployed configuration too large for delivery through a bodily opening (e.g., via catheter sheath 312) to the bodily cavity. The elongate members 304 may form part of a flexible circuit structure (e.g., also known as a flexible printed circuit board (PCB) circuit). The elongate members 304 can include a plurality of different material layers. Each of the elongate members 304 can include a plurality of different material layers. The structure 308 can include a shape memory material, for instance Nitinol. The structure 308 can include a metallic material, for instance stainless steel, or non-metallic material, for instance polyimide, or both a metallic and non-metallic material by way of non-limiting example. The incorporation of a specific material into structure 308 may be motivated by various factors including the specific requirements of each of the unexpanded or delivery configuration and expanded or deployed configuration, the required position or orientation (e.g., pose), or both of structure 308 in the bodily cavity or the requirements for successful ablation of a desired pattern.

Figure 4:
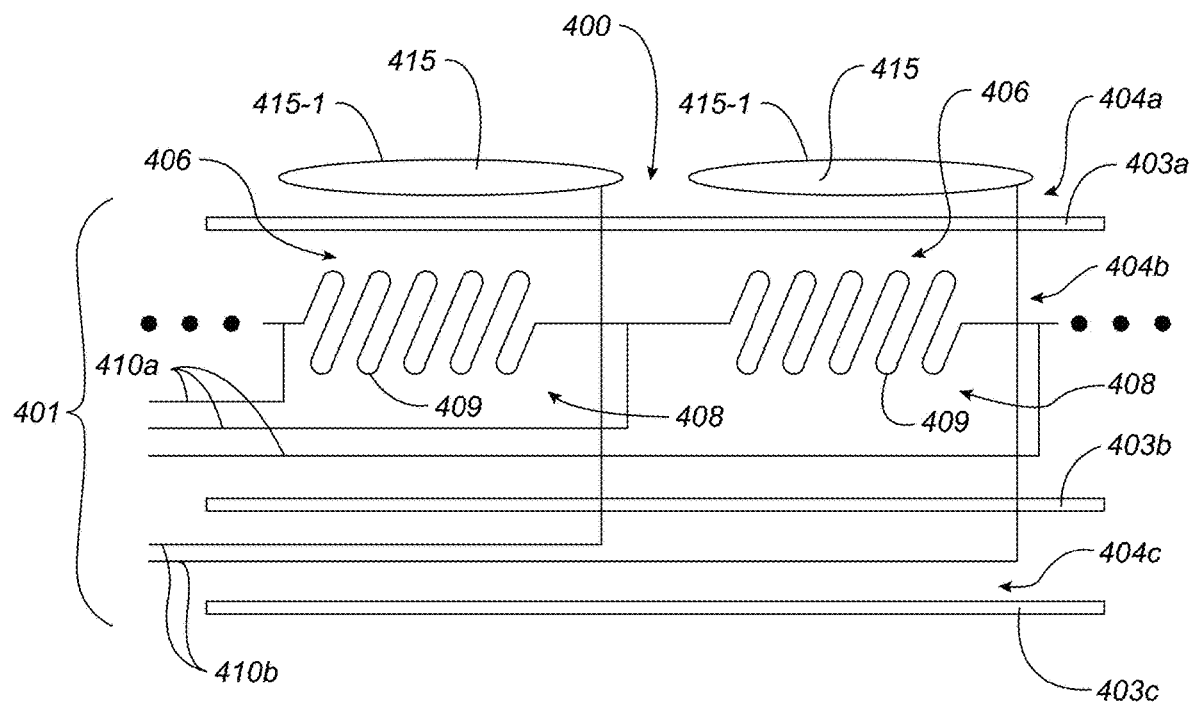
FIG. 4 includes a schematic representation of a transducer-based device that includes a flexible circuit structure according to various example embodiments.

FIG. 4 is a schematic side elevation view of at least a portion of a transducer-based device 400 that includes a flexible circuit structure 401 that is employed to provide a plurality of transducers 406 (two called out) according to an example embodiment. In some embodiments, the flexible circuit structure 401 may form part of a structure (e.g., structure 308) that is selectively movable between a delivery configuration sized for percutaneous delivery and expanded or deployed configurations sized too large for percutaneous delivery. In some embodiments, the flexible circuit structure 401 may be located on, or form at least part of, a structural component (e.g., elongate member 304) of a transducer-based device system.

The flexible circuit structure 401 can be formed by various techniques including flexible printed circuit techniques. In some embodiments, the flexible circuit structure 401 includes various layers including flexible layers 403a, 403b and 403c (e.g., collectively flexible layers 403). In some embodiments, each of flexible layers 403 includes an electrical insulator material (e.g., polyimide). One or more of the flexible layers 403 can include a different material than another of the flexible layers 403. In some embodiments, the flexible circuit structure 401 includes various electrically conductive layers 404a, 404b and 404c (collectively electrically conductive layers 404) that are interleaved with the flexible layers 403. In some embodiments, each of the electrically conductive layers 404 is patterned to form various electrically conductive elements. For example, electrically conductive layer 404a is patterned to form a respective electrode 415 of each of the transducers 406. Electrodes 415 have respective electrode edges 415-1 that form a periphery of an electrically conductive surface associated with the respective electrode 415. It is noted that other electrodes employed in other embodiments may have electrode edges arranged to form different electrodes shapes (for example, as shown by electrode edges 315-1 in FIG. 3C).

Electrically conductive layer 404b is patterned, in some embodiments, to form respective temperature sensors 408 for each of the transducers 406 as well as various leads 410a arranged to provide electrical energy to the temperature sensors 408. In some embodiments, each temperature sensor 408 includes a patterned resistive member 409 (two called out) having a predetermined electrical resistance. In some embodiments, each resistive member 409 includes a metal having relatively high electrical conductivity characteristics (e.g., copper). In some embodiments, electrically conductive layer 404c is patterned to provide portions of various leads 410b arranged to provide an electrical communication path to electrodes 415. In some embodiments, leads 410b are arranged to pass though vias in flexible layers 403a and 403b to connect with electrodes 415. Although FIG. 4 shows flexible layer 403c as being a bottom-most layer, some embodiments may include one or more additional layers underneath flexible layer 403c, such as one or more structural layers, such as a steel or composite layer. These one or more structural layers, in some embodiments, are part of the flexible circuit structure 401 and can be part of, e.g., elongate member 304. In some embodiments, the one or more structural layers may include at least one electrically conductive surface (e.g., a metallic surface) exposed to blood flow. In addition, although FIG. 4 shows only three flexible layers 403a-403c and only three electrically conductive layers 404a-404c, it should be noted that other numbers of flexible layers, other numbers of electrically conductive layers, or both, can be included.

In some embodiments, electrodes 415 are employed to selectively deliver RF energy to various tissue structures within a bodily cavity (e.g., an intra-cardiac cavity or chamber). The energy delivered to the tissue structures may be sufficient for ablating portions of the tissue structures. The energy delivered to the tissue may be delivered to cause monopolar tissue ablation, bipolar tissue ablation or blended monopolar-bipolar tissue ablation by way of non-limiting example.

Energy that is sufficient for tissue ablation may be dependent upon factors including transducer location, size, shape, relationship with respect to another transducer or a bodily cavity, material or lack thereof between transducers, et cetera. For example, a pair of electrodes that each is approximately 10 mm$^2$ in surface area and present along a same structural member (e.g., an elongate member 304 in various ones of FIG. 3) may be expected, in some circumstances, to sufficiently ablate intra-cardiac tissue to a depth of approximately 3.1 mm with 2 W of power and to a depth of approximately 4.4 mm with 4 W of power. For yet another non-limiting example, if each electrode in this pair instead has approximately 20 mm$^2$ of surface area, it may be expected that such pair of electrodes will sufficiently ablate intra-cardiac tissue to a depth of approximately 3.1 mm with 4 W of power and to a depth of approximately 4.4 mm with 8 W of power. In these non-limiting examples, power refers to the average power of each electrode summed together, and the depth and power values may be different depending upon the particular shapes of the respective electrodes, the particular distance between them, a degree of electrode-to-tissue contact, and other factors. It is understood, however, that for the same control or target temperature, a larger electrode will achieve a given ablation depth sooner than a smaller electrode. A smaller electrode (e.g., an electrode with a smaller surface area) may need to operate at a higher target temperature to achieve the same ablation depth as compared to a larger (e.g., surface area) electrode (a phenomenon driven by a greater divergence of heat flux of smaller electrodes). Put differently, a maximum ablation depth (e.g., reached when the temperature profile approaches steady state) of a relatively smaller electrode is typically shallower than that of a relatively larger electrode when ablating at the same control or target temperature, and consequently, a given, less than maximum, ablation depth typically is a larger proportion of the final, maximum, ablation depth for a relatively smaller electrode and typically is reached later in the ablation as compared to a relatively larger electrode. This circumstance may be associated with a lower total power provided to the relatively smaller electrode as compared to a relatively larger electrode, but, nonetheless, the power density present in the relatively smaller electrode may be expected to be somewhat higher as compared to the relatively larger electrode. The phrase "power density" in this context means output power divided by electrode area. Note that power density approximately drives the realized control or target temperature, but in various cases, this is a simplification, and as indicated above, the relationship between power density and realized control or target temperature may be modified by such factors as electrode size, shape, separation, and so forth. It is further noted that when a comparison is made between a relatively larger electrode operated at a lower control temperature versus a relatively smaller electrode operated at a higher temperature, further complications may arise when limits on compensation for electrode size with temperature are also dictated, at least in part, by a desire to reduce occurrences of thermal coagulation of blood or steam formation in the ablated tissue. It is noted that power levels in irrigated electrode systems are typically higher (e.g., in the tens of Watts) than those described above.

In some embodiments, each electrode 415 is employed to sense or sample an electrical potential in the tissue proximate the electrode 415 at a same or different time than delivering energy sufficient for tissue ablation. In some embodiments, each electrode 415 is employed to sense or sample intra-cardiac voltage data in the tissue proximate the electrode 415. In some embodiments, each electrode 415 is employed to sense or sample data in the tissue proximate the electrode 415 from which an electrogram (e.g., an intra-cardiac electrogram) may be derived. In some embodiments, each resistive member 409 is positioned adjacent a respective one of the electrodes 415. In some embodiments, each of the resistive members 409 is positioned in a stacked or layered array with a respective one of the electrodes 415 to form a respective one of the transducers 406. In some embodiments, the resistive members 409 are connected in series to allow electrical current to pass through all of the resistive members 409. In some embodiments, leads 410a are arranged to allow for a sampling of electrical voltage in between each resistive members 409. This arrangement allows for the electrical resistance of each resistive member 409 to be accurately measured. The ability to accurately measure the electrical resistance of each resistive member 409 may be motivated by various reasons including determining temperature values at locations at least proximate the resistive member 409 based at least on changes in the resistance caused by convective cooling effects (e.g., as provided by blood flow).

Referring to FIGS. 3A, 3B, 3C, and 3D transducer-based device 300 can communicate with, receive power from or be controlled by a transducer-activation system 322. In some embodiments, the transducer-activation system 322 represents one or more particular implementations of the system 100 illustrated in FIG. 1. In some embodiments, elongate members 304 can form a portion of an elongated cable 316 of leads 317 (e.g., control leads, data leads, power leads or any combination thereof), for example, by stacking multiple layers, and terminating at a connector 321 or other interface with transducer-activation system 322. The leads 317 may correspond to the electrical connectors 216 in FIG. 2 in some embodiments. The transducer-activation device system 322 may include a controller 324 that includes a data processing device system 310 (e.g., which may be a particular implementation of data processing device system 110 from FIG. 1) and a memory device system 330 (e.g., which may be a particular implementation of the memory device system 130 from FIG. 1) that stores data and instructions that are executable by the data processing device system 310 to process information received from transducer-based device 300 or to control operation of transducer-based device 300, for example, activating various selected transducers 306 to ablate tissue and control a user interface (e.g., of input-output device system 320) according to various embodiments including at least those described below with respect to various ones of FIGS. 5 and 6. Controller 324 may include one or more controllers.

Transducer-activation device system 322 includes an input-output device system 320 (e.g., which may be a particular implementation of the input-output device system 120 from FIG. 1) communicatively connected to the data processing device system 310 (e.g., via controller 324 in some embodiments). Input-output device system 320 may include a user-activatable control that is responsive to a user action. Input-output device system 320 may include one or more user interfaces or input/output (I/O) devices, for example, one or more display device systems 332, speaker device systems 334, one or more keyboards, one or more mice (e.g., mouse 335), one or more joysticks, one or more track pads, one or more touch screens or other transducers to transfer information to, from, or both to and from a user, for example, a care provider such as a physician or technician. For example, output from a mapping process may be displayed on a display device system 332. Input-output device system 320 may include one or more user interfaces or input/output (I/O) devices, for example, one or more display device systems 332, speaker device systems 334, keyboards, mice, joysticks, track pads, touch screens or other transducers employed by a user to indicate a particular selection or series of selections of various graphical information. Input-output device system 320 may include a sensing device system 325 configured to detect various characteristics including, but not limited to, at least one of tissue characteristics (e.g., electrical characteristics such as tissue impedance, tissue conductivity, tissue type, tissue thickness) and thermal characteristics such as temperature. In this regard, the sensing device system 325 may include one, some, or all of the transducers 306 (or 406 of FIG. 4) of the transducer based device 300, including the internal components of such transducers shown in FIG. 4, such as the electrodes 415 and temperature sensors 408.

Transducer-activation device system 322 may also include an energy source device system 340 including one or more energy source devices connected to transducers 306. In this regard, although various ones of FIG. 3 show a communicative connection between the energy source device system 340 and the controller 324 (and its data processing device system 310), the energy source device system 340 may also be connected to the transducers 306 via a communicative connection that is independent of the communicative connection with the controller 324 (and its data processing device system 310). For example, the energy source device system 340 may receive control signals via the communicative connection with the controller 324 (and its data processing device system 310), and, in response to such control signals, deliver energy to, receive energy from, or both deliver energy to and receive energy from one or more of the transducers 306 via a communicative connection with such transducers 306 (e.g., via one or more communication lines through catheter body or shaft 314, elongated cable 316 or catheter sheath 312) that does not pass through the controller 324. In this regard, the energy source device system 340 may provide results of its delivering energy to, receiving energy from, or both delivering energy to and receiving energy from one or more of the transducers 306 to the controller 324 (and its data processing device system 310) via the communicative connection between the energy source device system 340 and the controller 324.

In any event, the number of energy source devices in the energy source device system 340 is fewer than the number of transducers in some embodiments. The energy source device system 340 may, for example, be connected to various selected transducers 306 to selectively provide energy in the form of electrical current or power (e.g., RF energy), light or low temperature fluid to the various selected transducers 306 to cause ablation of tissue. The energy source device system 340 may, for example, selectively provide energy in the form of electrical current to various selected transducers 306 and measure a temperature characteristic, an electrical characteristic, or both at a respective location at least proximate each of the various transducers 306. The energy source device system 340 may include various electrical current sources or electrical power sources as energy source devices. In some embodiments, an indifferent electrode 326 is provided to receive at least a portion of the energy transmitted by at least some of the transducers 306. Consequently, although not shown in various ones of FIG. 3, the indifferent electrode 326 may be communicatively connected to the energy source device system 340 via one or more communication lines in some embodiments. In addition, although shown separately in various ones of FIG. 3, indifferent electrode 326 may be considered part of the energy source device system 340 in some embodiments. In various embodiments, indifferent electrode 326 is positioned on an external surface (e.g., a skin-based surface) of a body that comprises the bodily cavity into which at least transducers 306 are to be delivered.

It is understood that input-output device system 320 may include other systems. In some embodiments, input-output device system 320 may optionally include energy source device system 340, transducer-based device 300 or both energy source device system 340 and transducer-based device 300 by way of non-limiting example. Input-output device system 320 may include the memory device system 330 in some embodiments.

Structure 308 can be delivered and retrieved via a catheter member, for example, a catheter sheath 312. In some embodiments, a structure provides expansion and contraction capabilities for a portion of the medical device (e.g., an arrangement, distribution or array of transducers 306). The transducers 306 can form part of, be positioned or located on, mounted or otherwise carried on the structure and the structure may be configurable to be appropriately sized to slide within catheter sheath 312 in order to be deployed percutaneously or intravascularly. FIGS. 3A, 3B show one embodiment of such a structure. In some embodiments, each of the elongate members 304 includes a respective distal end 305 (only one called out in each of FIGS. 3A, 3B), a respective proximal end 307 (only one called out in each of FIGS. 3A, 3B) and an intermediate portion 309 (only one called out in each of FIGS. 3A, 3B) positioned between the proximal end 307 and the distal end 305. The respective intermediate portion 309 of each elongate member 304 includes a first or front surface 318a that is positionable to face an interior tissue surface within a bodily cavity and a second or back surface 318b opposite across a thickness of the intermediate portion 309 from the front surface 318a. In some embodiments, each of the elongate members 304 is arranged front surface 318a-toward-back surface 318b in a stacked array during an unexpanded or delivery configuration similar to that described in co-assigned International Application No.: PCT/US2012/022061 and co-assigned International Application No.: PCT/US2012/022062. In many cases a stacked array allows the structure 308 to have a suitable size for percutaneous or intravascular delivery. In some embodiments, the elongate members 304 are arranged to be introduced into a bodily cavity distal end 305 first. A flexible, elongated, catheter body 314 is used to deliver structure 308 through catheter sheath 312 according to some embodiments.

In a manner similar to that described in co-assigned International Application No.: PCT/US2012/022061 and co-assigned International Application No.: PCT/US2012/022062, each of the elongate members 304 is arranged in a fanned arrangement 370 in FIGS. 3C, 3D. In some embodiments, the fanned arrangement 370 is formed during the expanded or deployed configuration in which structure 308 is manipulated to have a size too large for percutaneous or intravascular delivery. In some embodiments, structure 308 includes a proximal portion 308a having a first domed shape 309a and a distal portion 308b having a second domed shape 309b. In some embodiments, the proximal and the distal portions 308a, 308b each include respective portions of elongate members 304. In some embodiments, the structure 308 is arranged to be delivered distal portion 308b first into a bodily cavity when the structure is in the unexpanded or delivery configuration as shown in FIGS. 3A, 3B. In various embodiments, the proximal and distal portions 308a, 308b do not include a domed shape in the delivery configuration (for example, as shown in FIGS. 3A, 3B). In some embodiments, the first domed shape 309a of the proximal portion 308a and the second domed shape 309b of the distal portion 308b are arranged in a clam shell configuration in the expanded or deployed configuration shown in FIGS. 3C, 3D.

The transducers 306 can be arranged in various distributions or arrangements in various embodiments. In some embodiments, various ones of the transducers 306 are spaced apart from one another in a spaced apart distribution in the delivery configuration shown in FIGS. 3A, 3B. In some embodiments, various ones of the transducers 306 are arranged in a spaced apart distribution in the deployed configuration shown in FIGS. 3C, 3D. In some embodiments, various pairs of transducers 306 are spaced apart with respect to one another. In some embodiments, various regions of space are located between various pairs of the transducers 306. For example, in FIG. 3D the transducer-based device 300 includes at least a first transducer 306a, a second transducer 306b and a third transducer 306c (all collectively referred to as transducers 306). In some embodiments each of the first, the second and the third transducers 306a, 306b and 306c are adjacent transducers in the spaced apart distribution. In some embodiments, the first and the second transducers 306a, 306b are located on different elongate members 304 while the second and the third transducers 306b, 306c are located on a same elongate member 304. In some embodiments, a first region of space 350 is between the first and the second transducers 306a, 306b. In various embodiments, a first region of space 350 is between the respective electrodes 315a, 315b of the first and the second transducers 306a, 306b. In some embodiments, the first region of space 350 is not associated with any physical portion of structure 308. In some embodiments, a second region of space 360 associated with a physical portion of device 300 (e.g., a portion of an elongate member 304) is between the second and the third transducers 306b, 306c. In various embodiments, the second region of space 360 is between the respective electrodes 315b, 315c of the second and the third transducers 306b, 306c. In some embodiments, each of the first and the second regions of space 350, 360 does not include a transducer of transducer-based device 300. In some embodiments, each of the first and the second regions of space 350, 360 does not include any transducer. It is noted that other embodiments need not employ a group of elongate members 304 as employed in the illustrated embodiment. For example, other embodiments may employ a structure having one or more surfaces, at least a portion of the one or more surfaces defining one or more openings in the structure. In these embodiments, a region of space not associated with any physical portion of the structure may extend over at least part of an opening of the one or more openings.

In some embodiments, a first transducer set (e.g., a first set including one or more of transducers 306) is arranged (e.g., axially, circumferentially, or both axially and circumferentially arranged) along, across, or over a portion of catheter body 314 while a second set (e.g., a second set including one or more of transducers 306) is located on structure 308 extending outwardly from a distal end 314a of catheter body 314. An example first transducer set 380 and example second transducer set 382 are shown in FIG. 3C according to some embodiments. In various example embodiments, transducer-based device 300 includes a first transducer set (e.g., first transducer set 380) located proximally of a distal end 314a of catheter body 314 while a second transducer set (e.g., second transducer set 382) is located on structure 308 extending outwardly from the distal end 314a of catheter body 314 (which is better seen in FIG. 3B). In some of these various example embodiments, structure 308 is selectively moveable between a delivery configuration (e.g., FIGS. 3A, 3B) in which the first transducer set 380 and the second transducer set 382 are concurrently arranged in respective arrangements sized for movement through a lumen of catheter sheath 312, and an expanded or deployed configuration (e.g., FIGS. 3C, 3D) in which the second transducer set 382 is arranged in a respective arrangement sized too large for delivery through the lumen of catheter sheath 312 while the first transducer set 380 is arranged in a respective arrangement sized for movement through the lumen of the catheter sheath 312. For example, in some embodiments of the expanded or deployed configuration, each of various transducers 306 in the first transducer set 380 is moveable inwardly into or outwardly from the lumen of catheter sheath 312 while the transducers 306 in the second transducer set 382 are arranged in an arrangement too large for movement inwardly into the lumen of the catheter sheath 312. Advantageously, these embodiments may allow particular transducers (e.g., transducers 306 in the first transducer set 380 to be introduced into or removed from a bodily cavity when the structure 308 is repositioned in the bodily cavity in the expanded or deployed configuration. Repositioning of the structure 308 in the bodily cavity may be required due to variances in a size of the cavity (e.g., a larger than expected size) or variances in an expected positioning of various anatomical landmarks. In either case, additional transducers 306 may be brought into play or out of play as the specific circumstance may require. Bringing a particular transducer 306 into play within a bodily cavity may include appropriately positioning the transducer for a desired sensing function, an energy transmission function, or a sensing and energy transmission function within the bodily cavity.

In FIG. 3C, structure 308 includes at least one elongate member 304a (also shown in FIG. 3A) according to some embodiments. At least one elongate member 304a is sized and arranged to position at least some of a first set of the transducers 306 (e.g., first transducer set 380) diametrically opposite from a portion 314b (best seen in FIG. 3B) of an outer surface of catheter body 314, the portion of the outer surface not including any transducer. In some example embodiments, portion 314b includes at least a semicircular portion of an outer surface of catheter body 314. In some embodiments, various ones of the elongate members 304 of structure 308 extend outwardly away from the distal end 314a of the catheter body 314 while at least one elongate member 304 (e.g., at least one elongate member 304a) extends outwardly from a location (e.g., location 314c) on the catheter body 314 spaced proximally inward from the distal end 314a of the catheter body 314. In some embodiments, one or more transducers 306 of the first transducer set 380 are located within a region of space between location 314c and distal end 314a. In some embodiments, elongate member 304a is sized and arranged to position first transducer set 380 along the catheter body 314 inwardly from the distal end 314a of the catheter body 314 while positioning a third transducer set 384 outwardly from the distal end 314a of catheter body 314, each of the first and the third transducer sets 380, 384 located on elongate member 304a. In some embodiments, elongate member 304a is sized and arranged to position at least some of transducers 306 over a twisted region 311 of each of at least some of the other elongate members 304. In some embodiments, respective portions of each of at least three of the elongate members 304 are arranged front surface 318a-toward-back surface 318b along a first direction (for example, indicated by arrow 318 in FIG. 3A) to form a stacked array in the delivery configuration (e.g., FIG. 3A), and at least one portion of the respective front surface 318a of at least one elongate member 304a is arranged to face in a direction (e.g., represented by arrow 319 in FIG. 3A) other than the first direction in the delivery configuration. In other example embodiments, other structures may be employed to support or carry transducers of a transducer-based device such as a transducer-based catheter. For example, an elongated catheter member may be used to distribute the transducers in a linear or curvilinear array. Basket catheters or balloon catheters may be used to distribute the transducers in a two-dimensional or three-dimensional array.

FIGS. 6A-6F include respective data generation and flow diagrams, which may implement various embodiments of method 600 by way of associated computer-executable instructions according to some example embodiments. In various example embodiments, a memory device system (e.g., memory device systems 130, 330) is communicatively connected to a data processing device system (e.g., data processing device systems 110 or 310, otherwise stated herein as "e.g., 110, 310") and stores a program executable by the data processing device system to cause the data processing device system to execute various embodiments of method 600 via interaction with at least, for example, a transducer-based device (e.g., transducer-based devices 200, 300, or 400). In these various embodiments, the program may include instructions configured to perform, or cause to be performed, various ones of the instructions associated with execution of various embodiments of method 600. In some embodiments, method 600 may include a subset of the associated blocks or additional blocks than those shown in FIGS. 6A-6F. In some embodiments, method 600 may include a different sequence indicated between various ones of the associated blocks shown in FIGS. 6A-6F.

Figure 5A:
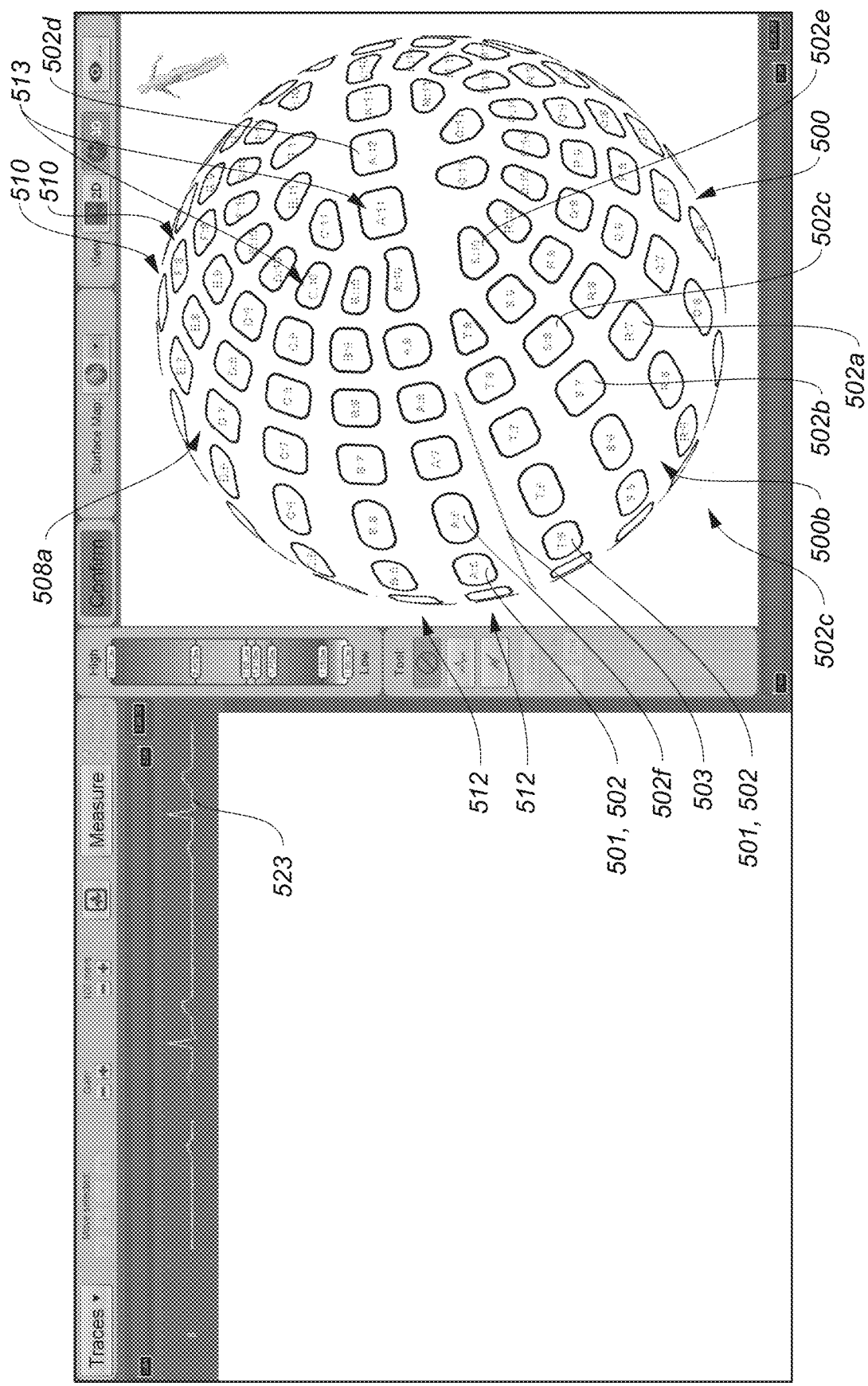
FIG. 5A includes a graphical interface providing a graphical representation according to various example embodiments, a depiction of at least a portion of a transducer-based device including a plurality of transducer graphical elements depicted among the graphical representation.

In some embodiments, block 604 is associated with computer-executable instructions (e.g., graphical representation instructions or graphical interface instructions or display instructions provided by a program) configured to cause an input-output device system (e.g., input-output device system 120 or 320) to display a graphical representation. FIG. 5A illustrates a graphical interface including a graphical representation 500 provided by the input-output device system according to one example embodiment provided in accordance with display instructions associated with block 604 in FIG. 6A. In some embodiments, the graphical representation 500 includes a three-dimensional graphical representation of at least a portion of a transducer-based device (e.g., structure 308 in FIG. 3) and is provided in accordance with the computer-executable program instructions associated with block 606. The instructions associated with block 606 may be configured to access a predefined model (e.g., a computer-aided-design ("CAD") or other computer-readable model stored in memory device system 130, 330) of the at least the portion of the transducer-based device and display the at least the portion of the transducer-based device according to such model. In some embodiments encompassing FIG. 5A, the representation of the transducer-based device is provided by or among various elements of graphical representation 500. In some embodiments, the graphical interface depicts the transducer-based device as including a first domed portion 508a associated with a first domed portion of the transducer-based device (e.g., proximal portion 308a when having the first domed shape 309a) and a second domed portion 508b associated with a second domed portion of the transducer-based device (e.g., distal portion 308b having the second domed shape 309b). A separation graphical element 503 may be employed between the first and the second domed portions 508a, 508b in some embodiments, but may be omitted in other embodiments. Various other transducer-based devices may be depicted according to the instructions associated with block 606 in other embodiments. FIGS. 5A, 5B, 5C, 5D, 5E, 5F, 5G, 5H, 5I, 5J, 5K, 5L, 5M, 5N, 5O, 5P, 5Q, 5R, 5S, 5T, 5U, 5V, 5W, and 5X (collectively FIG. 5) are presented in this disclosure in association with various embodiments. It is understood that each of these embodiments need not be associated with all of the FIG. 5, and in some cases will only be associated with a subset of the FIG. 5.

In some embodiments according to FIG. 5A, a plurality of graphical elements 501 (only two called out) are depicted (e.g., according to the instructions associated with block 606) among various elements of graphical representation 500. In various embodiments, each of the graphical elements 501 is respectively associated with a respective one of a plurality of transducer sets. Each respective transducer set includes at least one of a plurality of transducers included as part of the transducer-based device (e.g., transducer-based devices 200, 300, or 400) and each respective transducer set has at least one different transducer than another of the other transducer sets. In various particular embodiments, each respective transducer set has at least one different transducer than each of the other transducer sets.

Figure 5B:
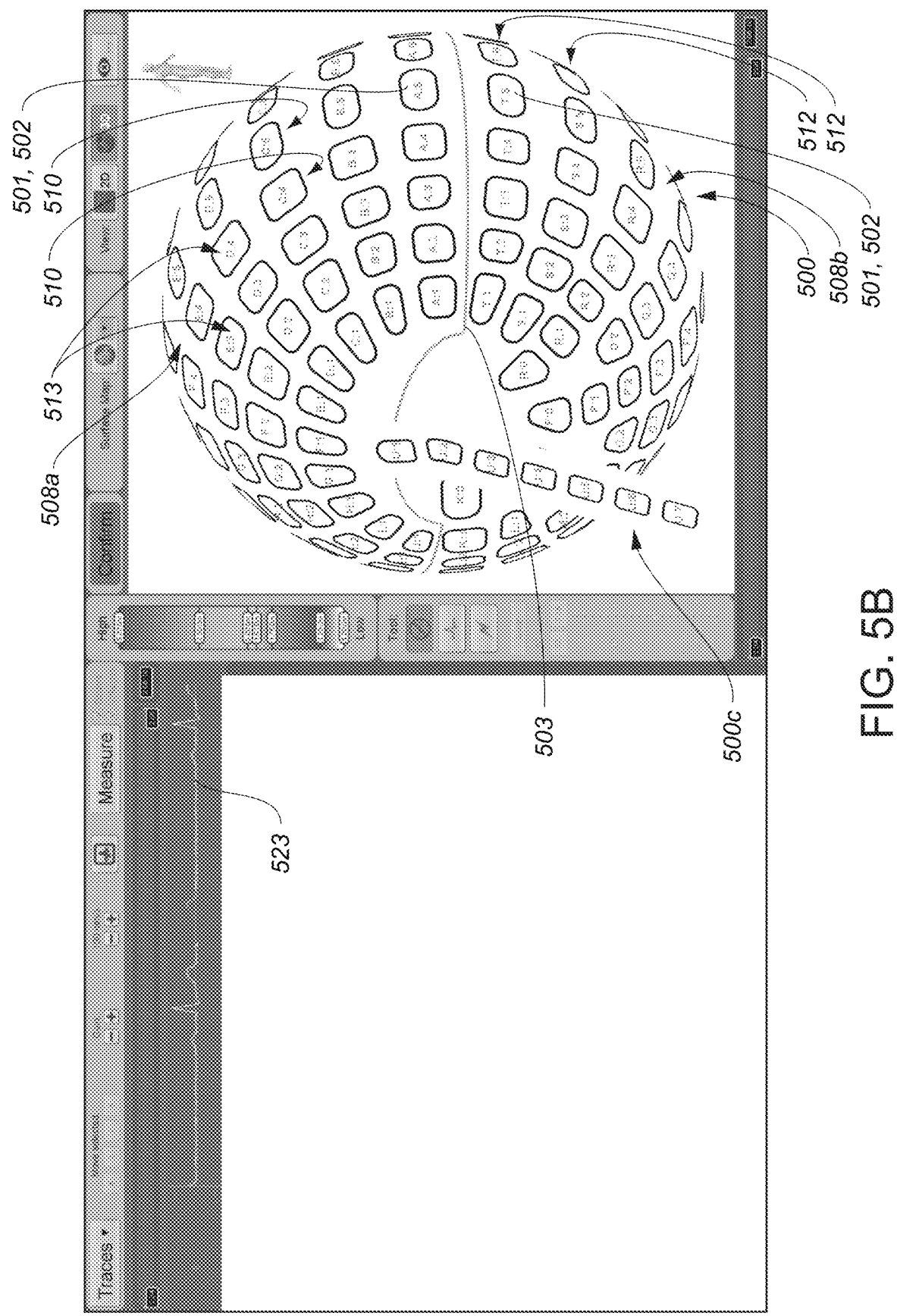
FIG. 5B includes the graphical interface of FIG. 5A with the portion of the transducer-based device depicted as viewed from a different viewing direction than that shown in FIG. 5A.

FIG. 5B shows the graphical interface in which the display instructions have been configured to cause (for example, in response to a user input via an input-output device system such as 120, 320) the three-dimensional graphical representation of the transducer-based device to be manipulated so as to be viewed from a different viewing angle than that shown in FIG. 5A. In some embodiments, the depiction of the transducer-base device may include various other elements thereof. For example, FIG. 5B depicts the transducer-based device as including an elongated portion 500c (e.g., extending from or toward domed portion 508a in some embodiments). In various embodiments, elongated portion 500c is representative of a particular element that is the same or similar to at least one elongate member 304a in various ones of FIG. 3B. It is noted that three-dimensional representations of at least portion of the transducer-based device are shown in FIGS. 5A, 5B, 5C, 5D, and 5R.

Referring to some embodiments encompassing FIG. 5A, each of at least some of the graphical elements 501 is provided by a respective one of a plurality of transducer graphical elements 502 that include at least a first transducer graphical element 502a, a second transducer graphical element 502b, and a third transducer graphical element 502c (e.g., all the transducer graphical elements forming part of a group of transducer graphical elements 502). In some embodiments, each transducer graphical element 502 is associated with a single respective transducer of the transducer-based device. In some example embodiments, each transducer graphical element 502 is representative of a respective transducer of the transducer-based device. In some example embodiments, each transducer graphical element 502 is representative of a location or position of a respective transducer of the transducer-based device. In some embodiments, the graphical representation 500 includes a first spatial relationship between the transducer graphical elements 502 that is consistent with a second spatial relationship between the corresponding transducers associated with the transducer graphical elements 502. For example, in some embodiments, the transducer graphical elements 502 in the three-dimensional graphical representation 500 in FIGS. 5A, 5B may exhibit a same spatial relationship that the transducers 306 exhibit in the transducer based device 300 in FIG. 3C. Or, in some embodiments, the transducer graphical elements 502 in other graphical representations 500 in others of FIG. 5 may exhibit a respective or corresponding spatial relationship that the transducers 306 exhibit in the transducer based device 300 in FIGS. 3C and 3D. In this regard, in some embodiments, the graphical representation 500 may include a first spatial relationship between the transducer graphical elements 502 that is consistent with a second spatial relationship between the corresponding transducers associated with the transducer graphical elements 502 when the corresponding transducers are arranged in a deployed configuration (e.g., FIGS. 3C, 3D). In some embodiments, each particular depicted transducer graphical element 502 is shown having a shape that is consistent with the particular transducer (or portion thereof) that the particular transducer graphical element 502 is representative of. For example, in FIG. 5A, transducer graphical element 502d includes an essentially square shape with rounded corners that is consistent with the square, rounder cornered shape of the electrode 315d of transducer 306d shown in FIG. 3D. Additionally, in FIG. 5A, transducer graphical element 502e includes an essentially triangular shape with rounded corners that is consistent with the triangular, rounded cornered shape of the electrode of transducer 306e shown in FIG. 3D. Further, in FIG. 5A, transducer graphical element 502f includes an essentially oval shape that is consistent with the oval shape of the electrode 315f of transducer 306f shown in FIG. 3D. Others transducer graphical elements 502 in FIGS. 5A and 5B have shapes that are consistent with respective ones of the electrodes shown in FIGS. 3C and 3D. A graphical representation 523 of an electrocardiogram (ECG/EKG) signal is also shown in the graphical interface of various ones of FIG. 5.

Figure 5C:
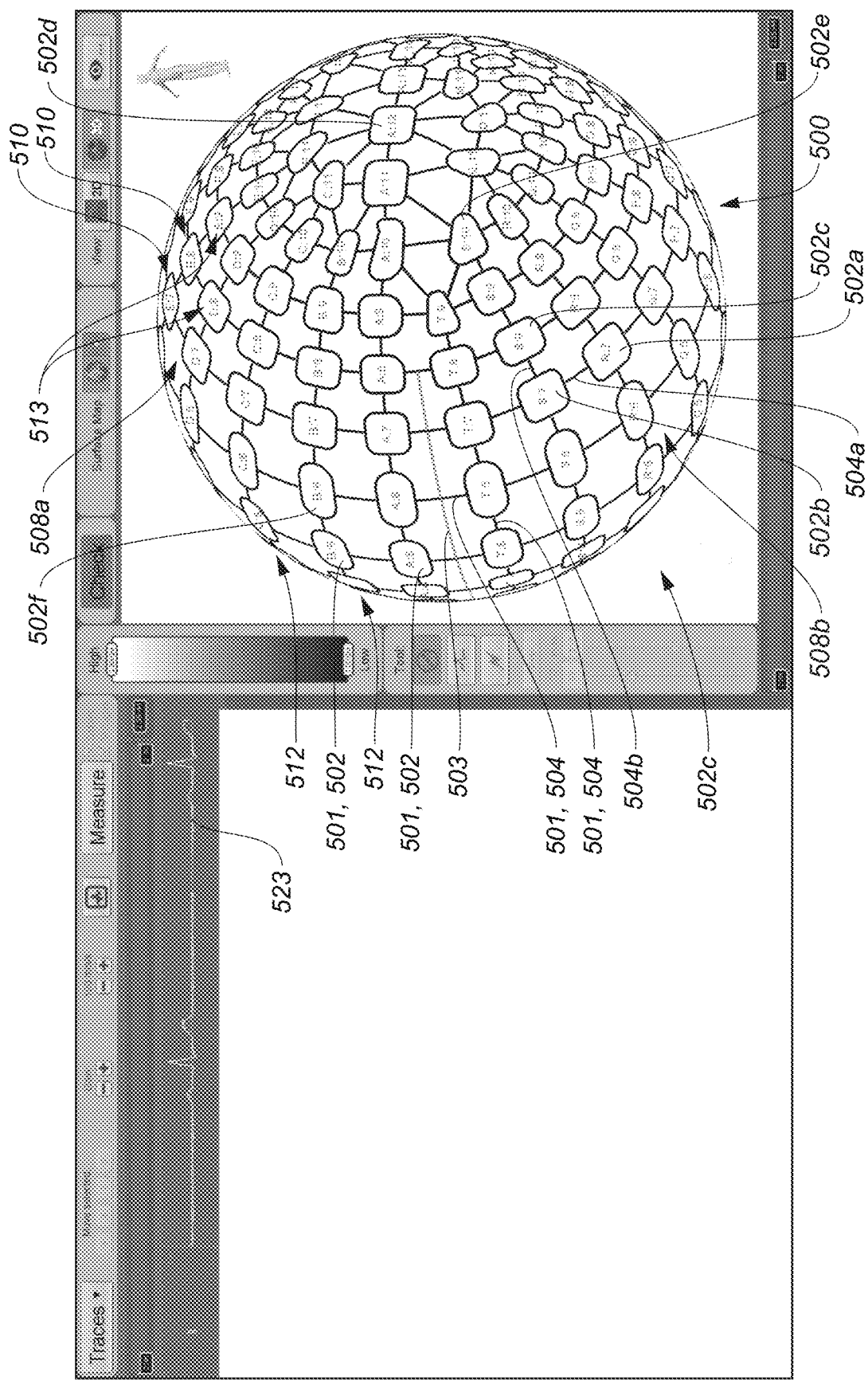
FIG. 5C includes the graphical representation provided by the graphical interface of FIG. 5A with the addition of various between graphical elements positioned between various ones of the transducer graphical elements.
Figure 5D:
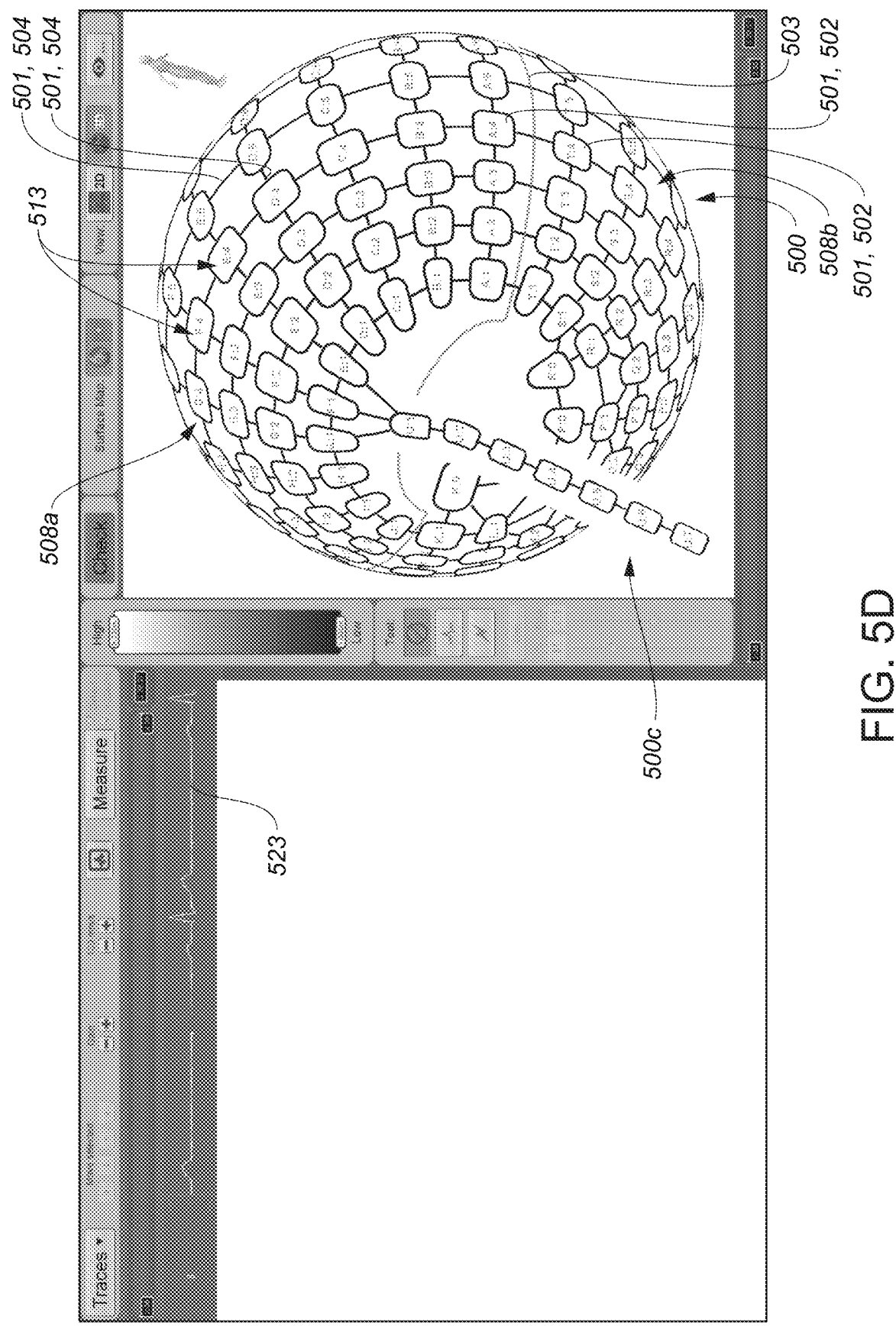
FIG. 5D includes the graphical representation provided by the graphical interface of FIG. 5C but with the portion of the transducer-based device depicted as viewed from a different viewing direction than that shown in FIG. 5C.

In some example embodiments, graphical elements 501 may include alternate or additional forms. For example, FIG. 5C shows an example embodiment in which each of at least some of the graphical elements 501 are provided by a respective one of a plurality of between graphical elements 504 including a first between graphical element 504a and a second between graphical element 504b (e.g., all the between graphical elements collectively referred to as between graphical elements 504). FIG. 5D shows an embodiment of the graphical interface in which the display instructions have been configured to cause (for example, in response to a user input via an input-output device system such as 120, 320) the depiction of the transducer-based device to manipulated so as to be viewed from a different viewing angle than that shown in FIG. 5C. In some embodiments, between graphical elements 504 are shown in addition to various ones of the transducer graphical 502 shown in FIGS. 5A and 5B. In some embodiments, between graphical elements 504 are provided separately or with other embodiments of graphical elements 501. In various embodiments, each of the between graphical elements 504 is associated with a set of at least two (e.g., a group) of the transducers of the transducer-based device. In some example embodiments, each of the between graphical elements 504 is associated with a pair of transducers in the transducer-based device. In some example embodiments, each between graphical element 504 is associated with a region of space between a respective pair of transducers in the transducer-based device. In some example embodiments, each between graphical element 504 is associated with a region of space between a respective pair of adjacent ones of the transducers in the transducer-based device.

In some embodiments, first transducer graphical element 502a is associated with a first transducer (e.g., first transducer 306a) of the transducer-based device, second transducer graphical element 502b associated with a second transducer (e.g., second transducer 306b) of the transducer-based device, and third transducer graphical element 502c associated with a third transducer (e.g., third transducer 306c) of the transducer-based device. In some embodiments, each of the transducer graphical elements 502a, 502b and 502c has a shape that is consistent with a shape of the respective electrode 315a, 315b, 351c of the corresponding one of the transducers 306a, 306b and 306c. In some embodiments, the first between graphical element 504a is associated with a first region of space that is between the first and the second transducers and the second between graphical element 504b is associated with a second region of space that is between the second and the third transducers. In some embodiments, the first region of space is a region of space that is not associated with any physical part of the transducer-based device (e.g., first region of space 350) and the second region of space is a region of space that is associated with a physical part of the transducer-based device (e.g., second region of space 360). In some embodiments, each of the first and the second between graphical elements 504a, 504b is associated with a region of space that does not include a transducer of the transducer-based device. In some embodiments, each of the first and the second between graphical elements 504a, 504b is associated with a region of space that does not include any transducer. It is understood that a "region of space" need not be a vacant space but can include physical matter therein.

In some embodiments, the first between graphical element 504a is positioned between the second and the first transducer graphical elements 502b, 502a among the graphical representation 500. In some embodiments, the second between graphical element 504b is positioned between the second and the third transducer graphical elements 502b, 502c among the graphical representation 500. In other example embodiments, other spatial relationships exist between the transducer graphical elements 502 and the between graphical elements 504 in the graphical representation.

The transducer graphical elements 502, the between graphical elements 504, or both may have different sizes, shapes or forms than those shown in the illustrated embodiment. In some embodiments, at least one particular one of the transducer graphical elements 502 may be depicted with a different shape, size, or form than the respective one of the shape, size or form of the respective portion of the particular transducer to which the particular one of the transducer graphical elements 502 corresponds. In some embodiments, different ones of the between graphical elements 504 may be depicted with different shapes, sizes, or forms.

With reference to various ones of FIG. 5, at least a portion of the transducer graphical elements 502, and at least a portion of the between graphical elements 504 are arranged in a plurality of rows 510 (two called out in FIG. 5A) and a plurality of columns 512 (two called out in FIG. 5A). In some embodiments, each row corresponds to a respective one of number "0", "1", "2", "3", "4", "5", "6", "7", "8", "9", "10", and "11", and each column 512 corresponds to a respective one of letters "A", "B", "C", "D", "E", "F", "G", "H", "I", "J", "K", "L", "M", "N", "O", "P", "Q", "R", "S", and "T", each of the numbers and letters used as part of the unique identifier 513 (only two called out with reference numeral 513 in FIG. 5A) of each transducer graphical element 504. In some embodiments, the plurality of rows 510 and columns 512 correspond to condition in which structure 308 is in the deployed configuration. In some embodiments, a portion of each of the columns 512 corresponds to region of space associated with a physical portion of the transducer-based device (e.g., an elongate member 304). In some embodiments, each of the columns 512 corresponds to at least a portion of the transducers located on a particular elongate member of a transducer-based device (e.g., an elongate member 304). In some embodiments, at least one of the columns 512 includes at least one transducer graphical element 502 having a shape that is different than the respective shape comprised by any of the transducer graphical elements 502 included in at least one other of the columns 512. For example, the "A" column 512 includes a transducer graphical element 502 identified as "A:10" that has a shape that is different than any of the transducer graphical elements 502 comprised by at least one of the other columns 512. In some embodiments, at least a first one of the rows 510 includes identically shaped transducer graphical elements 502 (e.g., row 510 that includes transducer graphical elements 502 identified as "A:6", "B:6", "C:6", "D:6", "E:6", "F:6", "G:6", "H:6", "I:6", "J6" "K:6", "L:6", "M:6", "N:6", "O:6", "P:6", "Q:6", "R:6", "S:6" and "T:6"), and at least a second one of the rows 510 includes differently shaped transducer graphical elements 502 (e.g., row 510 that includes transducer graphical elements 502 identified as "A:10", "B:10", "C:10", "D:10", "E: 10", "F:10", "G:10", "H:10", "I:10", "K:10", "L:10", "M:10", "N:10", "O:10", "P:10", "Q:10", "R:10", and "S:10"). In some example embodiments, a portion of each of the rows 510 corresponds to regions of space not associated with any physical portion of the transducer-based device (e.g., regions of space 350 between adjacent ones of the elongate members 304). In other example embodiments, different numbers of transducer graphical elements 502 and different numbers and spatial arrangements of between graphical elements 504 may be depicted in the graphical representation. In other example embodiments, different numbers and spatial arrangements of rows 510 and columns 512 may be depicted in the graphical representation. In various embodiments, each of the between graphical elements (e.g., between graphical elements 504) depicted in the graphical representation are representative of a respective physical path extending between a respective pair of transducers of the transducer-based device. Each of the physical paths may extend over a physical surface of the transducer-based device or over a portion of an opening defined by a physical surface of the transducer-based device. In the embodiment shown in FIG. 5C, each between graphical element 504 is representative of a respective physical path extending between the respective transducers associated with the adjacent pair of transducer graphical elements 502 that the between graphical element 504 extends between. In the embodiment shown in FIG. 5C, each adjacent pair of the transducer graphical elements 502 may be provided along a row 510 (two called out in FIG. 5C) of the graphical elements 501, along a column 512 (two called out in FIG. 5C) of the graphical elements 501, or diagonally between a row 510 and a column 512.

Referring back to FIGS. 5A, 5B, the plurality of rows 510 and the plurality of columns 512 are depicted as a three-dimensional arrangement in the graphical representation. In some embodiments, at least two of the plurality of columns 512 are depicted in the graphical representation extending along respective directions that converge with respect to one another. In some embodiments, at least two of the plurality of columns 512 are depicted in the graphical representation extending along non-parallel directions and at least two of the plurality of rows 510 are depicted extending along parallel directions. In some embodiments, the rows 510 and the columns 512 are depicted in the graphical representation in an arrangement in which the columns 512 are circumferentially arranged. In some embodiments, the rows 510 and the columns 512 are depicted in the graphical representation in an arrangement having a generally spherical shape. The plurality of columns 512 may be depicted like lines of longitude, and the plurality of rows 510 may be depicted like lines of latitude. Although the rows 510 and columns 512 are illustrated in FIGS. 5A-5D as circumferential lines (like lines of longitude and latitude), such rows 510 and columns 512 can take other forms, as shown, for example, in FIGS. 5E and 5F, discussed in more detail below, according to some embodiments.

Figure 5E:
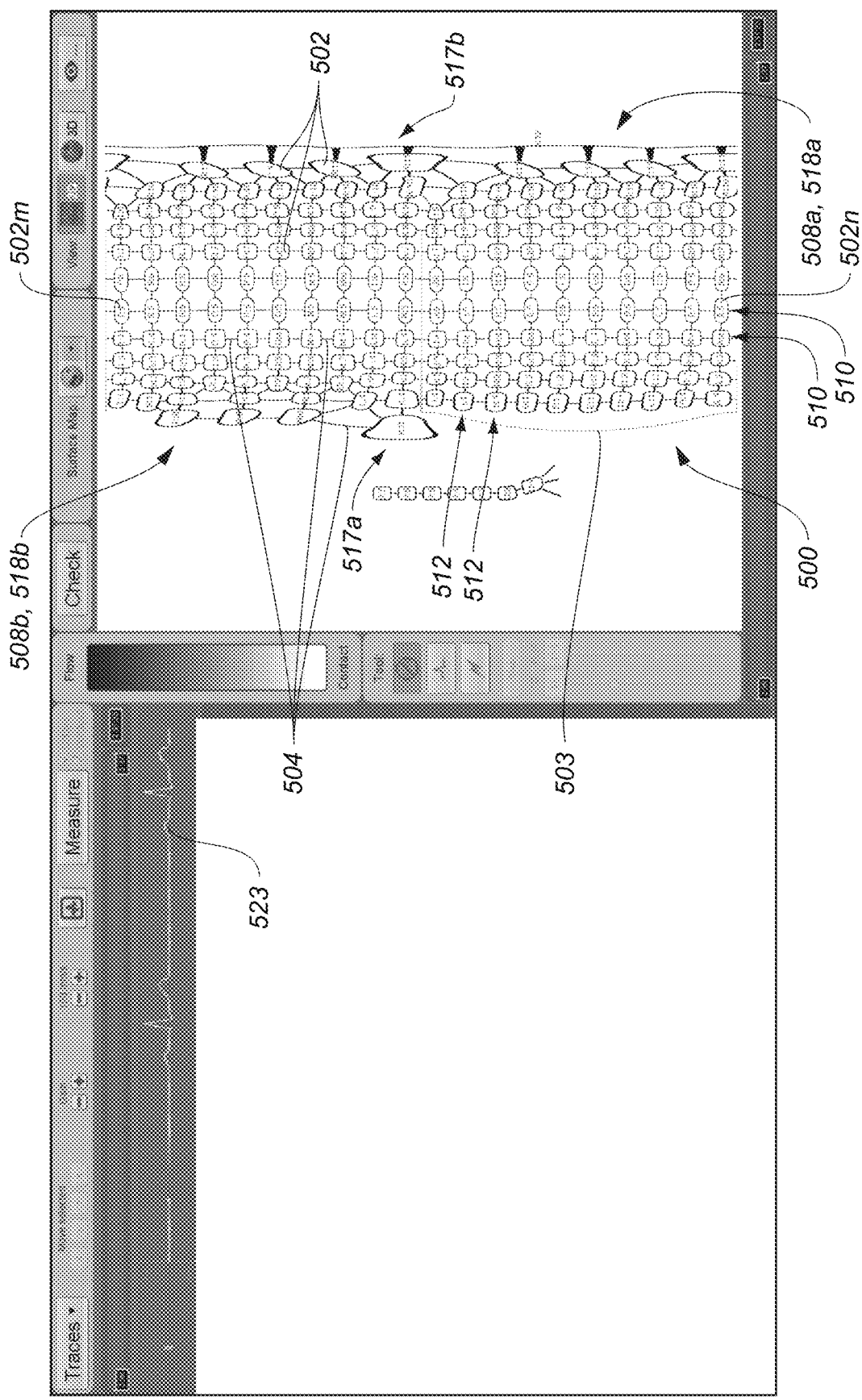
FIG. 5E includes the graphical representation provided by the graphical interface of FIGS. 5C and 5D depicted with one particular form of two-dimensional representation in accordance with various example embodiments.
Figure 5F:
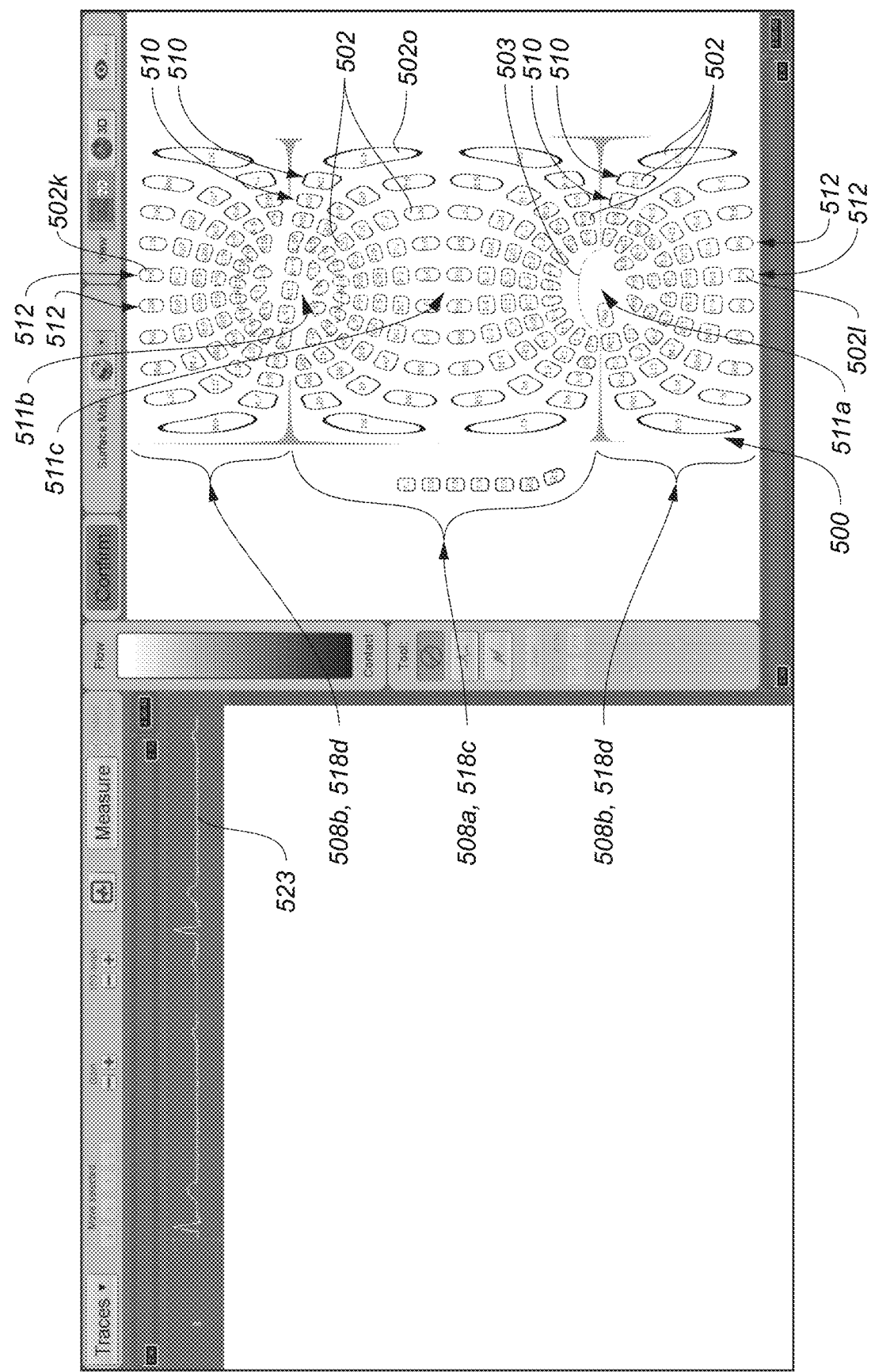
FIG. 5F includes the graphical representation provided by the graphical interface of FIGS. 5A and 5B depicted with another particular form of two-dimensional representation in accordance with various example embodiments.

The display instructions (e.g., according to block 604, 606, or both) may include instructions (e.g., instructions responsive to a user input made via an input-output device system) configured to vary the depiction of the portion of the transducer-based device between a three-dimensional representation (e.g., as depicted in various ones of at least FIGS. 5A, 5B, 5C, and 5D) and a two-dimensional representation (e.g., as depicted by at least FIG. 5E or 5F). Various two-dimensional representations are possible in various embodiments. For instance, the plurality of transducer graphical elements 502 may be arranged in the graphical representation 500 in a particular spatial distribution representing the three-dimensional distribution of transducers (e.g., 220 or 306) distorted onto a two-dimensional plane to form the two-dimensional representation. In this regard, in some embodiments, the two-dimensional representation of the three-dimensional distribution of transducers (e.g., 220 or 306) distorted onto a two-dimensional plane is not merely an isometric or other perspective view of the three-dimensional distribution of transducers, as such an isometric or other perspective view would be considered a three-dimensional representation, such as that shown in various ones of FIGS. 5A, 5B, 5C, and 5D. The two-dimensional representation may be generated according to the display instructions according to a conformal map or projection, such as a Mercator map or projection, a transverse Mercator map or projection, or other three-dimensional-to-two-dimensional map or projection, known in the art, according to some embodiments. According to various embodiments, a conformal mapping is a function that preserves local angles. For example, according to some embodiments, when a particular spatial relationship between the plurality of transducers 306 is conformally mapped to the graphical representation 500, an angle defined between a group of transducers (e.g., 306) according to the particular spatial relationship is preserved between the corresponding group of transducer graphical elements 502. In some embodiments, the two-dimensional representation need not be a projection or map from a three-dimensional model, and may merely be any two-dimensional representation, e.g., including an arrangement of transducers.

The two-dimensional representation depicted in FIG. 5E, according to some embodiments, represents the first domed portion 508a (e.g., shown in FIGS. 5C, 5D) of the depicted transducer-based device as first Mercator projection 518a and the second domed portion 508b (e.g., shown in FIGS. 5C, 5D) of the depicted transducer-based device as a second Mercator projection 518b. The first and the second Mercator projections 518a and 518b advantageously allow for simultaneous viewing of all the transducer graphical elements 502 and the between graphical elements 504. Columns 512 and rows 510 are depicted two-dimensionally in FIG. 5E. In some embodiments, separation graphical element 503 is also depicted in a two-dimensional configuration.

As discussed above, other two-dimensional representations may be implemented and may be user-selectable for viewing. For example, FIG. 5F illustrates a transverse Mercator projection employed according to some embodiments. In FIG. 5F, the transverse Mercator projection includes two portions 518c, 518d, each of the portions 518c, 518d representative of a respective one of first and second domed portions 508a and 508b in the corresponding three-dimensional representation. In FIG. 5F, portion 518d of the transverse Mercator projection is shown as two parts, each part at least depicting the transducer graphical elements 502 in a respective one of two parts of the domed portion 508b. In FIG. 5F, portion 518c is representative of first domed portion 508a. In some embodiments, various ones of the columns 512 radiate outwardly radially or quasi-radially from particular ones of a plurality of pole regions 511a and 511b represented in the graphical representation 500. In some embodiments, various ones of the rows 510 are circumferentially arranged about particular ones of a plurality of pole regions 511a and 511b.

In some embodiments, at least some of the between graphical elements 504 are not shown in various ones of the displayable two-dimensional representations. For example, in FIG. 5F, between graphical elements 504 have been selectively controlled, e.g., in response to user input, not to be visible among the graphical representation. In various embodiments, the transducer graphical elements 502 shown in each of the FIGS. 5E and 5F are arranged with respect to one another according to a spatial relationship that corresponds to a spatial relationship that the transducer graphical elements are arranged in the three-dimensional representations shown in various ones of FIGS. 5A, 5B, 5C, 5D, and 5R. In various embodiments, the transducer graphical elements 502 shown in each of the FIGS. 5E and 5F are arranged with respect to one another according to a spatial relationship that corresponds to a spatial relationship that particular transducers that the transducer graphical elements 502 correspond to, are arranged with respect to one another when a supporting structure (e.g., structure 308) is in a deployed configuration.

Various computer-executable instructions may be configured to control various input element control functions (e.g., mouse drag functions, touch screen drag functions) between various operating modes such as rotating and panning modes. A rotating mode may be advantageously used for manipulation of a three-dimensional representation of a transducer-based device or other portions of the graphical representation 500 to allow for viewing one or more portions of the three-dimensional representation of the transducer-based device or various portions of the graphical representation 500 that were not previously viewable (e.g., a manipulation between the views shown in FIGS. 5A and 5B or a manipulation between the views shown in FIGS. 5C and 5D). In some embodiments, a panning mode may be advantageously used for manipulation of a two-dimensional representation of the transducer-based device or other portions of the graphical representation 500 to allow for viewing of different arrangements of various graphical elements in the representation of a transducer-based device or other portions of the graphical representation 500. For example, in FIG. 5F, an up-down panning manipulation (e.g., caused in response to a mouse drag or touch screen drag function) may adjust a size of each of the portions 518d that are representative of domed portion 508b (e.g., one of the portions 518d increasing in size while the other portion 518d decreases in size) or in some cases combine the plurality of portions 518d into a fewer number of portions (e.g., a single portion 518d), or in some cases divide portion 518c representative of the first domed portion 508a into a plurality of portions 518c.

In some embodiments, a rotating mode may be advantageously used for manipulation of a two-dimensional representation of the transducer-based device or other portions of the graphical representation 500 to allow for viewing of different arrangements of various graphical elements in the transducer-based device or other portions of the graphical representation 500. For example, in FIG. 5F, a rotation mode (for example, caused in response to a mouse drag or touch screen drag function) may be employed to rotate or revolve various ones of the transducer graphical elements 502 or other elements of the graphical representation 500 about a selected one of two pole regions 511a and 511b. It is noted in some embodiments, a particular rotation of a first set of graphical elements about one of the pole regions 511a and 511b in a first particular rotational direction (e.g., a clockwise direction) may be automatically accompanied by a particular rotation of a second set of graphical elements about the other of the pole regions 511a and 511b in second particular rotation direction different than the first particular rotational direction (e.g., a counterclockwise direction).

It is noted that, even though an entirety of the representation of the transducer-based device may be shown in the two-dimensional representation, various panning or rotation modes such as described above may be employed to position various ones of the displayed graphical elements in a configuration that may provide a better understanding of a particular relationship between the graphical elements. For example, in some embodiments, the transducer graphical elements 502k and 502l respectively identified as "P:5" and "P:6" in FIG. 5F correspond to an adjacent pair of transducers, but are displayed apart from one another in the two portions 518d. A rotation (for example, as described above) about one of the two pole regions 511a, 511b may be used to position the transducer graphical elements 502k and 502l respectively identified as "P:5" and "P:6" closer together, for example, in the medial region 511c to better convey information describing the adjacency of the transducers corresponding to the transducer graphical elements 502k and 502l. In some example embodiments, a rotation (for example, as described above) about one of the two pole regions 511a, 511b may be used to position the transducer graphical elements 502k and 502l adjacently together without any others of the transducer graphical elements 502 positioned therebetween.

In some embodiments, the respective transducers of the adjacent pair of transducers (e.g., an adjacent pair of transducers 306) corresponding to transducer graphical elements 502k and 502l are located a same structural member (e.g., a same one of elongate members 304). In some embodiments, a region of space that includes a physical portion of the transducer-based device is located between the respective transducers of the adjacent pair of transducers (e.g., an adjacent pair of transducers 306) corresponding to transducer graphical elements 502k and 502l. In various embodiments, the rotation mode synchronizes rotation about one of the pole regions 511a, 511b with the rotation about the other of the pole regions 511a, 511b such that various transducer graphical elements 502 representative of an adjacent pair of transducers maintain a spatial relationship when rotated into the medial region 511c that is consistent with the spatial relationship of the corresponding adjacent transducers. In FIG. 5F, various columns of adjacent transducer graphical elements 502 radially extend or converge towards each of the pole regions 511a and 511b. The synchronized rotation about one of the pole regions 511a, 511b with the rotation about the other of the pole regions 511a, 511b allows each of the columns to continue to radially extend or converge towards each of the pole regions 511a and 511b at least while the columns are positioned in portion 518c.

In some embodiments, various ones of these manipulation modes may allow the user to better understand a relationship or interaction between the transducer graphical elements 502 and any displayed physiological information (e.g., intracardiac information) displayed in the graphical representation (e.g., as described below at least with respect to FIGS. 5G-5R). In some embodiments, various ones of these manipulation modes may allow the user to better understand a relationship of various ones of the transducers corresponding to various ones of the transducer graphical elements to facilitate a selection or non-selection thereof. It is noted that various ones of the manipulations modes are not limited to the two-dimensional representation of FIG. 5F and may be employed with other forms of two-dimensional representations. For example, in some embodiments, the transducer graphical elements 502m and 502n respectively identified as "T:5" and "A:5" in FIG. 5E correspond to an adjacent pair of transducers (e.g., an adjacent pair of transducers 306), but are displayed apart from one another. An up-down panning manipulation (for example, as described above) may be employed to better visualize the adjacency of the transducers corresponding to the transducer graphical elements 502m and 502n respectively identified as "T:5" and "A:5". In some embodiments, the respective transducers of the adjacent pair of transducers (e.g., an adjacent pair of transducers 306) corresponding to transducer graphical elements 502m and 502n are located on different structural members (e.g., different or separate ones of elongate members 304). In some embodiments, a region of space that does not include any physical portion of the transducer-based device is located between the respective transducers of the adjacent pair of transducers (e.g., an adjacent pair of transducers 306) corresponding to transducer graphical elements 502m and 502n.

A Mercator projection such as that employed in embodiments associated with FIG. 5E may include various distortions in some of the elements (e.g., transducer graphical elements 504) at least proximate the boundary regions 517a, 517b of the projection. In some embodiments, the columns 512 of graphical elements 501 act like converging lines of longitude in a three-dimensional representation (e.g., FIGS. 5A, 5B, 5C and 5D) and the distortions at least proximate the boundary regions 517a, 517b may be provided to account or compensate for the convergence of columns 512. It is noted, however, that a panning mode (e.g., a left-right panning mode) that may move one of the boundary regions 517a, 517b inwardly or centrally within the graphical representation may, in some embodiments, maintain the distortions in the various graphical regions that occupy or move along with the moved one of the boundary regions 517a, 517b. Moving these distorted regions inwardly or centrally within the field of view of the user may not provide, in some cases, a readably understandable representation of various facets of these graphical elements (e.g., a spatial relationship therebetween). The two-dimensional representation depicted in FIG. 5F, on the other hand, centralizes the graphical elements (e.g., transducer graphical elements 502) that are located in the boundary regions 517a, 517b of FIG. 5F centrally proximate the pole regions 511a, 511b of FIG. 5F with reduced levels of distortions. In this regard, the graphical representation of FIG. 5F provides a good understanding of the various relationships (e.g., spatial relationships) associated with "pole" areas (e.g., areas where the columns 512 converge like lines of longitude) of the corresponding three-dimensional representation. On the other hand, the graphical representation of FIG. 5E provides a good understanding of the various relationships (e.g., spatial relationships) associated with "equatorial areas (e.g., equatorial regions of columns 512 when acting like lines of longitude) of the corresponding three-dimensional representation. In some embodiments, two or more different two-dimensional representations are concurrently displayed via an input-output device system (e.g., 120, 320). In some embodiments, both of the two-dimensional representations shown in FIGS. 5E and 5F are concurrently displayed via an input-output device system (e.g., 120, 320).

In each of the FIGS. 5E and 5F, each of the transducer graphical elements 502 has a respective shape that is the same, or generally the same as, a shape of at least a portion of a corresponding transducer (e.g., transducer 306) that the transducer graphical element represents. In some embodiments, each of the transducer graphical elements 502 has a respective shape that is the same, or generally the same, as shape of an electrode (e.g., electrode 315) of a corresponding transducer (e.g., transducer 306) that the transducer graphical element represents. In each of the FIGS. 5E and 5F, the shape of each of at least some of the transducer graphical elements 502 is distorted and deviates in some aspects from the respective shape of a corresponding electrode. Unlike a distortion caused by the use of "perspective" (e.g., a varying of an appearance of objects in respect to their perceived relative distance and positions) in corresponding three-dimensional representations (e.g., FIGS. 5A, 5B, 5C, 5D), various graphical elements in FIGS. 5E and 5F employ other forms of distortion (for example, as described above in this description). For example, in FIG. 5F, increased levels of distortions (e.g., increased sizes or dimensions, increased stretching) accompany various ones of the transducer graphical elements 502 that are increasingly spaced from pole regions 511a and 511b. In FIG. 5E, increased levels of distortions (e.g., increased sizes or dimensions, increased stretching) accompany various ones of the transducer graphical elements 502 that are spaced relatively close to the boundary regions 517a, 517b as compared with various ones of the transducer graphical elements that are located relatively far from the boundary regions 517a, 517b. In either case, and unlike the perspective-based distortions employed in some three-dimensional representations, some of the more highly distorted transducer graphical elements 504 include enlarged shapes (e.g., relative to less distorted graphical elements 502 displayed centrally in each of two-dimensional representations) and correspond to transducers that would be spaced relatively farther from a viewer (e.g., with the less distorted transducer graphical elements 502 corresponding to transducers that would be spaced relatively closer to the viewer).

In some embodiments associated with FIG. 5F, a rotation mode may be employed to rotate at least some of the transducer graphical elements 502 about one of the pole regions 511a and 511b and changes in the shape or size of various ones of transducer graphical elements 502 during the rotation may occur. In some embodiments associated with FIG. 5F, a rotation mode may be employed to rotate at least some of the transducer graphical elements 502 about one of the pole regions 511a and 511b to vary a level of distortion comprised by various ones of transducer graphical elements 502. For example, the transducer graphical element 502o identified as "A:6" may, in some embodiments, be rotated about pole region 511b with its size or level distortion reducing as it rotates toward medial region 511c.

Referring back to FIG. 6A, the computer-executable display instructions associated with block 604 may include, in some embodiments, various instructions configured to allow for variations in the viewable content of the graphical representation. The computer-executable display instructions associated with block 604 may include various instructions (e.g., computer-executable instructions associated with block 606) configured to allow for selective inclusions of the transducer graphical elements 502 and the selective inclusion of the between graphical elements 504 among the graphical representation 500. (In this regard, although block 606 is shown separately from block 604, block 606 may be a particular implementation of block 604 and such block may be combined into a single block.) In some example embodiments, the display instructions associated with block 606 may include instructions that allow for the selective inclusion of identification labels 513 that identify various ones of the transducer graphical elements 502. In various example embodiments, each of the identification labels 513 employs an alpha-numeric format including a letter representative of the column 512 in which a corresponding transducer graphical element is located and a number representative of a location of the transducer graphical element 502 in the corresponding column 512. Other identification schemes may be employed in other embodiments.

Figure 6A:
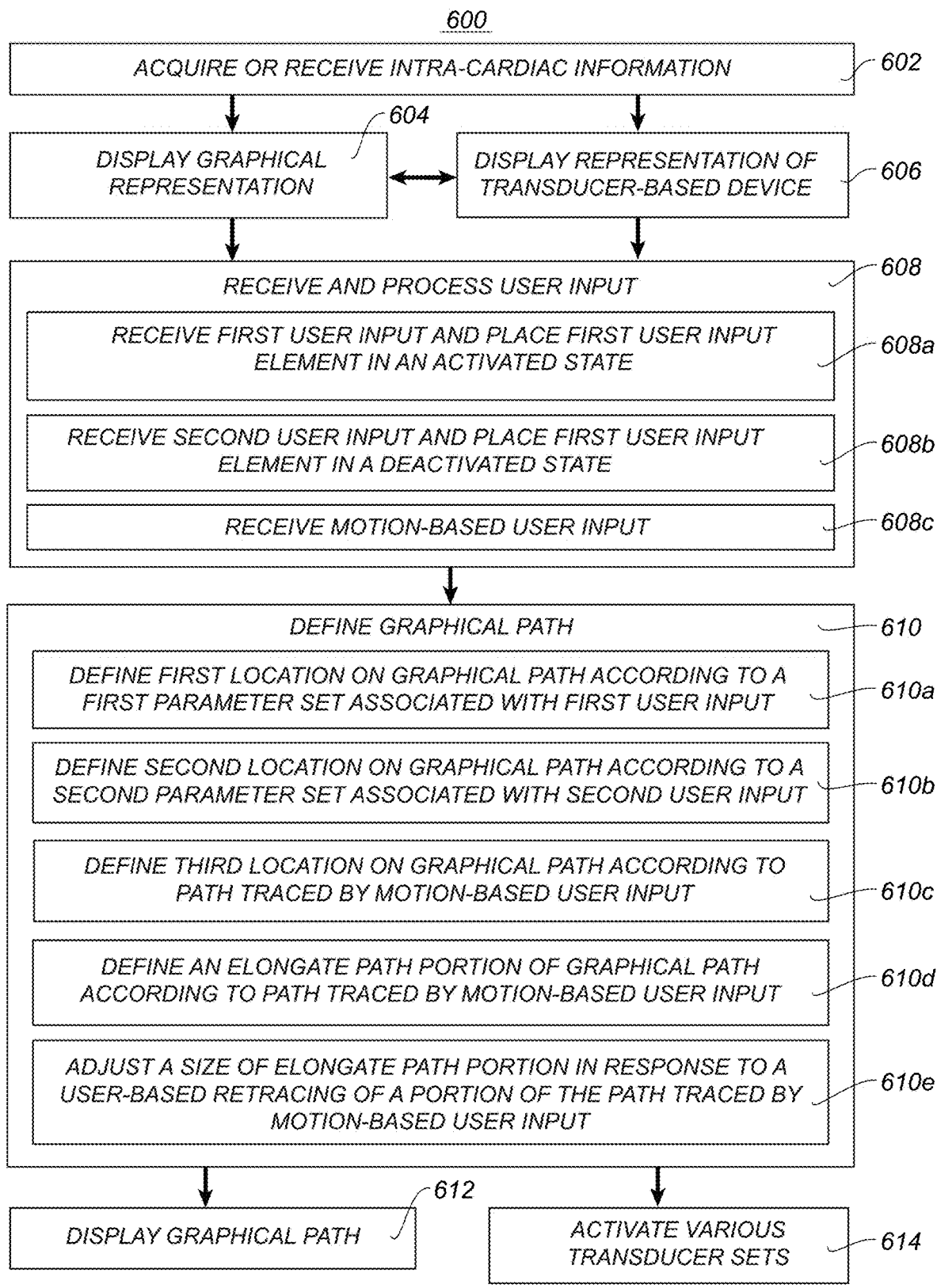
FIG. 6A includes a block diagram of a method for activating transducers of a transducer-based device according to some example embodiments.

Having discussed embodiments associated with blocks 604 and 606 in FIG. 6A, a discussion will now begin regarding embodiments where block 604 follows block 602. (Recall that block 606 may be included within block 604, in some embodiments.) Block 602, in some embodiments, is associated with instructions (e.g., input or acquisition instructions included in a program) that cause the data processing device system (e.g., data processing device systems 110 or 310) to acquire or receive intra-cardiac information. Intra-cardiac information can take various forms, including, but not limited to, e.g., electrical information or a derivation thereof (e.g., electrical potential information, such as intra-cardiac electrogram information; electrical impedance information, such as fluidic or non-fluidic cardiac tissue impedance information; electrical conductivity information, such as fluidic or non-fluidic cardiac tissue electrical conductivity), thermal information or a derivation thereof (e.g., temperature information), fluid property information or a derivation thereof (e.g., blood flow information, blood pressure information), force information or a derivation thereof (e.g., contact information), and mapping information or a derivation thereof (e.g., electrical mapping; physical feature mapping, such as anatomical feature mapping). In various embodiments, intra-cardiac information may be related to any physiological parameter information related to a heart chamber. In various embodiments, intra-cardiac information may include any information related to, or resulting from an interaction with intra-cardiac tissue. By way of non-limiting example, interaction with intra-cardiac tissue may include an interaction made by way of a diagnostic procedure or treatment procedure.

Figure 6B:
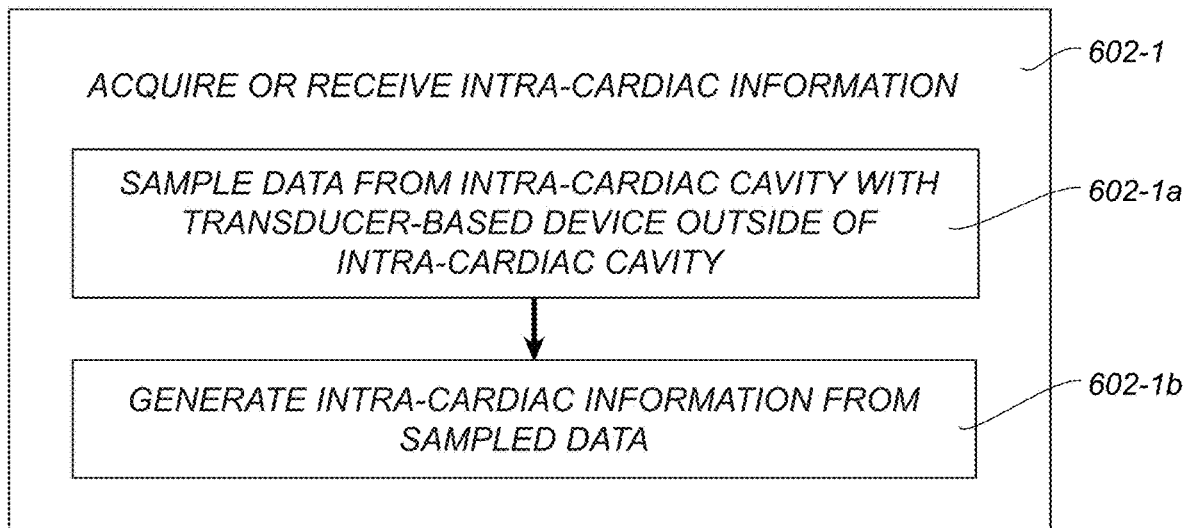
FIG. 6B includes an exploded view of some of the blocks of the block diagram of FIG. 6A according to some example embodiments.

Intra-cardiac information may be acquired or received by various methods and from various device systems. For example, FIG. 6B shows an exploded view of block 602, according to some embodiments. The particular implementation of block 602 illustrated in FIG. 6B is labeled as block 602-1. In this regard, FIG. 6B includes a sub-block 602-1a associated with computer-executable instructions that receive or acquire the intra-cardiac information via data sampling performed by a transducer-based device system (e.g., which may be at least part of the data input-output device system 120, 320) deployed externally from an intra-cardiac chamber or cavity (e.g., outside the chamber or cavity or outside a body comprising the chamber or cavity). In this regard, the method 600 may include a sub-block 602-1b in which the intra-cardiac information is generated (e.g., via generation instructions executable by a data-processing device system, e.g., 110, 310) from data provided or sampled (e.g., according to the computer-executable sampling instructions associated with block 602-1a) by the transducer-based device system deployed externally from the intra-cardiac chamber or cavity. Such generation according to block 602-1b, in some embodiments, may involve the associated instructions configuring the data processing device system (e.g., 110, 310) to recognize and identify (e.g., in memory device system 130, 330) the incoming sampled data or a derivation thereof as a set of respective intra-cardiac information (e.g., as an electrocardiogram or other form of intra-cardiac information discussed herein). By way of non-limiting example, various transducer-based device systems employed as per block 602-1a may include various fluoroscopy device systems, ultra-sound device system, magnetic resonance device systems, computerized tomography device systems, and transthoracic electrocardiographic mapping device systems. It is noted that some of the embodiments associated with block 602-1a are considered to employ non-invasive methods or technologies.

Figure 6C:
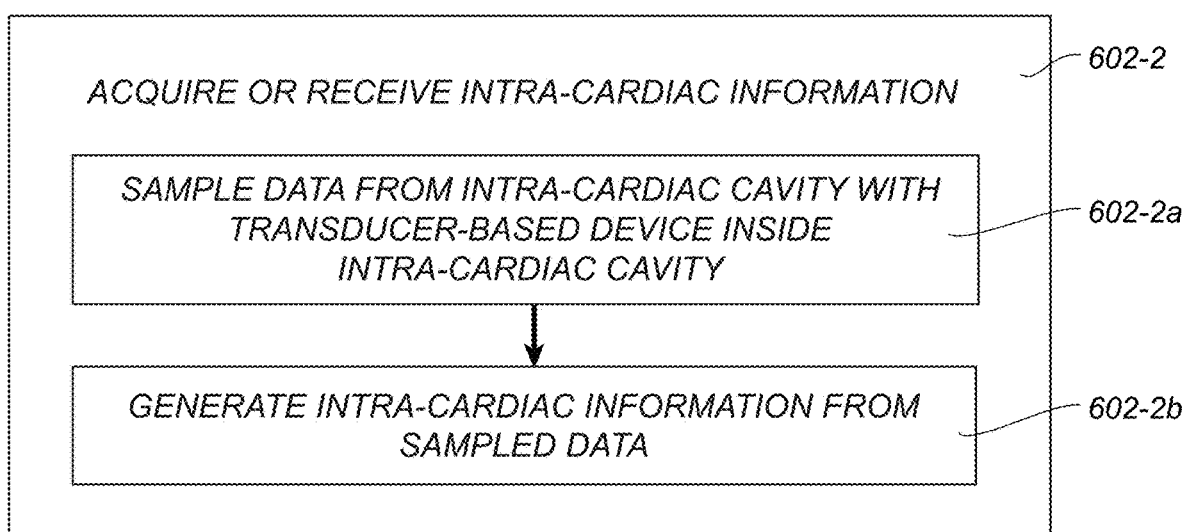
FIG. 6C includes an exploded view of some of the blocks of FIG. 6A according to some example embodiments.

FIG. 6C shows an exploded view of block 602, according to some embodiments. The particular implementation of block 602 illustrated in FIG. 6C is labeled as block 602-2. In this regard, FIG. 6C includes a sub-block 602-2a associated with computer-executable instructions that are configured to cause reception or acquisition of the intra-cardiac information via data sampling performed by a transducer-based device system (e.g., which may be at least part of the data input-output device system 120, 320) deployed internally to an intra-cardiac chamber or cavity. In this regard, the method 600 may include a sub-block 602-2b in which the intra-cardiac information is generated (e.g., via generation instructions executed by a data-processing device system (e.g., 110, 310) from data provided or sampled (e.g., by the sampling instructions associated with block 602-2a) by the transducer-based device system deployed internally within the intra-cardiac chamber or cavity (e.g., inside the chamber or cavity). Such generation according to block 602-2b, in some embodiments, may involve the associated instructions configuring the data processing device system (e.g., 110, 310) to recognize and identify (e.g., in memory device system 130, 330) the incoming sampled data or a derivation thereof as a set of respective intra-cardiac information (e.g., as an intra-cardiac electrogram or other form of intra-cardiac information discussed herein). By way of non-limiting example, various transducer-based device systems that may be internally deployed within an intra-cardiac chamber include by way of non-limiting example transducer-based device systems 200, 300, where data may be sampled according to the sampling instructions associated with block 602-2a by each of one or more transducers of the transducer-based device system, a portion of the transducer-based device system including the one or more transducers positionable in a cardiac chamber during the sampling, such that the generation instructions associated with block 602-2b may be configured to cause generation of the intra-cardiac information based at least in part on the sampled data. Various transducer-based device systems employed as per block 602-2a may include various intravascularly deployable or percutaneously deployable catheter device systems. Various transducer-based device systems employed as per block 602-2a may include detection capabilities, mapping capabilities, diagnostic capabilities, treatment capabilities, or any combination thereof. It is noted that some of the embodiments associated with block 602-2a may be considered to employ invasive methods or technologies.

Referring back to FIG. 6A, the displaying of the graphical representation according to the computer-executable instructions associated with block 604 may, in some embodiments, include causing displaying of a graphical representation of intra-cardiac information generated, acquired, or received according to the computer-executable instructions associated with block 602. Various embodiments may process or analyze (e.g., according to the instructions associated with block 604) the transducer data received by the data processing device system according to the computer-executable instructions associated with block 602 in order to, for example, generate and cause the displayed graphical representation 500 to include the intra-cardiac information. Various embodiments may process or analyze the transducer data received by the data processing device system according to the instructions associated with block 602 in order to, for example, generate and possibly cause the displayed graphical representation 500 to include a map of the intra-cardiac information. In various embodiments, the data is sampled by a transducer-based device system from a plurality of locations in a cardiac chamber and the generation instructions associated with block 602 cause mapping of each of a plurality of parts or values of the intra-cardiac information (which may represent a sensed tissue electrical characteristic or other information) to a respective one of the plurality of locations in the cardiac chamber. In some of these various embodiments, the display instructions associated with block 604 are configured to cause an input-output device system (e.g., 120, 320) to display the plurality of parts of the intra-cardiac information with a first spatial relationship that is consistent with a second spatial relationship between the plurality of locations in the cardiac chamber (e.g., a map of the parts of the intra-cardiac information is displayed). In some embodiments, the transducer-based device includes a plurality of transducers (e.g., transducer-based device 200, 300) and the sampling instructions (e.g., 602-1a, 602-2a) are configured to cause the sampled data to be sampled concurrently from the plurality of locations in the cardiac chamber.

It should be noted that some embodiments need not be limited to any particular form of processing or analysis of the transducer data received by the data processing device system according to the instructions associated with block 602. Although various display procedures can be implemented according to the computer-executable instructions associated with block 604 to display intra-cardiac information, these display procedures can be performed at other times, such as any time during the generation of or after the display of a graphical representation of at least a portion of a transducer-based device (e.g., as per the computer-executable instructions associated with block 606).

An example of a display of a graphical representation that at least depicts intra-cardiac information according to various embodiments (such as those represented by block 604 in FIG. 6A) would be a mapping locating the position of the ports of various bodily openings positioned in fluid communication with a cardiac chamber. For example, in some embodiments, it may be desired to determine intra-cardiac information indicating the locations of various ones of the pulmonary veins or the mitral valve that each interrupts an interior surface of an intra-cardiac cavity such as a left atrium.

In some example embodiments, the mapping is based at least on locating such bodily openings by differentiating between fluid and tissue (e.g., tissue defining a surface of a bodily cavity). There are many ways to differentiate tissue from a fluid such as blood or to differentiate tissue from a bodily opening in case a fluid is not present. Four approaches may include by way of non-limiting example:

1. The use of convective cooling of heated transducer elements by fluid. A slightly heated arrangement of transducers that is positioned adjacent to the tissue that forms the interior surface(s) of a bodily cavity and across the ports of the bodily cavity will be cooler at the areas which are spanning the ports carrying the flow of fluid.

2. The use of tissue impedance measurements. A set of transducers positioned adjacently to tissue that forms the interior surface(s) of a bodily cavity and across the ports of the bodily cavity can be responsive to electrical tissue impedance. Typically, heart tissue will have higher associated tissue impedance values than the impedance values associated with blood.

3. The use of the differing change in dielectric constant as a function of frequency between blood and tissue. A set of transducers positioned around the tissue that forms the interior surface(s) of the atrium and across the ports of the atrium monitors the ratio of the dielectric constant from 1 KHz to 100 KHz. Such can be used to determine which of those transducers are not proximate to tissue, which is indicative of the locations of the ports.

4. The use of transducers that sense force (e.g., force sensors). A set of force detection transducers positioned around the tissue that forms the interior surface of the bodily cavity and across the bodily openings or ports of the bodily cavity can be used to determine which of the transducers are not engaged with the tissue, which is indicative of the locations of the ports.

Figure 5G:
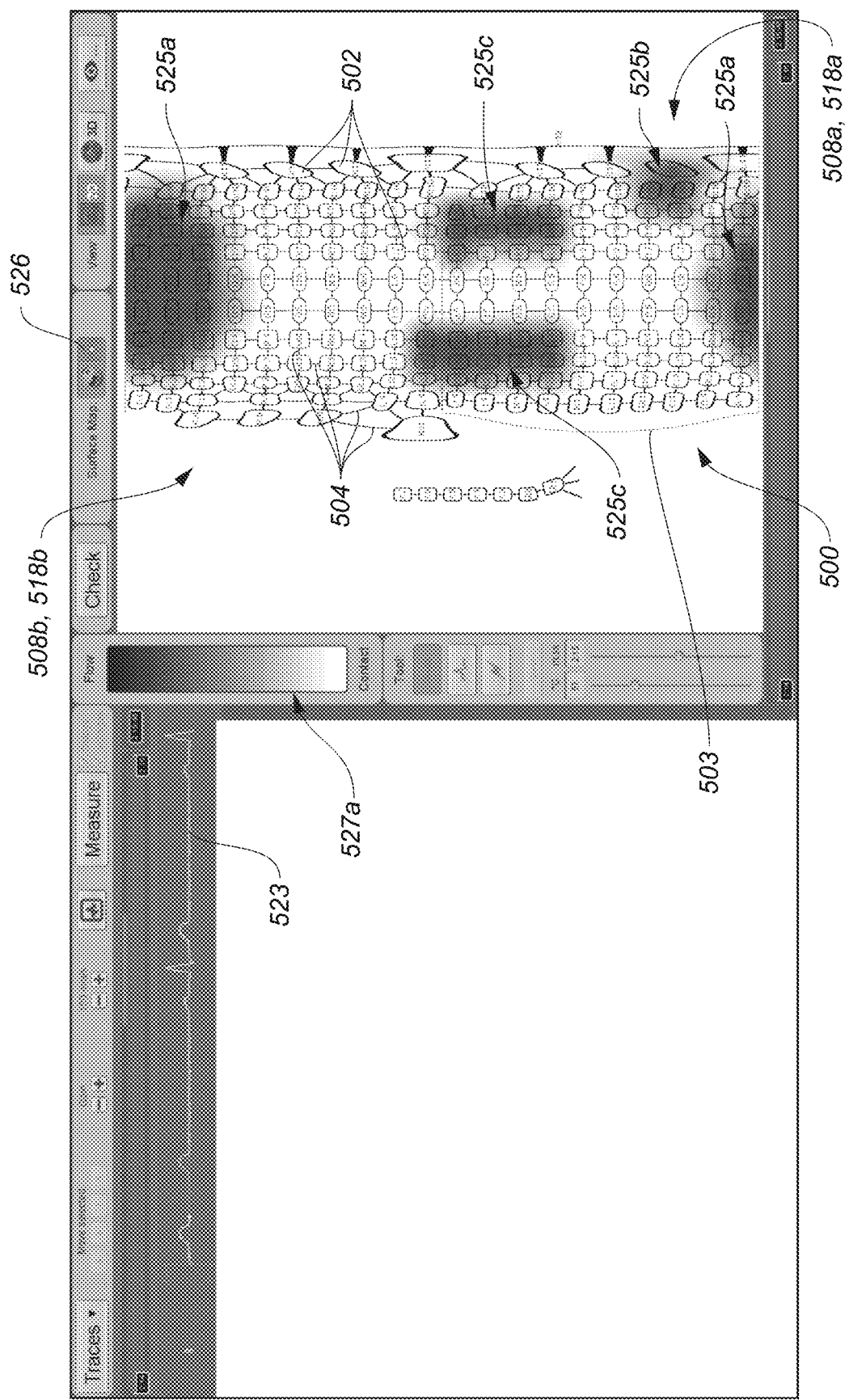
FIG. 5G includes the graphical representation provided by the graphical interface of FIG. 5E with the addition of various intra-cardiac information including various regions determined on the basis of flow data.

The graphical interface of FIG. 5G includes various regions 525a, 525b, and 525c (e.g., part of a plurality if regions collectively referred to as regions 525) added to the graphical representation 500 shown in FIG. 5E. The regions 525 could be displayed according to the instructions associated with block 604 in FIG. 6A in some embodiments. Although, such regions 525 could be displayed at other times or according to other instructions. In some embodiments, the graphical interface depicted in FIG. 5G is generated after the transducer-based device is received in a bodily cavity having various anatomical features of interest and the drop-down selection box 526 identified as "Surface Map" is activated via the input-output device system to select a mode referred to as "Flow". Techniques for flow-based mapping techniques are disclosed in commonly assigned U.S. Patent Application Publication No.: US 2008/0004534. In various embodiments associated with various ones of FIG. 5, the anatomical features of interest are ports of a mitral valve and various pulmonary veins positioned in fluid communication with an intra-cardiac cavity (e.g., a left atrium in some embodiments). In these various embodiments, the transducers of the transducer-based device are distributed adjacent respective regions in the intra-cardiac cavity that can include relatively lower blood flow regions (e.g., adjacent a tissue surface of the intra-cardiac cavity) and relatively higher flow regions (e.g., over the ports of the intra-cardiac cavity). It is noted that relatively lower blood flow regions in the intra-cardiac cavity may occur when a transducer is positioned in contact with a tissue surface to restrict blood flow at the contacted tissue. In some example embodiments, a relatively large number of transducers in the distribution advantageously allow for each of the transducers to be positioned adjacent their corresponding regions with little or no repositioning of the transducer-based device thereby facilitating an obtaining of transducer-based data concurrently from multiple locations in the bodily cavity.

Figure 5H:
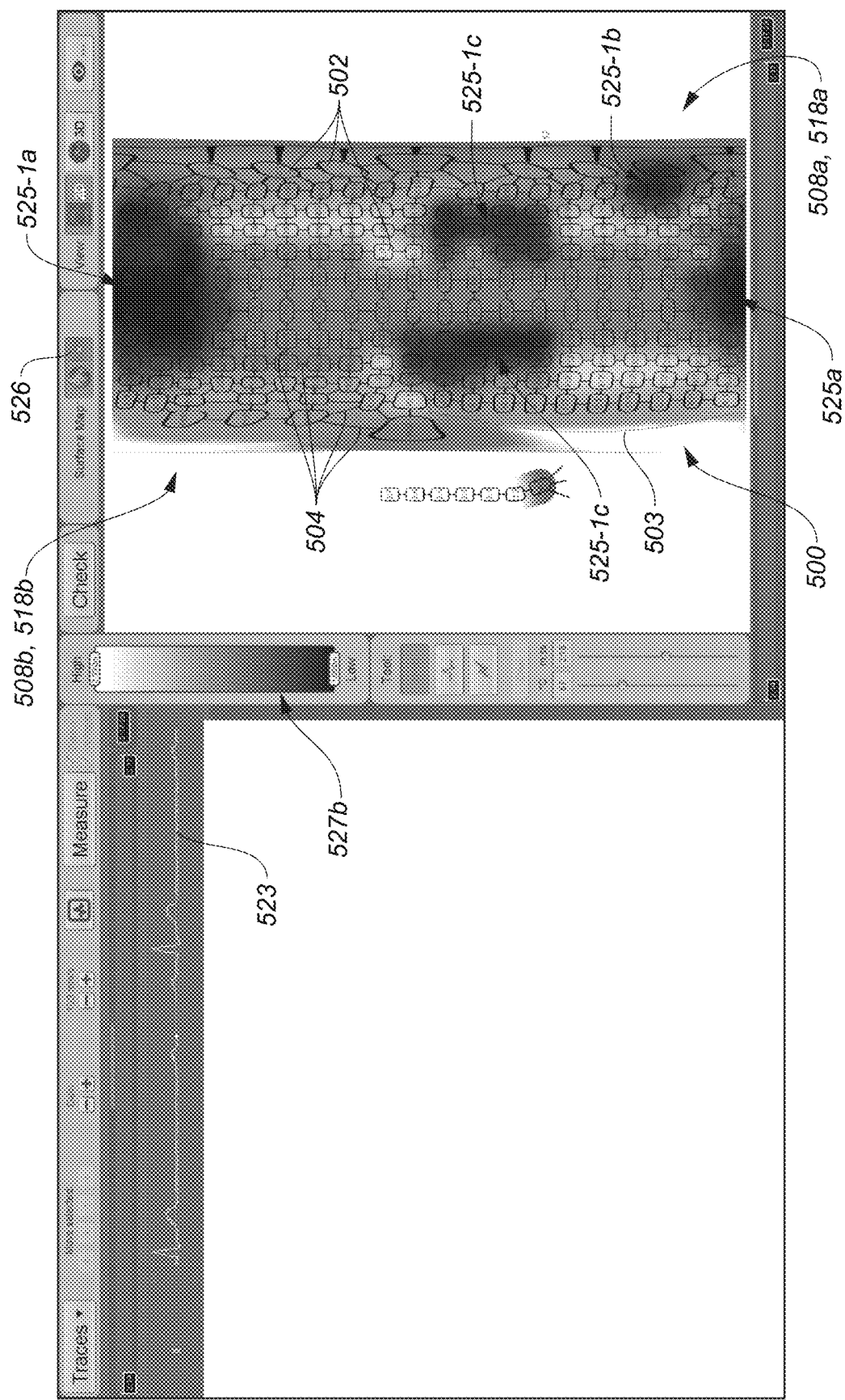
FIG. 5H includes the graphical representation provided by the graphical interface of FIG. 5E with the addition of various intra-cardiac information including various regions determined on the basis of electrical data.

One or more of the above-discussed mapping procedures may be implemented according to instructions associated with block 604 to display a graphical representation 500 that includes intra-cardiac information that indicates at least a portion of one or more anatomical features based at least on an analysis of the transducer data acquired or received according to block 602. In some of these embodiments, the one or more anatomical features are the ports of various bodily openings (e.g., pulmonary veins, left atrial appendage, mitral valve) positioned in fluid communication with the intra-cardiac cavity and the transducer data includes data containing various blood flow data within the bodily cavity. In various embodiments, the data sampled according to block 602 is temperature data and the graphical representation 500 includes a graphical representation of at least some of the temperature data or a derivation thereof (e.g., a map of temperature distribution in the cardiac chamber). For example, in various embodiments in which the use of convective cooling of heated transducer elements by fluid is employed to distinguish blood flow adjacent to the tissue that forms the interior surface(s) of a cardiac chamber from blood flow across the ports of the cardiac chamber, temperature data associated with the convective cooling can be sampled and displayed to provide the graphical representation of the intra-cardiac information. In FIG. 5G, the relatively large region 525a (e.g., shown as two parts in this particular orientation of the two-dimensional representation) is associated with the mitral valve, region 525b is associated with the left atrial appendage, and regions 525c are associated with various pulmonary vein groups. Each of the regions 525 is depicted in the graphical representation 500 with a graduated pattern provided by the flow identifier 527a in the graphical interface of FIG. 5G. In some embodiments, flow identifier 527a provides a graduated scale from a condition indicated as "Contact" (e.g., when a transducer is contact with cardiac tissue) to a condition indicated as "Flow" (e.g., when a transducer overlies a port in the cardiac chamber). A graduated pattern can be employed to indicate various regions in the graphical representation corresponding to different regions of flow in the intra-cardiac cavity. The identified regions 525 may be identified by any suitable methods including the use of gray-scale patterns, different colors, different opacities, different intensities and different shapes. It is understood that other embodiments may employ other techniques to identify regions in the graphical representation corresponding to a desired anatomical feature. For example, transducer-based data containing blood and tissue impedance information may be employed to determine regions 525 as shown in FIG. 5H. In various embodiments, drop-down selection box 526 may be operated to allow for the selective inclusion in the graphical representation of impedance data (e.g., tissue impedance data) or conductivity data (e.g., tissue conductivity data) sampled according to the instructions associated with block 602. In FIG. 5H, the relatively large region 525-1a (e.g., shown as two parts in this particular orientation of the two-dimensional representation) is associated with the mitral valve, region 525-1b is associated with the left atrial appendage, regions 525-1c are associated with various pulmonary vein groups. Each of the regions 525 is depicted in the graphical representation 500 with a graduated pattern provided by the impedance identifier 527b in the graphical interface of FIG. 5H. In some embodiments, impedance identifier provides a graduated scale from a condition indicated as "Low" (e.g., when a transducer overlying a port in the cardiac chamber is used to measure the electrical impedance of blood) to a condition indicated as "High" (e.g., when a transducer adjacent cardiac tissue is used to measure the electrical impedance of cardiac tissue). A graduated pattern can be employed to indicate various regions in the graphical representation corresponding to different regions of impedance in the intra-cardiac cavity. The identified regions 525 may be identified by any suitable methods including the use of gray-scale patterns, different colors, different opacities, different intensities, and different shapes. It is understood that other embodiments may employ other techniques to identify regions in the graphical representation corresponding to a desired anatomical feature.

Identification of the regions 525, which may represent anatomical features, may be motivated for various reasons. For example, in embodiments in which transducers of transducer-based device are activated to treat, diagnose, or investigate various regions in a bodily cavity, the mapping of various regions 525 and their spatial relationship relative to one another may impact the efficacy of the treatment, diagnostic, or investigative procedure. For example, in situations in which at least some of the transducers of a transducer-based device are employed to ablate various regions within an intra-cardiac cavity (e.g., to treat atrial fibrillation), ablation of a pulmonary vein may result in an undesired condition referred to as pulmonary stenosis. Identification of various ones of the regions 525c (e.g., 525-1c) in the graphical representation along with their spatial relationship with various ones of the transducers at various times may be employed to reduce occurrences of this undesired condition.

Without limitation, other forms of intra-cardiac data (e.g., as received, acquired, provided, generated, or sampled per block 602) that may form part of the graphical representation 500 may include pressure data (e.g., blood pressure data, contact pressure data), electrophysiological activation timing data, isochronal data, propagation data, electrophysiological isopotential data, and other electrophysiological voltage data. Without limitation, various maps of intra-cardiac data may include tissue contact maps (e.g., contact maps inferred from flow data, impedance data, conductivity data, which may map an interior tissue surface region of a cardiac chamber), activation maps indicating the local activation times associated with a particular cardiac event, isochronal maps where contour lines may delineate regions of equal activation times associated with a particular cardiac event, propagation maps providing a dynamic representation of the moving activation wave-front associated with a particular cardiac event, isopotential maps, and various other voltage maps associated with intra-cardiac electrical activity. Various representations (e.g., maps) of intra-cardiac information may include portions corresponding to values measured at specific locations within an intra-cardiac cavity and portions corresponding to values that are interpolated (for example, interpolated from values measured at specific locations within an intra-cardiac cavity).

Figure 5I:
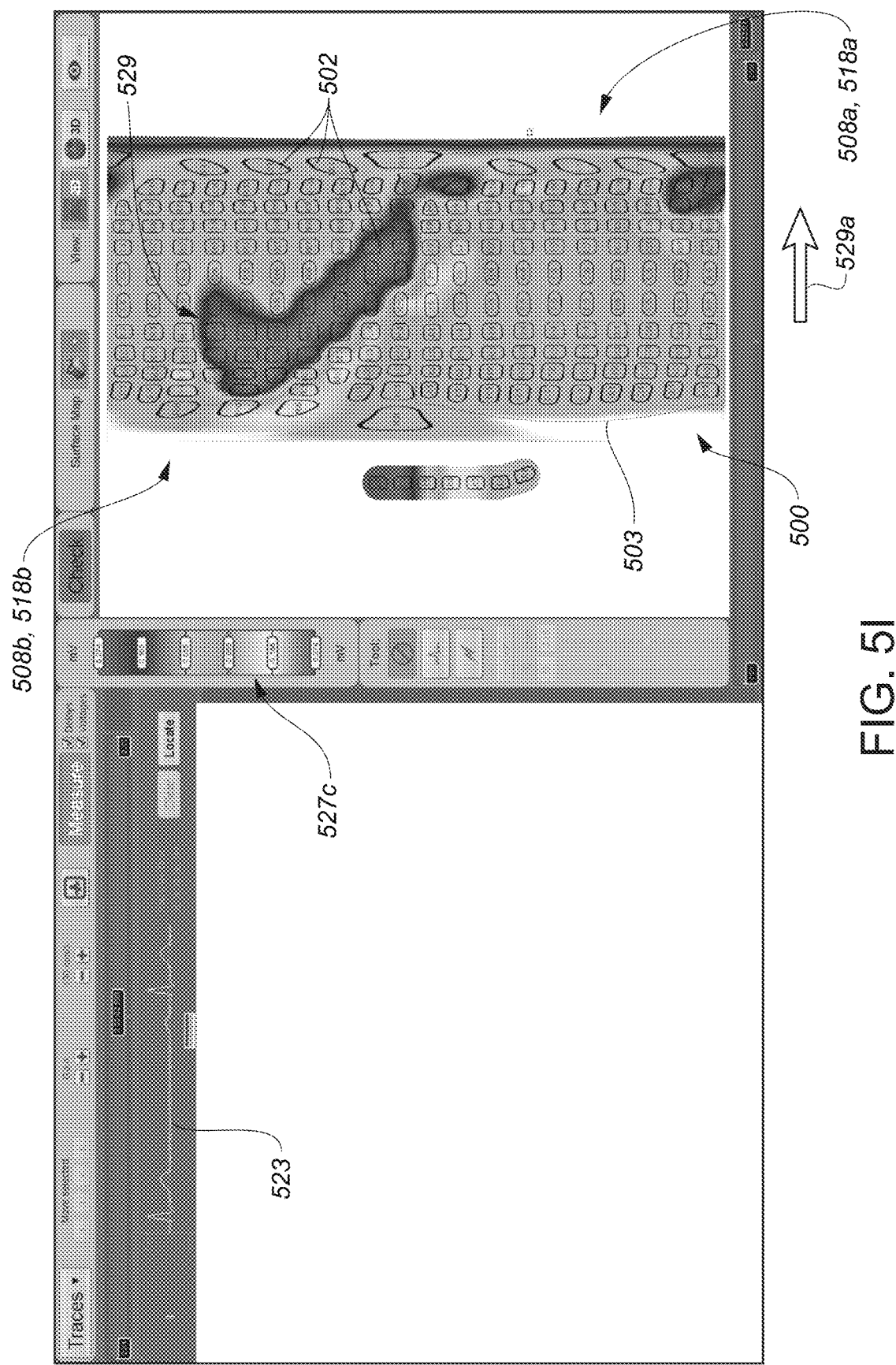
FIGS. 5I, 5J and 5K include the graphical representation provided by the graphical interface of FIG. 5E including changes in intra-cardiac information occurring during three successive times during a display period.
Figure 5J:
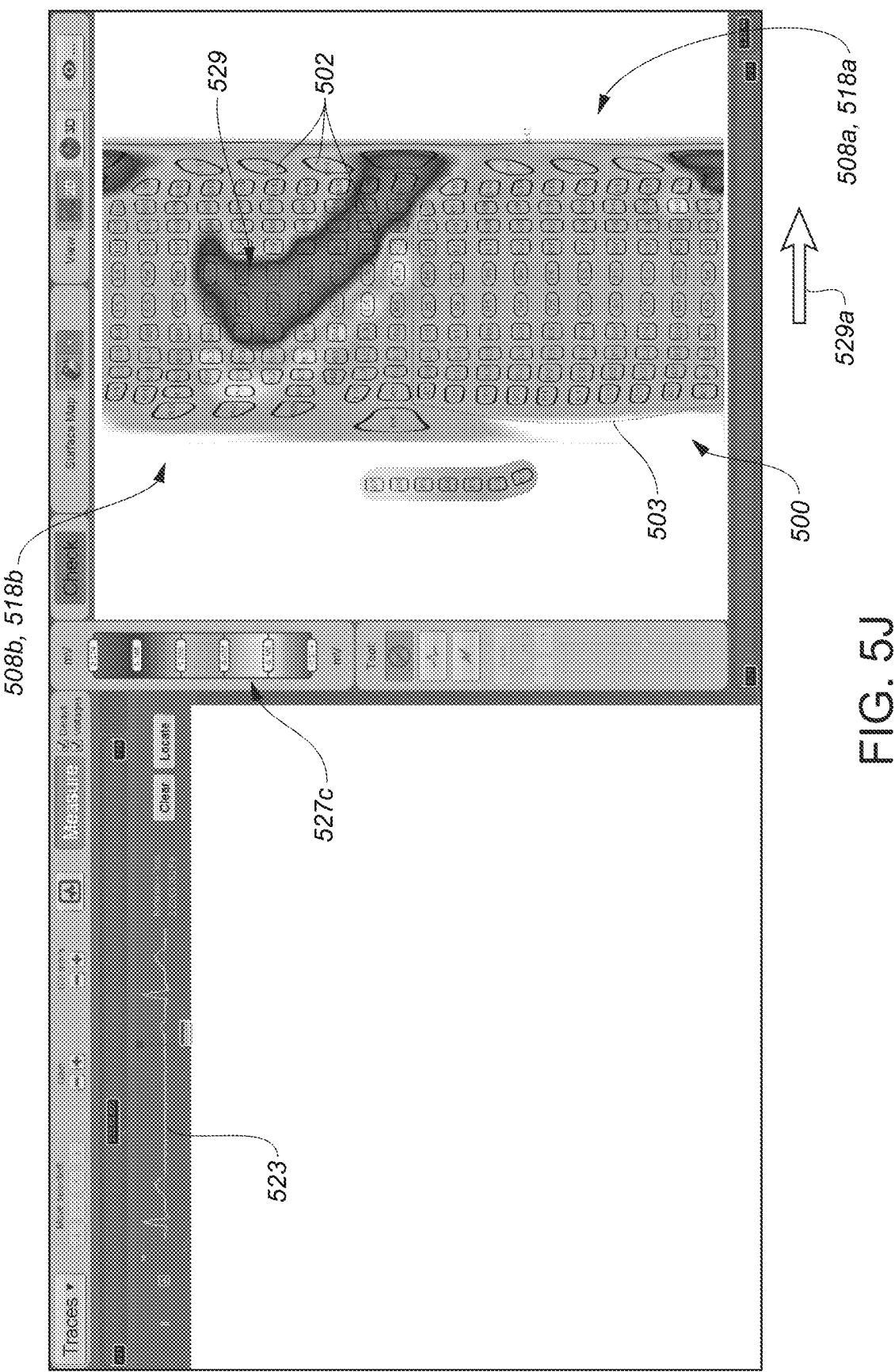
Figure 5K:
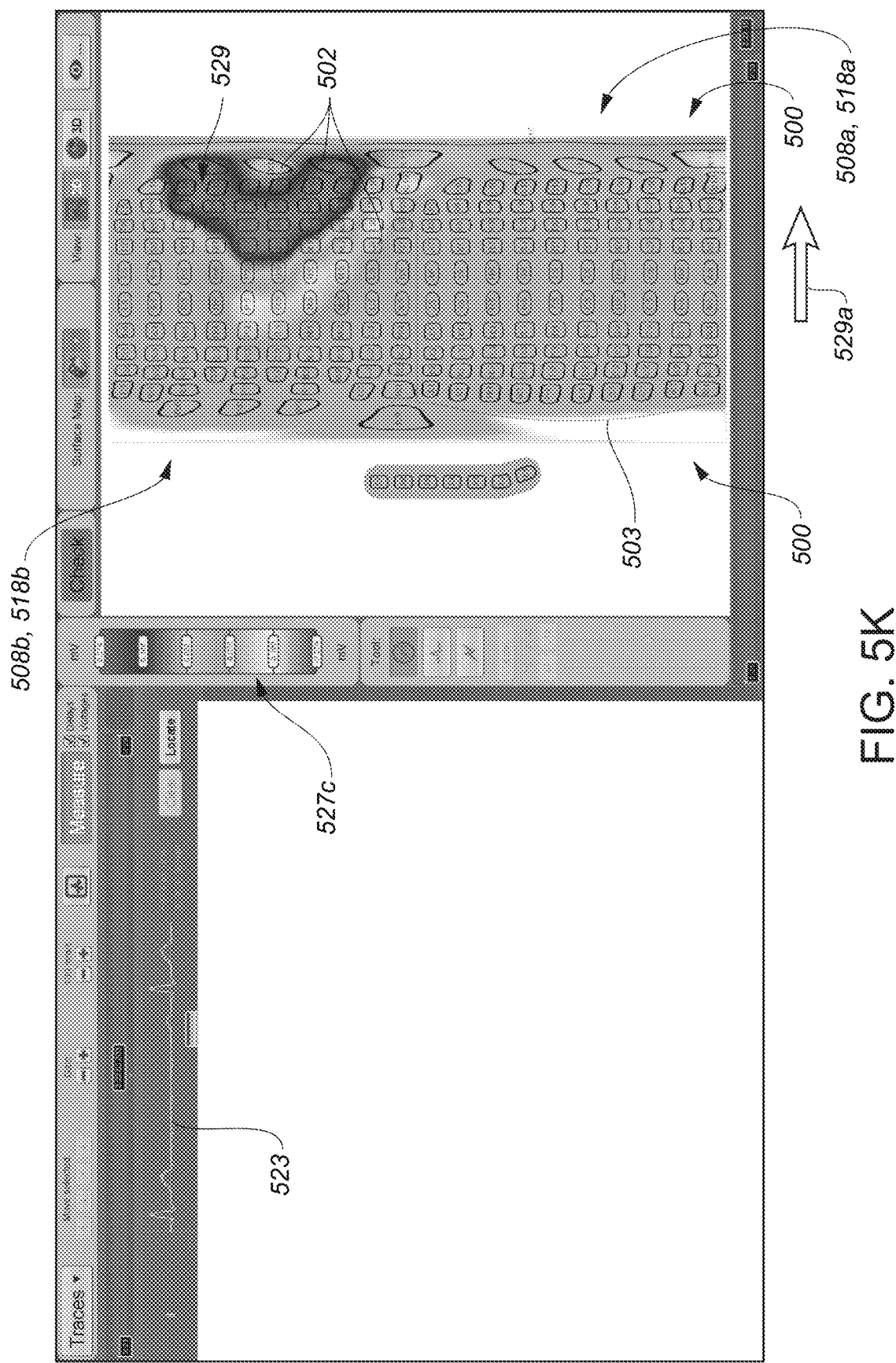

In some embodiments, intra-cardiac information is depicted in the graphical representation statically or relatively statically. That is, the displayed intra-cardiac data remains unaltered or relatively unaltered during a defined display period. In some embodiments, intra-cardiac information is depicted in the graphical representation 500 such that variances in the intra-cardiac information are shown occurring over a defined display period. In some embodiments, the graphical representation includes an animation of changes in intra-cardiac information. FIGS. 5I, 5J, and 5K show graphical representation 500 including changes in intra-cardiac information occurring at three successive particular times during a display period. In some embodiments, the intra-cardiac information displayed in each of FIGS. 5I, 5J, and 5K includes intra-cardiac voltage data showing a distribution of voltage values of intra-cardiac electrogram voltage data sampled (e.g., using a transducer-based device system 200, 300, e.g., according to the instructions associated with block 602) at a particular time (e.g., each of the FIGS. 5I, 5J, and 5K associated with a respective different particular time), each of the voltage values associated with intra-cardiac electrogram data or information sampled at the particular time at a respective one of a plurality of locations in an intra-cardiac cavity (e.g., by respective transducers).

In some embodiments, the displayed voltage values include positive values, negative values, or both positive and negative values. For example, various positive and negative voltage values are indicated in the graphical representation 500 shown in each of FIGS. 5I, 5J, and 5K, a magnitude and positive or negative indication varying in accordance with the voltage identifier 527c. The voltage values shown in FIGS. 5I, 5J, and 5K may be identified by any suitable methods including the use of gray-scale patterns, different colors, different opacities, different intensities, and different shapes. In some embodiments, a grey-scale or color-scale pattern extending across both a positive and negative range is employed to represent the various voltage values or ranges of voltage values. In various embodiments, at least some of the displayed voltage values may include a peak value corresponding to a peak amplitude portion of a waveform representative of the intra-cardiac electrogram data or information associated with the particular displayed voltage values. In various embodiments, at least some of the displayed voltage values may include a non-peak value corresponding to non-peak amplitude portion of a waveform representative of the intra-cardiac electrogram data or information associated with the particular displayed voltage values. Without limitation, various ones of the displayed voltage values may include derivations of the actual measured voltage values (e.g., values derived from the actual measured voltage values) including RMS values, peak-to-peak values.

In various embodiments, the sequence depicted in FIGS. 5I, 5J, and 5K shows time-varying changes in the voltage values associated with the intra-cardiac voltage data or information sampled at respective ones of a plurality of locations in an intra-cardiac cavity. By concurrently sensing intra-cardiac voltage data at each of plurality of locations within an intra-cardiac cavity at various successive times, a relationship indicating changes among all the voltage values associated the intra-cardiac voltage data or information sampled at various successive times across all of a plurality of locations in an intra-cardiac cavity is shown. For example, FIGS. 5I, 5J, and 5K include a depiction of various voltage values represented by moving wave-front 529 (sometimes referred to as propagation 529). In this case, the moving wave-front 529 of voltage values propagates generally in a direction indicated by arrow 529a (not part of the graphical representation 500 but provided to clarify the direction of propagation of wave-front 529 shown in the sequence depicted in FIGS. 5I, 5J, and 5K). It is understood that the propagation of the wave-front 529 of voltage values is not limited to the direction indicated by arrow 529a, but rather, is influenced by various physiological factors associated with the flow of various electrical signals within the cardiac tissue.

In some embodiments, the appearance of a propagating wave-front 529a is caused by changes in the voltage values at each of a plurality of locations in the graphical representation 500, the changes at each particular location represented by changes in a visual characteristic of the voltage value at that particular location. In this regard, an essentially real-time or quasi-real-time representation of the propagation of various electrical signals within an intra-cardiac cavity may be depicted.

It is noted that in various example embodiments such as those associated with various ones of FIGS. 5G, 5H, 5I, 5J, and 5K, at least some of the graphical elements 501 (e.g., transducer graphical elements 502, between graphical elements 504) are depicted as overlaid or superimposed on the displayed graphical representation 500 that includes a depiction of the acquired intra-cardiac information. In various embodiments, various ones of the graphical elements 501 (e.g., various ones of the transducer graphical elements 502) are depicted with a transparent, semi-transparent, or translucent appearance that allows a user to view regions of the intra-cardiac information that underlie each of the various ones of the graphical elements 501 or visual changes in the regions of the intra-cardiac information that underlie each of the various ones of the graphical elements 501. This configuration can be especially advantageous when one hundred, two hundred, or even more transducers are employed percutaneously to sample or gather the intra-cardiac information from a cardiac chamber. A graphical representation 500 that employs a similar, equal, or greater number of graphical elements 501 (e.g., transducer graphical elements 502, between graphical elements 504 or both transducer graphical elements 502 and between graphical elements 504) may obstruct a required viewing of the displayed intra-cardiac information, especially when transducer graphical elements 502 having a shape consistent with the shapes of corresponding ones of the transducers are employed or when transducer graphical elements having distorted appearances (e.g., enlarged distorted appearances described above) are employed. These situations may be effectively mitigated by the use of various graphical elements 501 having a transparent, semi-transparent, or translucent appearance.

Having described examples of the graphical representation (e.g., 500) displayed according to the instructions associated with block 604 in FIG. 6A, the definition of a graphical path (e.g., via input-output device system 120, 320) within or among such graphical representation (e.g., 500) will be described, according to some embodiments. In this regard, instructions associated with block 610 in FIG. 6A may configure a data processing device system (e.g., 110, 310) to define, display, or both define and display such a graphical path. In various embodiments, the graphical path is defined, displayed, or both defined and displayed as including a plurality of the graphical elements 501, according to the instructions associated with block 610.

Figure 5L:
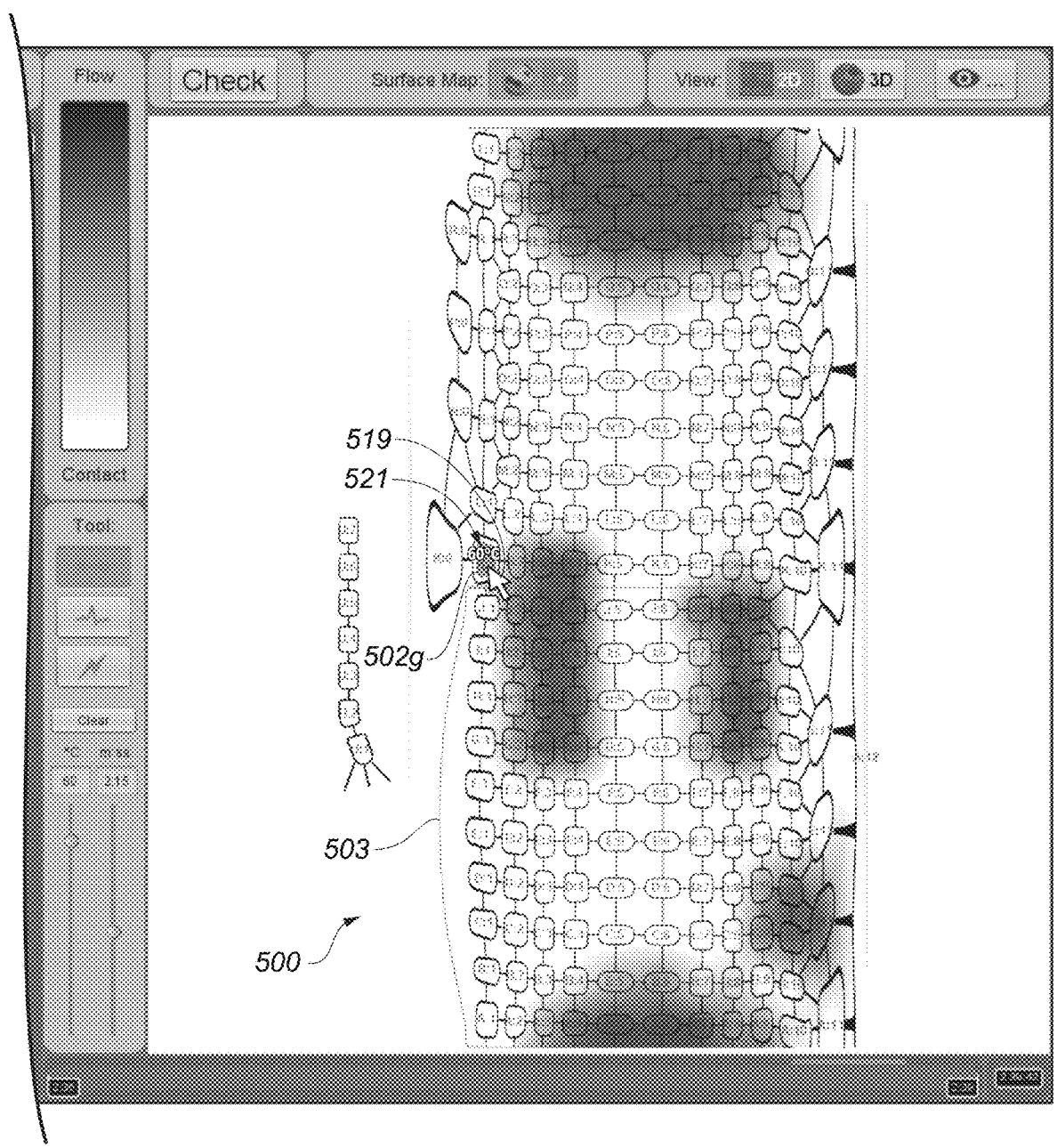
FIGS. 5L, 5M, 5N, 5O, 5P and 5Q show a sequence in which a plurality of portions of a graphical path are selected according to the sequence, each selected portion of the graphical path indicating a selection of at least one graphical element or at least one graphical-path-element.
Figure 5M:
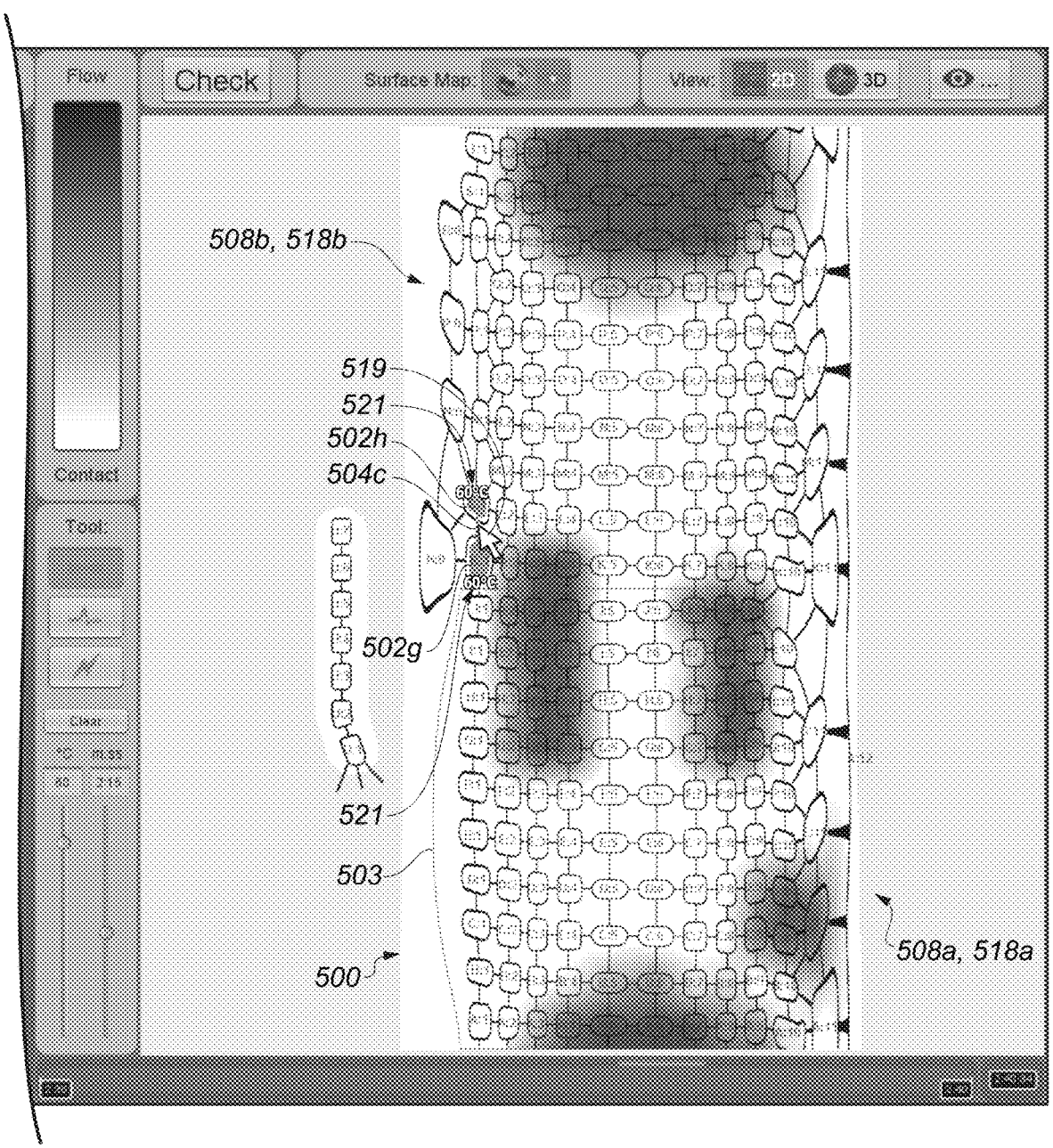
Figure 5N:
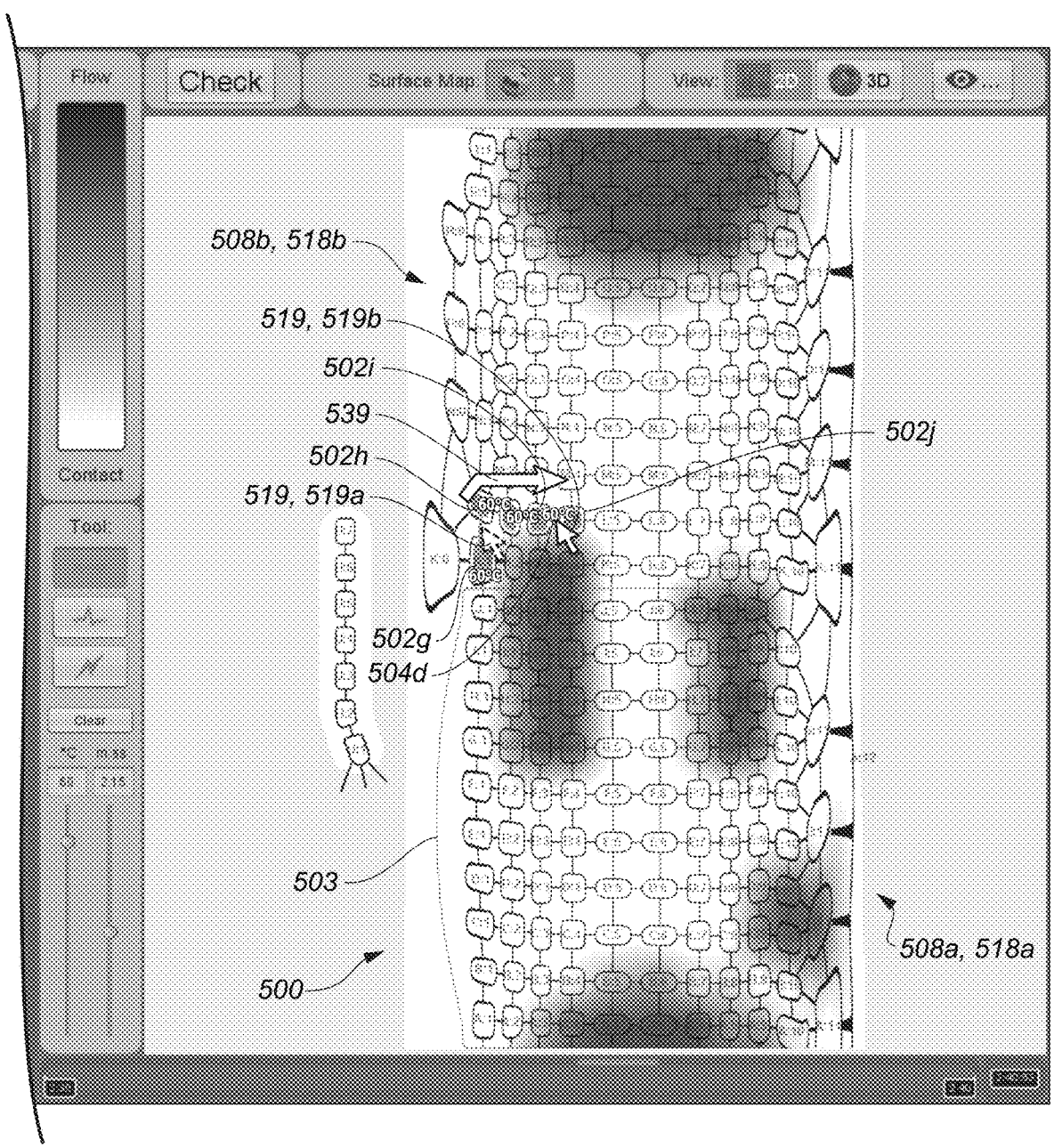
Figure 5O:
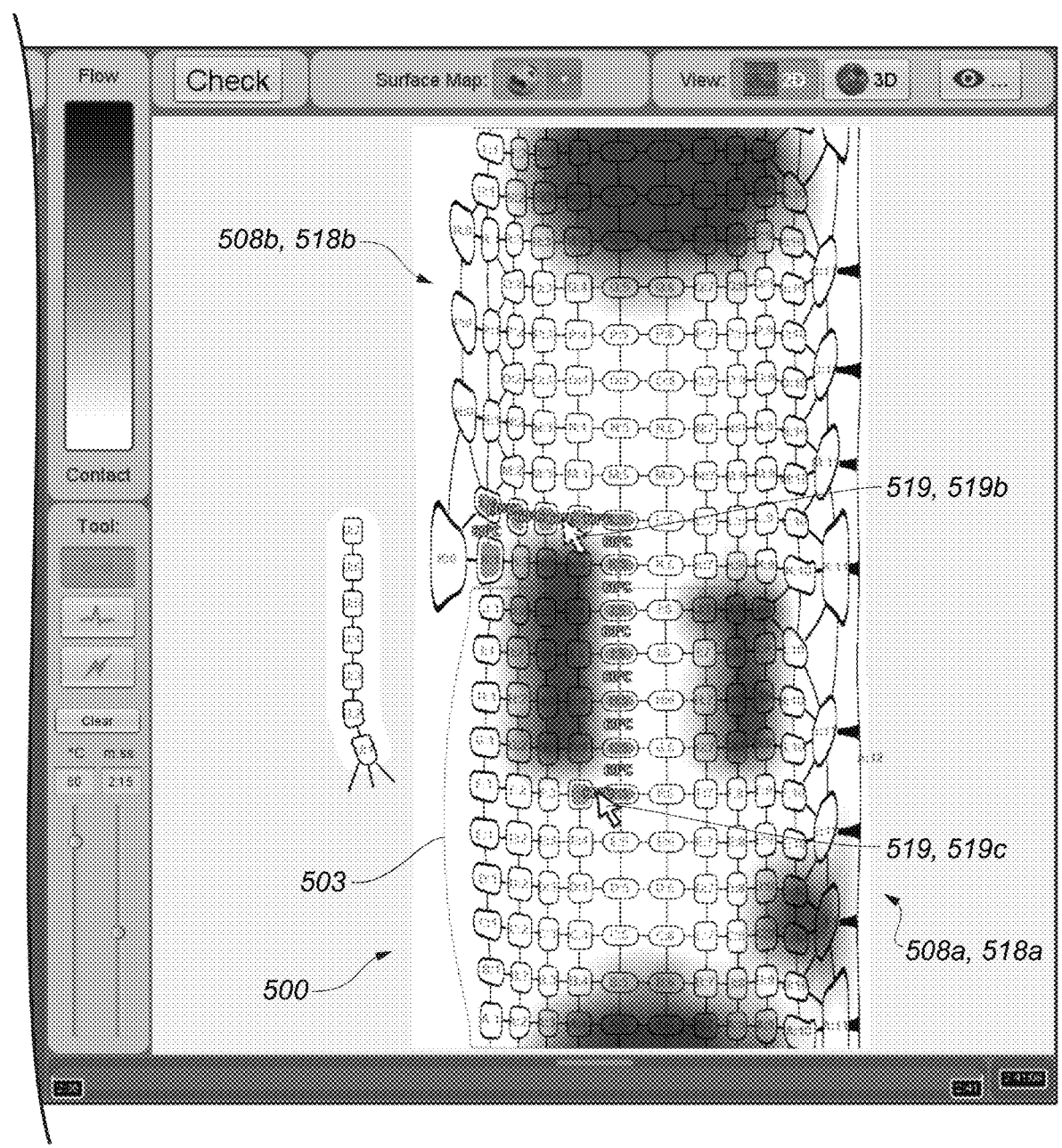
Figure 5P:
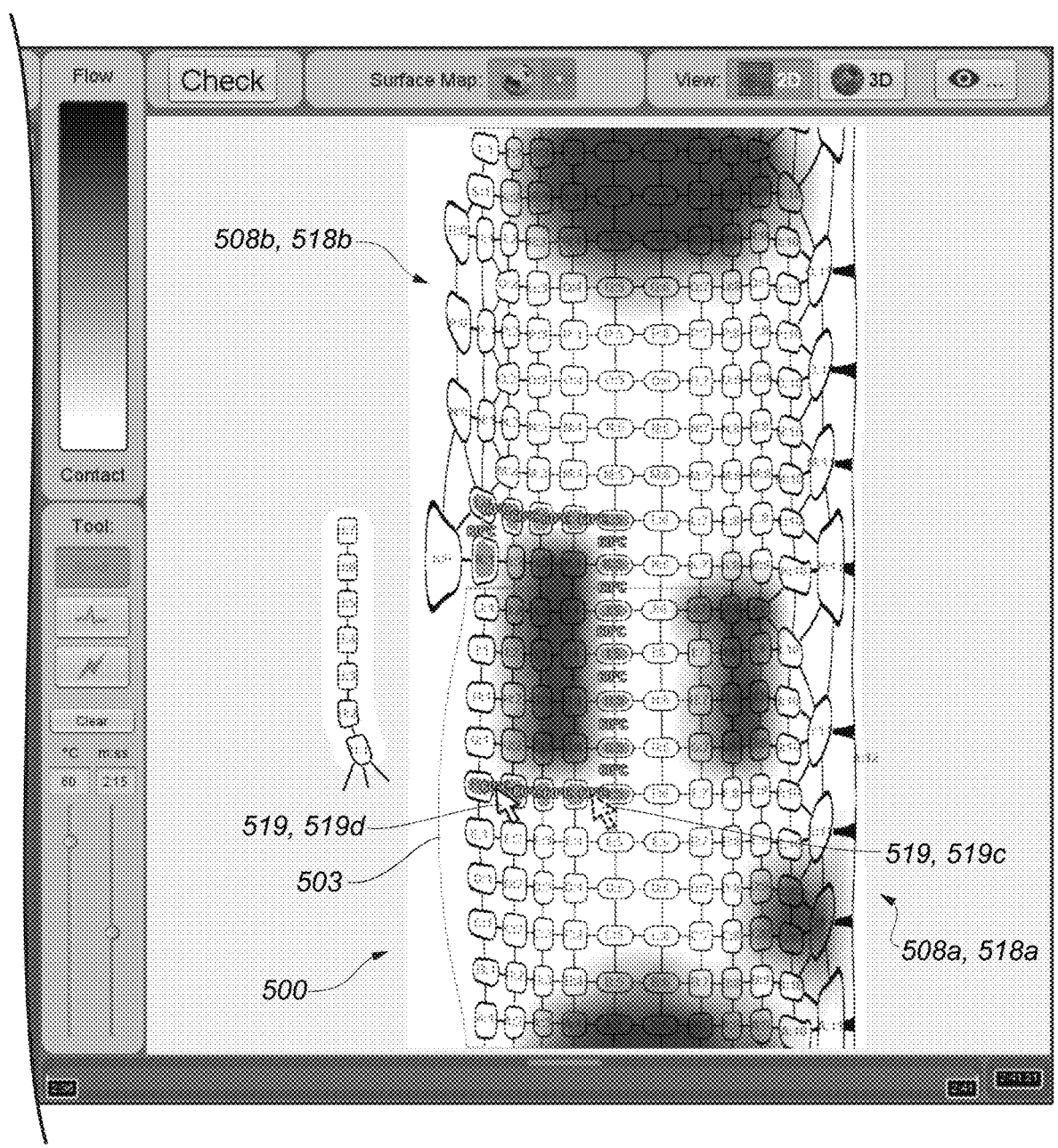
Figure 5Q:
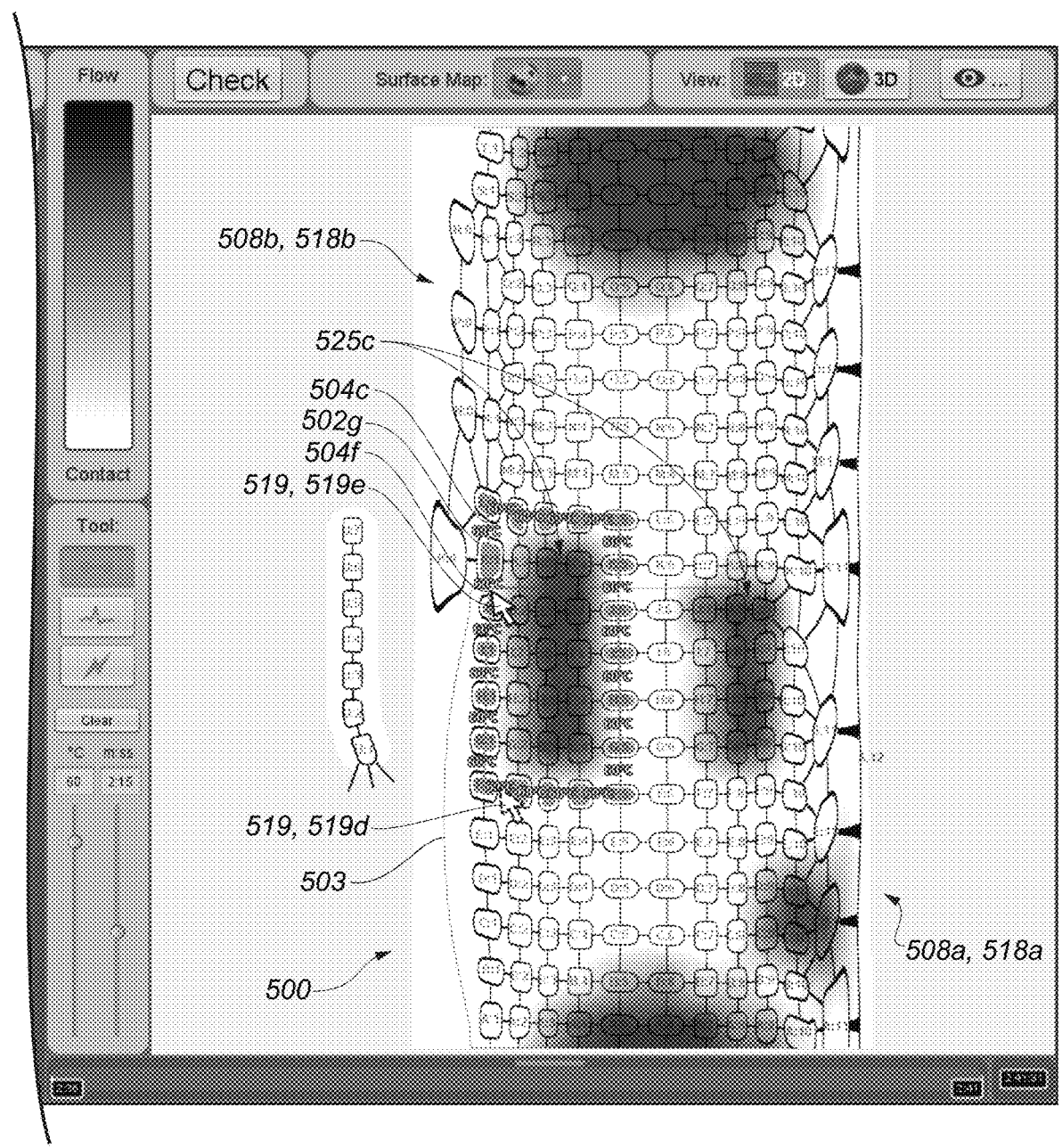
Figure 5R:
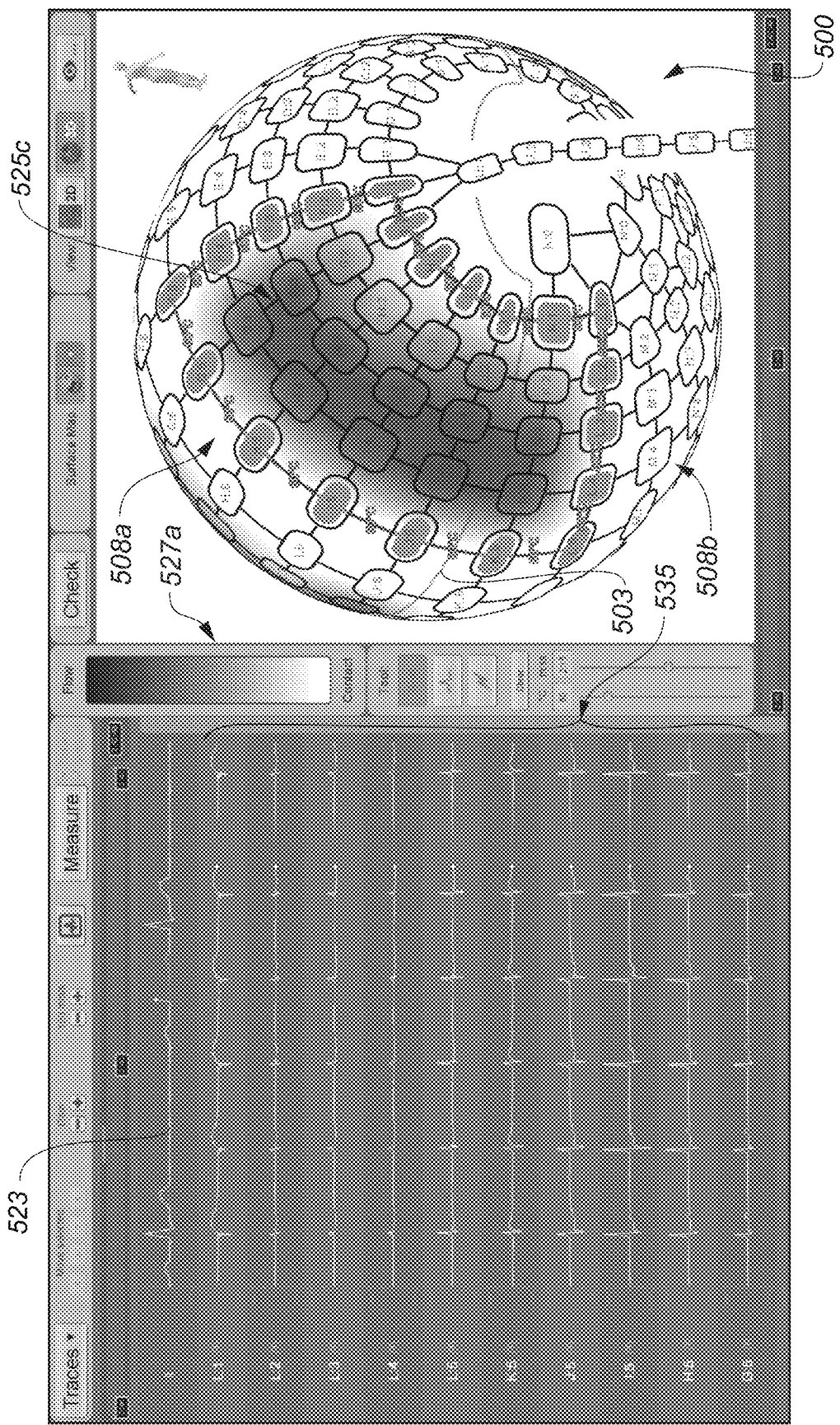
FIG. 5R includes the graphical representation provided by the graphical interface of FIG. 5Q but depicted three-dimensionally according to various example embodiments.

For example, as shown in FIG. 5L, a user may locate a mouse cursor over a transducer graphical element 502g, depress a mouse button at that time, and while continuing to depress the mouse button (e.g., maintaining its activated state), move the mouse cursor 519 over transducer graphical element 502h (FIG. 5M), then to transducer graphical element 502j (e.g., from location 519a to location 519b generally following a path indicated by arrow 539 (not part of the displayed output) in FIG. 5N), then around a loop back to transducer graphical element 502g (e.g., from location 519b around the graphical path corners to location 519c in FIG. 5O, then to location 519d in FIG. 5P and location 519e (e.g., ending at between graphical element 504f) in FIG. 5Q) to define the rectangular-shaped graphical path shown by highlighted transducer graphical elements (FIGS. 5M-5Q), and at such time, release the mouse button (e.g., causing its deactivated state), according to some embodiments. According to some embodiments, the progression of movements of the mouse cursor 519 from FIG. 5L-5Q progressively selects the respective graphical elements (transducer graphical elements 502 in this example, but also or instead, between graphical elements 504 in other embodiments). (For clarity, only part of the graphical interface shown in other various ones of FIG. 5 is shown in FIGS. 5L, 5M, 5N, 5O, 5P and 5Q.) The data processing device system (e.g., 110, 310) may be configured by the instructions associated with block 610, according to some embodiments, to interpret at least (a) the initial depression of the mouse button and the location of the mouse cursor at that time to be the initiation of a definition of a graphical path at the graphical element 501 closest to the location of the mouse cursor; (b) the subsequent movement of the mouse cursor while the mouse button is depressed to be the definition of an intermediate portion of the graphical path, which may include an intermediate location at a particular graphical element 501 or may include at least one elongate path portion including a plurality of graphical elements 501 in a row; and (c) the release of the mouse button to be the termination of the definition of the graphical path at a graphical element 501 closest to the location of the mouse cursor at the time of the release of the mouse button. It is noted that the use of mouse cursor 519 is employed in FIG. 5 merely for the convenience of discussion, and other embodiments may employ other forms of motion-based user input elements (e.g., sliding of contact across a touch screen or touch pad or the movement of other pointing-based interfaces) of other forms of indicators employed by various motion-based user input elements. In addition, other or additional user input or inputs than those discussed above may be required to enable definition of a graphical path. In this regard, it should be noted that various other embodiments are not limited to the details of these embodiments, which are referred to for purposes of illustration only.

Further in this regard, the graphical path defined in accordance with the instructions associated with block 610 may be displayed in various forms, shapes, or configurations including embodiments that include, by way of non-limiting example, an elongated portion, a continuous portion, an interrupted portion, a linear portion, an arcuate portion, a portion defining an obtuse angle, a portion defining an acute angle, a beginning portion (e.g., a portion defining or associated with a beginning or start of the definition of the graphical path), an end portion (e.g., a portion defining or associated with an end or termination of the definition of the graphical path), an open or closed circumferential portion, or any combination thereof. In various embodiments, a graphical path defined in accordance with the instructions associated with block 610 may include a plurality of graphical-path-elements, which may be graphical elements 501, such as transducer graphical elements 502, between graphical elements 504, or both. In various embodiments, a graphical path defined in accordance with the instructions associated with block 610 may include selection of some but not all of a plurality of selectable graphical-path-elements, such as graphical elements 501.

The definition of the graphical path in accordance with the instructions associated with block 610 may be accomplished at least in part by execution of such instructions by the data processing device system (e.g., 110, 310) in response to various user instructions, inputs, or actions. For instance, in some embodiments, a user instruction, input or action may originate from a user clicking a mouse button over a particular region or regions of graphical representation 500. In this case, various instructions may configure the data processing device system to recognize this user instruction when it is received via an input-output device system (e.g., 120, 320) as a user instruction to form or define at least a portion of the graphical path. In some embodiments, the definition of the graphical path need not be defined according to user-input and, in some embodiments, may be automatically defined, e.g., based on anatomical feature locations (e.g., one or more regions 525—see FIG. 5Q, e.g.).

In some embodiments where user input facilitates graphical path definition, method 600 may include a block 608 associated with input-processing instructions indicating reception or reception and processing of various user inputs. In some embodiments, the instructions associated with block 608 include instructions (e.g., associated with block 608*a*) configured to cause reception of first user input via an input-output device system (e.g., 120, 320, such as a mouse button click), and in response to receiving the first user input, place a first user input element in an activated state (e.g., the data processing device system 110, 310 records in memory device system 130, 330 that the mouse button is in an activated state due to reception of an indication of the mouse button click). In some embodiments, input-processing instructions associated with block 608 include instructions (e.g., associated with block 608*b*) configured to cause reception of second user input via an input-output device system (e.g., 120, 320, such as a release of the mouse button), and in response to receiving the second user input, place the first user input element in a deactivated state (e.g., the data processing device system (e.g., 110, 310) records in memory device system (e.g., 130, 330) that the mouse button is in a deactivated state due to reception of an indication of the mouse button release). In some embodiments, input-processing instructions associated with block 608 include instructions (e.g., associated with block 608*c*) configured to cause reception of motion-based user input via an input-output device system (e.g., 120, 320, such as movement of the mouse cursor).

In various embodiments, the graphical path definition instructions associated with block 610 are configured to define a graphical path among the displayed graphical representation (e.g., 500) including a first location, a second location, and a third location, according to the instructions associated with blocks 610*a*, 610*b*, and 610*c*. In some embodiments, the instructions associated with block 610*a* configure the data processing device system (e.g., 110, 310) to define the first location (e.g., an initial or first graphical element or element set (e.g., 502*g* in the example of FIG. 5L)) on the graphical path being defined according to a first parameter set associated with the first user input (e.g., a location (an example of a parameter) of the mouse cursor when the mouse button is clicked (an example of the first user input)). In some embodiments, the instructions associated with block 610*b* configure the data processing device system to define the second location (e.g., a terminating or second graphical element or element set (e.g., 502*g* closing the loop in the example of FIG. 5Q)) on the graphical path according to a second parameter set associated with the second user input (e.g., a location (an example of a parameter) of the mouse cursor when the mouse button is released (an example of the second user input)). In some embodiments, the instructions associated with block 610*c* configure the data processing device system to define the third location (e.g., a third or internal or intermediate graphical element or element set between the initial and terminating graphical elements or graphical element sets (e.g., 502*i* in the example of FIG. 5N) on the graphical path other than the first and the second locations according to a path traced by the motion-based user input (e.g., movement of the mouse cursor). In some embodiments, the third, intermediate location on the graphical path is part of an elongate path portion of the graphical path (e.g., the row of four transducer graphical elements including transducer graphical elements 502*h*, 502*i*, and 502*j* in the example of FIG. 5N). In this regard, the instructions associated with block 610*d* may configure the data processing device system to define the elongate path portion on the graphical path according to the path traced by the motion-based user input. However, in some embodiments, the elongate path portion and the third location may be distinct.

In various embodiments, as discussed above, the first user input (e.g., a mouse button click) precedes the motion-based user input (e.g., the movement of the mouse cursor) in the definition of the graphical path. Also, as discussed above, in some embodiments, the first and the second locations defined on the graphical path indicate respective ends or terminations of the graphical path. In some embodiments, one of the first and the second locations may be a location of a portion of the graphical path defined first during the definition of the graphical path and the other of the one of the first and the second locations may indicate a location of a portion of the graphical path defined last during the definition of the graphical path. In some embodiments, one of the first and the second locations may be a location of a portion of the graphical path displayed first (e.g., via in the input-output device system (e.g., 120, 320) in accordance with display instructions associated with block 612) during a display of the graphical path, and the other of the first and the second locations may be a location of a portion of the graphical path displayed last (e.g., via in the input-output device system (e.g., 120, 320) in accordance with the display instructions associated with block 612) during the display of the graphical path. In some embodiments, the first and the second locations indicate a same location or substantially the same location on the graphical path, such as when the graphical path is a closed path (e.g., a path having a closed form or continuous form, a looped form or circumferential form, like the example of FIG. 5Q). In some embodiments involving a closed path or substantially closed path, one of the first and the second locations may be a location of a portion of the graphical path defined or displayed first and the other of the first and the second locations may indicate a location of a portion of graphical path defined or displayed last, the first and the second locations sufficiently close to one another to impart a closed form or the appearance of the closed form onto the graphical path.

Definition of the graphical path may be motivated by different reasons. For example, in some embodiments, an activation (e.g., according to instructions associated with block 614) of various transducer sets of a transducer-based device (e.g., 200, 300, or 400), initiated during or after the completion of the definition of the graphical path according to the instructions associated with block 610, may cause energy sufficient for tissue ablation along an ablation path corresponding to the defined graphical path. In other words, for example, transducers in the transducer-based device that correspond to the selected transducer graphical elements 502 in the graphical path may be activated, such as being caused to transmit energy sufficient for tissue ablation along an ablation path corresponding to the defined graphical path, according to some embodiments. Advantageously, in some embodiments, the ability to define a graphical path based at least on a graphical representation that includes at least a representation of intra-cardiac information may allow for enhanced results, or a possible reduction in undesired results during a subsequent ablation of cardiac tissue within an intra-cardiac cavity (e.g., an intra-cardiac cavity that is the source of the intra-cardiac information discussed above) when the graphical path acts as a template for a desired ablation path. In this regard, a desired ablation path may be defined based at least on a modeled graphical path that may be generated based at least on various possible constraints indicated by the graphical representation of the intra-cardiac information. For example, various representations of intra-cardiac information that indicate at least a portion of one or more anatomical features (e.g., regions 525, which may represent various cardiac ports provided by the pulmonary veins, left atrial appendage, or mitral valve as shown in FIGS. 5G and 5H by way of non-limiting example) may be used to assist a user or the data processing device system (e.g., 110, 310) in defining a graphical path that acts as a basis for a subsequent ablation path that takes into consideration (e.g., avoids) these anatomical features and reduce occurrences of undesired complications (e.g., stenosis which may arise if ablative energy is applied to particular ones of these anatomical features).

In various embodiments, as discussed above, the graphical representation 500 may include a representation of various transducers (e.g., by way of transducer graphical elements 501) of a transducer-based device (e.g., 100, 200, 300 or 400) positioned within the intra-cardiac cavity. For example, a mapping indicating a particular positioning, pose, or orientation of the transducer-based device in the intra-cardiac cavity, and in particular, a spatial positioning between various ones of the transducers and various regions of the depicted intra-cardiac information may be displayed. In some of these various embodiments, the graphical representation 500 may form a basis for the definition of a particular graphical path that identifies particular ones of the transducers that may be suitable to perform ablation along an ablation path corresponding to the defined graphical path. Other motivations may drive the definition of the graphical path in other embodiments. In some embodiments, various combinations of the display instructions associated with block 604, the display instructions associated with block 606, and the display instructions associated with block 612 are provided by a same set of display instructions.

Referring back to the examples of FIGS. 5L-5Q, in some embodiments, the first user input (e.g., which may initiate the definition of a new graphical path) includes at least engaging a first user input element, and the second user input (e.g., which may indicate the termination of the definition of the graphical path) includes at least disengaging the first user input element. For example, the first user input element may include a keyboard key, a mouse button, a touch screen, or any other user input element capable of being engaged and disengaged. In some embodiments where the first user input includes an engaging of the first user input element, the first user input may include a pressing (or otherwise engaging with) the keyboard key, the mouse button, or the touch screen, for example. In the case of a touch screen, the engaging may include an initiation of user-contact with the touch screen, although the touch screen may be configured to interact with other entities, such as a stylus. In some embodiments where the second user input includes a disengaging of the first user input element, the second user input may include a releasing (or otherwise disengaging) the keyboard key or the mouse button, or a cessation of contact from the touch screen, for example. In either or both of the engaging and disengaging cases, the data processing device system (e.g., 110, 310) may be configured to register in a memory device system (e.g., 130, 330)) that the user input element is in an activated or deactivated state, respectively, in response to registering or identifying that the engaging or disengaging of the first user input element has occurred. It is noted that other embodiments are not limited to the above example embodiments of first user input elements.

In some embodiments, the first user input includes engaging at least two user input elements (e.g., to initiate the definition of a new graphical path, according to some embodiments) of an input-output device system (e.g., 120, 320). For example, a combination of an engaging of a keyboard key and a mouse click, or some other combination of user input elements may be required to initiate the definition of a new graphical path, according to some embodiments. In some of these embodiments, the second user input may include at least a disengaging at least one but not all of the at least two user input elements.

Figure 6D:
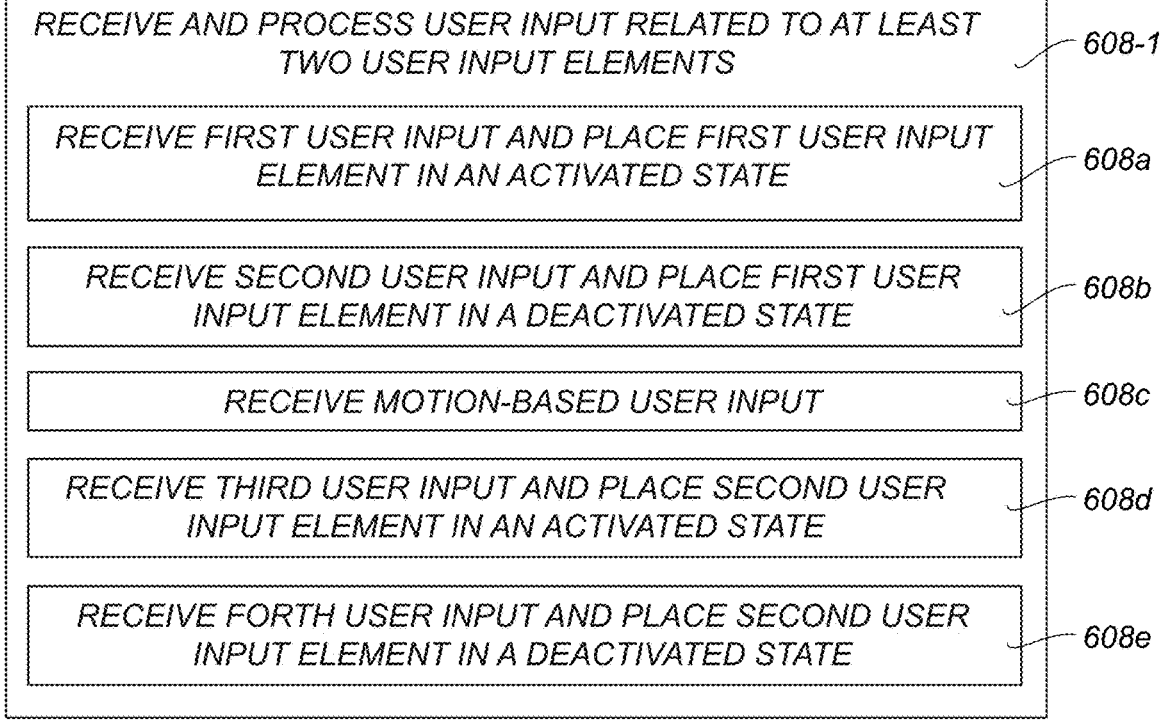
FIG. 6D includes an exploded view of some of the blocks of FIG. 6A according to some example embodiments.

In this regard, the data processing device system (e.g., 110, 310) may be configured to require particular user input to enable the definition of a graphical path prior to or concurrently with receiving user input that defines an initial location on the graphical path. FIG. 6D illustrates various blocks associated with instructions that may configure the data processing device system to operate in this manner. In particular, FIG. 6D illustrates various embodiments of the input-processing instructions associated with block 608 (e.g., identified as 608-1 in FIG. 6D) in which at least two user input elements are employed, according to some embodiments. Block 608-1 in FIG. 6D includes additional sub-blocks 608d and 608e, as compared to block 608 in FIG. 6A.

The input-processing instructions associated with sub-block 608d may be configured to cause reception of a third user input other than the first user input (e.g., which may facilitate definition of a first location in a new graphical path; see, e.g., block 608a), the second user input (e.g., which may facilitate definition of a terminating location of the graphical path; see, e.g., block 608b) and the motion-based user input (e.g., which may facilitate definition of the intermediate locations of the graphical path; see, e.g., block 608c). In various embodiments, the graphical path definition instructions associated with block 610 are configured to require the reception of the third user input in order to enable definition of some or all of the graphical path.

For example, in user interfaces where functionality of a user input element is overloaded (e.g., has many functions), or in implementations where the definition of a graphical path has important consequences (e.g., being a precursor to causing tissue ablation), it may be beneficial to require an additional user input element into an activated state in order to allow definition of some or all of the graphical path. For instance, instead of requiring only a mouse click (an example of a first user input element) to begin definition of a graphical path, it may be beneficial to require the pressing of a particular keyboard key (an example of a second user input element) prior to or concurrently with the mouse click to enable the definition of the graphical path.

In some embodiments, the data processing device system (e.g., 110, 310) is configured to require an engaging of the second user input element (e.g., placing it into an activated state) to enable definition of the intermediate portion or location(s) in the graphical path. For example, engaging of the second user-input (e.g., a depression of a particular keyboard key) need not be required to allow definition of the initial location in the graphical path (e.g., by a mouse click), but may be required to allow the definition of the intermediate locations (e.g., third location per block 610*c*, elongate path portion per block 610*d* (or 610*e* discussed below)) by way of a path traced by the motion-based user input, according to some embodiments. Such a circumstance may allow, e.g., selection of the transducer graphical element 502*g* in FIG. 5L by way of a mouse click at the location of the cursor 519, but would not allow selection of the transducer graphical element 502*h* in FIG. 5M (or the subsequent transducer graphical elements in FIGS. 5N-5Q) by the motion-based user input until the second user input is engaged (e.g., by depression of a particular keyboard key), according to some embodiments. Such circumstance may provide a user with feedback acknowledging an intent to form a new graphical path by allowing selection of transducer graphical element 502*g*, but may require the user to more intently focus on forming the path traced by the motion-based user input, which can be erratic, to form the intermediate portions of the graphical path, by requiring the engagement of the second user input element to do so.

In this regard, in some embodiments, the input-processing instructions associated with block 608-1 (sub-block 608*d*) are configured to cause the second user input element to be placed in a respective activated state in response to receiving the third user input. For example, the third user input might be the depression of a particular keyboard key, which may be an example of the second user input element. In some embodiments, the second user input element may be another keyboard key other than a keyboard key employed as the first user input element. The second user input element may, in some embodiments, be a selectable region of a touch screen other than a particular region of the touch screen employed as the first user input element. Accordingly, it should be noted that various embodiments are not limited to any particular user input elements or combinations thereof. In various embodiments, the graphical path definition instructions associated with block 610 may be configured to require that the first user input element and the second user input element be in their respective activated states in order to at least enable a definition of at least a portion of the graphical path. In some embodiments, the third user input may be required in addition to at least the first user input to enable the graphical path definition instructions associated with block 610 to cause a definition of at least part of the graphical path. It is noted that, in some embodiments, the presence of the third user input (or the second user input element being in an activated state) may be required to enable initiation of definition of at least a portion of the graphical path, but may not be required to allow a subsequent definition of at least a portion of the graphical path (e.g., an intermediate location or elongate path portion thereof). For example, the data processing device system (e.g., 110, 310) may be configured to require depression of a particular keyboard key (e.g., to place that keyboard key in an activated state) to initiate definition of the graphical path, but may allow release of the particular keyboard key (e.g., to place that keyboard key in a deactivated state) during subsequent definition of the graphical path while continuing to allow such subsequent definition.

The release of the second user input element may be considered a fourth user input, according to some embodiments. In this regard, the input-processing instructions associated with block 608-1 may further include instructions associated with sub-block 608*e*, which configure the data processing device system (e.g., 110, 310) to receive a fourth user input other than the motion-based user input and the first, the second, and the third user inputs. Such input-processing instructions may be configured to cause the second user input element to be placed in a respective deactivated state in response to receiving the fourth user input. In some embodiments, the path definition instructions associated with block 610 are configured to cause definition or further definition of the elongate path portion of the graphical path according to the path traced by the motion-based user input (e.g., via the instructions associated with block 610*d*) even though the fourth user input has been received and the second user input element has, consequently, been placed in the respective deactivated state. In this regard, the fourth user input may be received by the data processing device system (e.g., 110, 310) before or during the motion-based user input. However, such timing is not required, and the fourth user input may be received after conclusion of the motion-based user input (e.g., when the second user input is received, which may terminate definition of the graphical path).

In this regard, the above discussion mentions that the graphical-path-enabling user input (e.g., the third user input that places the second user input element in the activated state) occurs prior to or concurrently with the graphical-path-initiating user input (e.g., the first user input that places the first user input element in the activated state), according to some embodiments, but this timing is not required. For example, in some embodiments, the first user input-element may be in an activated state prior to receipt of the graphical-path-enabling user input. In such a circumstance, the enabling of the graphical path does not occur until both the first user input element and the second user input element are in activated states, according to some embodiments.

It is noted that in various embodiments, the first user input element remains in the activated state (e.g., as per the instructions associated with block 608*a*) during the motion-based user input. In some embodiments, placement of the first user input element into its activated state as per the instructions associated with block 608*a* precedes a selection of a set of one or more graphical elements or a set of one or more graphical-path-elements. In some embodiments, placement of the first user input element into its activated state as per the instructions associated with block 608*a* is required at least in part to move a particular user input element from a first state that does not allow for a selection of a set of one or more graphical elements or a set of one or more graphical-path-elements to be made to a second state that does allow for a selection of a set of one or more graphical elements or a set of one or more graphical-path-elements to be made. In various embodiments, where a graphical path is traced in accordance with a motion-based user input, a selection of various graphical elements along the path may occur solely on the basis of the motion-based user input without the requirement for the activation or deactivation of a particular user input element (e.g., a particular user input element employed to at least in part provide the motion-based user input or a particular user input element that is not employed to at least in part provide the motion-based user input).

Figure 6E:
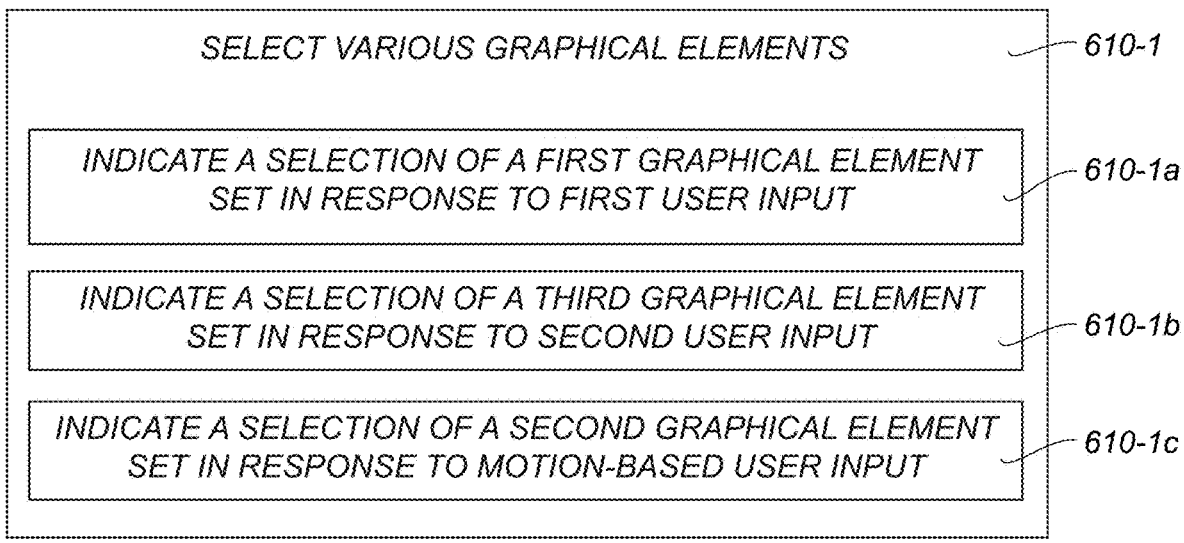
FIG. 6E includes an exploded view of some of the blocks of FIG. 6A according to some example embodiments.

In some embodiments, each of the first user input (e.g., a graphical-path-initiating input) and the second user input (e.g., a graphical path termination input) may facilitate identification or selection of more than one graphical element 501. FIG. 6E shows examples of at least a portion of the path definition instructions associated with block 610 (e.g., identified as 610-1 in FIG. 6E) employed according to some embodiments to configure a data processing device system (e.g., 110, 310) to accommodate such multi-graphical-element identification or selection. For example, in some embodiments, the first user input (e.g., a depression of a mouse button) might occur over a between graphical element 504 (e.g., 504c in FIG. 5M) associated with a respective plurality of transducer graphical elements 502 (e.g., between a pair of transducer graphical elements 502g, 502h in FIG. 5M). In this case, in some embodiments, the instructions associated with at least block 610-1 may configure the data processing device system (e.g., 110, 310) to indicate a selection of the associated respective plurality of transducer graphical elements 502 (e.g., 502g, 502h; an example of a graphical element set) in response to receiving the first user input (e.g., according to the instructions associated with block 610-1a).

A corresponding configuration may apply to the second user input, where the second user input (e.g., a release of the mouse button) occurs over a between graphical element 504. In this case, in some embodiments, the instructions associated with at least block 610-1 may configure the data processing device system (e.g., 110, 310) to indicate a selection of the respective plurality of transducer graphical elements 502 (an example of a graphical element set) associated with the between graphical element 504 in response to receiving the second user input (e.g., according to the instructions associated with block 610-1b). In some embodiments, the graphical element set selected according to the second user input includes at least one transducer graphical element 502 that is other than a transducer graphical element 502 selected according to the first user input. For example, the first user input might cause selection of transducer graphical elements 502g, 502h in FIG. 5M, and the second user input might cause selection of transducer graphical elements 502g and the transducer graphical element adjacent 502g, but on the opposite side compared to transducer graphical element 502h. Or, the graphical path need not be closed loop like that shown in FIG. 5Q, which may cause the transducer graphical elements selected according to the first user input and the second user input to be mutually exclusive, according to some embodiments.

The motion-based user input (e.g., movement of the mouse cursor 519) may also facilitate identification or selection of a plurality of graphical elements 501, such that the instructions associated with at least block 610-1 may configure the data processing device system (e.g., 110, 310) to indicate a selection of the respective plurality of graphical elements 501 (an example of a graphical element set) in response to receiving the motion-based user input (e.g., according to the instructions associated with block 610-1c). In some embodiments, the graphical element set selected according to the motion-based user input includes at least one transducer graphical element 502 that is other than a transducer graphical element 502 selected according to the first user input.

It should be noted that, although the above examples refer to the selection of a between graphical element 504 to cause the selection of a plurality of other graphical elements (e.g., transducer graphical elements 502), other embodiments are not limited to any particular technique for selecting a plurality of graphical elements. Further, although these examples refer to a plurality of graphical elements 501 being a graphical element set, a graphical element set may only include a single graphical element in various embodiments.

In this regard, in some embodiments, the graphical element set selected according to the first user input (e.g., block 610-1a), the graphical element set selected according to the second user input (e.g., block 610-1b), the graphical element set selected according to the motion-based user input (e.g., block 610-1c), or a combination of some or all of the first user input, the second user input, and the motion-based user input may include a group of transducer graphical elements. In this regard, each group of transducer graphical elements may correspond to a respective one of a plurality of groups of adjacent transducers, according to some embodiments. For example, the first user input might cause selection of a group of adjacent transducer graphical elements 502g, 502h in FIG. 5M, which may correspond to a respective group of adjacent transducers 306 in FIG. 3C, according to some embodiments. Similar examples apply to the second user input and the motion-based user input.

As discussed above, in various embodiments, a graphical path defined in accordance with the instructions associated with block 610 may include a selection of various ones of a plurality of selectable graphical-path-elements, which may be graphical elements 501. Each of the selected graphical-path-elements may be arranged along the graphical path. In various embodiments, a graphical path defined in accordance with the instructions associated with block 610 may include a selection of various ones of a plurality of selectable graphical-path-elements, each selected one of the selectable graphical-path-elements defining a respective portion of the graphical path.

In this regard, the selection according to the instructions associated with block 610-1 includes, in some embodiments, multiple constituent or sub-selections (although in other embodiments, the selection according to the instructions associated with block 610-1 includes selection instructions configured to cause, due to execution of the selection instructions by the data processing device system (e.g., exemplified by data processing device systems 110 or 310), selection of a graphical element. In some embodiments, such selection instructions include a first group of instructions configured to cause the data processing device system to receive or process, via the input-output device system, a user instruction to select a graphical element. In some of these embodiments, such selection instructions also include a second group of instructions configured to cause the data processing device system to perform its own selection of the graphical element in response to receiving the user instruction. For instance, the user instruction to select the graphical element might originate from a user clicking a mouse button (e.g., a first constituent selection) while a cursor is above or within a display region of a user-selected graphical element. In this case, the first group of instructions could configure the data processing device system to recognize this user instruction when it is received via the data input-output device system as a user instruction to select the user-selected graphical element below the cursor at the time of the mouse-button click. In some embodiments, the second group of instructions may configure the data processing device system, in response to the first group of instructions recognizing this user instruction, to perform its own selection (e.g., a second constituent selection) of the user-selected graphical element at least by causing, via the input-output device system, the display of the user-selected graphical element to change one or more visual characteristics of the user-selected graphical element. Accordingly, the selection according to various ones of the instructions associated with block 610-1 may be deemed, in some embodiments, to involve a first, user-based constituent selection and a second, machine-based or automatic constituent selection triggered by the user-based constituent selection.

Although a mouse click was provided above as an example of a user-based constituent selection, and the changing of a visual characteristic of the user-selected graphical element was provided as an example of a machine-based constituent selection, it should be noted, however, that any form of user-based selection or machine-based selection of a graphical element known in the art can be used. In this regard, direct interaction with a graphical element itself (e.g., by way of a mouse click on the graphical element) is not required to directly select the graphical element or its corresponding transducer. For example, in some embodiments, a user might type a unique identifier associated with a graphical element or transducer via a keyboard, which can cause direct selection of that graphical element or transducer.

Further, although a user-based constituent selection of a user-selected graphical element followed by a machine-based constituent selection of that user-selected graphical element was provided above as an example of constituent selections involved with block 610-1, it should be noted that a user-based constituent selection of a first user-selected graphical element can also cause a machine-based constituent selection of a second, different, non-user-selected graphical element. For example, in some embodiments, a user-performed mouse click while the mouse cursor is above or within a display region of a user-selected between graphical element 504 (e.g., a user-based constituent selection) can cause, possibly among other things, a machine-based constituent selection of the non-user-selected transducer graphical elements 502 at each end of the user-selected between graphical element 504. In this regard, the phrase, "user-selected", when used herein to describe a selected graphical element (e.g., a transducer graphical element or a between graphical element), is intended to refer to a graphical element directly selected by a user, as opposed to a non-user-selected graphical element, which is a machine-selected graphical element that is machine-selected either in response to no user instruction to select any graphical element or in response to a user instruction to select a user-selected graphical element different than the machine-selected graphical element. In cases where a user selection of a user-selected graphical element causes a machine-selection of a different graphical element, it can be said that the different graphical element is indirectly selected by the user.

Further still, although a user-based constituent selection followed by a machine-based constituent selection was provided above as an example of constituent selections involved with block 610-1, it should be noted that any number of constituent selections, whether user-based or machine-based, can be involved with block 610-1. For example, depending upon how the user interface is structured, one or more user-based constituent selections may result in one or more machine-based constituent selections. For instance, multiple user gestures might be required to identify a particular user-selected graphical element in order to cause the data processing device system to change the visual characteristics of (or provide another form of selection of) the particular user-selected graphical element. For example, according to some embodiments, the above-discussed first user input (e.g., block 610-1*a*) might be a combination of the pressing of two keyboard keys, at least in part, concurrently, to place the first user input element (e.g., the two keyboard keys) in an activated state to change the visual characteristics of a correspondingly selected transducer graphical element (e.g., 502*g* in FIG. 5L). If the same multi-key approach was applied to the selection of a between graphical element (e.g., 504*c* in FIG. 5M), the data processing device system (e.g., 110, 310) may be configured to respond with at least two machine-based constituent selections to change the visual characteristics of the corresponding transducer graphical elements (e.g., 502*g*, 502*h* in FIG. 5M), according to some embodiments.

Further still, although one or more user-based constituent selections followed by one or more machine-based constituent selections was provided above as an example of constituent selections involved with block 610-1, it should be noted that block 610-1 might not involve any user-based constituent selections in some embodiments. For example, graphical element selection according to block 610-1*a* might occur based upon data received from transducers, and this data might result in one or more machine-based or automatic constituent selections performed by the data processing device system.

It should be noted that, whenever a selection of a graphical element is discussed herein, such selection, in some embodiments, may include the above-discussed constituent selections, according to some embodiments. However, the above-discussed constituent selections are not limited to just selections of graphical elements and can apply to any selection described herein. For example, one or more user-based constituent selections of a user-selected graphical element can lead to one or more machine-based constituent selections of the user-selected graphical element or some other graphical element(s), which can lead to one or more machine-based selections of one or more transducers corresponding to the machine-selected graphical elements, the machine-based selection(s) of the one or more transducers possibly causing an activation of the one or more transducers. For another example, one or more user-based constituent selections of a user-selected graphical element can lead to one or more machine-based constituent selections of one or more data objects associated with the user-selected graphical element, one or more other associated graphical elements, one or more transducers associated with the user-selected graphical element, or one or more other objects associated with the user-selected graphical element, such as for purposes of viewing or changing properties of the one or more data objects or causing an activation based upon information provided by the one or more data objects.

In some embodiments, the graphical path defined according to the instructions associated with block 610 (e.g., by way of the first user input, the second user input, the motion-based user input, or a combination of some or all of the first, second, and motion-based user inputs) includes transducer graphical elements 502, between graphical elements 504, or both transducer graphical elements 502 and between graphical elements 504. In some embodiments, the graphical path includes a continuous series of selected transducer graphical elements 502 and selected between graphical elements 504. In some embodiments, the between graphical elements 504 forming at least part of the graphical path are interleaved with the transducer graphical elements 502 forming at least part of the graphical path.

In some embodiments, at least selected ones of the between graphical elements 504 include an elongated portion extending between two respective ends, each of the respective ends located at least proximate a respective one of two transducer graphical elements 502, according to some embodiments. For example, various ones of FIG. 5 illustrate each between graphical element 504 as a line between two transducer graphical elements 502. However, the invention is not limited to such a representation of a between graphical element 504, and between graphical elements 504 need not be lines (or elongated portions) or contact their respective transducer graphical elements 502. In some embodiments where an intermediate portion of the graphical path includes an elongate path portion, an elongated portion of each of at least some of the selected between graphical elements 504 may provide at least part of the elongate path portion.

As discussed above with respect to FIG. 3D and regions of space 350, 360, at least some between graphical elements 504 (e.g., 504c) may each be associated with a region of space that is not associated with any physical part or portion of the corresponding transducer-based device system. In some embodiments, at least some between graphical elements 504 (e.g., 504c) may each be associated with a region of space that does not include any transducer (e.g., either between elongate members 304 or along a same elongate member 304), the region of space being between transducers in a group of adjacent transducers (e.g., transducers 306 corresponding to transducer graphical elements 502g, 502h, in the case of between transducer graphical element 504c in FIG. 5M). In some embodiments, at least some between graphical elements 504 (e.g., 504d in FIG. 5N) may each be associated with a region of space that is associated with a physical part or portion of the transducer-base system (e.g., a region of space along a same elongate member 304 between transducers 306 associated with transducer graphical elements 502i, 502j, in the case of between graphical element 504d in FIG. 5N).

According to some embodiments, block 612 in FIG. 6A is associated with instructions configured to cause the data processing device system (e.g., 110, 310) to display the graphical path defined according to the instructions associated with block 610. As discussed above, the graphical path defined in accordance with the instructions associated with block 610 may be displayed according to the instructions associated with block 612 in various forms, shapes, or configurations including embodiments that include, by way of non-limiting example, an elongated portion, a continuous portion, an interrupted portion, a linear portion, an arcuate portion, a portion defining an obtuse angle, a portion defining an acute angle, a beginning portion (e.g., a portion defining or associated with a beginning or start of the definition of the graphical path), an end portion (e.g., a portion defining or associated with an end or termination of the definition of the graphical path), an open or closed circumferential portion or path, or any combination thereof.

In cases where the graphical path is represented at least in part in an interrupted form including at least an interrupted portion, such interrupted portion may be caused, at least in part, by between graphical elements 504 that do not connect to their associated transducer graphical elements 502, unlike the connecting between graphical elements 504 as shown in various ones of FIG. 5 (e.g., each of FIG. 5L-5Q). Non-connecting between graphical elements 504 may be represented as line segments, double-line segments, squares, dots, or any other shape that does not contact at least on adjacent transducer graphical element 502, according to some embodiments. In cases where the graphical path is displayed at least in part as a circumferential path, such circumferential path may enclose or surround a region (e.g., 525c in FIG. 5Q corresponding to a pulmonary vein) in a graphical representation of intra-cardiac information.

The instructions associated with block 612 may be configured to cause at least one visual characteristic set of each of various ones of the graphical elements 501 to change upon or after selection (e.g., by way of the first, second, or motion-based user inputs) and inclusion in the graphical path according to the instructions associated with blocks 608 and 610, according to various embodiments. For example, at least each of FIGS. 5L-5Q show the changing of an interior color of each selected transducer graphical elements 502 as the graphical path is defined and displayed over time. Similarly, a color or other visual characteristic of between graphical elements 504 selected for inclusion in the graphical path may change when or as the graphical path is displayed. In some embodiments, selected transducer graphical elements 502, selected between graphical elements 504, or both, in the graphical path have different visual characteristics than unselected or non-selected respective ones of the transducer graphical elements 502, the between graphical elements 504, or both.

In some embodiments, the graphical path may be defined according to selection of any selectable graphical-path-element. In some embodiments, the selectable graphical-path-elements are graphical elements 501, including transducer graphical elements 502, between graphical elements 504, or both. However, other selectable graphical-path-elements may be used.

In some embodiments, the selectable graphical-path-elements are provided by or among a displayed graphical representation (e.g., 500). The selectable graphical-path-elements may be arranged in the graphical representation (e.g., 500) in an arrayed configuration (e.g., a depicted two-dimensional or depicted three-dimensional arrayed configuration). In some embodiments, the selectable graphical-path-elements are arranged in a grid or grid-like configuration. Various ones of FIG. 5 show two-dimensional or three-dimensional arrangements of selectable graphical-path-elements according to some embodiments.

It is noted that the display of the selectable graphical-path-elements or the defined graphical path is not limited to two-dimensional representations as shown, for example, in various ones of FIG. 5. In this regard, FIG. 5R shows the graphical path generated in FIGS. 5L-5Q three-dimensionally. A graphical representation of intra-cardiac information (e.g., blood flow information) is also depicted three-dimensionally in FIG. 5R. In embodiments encompassing FIG. 5R, a plurality of graphical representations of intra-cardiac electrograms 535 may be additionally displayed by the graphical interface, each of the electrograms 535 derived from data sampled by a respective transducer (e.g., transducer 306, 406) corresponding to a particular one of the transducer graphical elements 502 selected along the graphical path. In various embodiments, each of the electrograms 535 is a unipolar or monopolar electrogram.

In some embodiments, as discussed above with respect to FIG. 5A, each of at least some of the transducer graphical elements 502 includes a shape that is consistent with a shape of the respective electrode (e.g., 315, 415) of the transducer (e.g., 306, 406) to which the transducer graphical element 502 corresponds. In this regard, different transducer graphical elements 502 may have different shapes, like their respective transducers (e.g., 306, 406) or electrodes (e.g., 315, 415) thereof.

In some embodiments, the display instructions associated with block 612 in FIG. 6A configure the data processing device system (e.g., 110, 310) to cause the input-output device system (e.g., a display device of 120, 320) to display the graphical path among a graphical representation of intra-cardiac information (see, e.g., FIGS. 5L-5R). Such intra-cardiac information has been described above with respect to at least FIGS. 5G-5K. In this regard, according to some embodiments, the display instructions associated with block 612 may be configured to cause the input-output device system to display a plurality of between graphical elements 504 concurrently with transducer graphical elements 502, the graphical path, and the graphical representation of the intra-cardiac information.

It is noted that in various embodiments, the intra-cardiac information that is displayed (e.g., via the instructions associated with block 604) need not be static and may include changes in the displayed appearance thereof. For example, the display instructions associated with block 604 may be configured to, in some embodiments, cause an input-output device system (e.g., 120, 320) to graphically display changes in the intra-cardiac information (for example, as depicted in FIGS. 5I, 5J and 5K) during: a) reception of the first user input (e.g., block 608*a*), b) reception of the second user input (e.g., block 608*b*), c) reception of the motion-based user input (e.g., block 608*c*), or any combination of a), b) and c). In some embodiments encompassing FIGS. 5L and 5M, additional information 521 (which may be another form of graphical representation of intra-cardiac information) is displayed upon a selection indicating a particular one of the graphical elements 501. In at least some of these particular embodiments, the information 521 includes target temperature information associated with each of the transducers corresponding to the particular ones of the selected transducer graphical elements 502. In some embodiments, the information 521 is related to, or reflective of systems-based or hardware-based information. In some embodiments, the information 521 is related to, or reflective of physiological parameter information. In some embodiments, the information 521 may represent target temperature information to monitor or control the transmittance of tissue ablation energy from a particular one of the transducers. In various embodiments, temperature data is sensed by a particular temperature sensor (e.g., temperature sensor 408) provided by a particular transducer. The temperature data may, in some embodiments, be compared with the target temperature to monitor or control the transmittance of tissue ablation energy from the particular transducers. Other forms of information 521 may be displayed in other embodiments. It is noted that displayed information 521 need not solely arise from a selection indicated by the first user input, but may, in some embodiments, arise as a result of other user inputs (e.g., a second user input or a motion-based input as described herein). It is noted that in some embodiments, the display of information 521 occurs in response to a selection of various ones of the graphical elements 501. Advantageously, the selective inclusion of information 521 only for the selected ones of the graphical elements 501 may reduce cluttering the display region if the information 521 were provided for a significant number of (e.g., a majority) or all of the selectable graphical elements 501. This is especially important when several hundreds of selectable graphical elements 501 are displayed.

Having the graphical path displayed among a graphical representation of intra-cardiac information (e.g., FIGS. 5L-5R) may facilitate better judgments regarding or improve the effectiveness or operational implementation of transducer activation (e.g., sensing, tissue ablation, both, or some other activation) within the cardiac cavity. In some embodiments, activation instructions associated with block 614 in FIG. 6A are configured to cause activation of various transducer sets. In some embodiments, these various transducer sets include or are the transducers corresponding to those transducer graphical elements 502 included in the graphical path.

In some embodiments, the activation instructions associated with block 614 are configured to cause transmission, initiated during or after completion of the definition of the graphical path (e.g., according to the instructions associated with block 610), of energy sufficient for tissue ablation (e.g., via energy source device system 340) from each of at least one of the respective transducers (e.g., 220, 306, 406) corresponding to graphical elements 501 in the graphical path, such as transducer graphical elements 502, between graphical elements 504, or both, selected by the first user input (e.g., blocks 608*a*, 610*a*), the motion-based user input (e.g., blocks 608*c*, 610*c*), or the second user input (e.g., blocks 608*b*, 610*b*).

In some embodiments, the activation instructions associated with block 614 are configured to cause transmission, initiated during or after completion of the definition of the graphical path, of energy sufficient for tissue ablation from at least each respective transducer corresponding to a first transducer graphical element selected, e.g., based on a graphical-path-initiating first user input according to the instructions associated with block 608*a* in FIG. 6A, a second transducer graphical element selected, e.g., based on motion-based user input according to the instructions associated with block 608*c* in FIG. 6A, and a third transducer graphical element selected, e.g., based on graphical-path-terminating second user input according to the instructions associated with block 608*b* in FIG. 6A.

Similarly, in some embodiments, the activation instructions associated with block 614 are configured to cause transmission, initiated during or after completion of the definition of the graphical path (e.g., according to the instructions associated with block 610), of energy sufficient for tissue ablation from at least each respective transducer (e.g., 220, 306, 406) corresponding to each transducer graphical element 502 in each of a first transducer graphical element set selected, e.g., based on a graphical-path-initiating first user input according to the instructions associated with block 610-1*a* in FIG. 6E, a second transducer graphical element set selected, e.g., based on motion-based user input according to the instructions associated with block 610-1*c* in FIG. 6E, and a third transducer graphical element set selected, e.g., based on graphical-path-terminating second user input according to the instructions associated with block 610-1*b* in FIG. 6E.

In some embodiments, the activation instructions associated with block 614 are configured to cause transmission, initiated during or after completion of the definition of the graphical path, of energy sufficient for tissue ablation from at least each transducer (e.g., 220, 306, 406) of a respective one of a plurality of groups of adjacent ones of the transducers corresponding to a selected at least one of the between graphical elements 504. For example, if between graphical element 504 in FIG. 5M is selected, which causes inclusion of adjacent transducer graphical elements 502*g* and 502*h* in the graphical path, the group of adjacent transducers 306 corresponding to transducer graphical elements 502*g* and 502*h* may be caused to transmit tissue-ablative energy (e.g., via energy source device system 340) in accordance with the instructions associated with block 614, according to some embodiments.

Advantageously, activating a set of two or more of the transducers based on a selection of a single graphical element (e.g., between graphical element 504) provides for a workflow that may be less cumbersome and more expeditious than individually selecting the respective graphical elements (e.g., transducer graphical elements 502) associated with each transducer of the set of two or more of the transducers, especially when 50, 100, 200 or even over 300 or more transducer graphical elements are provided in the graphical representation. This configuration may be even more advantageous, when a single graphical element (e.g., between graphical element 504) provides additional information (e.g., spatial information) relating each of the transducers in the set of two or more of the transducers. For example, a between graphical element 504 may indicate a distance between or acceptability-of-activation of transducers of a corresponding transducer pair, and, accordingly, the between graphical element 504 provides, in some embodiments, information about the corresponding group (e.g., pair) of transducers and, thereby, makes the selection process more efficient. In addition, allowing selection of the between graphical elements for corresponding transducer activation can provide a more intuitive user interface in certain applications. For example, such an arrangement allows a user to make selections along an ablation path or a path along which data is to be obtained, without having to focus on the transducers required to make that ablation path or acquire that data. The user may, for example, just select a path using between graphical elements (e.g., user-based selection(s)/constituent selection(s)), and the corresponding transducers are automatically selected (e.g., machine-based selection(s)/constituent selection(s)) in response. Since various ones of the between graphical elements need not be tied to any physical portion of the transducer-based device, they can be freely designed to reflect a path (e.g., over tissue or fluid) along which their corresponding transducers will interact when activated (e.g., by causing ablation). In this regard, if the between graphical elements are configured to accurately represent their respective path segments in which ablation or data gathering will occur, according to some embodiments, the user can gain an even better understanding of the expected results of activation of the corresponding transducers. This configuration may advantageously increase the likelihood that an ablation path that is consistent with the displayed graphical path will result.

Activation of transducers according to the instructions associated with block 614 may occur when the definition, display, or both of the graphical path has not yet completed. For example, if FIG. 5Q represents the completion of definition and display of the graphical path, and FIGS. 5L-5P represent times during the definition and display of the graphical path (e.g., after a graphical-path-initiating first user input and during the motion-based user input), transducers associated with selected transducer graphical elements 502g and 502h may be activated according to the instructions associated with block 614 at the time represented by FIG. 5M or any time thereafter (e.g., at the time of FIG. 5M, 5N, 5O, 5P, 5Q, or thereafter). In some embodiments, all of the transducers corresponding to selected transducer graphical elements 502 may be concurrently queued for activation according to the instructions associated with block 614 by a particular user input. For example, after the graphical path of FIG. 5Q is completed, the user may engage an "ablate" software button on the user interface to queue all of the transducers corresponding to the highlighted transducer graphical elements 502 in FIG. 5Q to cause tissue ablation. In some embodiments, such an "ablate" software button (or, more generally, the activation instructions associated with block 614) may be enabled for operation at least in response to a reception of a graphical-path-terminating second user input. Such an "ablate" software button need not be engaged only after path definition, however, and could be engaged during graphical path definition, display, or both, as discussed above. Note that queuing transducers for activation does not necessarily mean that all transducers will be activated concurrently or immediately, although this may be so in some embodiments. For example, in some embodiments, when a group of transducers are queued for tissue ablation, the transducers in the group are not activated for ablation concurrently, but are activated for ablation according to a sequence of sets of transducers to ensure proper tissue ablation and operate within hardware and driving constraints. For instance, if ablation occurs by way of delivery of energy from an energy source device system (e.g., energy source device system 340) to the respective transducers, it may be that the energy source device system is capable of transmitting tissue-ablative energy to (e.g., "driving") a predetermined number of transducers simultaneously, according to some embodiments. For example, if 20 transducers are queued for ablation, but only 8 transducers can be driven electrically at a time by the energy source device system, then the 20 transducers may be activated for ablation in sequential groups of 8, 8, and 4 or some other sequential grouping within the hardware constraints.

In some embodiments, the activation caused according to the instructions associated with block 614 is concurrent monopolar activation, initiated during or after completion of the definition of the graphical path. Monopolar activation can include activation for monopolar ablation or monopolar electrogram generation by way of non-limiting example. In some embodiments, an indifferent electrode (e.g., indifferent electrode 326) is provided (e.g., usually to an external surface or skin-based surface of a body) while the transducer-based device (e.g., 200, 300, 400) is received in a bodily cavity within the body. A portion of the tissue-ablating energy delivered to the respective transducer (e.g., 306, 406) corresponding to the selected transducer graphical element (e.g., 502) may be transmitted from the respective transducer to the indifferent electrode in a process typically referred to as monopolar ablation. In some embodiments, the activation caused according to the instructions associated with block 614 is bipolar tissue ablation, initiated during or after completion of the definition of the graphical path.

In some embodiments, (a) a portion of the energy delivered to a first transducer of the respective set of two or more of the transducers (e.g., first transducer 306) is transmitted by the first transducer, (b) a portion of the energy delivered to a second transducer of the respective set of two or more of the transducers (e.g., second transducer 306) is transmitted by the second transducer, or both (a) or (b). In some embodiments, (a) a portion of the energy delivered to a first transducer of the respective set of two or more of the transducers (e.g., first transducer 306) is transmitted by the first transducer to a second transducer of the respective set of two or more of the transducers (e.g., second transducer 306), (b) a portion of the energy delivered to the second transducer of the respective set of two or more of the transducers is transmitted by the second transducer to the first transducer, or both (a) or (b). In some example embodiments, a selected between graphical element (e.g., between graphical element 504) is representative of a physical path extending between a respective pair of the transducers associated with the selected between graphical element and the energy is sufficient for ablating a portion of tissue extending along the physical path. A portion of the tissue-ablating energy may be transmitted between the respective pair of the transducers in a process typically referred to as bipolar ablation. In some embodiments, an indifferent electrode (e.g., indifferent electrode 326) is provided (e.g., usually to an external surface of a body) while the transducer-based device is received in a bodily cavity within the body. Some of the tissue-ablating energy may be transmitted between the respective pair of the transducers while some of the tissue-ablating energy may be transmitted from various ones of the respective pair of the transducers to the indifferent electrode in a process typically referred to as blended monopolar-bipolar ablation. The term "bipolar ablation" as used in this disclosure is to be interpreted broadly to include blended monopolar-bipolar ablation in some embodiments.

In addition to embodiments where the instructions according to block 614 are configured to cause a data processing device system to cause bipolar ablation, the instructions according to block 614, in some embodiments, are configured to cause a data processing device system to cause multi-transducer monopolar ablation with the respective set of two or more of the transducers, e.g., dual monopolar ablation for two transducers, or triple monopolar ablation for three transducers. In such cases, for example, the respective set of two or more of the transducers may be 'queued' for monopolar ablation, such that monopolar ablation occurs for each transducer in the respective set of two or more of the transducers within some period of time, but not necessarily at the same time or even one immediately after another. In this regard, references herein to the occurrence of monopolar ablation for more than one transducer may include this multi-transducer monopolar ablation according to some embodiments. In addition, any reference herein to the occurrence of bipolar ablation may be replaced with the occurrence of dual monopolar ablation (or other multi-transducer monopolar ablation when more than two transducers are involved), according to some embodiments. In some cases in which multi-monopolar ablation is employed, energy transfer sufficient to cause tissue ablation is not transferred between the particular transducers employed by the multi-monopolar ablation. Rather, in these cases energy sufficient for tissue ablation is transmitted between each of these particular transducers and an indifferent electrode (e.g., indifferent electrode 326).

The activation according to the instructions associated with block 614 need not be for tissue ablation. In some embodiments, a sensing device system (e.g., provided at least in part by a number of the transducers 306, 406) is arranged to sense intra-cardiac information or physiological parameter information at a respective location at least proximate the respective transducer corresponding to a selected transducer graphical element with the energy delivered to the transducer as at least part of the activation. In this regard, in some embodiments, the instructions associated with block 614 that are, in some embodiments, configured to activate a respective transducer (e.g., 306, 406) corresponding to a selected transducer graphical element (e.g., 502) include instructions that are configured to cause a sensing device system (e.g., sensing device system 325) to detect electrophysiological activity (an example of intra-cardiac information in some embodiments) in an intra-cardiac cavity at a location at least proximate the respective transducer. The detected electrophysiological activity can be displayed as an intra-cardiac electrogram via the input-output device system (e.g. electrograms 535 shown in FIG. 5R). In some embodiments, detection of electrophysiological activity in an intra-cardiac cavity at a location at least proximate various ones of the transducers occurs continuously. In some embodiments, a sensing device system (e.g., sensing device system 325) is arranged to sense at least one tissue electrical characteristic (e.g., an example of intra-cardiac information) at respective locations at least proximate each transducer of the respective set or group of two or more of the transducers with the energy delivered to the respective set of two or more of the transducers. Other forms of activation of the respective transducer corresponding to the selected transducer graphical element are possible in other embodiments.

In some embodiments, the above-discussed sensing functionality of one or more transducers (e.g., 306, 406) occurs simultaneously with tissue-ablation performed by such one or more transducers, e.g., according to the instructions associated with block 614.

In some embodiments, the initiation, evolution, conclusion, or a combination thereof of the activation caused according to the instructions associated with block 614 may be represented in a displayed user interface (e.g., like that shown in various ones of FIG. 5) by a change in a visual characteristic set of the activated transducer graphical elements (e.g., 502). For example, FIG. 5X shows the various particular transducer graphical elements 502 and between graphical elements 504 selected as per various embodiments associated with various one of FIGS. 5L, 5M, 5N, 5P, 5P, 5Q, and 5R but after the corresponding transducers (e.g., 306, 406) have been activated (e.g., to transmit tissue ablation energy). In FIG. 5X, a visual characteristic set of the various particular transducer graphical elements 502 and between graphical elements 504 has changed (e.g., thicker and darker shading as compared with FIG. 5Q) indicating a particular state (e.g., initiation, an intermediate state, or a completion) associated with the activation of each of the corresponding transducers.

It should be noted that, with respect to every discussion of a change of visual characteristic or visual characteristic set discussed herein in various embodiments, other embodiments are not limited to any particular visual characteristic that may be changed. For example, such a visual characteristic may be, without limitation, a color, a color density, a shape, a texture, a location, etc. A visual characteristic set may be one or more visual characteristics, such that a change in a visual characteristic set may be a change in one or more visual characteristics.

In various embodiments, the graphical path is defined, at least in part, based on (a) a positional relationship between various ones of the graphical elements 501, (b) a positional relationship between various regions (e.g., 525) of a graphical representation of intra-cardiac information, (c) a positional relationship between various ones of the graphical elements 501 and various regions of the graphical representation of the intra-cardiac information, or a combination of two or more of (a), (b) and (c). Enhanced or more efficient selection of various graphical elements 501 may be achieved in some embodiments, which allow a respective graphical element 501 to be selected if user input (e.g., graphical-path-initiating first user input, motion-based user input, or graphical-path-terminating second user input, e.g., respectively pursuant to blocks 608a, 608b, and 608c) occurs within a display region associated with the respective graphical element 501, the display region including at least a portion that extends beyond at least a portion of its respective graphical element 501.

Figure 5S:
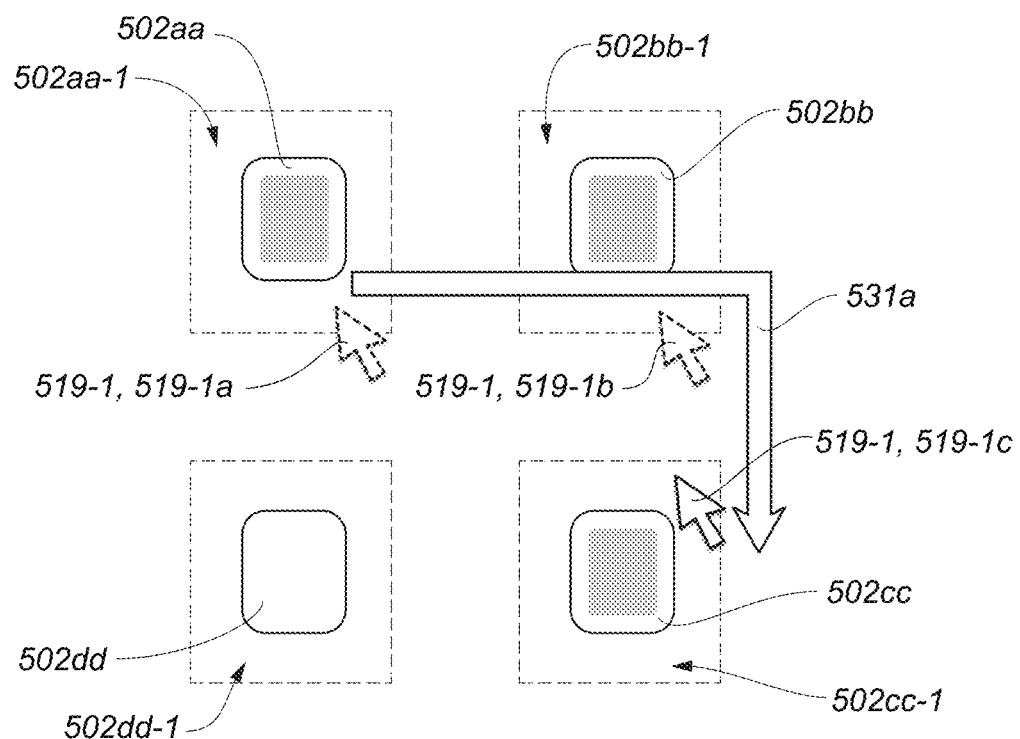
FIG. 5S shows a selection of particular transducer graphical elements made in response of a first motion-based user input according to various example embodiments.
Figure 5T:
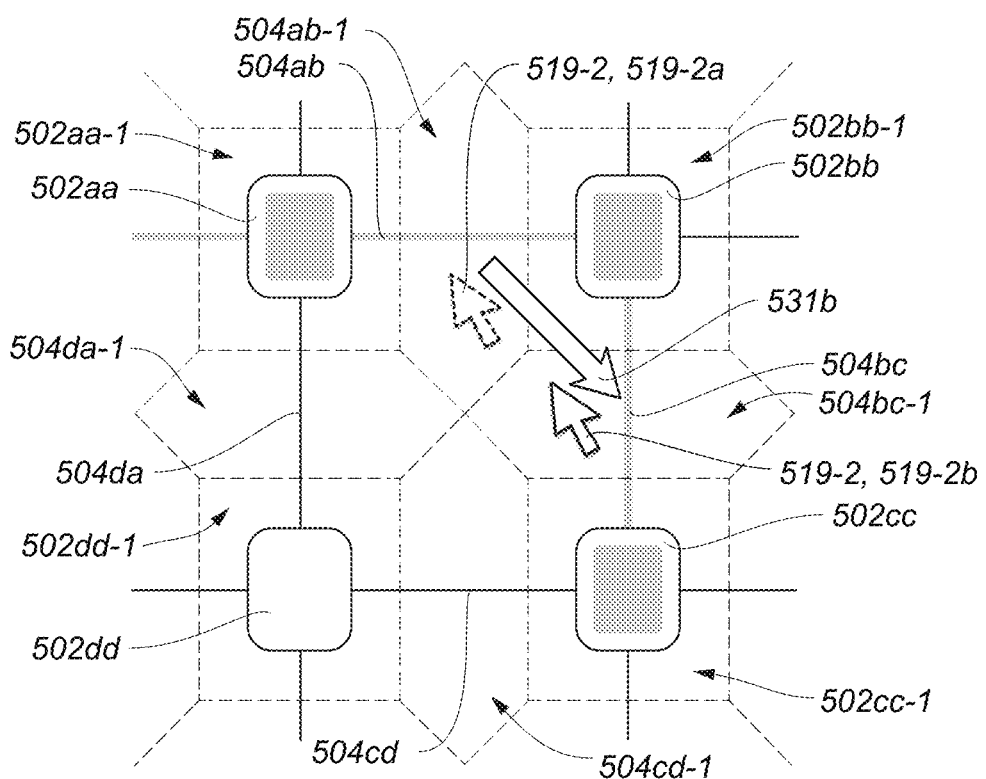
FIG. 5T shows a selection of the particular transducer graphical elements of FIG. 5S but selected in response of a second motion-based user input according to various example embodiments.

For example, each of FIGS. 5S and 5T shows a plurality of transducer graphical elements (e.g., similar to some transducer graphical elements 502 shown in various other ones of FIG. 5) including transducer graphical elements 502aa, 502bb, 502cc, 502dd (collectively, transducer graphical elements 502). Each of the transducer graphical elements 502aa, 502bb, 502cc, 502dd resides, at least in part, within a respective one of display regions 502*aa*-1, 502*bb*-1, 502*cc*-1, and 502*dd*-1 (e.g., shown in broken lines in these particular illustrated embodiments). In these embodiments, each of the transducer graphical elements 502 does not occupy the entirety, or all, of its respective display region. In addition to the transducer graphical elements included in FIG. 5S, FIG. 5T additionally includes a plurality of between graphical elements (e.g., similar to some between graphical elements shown in various other ones of FIG. 5) including between graphical elements 504*ab*, 504*bc*, 504*cd*, and 504*da* (collectively, between graphical elements 504), each of the between graphical elements arranged between a respective adjacent pair of the transducer graphical elements 502. In FIG. 5T, each of the between graphical elements 504*ab*, 504*bc*, 504*cd*, and 504*da* resides, at least in part, within a respective one of the display regions 504*ab*-1, 504*bc*-1, 504*cd*-1, and 504*da*-1 (e.g., shown in broken lines in these particular illustrated embodiments). In these embodiments, each of the between graphical elements 504 does not occupy the entirety, or all, of its respective display region. It should be noted that, in some embodiments that do not include between graphical elements 504, which may be represented by FIG. 5S, in some embodiments, the display regions associated with the transducer graphical elements 502 may contact each other, unlike FIG. 5S.

In some embodiments encompassing FIGS. 5S and 5T, a selection of transducer graphical elements is indicated at least by user input, such as, but not limited to first user input (e.g., graphical-path-initiating first user input), motion-based user input, or second user input (e.g., graphical-path-terminating second user input), e.g., respectively pursuant to blocks 608*a*, 608*b*, and 608*c* in FIG. 6A. For example, first user input (e.g., a graphical-path-initiating first user input) according to block 608*a* may occur at the display-screen-location 519-1*a* where the broken-line cursor 519-1 in FIG. 5S is located. In this regard, the instructions associated with block 610*a* in FIG. 6A may be configured to cause the data processing device system (e.g., 110, 310) to analyze such display-screen-location (an example of a parameter in a first parameter set associated with the first user input) in relation to one or more of the transducer graphical elements 501. For example, in some embodiments, the data processing device system may compare such display-screen-location to the display regions associated with the graphical elements to determine a display region in which the display-screen-location of the first user input occurs. In the example of FIG. 5S, the display-screen-location 519-1*a* associated with the first user input is determined to be located in region 502*aa*-1 associated with transducer graphical element 502*aa*. Consequently, the instructions associated with block 610*a* in FIG. 6A may configure the data processing device system to identify the transducer graphical element 502*aa* as the first location on the graphical path.

Similarly, because the motion-based user input (e.g., according to block 608*c*) passes through display region 502*bb*-1 (e.g., includes a display-screen-location 519-1*b*, which is an example of a parameter in a parameter set, within such display region 502*bb*-1), as shown by broken-line cursor 519-1 in the direction illustrated by arrow 531*a*, the instructions associated with block 610*c* in FIG. 6A may configure the data processing device system to identify the transducer graphical element 502*bb* as another location on the graphical path, according to some embodiments. Further, a second user input (e.g., a graphical-path-terminating second user input) might occur at the display-screen-location 519-1*c* (an example of a parameter in a second parameter set associated with the second user input) of cursor 519-1, which is within the display region 502*cc*-1 of transducer graphical element 502*cc*. In this regard, the instructions associated with block 610*b* in FIG. 6A may configure the data processing device system to identify the transducer graphical element 502*cc* as yet another location on the graphical path, according to some embodiments. As shown in FIGS. 5S and 5T, a visual characteristic set of each of transducer graphical elements 502*aa*, 502*bb*, and 502*cc* has been changed (for example, as compared with unselected transducer graphical element 502*dd*) in a manner similar to, or the same as, that indicated by various other selected transducer graphical elements 502 shown in various other ones of FIG. 5. Additional information 521 is not shown in FIGS. 5S and 5T for clarity, although it is understood that information 521 may or may not be included in other embodiments.

In FIG. 5T, transducer graphical elements 502*aa*, 502*bb*, and 502*cc* are selected by employing a motion-based user input that moves a mouse cursor 519-2 along a path (e.g., schematically represented by arrow 531*b* in some embodiments) sequentially through display regions 504*ab*-1 and 504*bc*-1 of between graphical elements 502*ab*-1 and 502*bc*-1. That is, in some embodiments, transducer graphical elements 502*aa*, 502*bb*, and 502*cc* may be indirectly selected in response to a user selection of between graphical elements 504*ab* and 504*bc*. Advantageously, the user-input(s) required to select transducer graphical elements 502*aa*, 502*bb*, and 502*cc* in FIG. 5T may be simpler and shorter (e.g., as schematically represented by the non-jogged shape of arrow 531*b* and the overall length of arrow 531*b*) as compared with the user input(s) required to individually select transducer graphical elements 502*aa*, 502*bb*, and 502*cc* in FIG. 5S (e.g., as schematically represented by the jogged shape of arrow 531*a* and the longer overall length of arrow 531*a*). It is noted that, in some embodiments, upon selection, a visual characteristic set of each directly selected between graphical element 504*ab* and 504*bc* is changed (e.g., as compared with unselected between graphical elements 504*cd* and 504*da*) along with a change in a visual characteristic set of transducer graphical elements 502*aa*, 502*bb*, and 502*cc*. Changes in the visual characteristic set of various graphical elements in FIGS. 5S and 5T may be made in accordance with the instructions associated with block 612 in some embodiments. In FIG. 5T at least one of the display regions (e.g., 502*aa*-1) has different dimensions or sizes than another of the display regions (e.g., 504*ab*-1). In FIG. 5T at least one of the display regions (e.g., 502*aa*-1) has a different shape than another of the display regions (e.g., 504*ab*-1).

In some embodiments associated with FIGS. 5S and 5T, each of the selections (e.g., direct or indirect) of transducer graphical elements 502*aa*, 502*bb* and 502*cc* may be made in response to the path traced by the motion-based user input without any additional control element activation or deactivation (e.g., a mouse button click or de-click). It is noted that, intra-cardiac information similar to that shown in various other ones of FIG. 5 is not displayed in FIGS. 5S and 5T for clarity. Intra-cardiac information may or may not be additionally displayed in various embodiments.

Figure 5U:
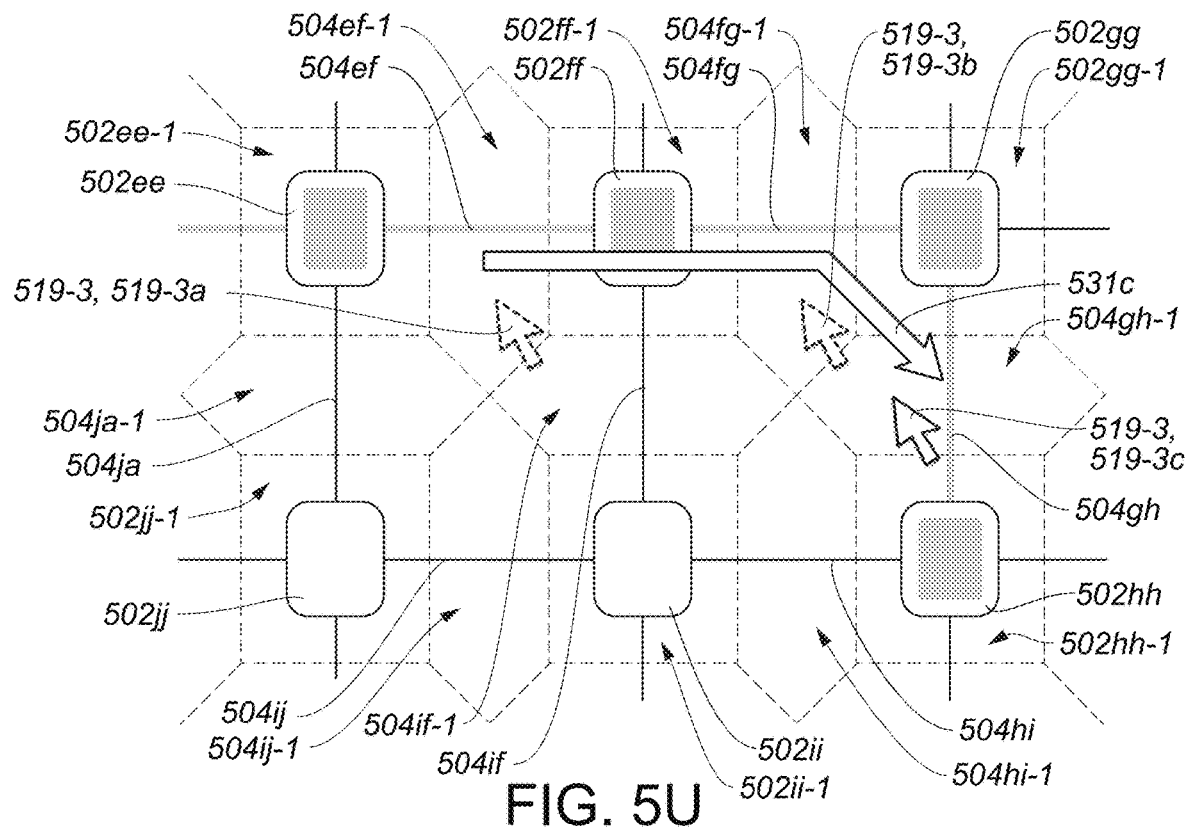
FIG. 5U shows a set of graphical elements or graphical-path-elements selected according to an interim-path definition of a graphical path.
Figure 5V:
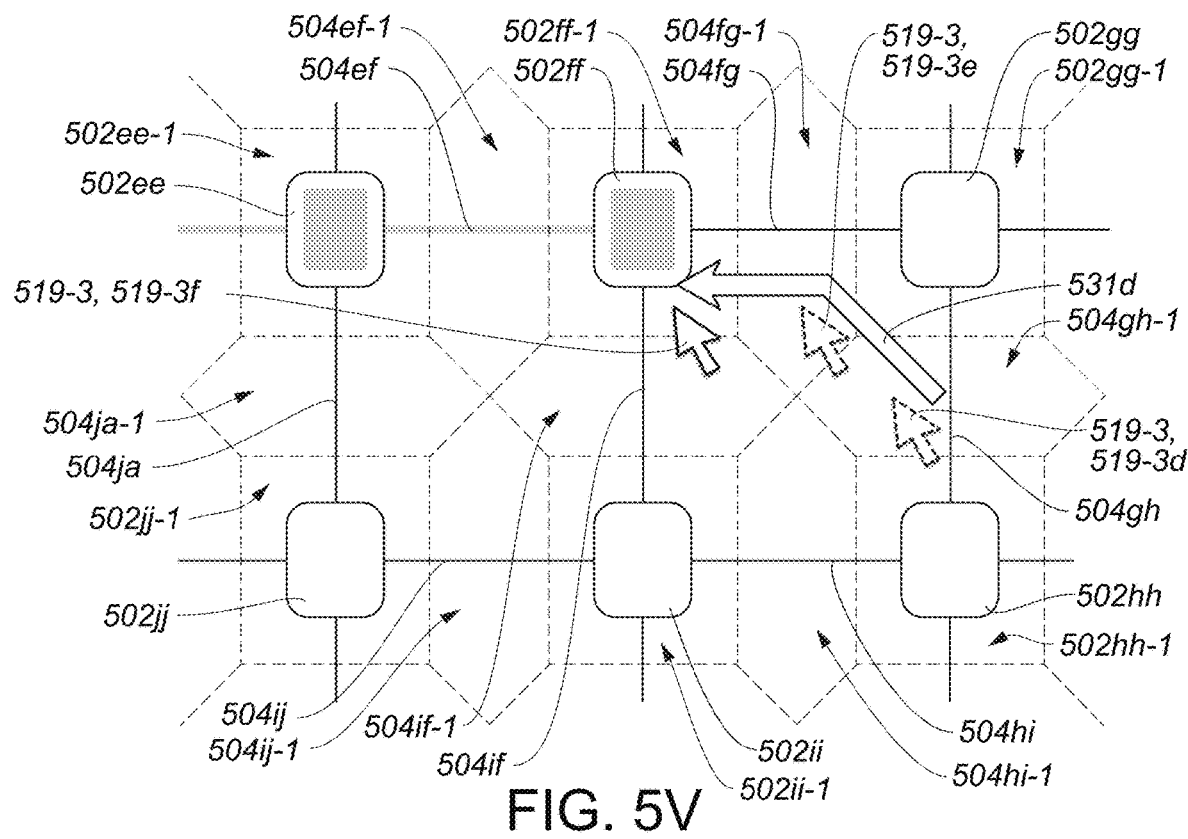
FIG. 5V shows at least some of the graphical elements or graphical-path-elements selected in FIG. 5U deselected according to a modified-interim-path definition of the graphical path.
Figure 5W:
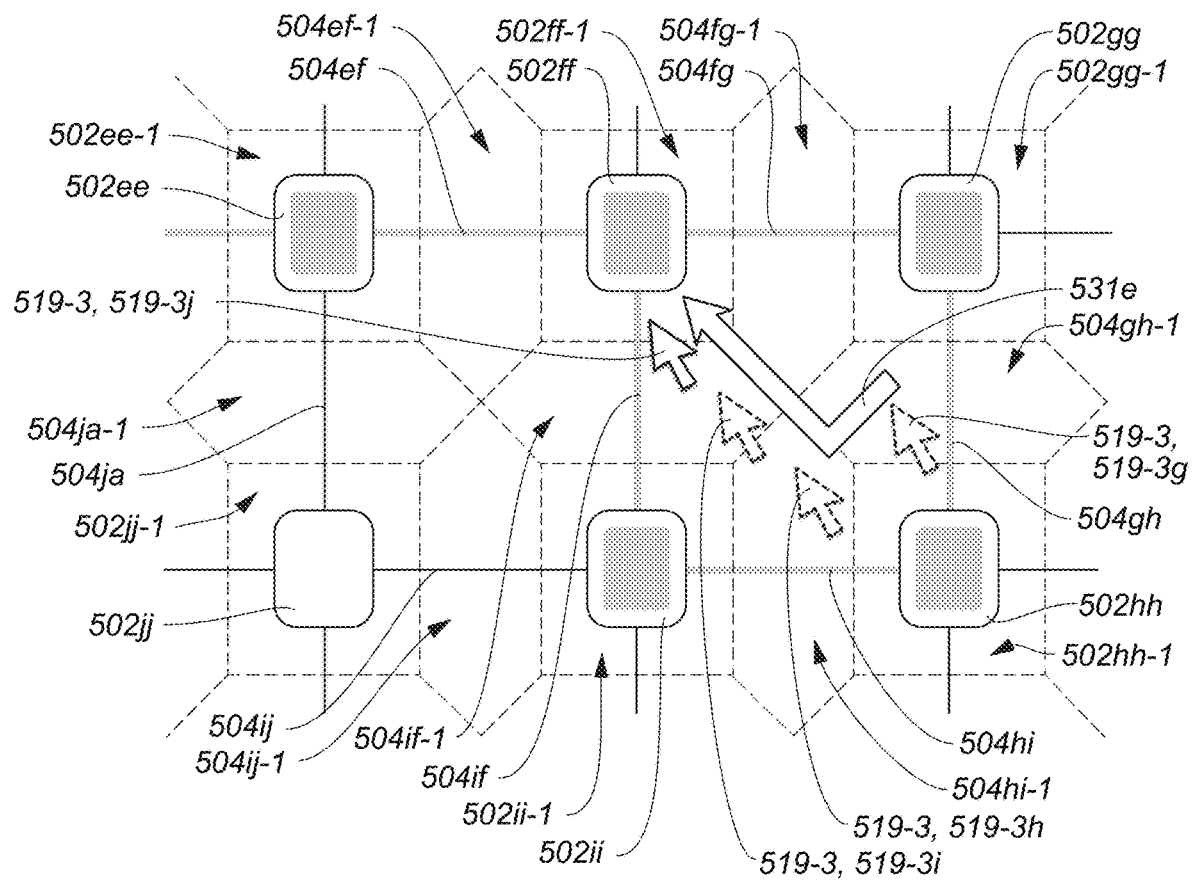
FIG. 5W shows each of the graphical elements or graphical-path-elements selected in FIG. 5U remaining selected when a portion of the graphical path is not retraced through the respective display regions of various ones of the graphical elements or graphical-path-elements.
Figure 5X:
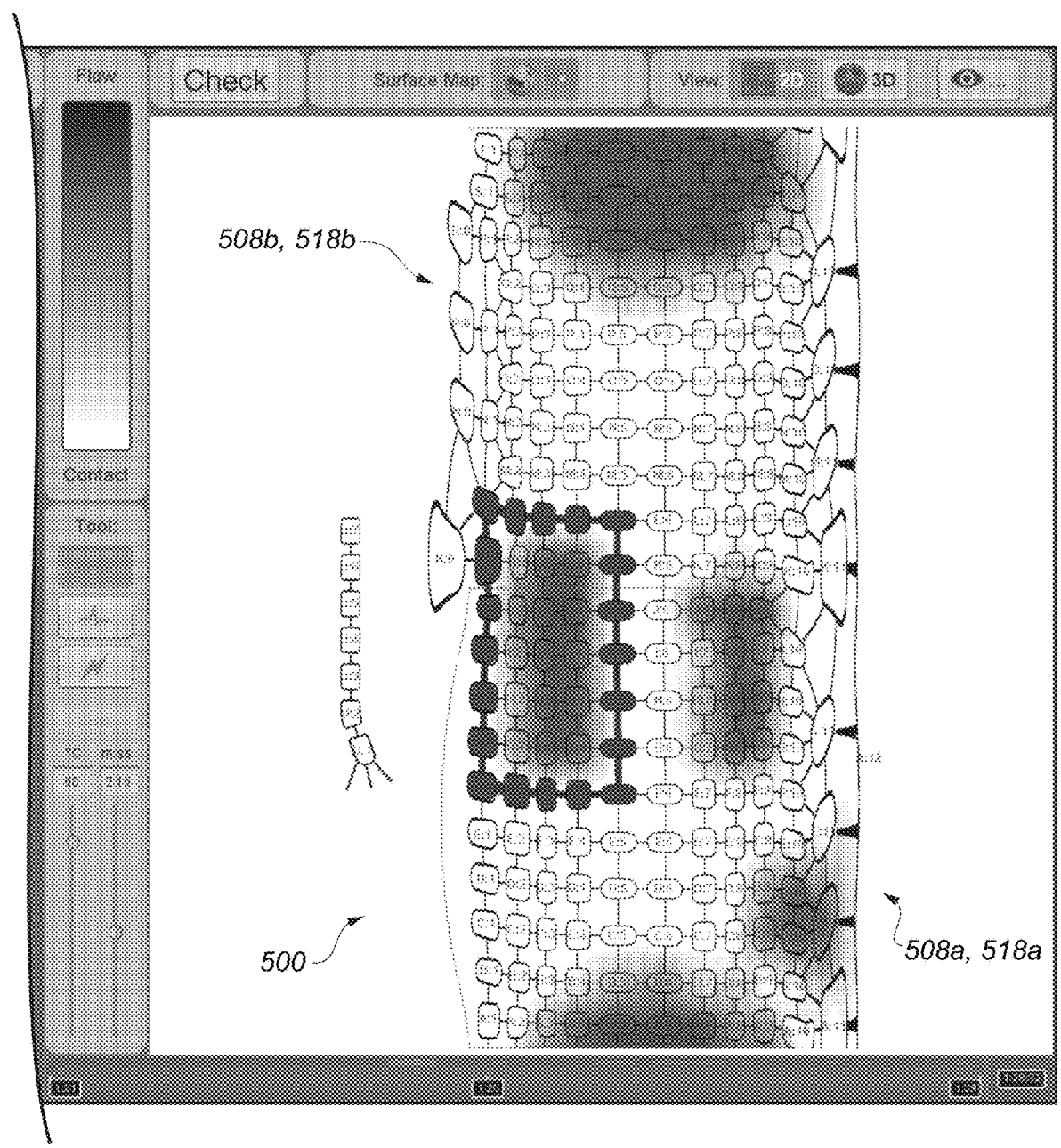
FIG. 5X illustrates the graphical representation provided by the graphical interface of FIG. 5Q but with change in visual characteristic set of the selected graphical elements or selected graphical-path-elements.

With respect to FIGS. 5U, 5V, and 5W, in some embodiments, each of a plurality of transducer graphical elements 502*ee*, 502*ff*, 502*gg*, 502*hh*, 502*ii*, and 502*jj* resides, at least in part, within a respective one of display regions 502*ee*-1, 502*ff*-1, 502*gg*-1, 502*hh*-1, 502*ii*-1, and 502*jj*-1 (e.g., shown in broken lines in these particular illustrated embodiments). In addition to these transducer graphical elements, FIGS. 5U, 5V, and 5W includes a plurality of between graphical elements (e.g., similar to some between graphical elements shown in various other ones of FIG. 5) including between graphical elements 504*ef*, 504*fg*, 504*gh*, 504*hi*, 504*ij*, 504*ja*, and 504*if* (collectively, between graphical elements 504), each of the between graphical elements arranged between a respective adjacent pair of the transducer graphical elements 502. In FIGS. 5U, 5V, and 5W, each of the between graphical elements 504*ef*, 504*fg*, 504*gh*, 504*hi*, 504*ij*, 504*ja*, and 504*if* resides, at least in part, within a respective one of the display regions 504*ef*-1, 504*fg*-1, 504*gh*-1, 504*hi*-1, 504*ij*-1, 504*ja*-1, and 504*if*-1 (e.g., shown in broken lines in these particular illustrated embodiments). In these embodiments, each of the transducer graphical elements 502 and each of the between graphical elements 504 does not occupy the entirety, or all, of its respective display region.

With respect to FIG. 5U, in some embodiments, a plurality of selectable graphical-path-elements (e.g., at least 504*ef*, 502*ff*, 504*fg*) are concurrently displayed with the graphical representation of intra-cardiac information (not shown in FIG. 5U, but shown, e.g., with respect to FIGS. 5G-5R and 5X). In this regard, in some embodiments, the graphical path includes a group of the graphical-path-elements (e.g., at least 504*ef*, 502*ff*, 504*fg*) in response to a path traced by motion-based user input or a portion thereof (e.g., at least a portion of the path traced by mouse cursor 519-3 from location 519-3*a* to location 519-3*b*) passing through a respective predetermined display region associated with each of at least one graphical-path-element of the group of graphical-path-elements (e.g., at least region 504*ef*-1, region 502*ff*-1, or region 504*fg*-1), the respective predetermined display regions of at least two of the group of the graphical-path-elements having different shapes (e.g., region 504*fg*-1 has a different shape than region 502*ff*-1). In some embodiments, one of the plurality of graphical-path-elements (e.g., graphical element 502*ff*) includes the third location (e.g., an internal or intermediate location in the graphical path) defined according to the instructions associated with block 610*c*.

In various embodiments, the analysis (which may be included as part of the instructions associated with blocks 610*a*, 610*b*, 610*c*) of the display-screen location (e.g., a display-screen location associated with a first user input, motion-based user input, or second user input, e.g., respectively pursuant to blocks 608*a*, 608*b*, and 608*c*) in relation to one or more of the graphical elements 501 (e.g., one or more transducer graphical elements 502 or one or more between graphical elements 504) includes determining a proximity between the display-screen location and each of one or more graphical elements 501. The one or more graphical elements may include, in some embodiments, two or more of the graphical elements (e.g., two or more of the transducer graphical elements 502 or two or more of the between graphical elements 504), and the analysis of the display-screen location in relation to the two or more of the graphical elements 501 may include defining the respective location (e.g., first location, second location, or third location pursuant to blocks 610*a*, 610*b*, 610*c*) on the graphical path as a location of a particular one of the two or more graphical elements 501 in closest proximity to the display-screen location.

For example, a first user input at display-screen location 519-1*a* in FIG. 5S is closest to transducer graphical element 502*aa*, so transducer graphical element 502*aa* may be determined by the data processing device system, according to the instructions associated with block 610*a*, to be a first location in the graphical path, according to some embodiments. For another example, a user input occurring at cursor location 519-2*a* in FIG. 5T is closest to between graphical element 504*ab*, so between graphical element 504*ab* may be determined by the data processing device system, according to the instructions associated with block 610*c*, to be a location in the graphical path, according to some embodiments. Continuing this example, according to some embodiments, since the closest graphical element is a between graphical element 504*ab*, the data processing device system may be configured to also determine that the transducer graphical elements 502*aa* and 502*bb* associated with the between graphical element 504*ab* are to be included in the graphical path. Since transducer graphical elements 502*aa* may have already been part of the graphical path (e.g., due to an earlier selection via the motion-based user input, or in some other embodiments via a previous first user input), such transducer graphical elements 502*aa* may be neglected, and only transducer graphical element 502*bb* would additionally be added to the graphical path, according to some embodiments.

In view of the above-discussions with respect to FIGS. 5S and 5T, when a path traced by motion-based user input (e.g., per arrow 531*a* or arrow 531*b*) is away from an adjacent or closest graphical element (e.g., 501), the path traced by the motion-based user input may be considered to "snap" to the adjacent or closest graphical element due to the change in visual characteristics and inclusion of the adjacent or closest graphical element. For example, although the path traced by the motion-based user input in FIG. 5T moves in a diagonal direction according to arrow 531*b*, the graphical path follows a slightly different route including transducer graphical element 502*aa*, between graphical element 504*ab*, transducer graphical element 502*bb*, between graphical element 504*bc*, and transducer graphical element 502*cc*. In this regard, it may be considered that the path traced by the motion-based user input snaps to the defined and displayed graphical path, according to some embodiments. Similarly, it may be considered that the user input at the location 519-2*a* of cursor 519-2 snaps to between graphical element 504*ab*, and that the user input at the location 519-2*b* of cursor 519-2 snaps to between graphical element 504*bc*, according to some embodiments. In some embodiments, a snapping to a between graphical element (e.g., 504*ab*) also causes a concurrent snapping to one or more associated transducer graphical elements (e.g., at least 502*bb*).

In some embodiments, path definition instructions (e.g., associated with block 610*c* or 610-1*c*) are configured to cause the path traced by the motion-based user input or a portion thereof to snap to a transducer graphical element (e.g., 502) or a portion thereof in response to the path traced by the motion-based user input or the portion thereof being away from the transducer graphical element but within a predetermined distance from the transducer graphical element or a part thereof. The predetermined distance may define the outer limits of the respective display region (e.g., 502*aa*-1 for transducer graphical element 502*aa*), according to some embodiments.

In some embodiments, the path definition instructions are configured to cause an elongate path portion of the graphical path (e.g., defined according to motion-based user input per, e.g., blocks 608*c* and 610*d* in FIG. 6A) to include a transducer graphical element (e.g., 502) or a portion thereof in response to the path traced by the motion-based user input or a portion thereof being away from the transducer graphical element but within a predetermined display region associated with the transducer graphical element. In this regard, it should be noted that a graphical path might include only a portion of a graphical element (e.g., 501) in some embodiments. For example, FIG. 5T shows a graphical path portion represented, at least in part, by highlighting of transducer graphical element 502*aa*, between graphical element 504*ab*, transducer graphical element 502*bb*, between graphical element 504*bc*, and transducer graphical element 502*cc*. In this regard, the highlighting in each of transducer graphical elements 502*aa*, 502*bb*, and 502*cc* does not occupy the entirety of the interior region of the respective transducer graphical elements. Such a circumstance is an example where the graphical path includes only a portion of a graphical element included in the graphical path. In this regard, the graphical path illustrated in FIG. 5T by highlighting of respective graphical elements is an example of a graphical path having an interrupted form, because the highlighting of the respective transducer graphical elements 502 does not contact the highlighting of the adjacent between transducer graphical element(s) 504. For another example, FIG. 5S shows highlighting within selected transducer graphical elements 502*aa*, 502*bb*, and 502*cc*, with non-highlighted gaps between respective display regions 502*aa*-1, 502*bb*-1, and 502*cc*-1, such gaps adding to an interrupted form of a graphical path, in some embodiments.

In some embodiments, the path definition instructions are configured to cause the elongate path portion of the graphical path to include a transducer graphical element or a portion thereof in response to the path traced by the motion-based user input or a portion thereof passing through a predetermined display region associated with the transducer graphical element, the predetermined display region including at least a part of the transducer graphical element, and the transducer graphical element not occupying all of the predetermined display region.

In some embodiments, the path definition instructions are configured to cause the elongate path portion of the graphical path to include a transducer graphical element or a portion thereof in response to the path traced by the motion-based user input or a portion thereof being away from the transducer graphical element but within a predetermined distance from the transducer graphical element or a part thereof.

In some embodiments, the path definition instructions are configured to cause the path traced by the motion-based user input or a portion thereof to snap to a particular between graphical element (e.g., 504) or a portion thereof in response to the path traced by the motion-based user input or the portion thereof being away from the particular between graphical element but within a predetermined distance from the particular between graphical element or a part thereof.

In some embodiments, the path definition instructions are configured to cause an elongate path portion of the graphical path (e.g., defined according to motion-based user input per, e.g., blocks 608*c* and 610*d* in FIG. 6A) to include a particular between graphical element or a portion thereof in response to the path traced by the motion-based user input or a portion thereof being away from the particular between graphical element but within a predetermined display region associated with the particular between graphical element.

In some embodiments, the path definition instructions are configured to cause the elongate path portion of the graphical path to include a particular between graphical element or a portion thereof in response to the path traced by the motion-based user input or a portion thereof passing through a predetermined display region associated with the particular between graphical element, the predetermined display region including at least a part of the particular between graphical element, and the particular between graphical element not occupying all of the predetermined display region.

In some embodiments, the path definition instructions are configured to cause the elongate path portion of the graphical path to include a particular between graphical element or a portion thereof in response to the path traced by the motion-based user input or a portion thereof being away from the particular between graphical element but within a predetermined distance from the particular between graphical element or a part thereof.

In some embodiments, the above-discussed 'snapping' of a user-input display screen location to a graphical element, when the user-input display screen location is away from the graphical element but within a predetermined display region associated with the graphical element, need not only apply to motion-based user input. In this regard, such 'snapping' may apply to stationary user input, in some embodiments, such as a mouse click, a touch-screen contact, or other user input associated with a display screen location, to select a graphical element that is away from the display screen location, but the display screen location is within a predetermined display region associated with the graphical element.

In some cases, a user may desire to adjust or revise the graphical path during the definition or generation of the graphical path. For example, in some embodiments employing arrays of hundreds of graphical elements such as those shown in various graphical elements 501 of FIG. 5, numerous choices are presented to a user (e.g., a health care practitioner or technician) as to which of these numerous graphical elements should or should not be located on the graphical path or form part of the graphical path. In many cases, a particular set of one or more graphical elements may be deemed to be incorrectly chosen. For example, one or more graphical elements may be mistakenly chosen through an unintended manipulation of a particular user input control element or upon receipt of updated intra-cardiac information (e.g., physiological information) during or after the selection, the updated intra-cardiac information indicating or suggesting that a better selection can be made. In some embodiments, the graphical path definition instructions associated with block 610 further include path adjustment instructions (e.g., associated with block 610*e*) configured to adjust (e.g., reduce) a size of at least an elongate path portion (e.g., defined according to motion-based user input per, e.g., 610*d*) of the graphical path.

In various embodiments, the path adjustment instructions associated with block 610*e* are configured to adjust a size of the elongate path portion in response to a user-based retracing of a portion of the path traced by the motion-based user input. Adjusting a size of the elongate path portion may include a path reduction that still allows for at least some of the elongate path portion or at least some part of the graphical path to be maintained. In some embodiments, the instructions associated with block 610*e* are configured to adjust the size of the elongate path portion of the graphical path so long as a graphical path terminating input (e.g., a second user input that places the first user input element in a deactivated state) has not been received (for example, as per the instructions associated with block 608*b*). For example, in some embodiments, various instructions that, in response to the reception of the second user input, indicate a termination point in the graphical path or indicate a termination of the graphical path generation process, may preclude reducing a size of the elongate path portion at least based on a retracing of a portion of the path traced by the motion-based user input. In this regard, in some embodiments, the instructions associated with block 610e are configured to adjust (e.g., reduce) the size of the elongate path portion of the graphical path so long as a second location or locations (e.g., a set of graphical elements 501) on the graphical path has not been defined according to a second parameter set associated with a graphical-path-terminating second user input (for example, as per the instructions associated with block 610b). In some embodiments, other adjustment instructions responsive to other user inputs may be configured to adjust (e.g., reduce) a portion of the graphical path. For example, other instructions may include instructions that may cause an undoing of at least the entirety of the elongate path portion.

In some embodiments, the motion-based user input (e.g., according to the instructions associated with block 608c) indicates a selection of a group of transducer graphical elements (e.g., 502). In some of these embodiments, the instructions associated with block 610e may include de-selection instructions configured to deselect at least one transducer graphical element in the group of the transducer graphical elements in response to a user-based retracing of a portion of the path traced by the motion-based user input.

Figure 6F:
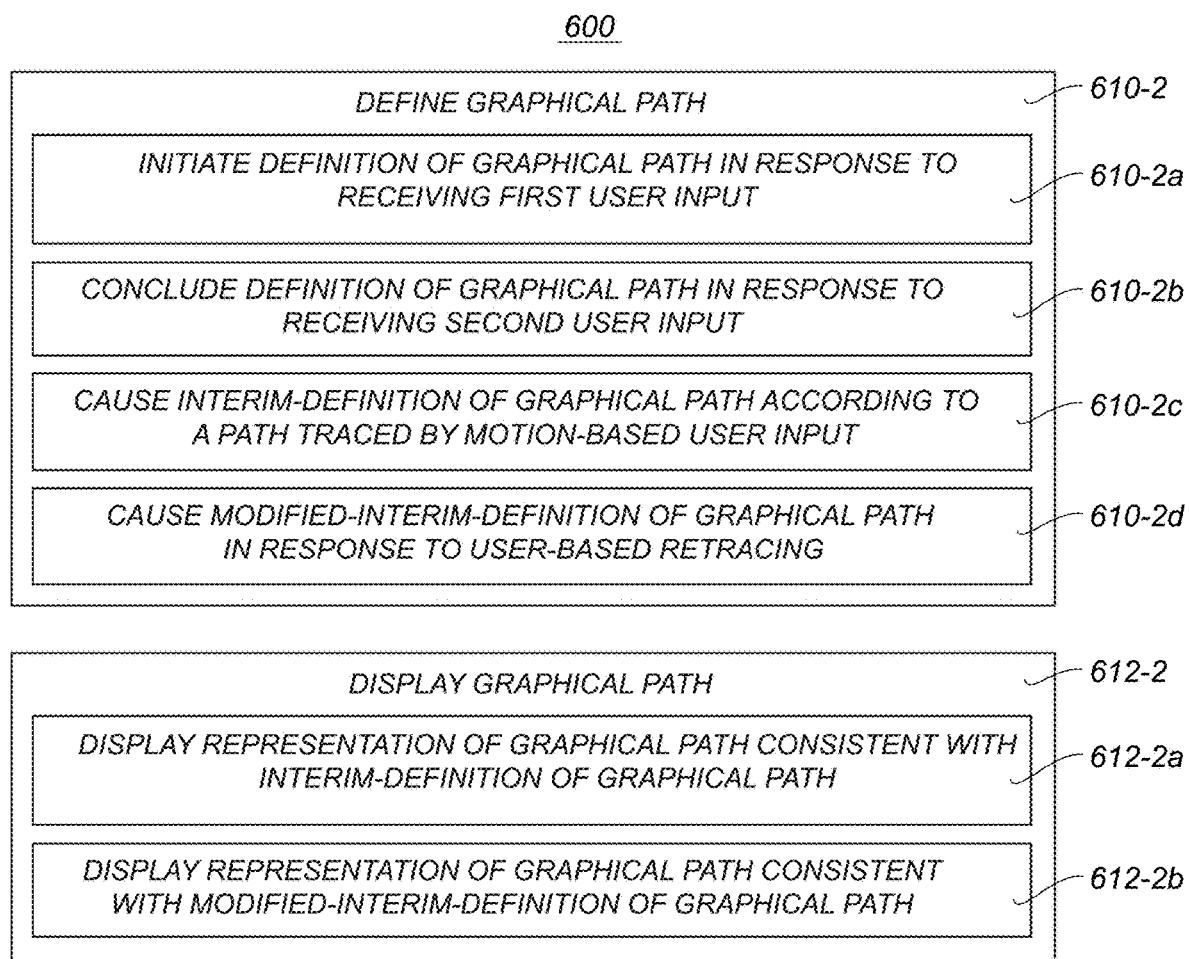
FIG. 6F includes an exploded view of some of the blocks of FIG. 6A according to some example embodiments.

FIG. 6F shows an exploded view of blocks of at least some of the instructions of method 600 employed according to various aspects of block 610e in FIG. 6A, according to some embodiments. FIG. 6F includes a set of instructions associated with block 610-2 and a set of instructions associated with block 612-2. Block 610-2 shows an exploded view of path definition instructions of block 610 as employed in some embodiments. Block 612-2 shows an exploded view of the graphical path display instructions associated with block 612 as employed in some embodiments. The instructions associated with block 610-2 define a graphical path that includes a plurality of elements or graphical-path-elements in some embodiments. For the ease of convenience, reference is made to various ones of graphical elements 501 (e.g., various ones of transducer graphical elements 502, various one of between graphical elements 504, or both). It is understood however, that other embodiments may employ other forms of graphical elements or graphical-path-elements. Additionally, it is noted in various embodiments, a particular graphical element or graphical-path element may not necessarily be visible (e.g., visibly displayed by an input-output device system) prior to selection. For example, in some embodiments, various graphical elements along the path or various graphical-path-elements forming at least part of the path may not be made visible until indicated by some form of user input (e.g., a motion-based user input received, for example, in accordance with the instructions associated with block 608c).

Block 610-2a is associated with, in some embodiments, instructions configured to initiate the graphical path at least in response to receiving first user input (e.g., first user input that places a first user input element into an activated state, for example, as received by the instructions associated with block 608a). In this regard, block 610-2a may encompass at least block 610a in FIG. 6A, 610-1a in FIG. 6E, or both. Block 610-2c is associated with, in some embodiments, instructions configured to define an interim-definition of the graphical path according to a path traced by motion-based user input (e.g., motion-based user input received in accordance with the instructions associated with block 608c). In this regard, block 610-2c may correspond at least to or encompass at least block 610c in FIG. 6A, 610-1c in FIG. 6E, or both. The displayed graphical representation of the graphical path, as defined by the interim-definition, is discussed below with respect to FIG. 5U. Block 610-2b is associated with, in some embodiments, instructions configured to cause conclusion of the definition of the graphical path in response to receiving second user input (e.g., second user input that places a first user input element into a deactivated state, for example, as received by the instructions associated with block 608b). In this regard, block 610-2b may encompass at least block 610b in FIG. 6A, 610-1b in FIG. 6E, or both.

In various embodiments, each of the graphical elements or graphical-path-elements includes a respective display region, and an indication or identification or a status determination (e.g., visible/non-visible or selected/not selected) of each of the graphical elements or graphical-path-elements occurring in response to the selection of the respective display region. In some embodiments, each display region includes at least a portion of a respective graphical element or graphical-path-element. In some embodiments, each display region includes all of a respective graphical element or respective graphical-path-element. In some embodiments, the respective graphical element or graphical-path-element occupies all of its respective display region. In some embodiments, the respective graphical element or respective graphical-path-element does not occupy all of its respective display region.

In various embodiments, display instructions (e.g., display instructions associated with block 612-2a) are provided and are configured to cause an input-output device system (e.g., 120, 320) to display, prior to the conclusion of the definition of the graphical path, a graphical representation of the graphical path including the identified plurality of graphical elements or the identified plurality of graphical-path-elements consistent with the interim-definition (e.g., block 610-2c) of the graphical path. In some embodiments, a visual characteristic set of the respective graphical element or respective graphical-path-element changes upon selection (e.g., a selection made on the basis of the first user input, the second user input, or the motion-based user input as described above).

In various embodiments, the instructions associated with block 610-2d are configured to cause generation of a modified-interim-definition of the graphical path prior to the conclusion of the definition of the graphical path. In this regard, block 610-2d may correspond at least to or encompass at least block 610c in FIG. 6A, 610-1c in FIG. 6E, or both. The displayed graphical representation of the graphical path, as defined by the modified-interim-definition, is discussed below with respect to FIG. 5V. In various embodiments, the modified-interim-definition of the graphical path excludes at least one of the identified plurality of graphical elements or graphical-path-elements in response to a user-based retracing of a portion of the path traced by the motion-based user input. In some of these various embodiments, the excluded at least one of the identified plurality of graphical elements or graphical-path-elements are those whose associated display regions have been passed through by the retracing of the portion of the path traced by the motion-based user input. In various embodiments, the display instructions (e.g., display instructions associated with block 612) are configured to cause the input-output device system (e.g., 120, 320) to change the display of the graphical representation of the graphical path to account for the excluded at least one of the identified plurality of the graphical elements or graphical-path-elements consistent with the modified-interim-definition of the graphical path.

For example, in FIG. 5U, a graphical representation of graphical path including a plurality of graphical elements or graphical-path-elements is displayed prior to the conclusion of the definition of the graphical path (e.g., prior to an execution of the instructions associated with block 610-2*b*), the selection of graphical elements or graphical-path-elements identified or indicated as per an interim-definition of the graphical path generated according to a path traced by a motion-based user input (for example, as per the instructions associated with block 610-2*c*). In particular, the interim-definition of the graphical path identifies a selection of transducer graphical elements 502*ee*, 502*ff*, 502*gg*, and 502*hh* (e.g., selected from a group of transducer graphical elements 502*ee*, 502*ff*, 502*gg*, 520*hh*, 502*ii*, and 502*jj* (collectively transducer graphical elements 502) in FIG. 5U). It is noted that, upon selection, a visual characteristic set of each of transducer graphical elements 502*ee*, 502*ff*, 502*gg*, and 502*hh* has been changed (for example, as compared with unselected transducer graphical elements 502*ii*, 502*jj*) in a manner similar to, or the same as that indicated by various other selected transducer graphical elements 502 shown in various other ones of FIG. 5. Additional information 521 is not shown in FIGS. 5U, 5V and 5W for clarity, although it is understood that information 521 may or may not be included in other embodiments.

In FIG. 5U, transducer graphical elements 502*ee*, 502*ff*, 502*gg*, and 502*hh* are selected by employing a motion-based user input that moves a mouse cursor 519-3 along a path (e.g., schematically represented by arrow 531*c* in some embodiments) sequentially through display regions 504*ef*-1, 504*fg*-1, and 504*gh*-1 of between graphical elements 504*ef*, 504*fg*, and 504*gh*. That is, in some embodiments, transducer graphical elements 502*ee*, 502*ff*, 502*gg*, and 502*hh* are indirectly selected in response to a user selection of between graphical elements 504*ef*, 504*fg*, and 504*gh*. In some embodiments, between graphical elements 504*ef*, 504*fg*, and 504*gh* also form part of the graphical elements or graphical-path-elements identified or indicated by the interim-definition of the graphical path. In some embodiments, each of the between graphical elements 504*ef*, 504*fg*, and 504*gh* along with each of the transducer graphical elements 502*ee*, 502*ff*, 502*gg*, and 502*hh* is identified or indicated as a graphical element or graphical-path-element forming part of, or included in the graphical path in accordance with the interim definition of the graphical path.

In some embodiments, each of the between graphical elements 504*ef*, 504*fg*, and 504*gh* along with each of the transducer graphical elements 502*ee*, 502*ff*, 502*gg*, and 502*hh* is selected as the mouse cursor 519-3 moves along sequentially from position 519-3*a* (indicated by mouse cursor 519-3 shown in broken lines) to 519-3*b* (indicated by mouse cursor 519-3 shown in broken lines) to 519-3*c* (indicated mouse cursor 519-3 shown in solid lines) along a path (e.g., schematically represented by arrow 531*c*) traced by the motion-based user input, thereby providing the interim-definition of the graphical path. In some embodiments, each of the locations 519-3*a*, 519-3*b*, and 519-3*c* is in a respective one of the display regions 504*ef*-1, 504*fg*-1, and 504*gh*-1 associated with between graphical elements 504*ef*, 504*fg*, and 504*gh*. In some embodiments, each of between graphical elements 504*ef*, 504*fg*, and 504*gh* does not occupy the entirety of a respective one of display regions 504*ef*-1, 504*fg*-1, and 504*gh*-1.

It is noted in some embodiments, that, upon selection, a visual characteristic set of each of the directly selected between graphical elements 504*ef*, 504*fg*, and 504*gh* may be changed (e.g., as compared with unselected between graphical elements 504*hi*, 504*ij* and 504*ja*) along with a change in a visual characteristic set of transducer graphical elements 502*ee*, 502*ff*, 502*gg*, and 502*hh*. Changes in a visual characteristic set of various graphical elements in FIGS. 5V and 5W (described below) may be made in accordance with the instructions associated with block 612 in some embodiments.

In FIG. 5V, a modified-interim-definition of the graphical path is generated (for example, by execution of the instructions associated with block 610-2*d*). In various embodiments, the modified-interim-definition of the graphical path is generated prior to the conclusion of the definition of the graphical path. In FIG. 5V, the modified interim definition of the graphical path excludes at least some of the selected graphical elements or graphical-path-elements (e.g., transducer graphical elements 502 and between graphical elements 504) shown in FIG. 5U in response to a user-based retracing of a portion of the motion-based user input employed to generate the interim-definition of the graphical path shown in FIG. 5U. In various embodiments, the excluded graphical elements or excluded graphical-path-elements are those whose display regions have been passed through by the retracing of the portion of the path traced by the motion-based user input during the interim-definition of the graphical path.

In various embodiments, display instructions (e.g., instructions associated with block 612-2*b*) are configured to cause an input-output device system (e.g., 120, 320) to change the display of the graphical representation of the graphical path (for example, as provided by the interim-definition of the graphical path) to account for at least one of the identified excluded graphical elements or at least one of the identified excluded graphical-path-elements. In various embodiments, display instructions (e.g., instructions associated with block 612-2*b*) are configured to cause an input-output device system (e.g., 120, 320) to change the display of the graphical representation of the graphical path (for example, as provided by the interim-definition of the graphical path) to account for at least one of the identified excluded graphical elements or at least one of the identified excluded graphical-path-elements in manner consistent with the modified-interim-definition of the graphical path. In various embodiments, display instructions (e.g., instructions associated with block 612-2*b*) are configured to cause an input-output device system (e.g., 120, 320) to change the display of the graphical representation of the graphical path (for example, as provided by the interim-definition of the graphical path) to account for at least one of the identified excluded graphical elements or at least one of the identified excluded graphical-path-elements prior to a conclusion of the definition of the graphical path.

In some embodiments encompassing FIG. 5V, transducer graphical elements 502*hh* and 520*gg* along with between graphical elements 504*gh* and 5094*fg* are excluded to generate the modified-interim-definition of the graphical path. In some embodiments, user-based retracing of a portion of the motion-based user input that results in the exclusion of transducer graphical elements 502*hh* and 520*gg* and between graphical elements 504*gh* and 504*fg* includes a movement of mouse cursor 519-3 along a path (e.g., schematically represented by arrow 531*d* in some embodiments) sequentially from position 519-3*d* (indicated by mouse cursor 519-3 shown in broken lines) to position 519-3*e* (indicated by mouse cursor 519-3 shown in broken lines) to position 519-3*f* (indicated by mouse cursor 519-3 shown in solid lines). In some embodiments, each of locations 519-3*d* and 519-3*e* are located in a respective one of the display regions 504*gh*-1 and 504*fg*-1 that were previously passed through during the interim definition of the graphical path in FIG. 5U. In this regard, particular ones of the graphical elements or graphical-path-elements selected by passing through their respective display regions during the interim-definition of the graphical path in FIG. 5U are deselected by retracing through the same respective display regions during the modified-interim-definition of the graphical path in FIG. 5V. For example, when the mouse cursor 519-3 is retraced along a path extending from location 519-3*d* in display region 504*fg*-1 to location 519-3*e* in display region 504*fg*-1, between graphical element 504*gh* and transducer graphical element 502*hh* (e.g., originally selected as part of the graphical elements or graphical-path-elements in FIG. 5U) are deselected. It is noted, in various embodiments, that transducer graphical element 502*gg* may be directly selected along with transducer graphical element 502*hh* when between graphical element 504*gh* is selected in accordance with a path traced by the motion-based user input (for example, as per the embodiment of FIG. 5U).

In some of these various embodiments, transducer graphical element 502*gg* is not immediately deselected when the mouse cursor 519-3 is retraced out of the display region 504*gh*-1 for various reasons. For example, in some embodiments, transducer graphical element 502*gg* was indirectly selected e.g., when between graphical element 504*fg* was selected in accordance with a path traced by the motion-based user input as shown in FIG. 5U, and is not deselected until the retracing moves mouse cursor 519-3 into and out of the display region 504*fg*-1 of between graphical element 504*fg*. For example, in FIG. 5V, each of transducer graphical elements 502*hh*, 502*gg* and between graphical elements 504*gh*, 504*fg* are shown as deselected (e.g., via a change in their visual characteristics as compared with their selected state in FIG. 5U) when mouse cursor 519-3 is moved to location 519-3*f* in display region 502*ff*-1.

It is noted in some embodiments, retracing may occur through various display regions whose respective graphical elements or graphical-path-elements occupy the entirety thereof. It is noted that an exact retracing of the motion-based user input employed during the interim-definition of the graphical path need not be required during the modified-interim-definition of the graphical path (e.g., location 519-3*d* need not be the same as location 519-3*c* and location 519-3*e* need not be the same as location 519-3*b*).

In some embodiments, particular ones of graphical elements or graphical-path-elements are not deselected during the modified-interim-definition of the graphical path unless the path traced by the motion-based-user input during the selection of the particular ones of graphical elements or graphical-path-elements and the portion of the path retraced to deselect the particular ones of graphical elements or graphical-path-elements pass through the same ones of the display regions associated with the particular ones of graphical elements or graphical-path-elements. In some embodiments, particular ones of graphical elements or graphical-path-elements are not deselected during the modified-interim-definition of the graphical path unless the path traced by the motion-based-user input during the selection of the particular ones of graphical elements or graphical-path-elements and the portion of the path retraced to deselect the particular ones of graphical elements or graphical-path-elements pass through the same ones of the display regions associated with the particular ones of graphical elements or graphical-path-elements in a reverse order that the display regions associated with the particular ones of graphical elements or graphical-path-elements were passed through during the interim-definition of the graphical path. For example, in FIG. 5W, each of transducer graphical elements 502*hh*, 502*gg* and between graphical elements 504*gh* and 504*fg* that were selected according to the embodiment of FIG. 5U are not deselected, according to some embodiments, when a retracing of a portion of the path traced by the motion-base user input in the embodiment associated with FIG. 5U is attempted to be retraced along a path (e.g., represented by arrow 531*e*) generally different than the portion of the path originally employed to select transducer graphical elements 502*hh*, 502*gg* and between graphical elements 504*gh*, 504*fg*. The retrace path indicated in FIG. 5W does not pass from display region 504*gh*-1 to display region 504*fg*-1 to display region 502*ff*-1 (for example, as shown in FIG. 5V) and each of transducer graphical elements 502*hh*, 502*gg* and between graphical elements 504*gh*, 504*fg* are not deselected (e.g., as indicated by a lack of change in their visible characteristics as compared with FIG. 5U) according to some embodiments. The attempted retrace path indicated in FIG. 5W does not pass from display region 504*gh*-1 to display region 504*fg*-1 to display region 502*ff*-1 in a reverse order that these particular display regions were passed through by the path traced by the motion-based user input employed to select particular ones of the graphical elements corresponding to these particular display regions in FIG. 5U, and, consequently, in accordance with some embodiments, these particular graphical elements are not deselected during the retracing.

In FIG. 5W, the retraced path moves from location 519-3*g* (indicated by mouse cursor 519-3 in broken lines) in display region 504*gh*-1 to location 519-3*h* (indicated by mouse cursor 519-3 in broken lines) in display region 504 *hi*-1 to location 519-3*i* (indicated by mouse cursor 519-3 in broken lines) in display region 504*if*-1 to location 519-3*j* (indicated by mouse cursor 519-3 in un-broken lines) in display region 502*ff*-1. Rather than deselecting various graphical elements or graphical-path-elements (e.g., transducer graphical elements 502*hh*, 502*gg* and between graphical elements 504*gh* and 504*fg*) selected during the interim-definition of the graphical path in FIG. 5U, additional graphical elements or graphical-path-elements are selected in response to the attempted retracing according to some embodiments. For example, between graphical elements 504*hi* and 504*if* and transducer graphical element 502*ii* are shown selected (e.g., as indicated by change in their visual characteristics as compared with their unselected state in FIG. 5U) in response to the attempted retracing.

Improved mechanisms by which a user can efficiently manipulate the map of transducers 306 via transducer graphical elements 502 in graphical representation 500 will now be described with respect to FIGS. 7 and 8A-8C, according to various embodiments. In some embodiments, the improved mechanisms allow a user to efficiently cause an automatic repositioning of a desired graphical element, such as a transducer graphical element 502, to facilitate better viewing. Since viewing and interaction with the transducer graphical elements 502 to control a transducer based device, such as transducer-based device 300, may occur during a medical procedure, time can be of the essence, and access to desired information may need to occur as quickly as possible. Accordingly, the present inventors have developed mechanisms by which a user, such as a physician or other medical professional, can efficiently and accurately reposition the map of transducers 306 via transducer graphical elements 502 in graphical representation 500 so that the user can better view needed information quickly.

Figure 7:
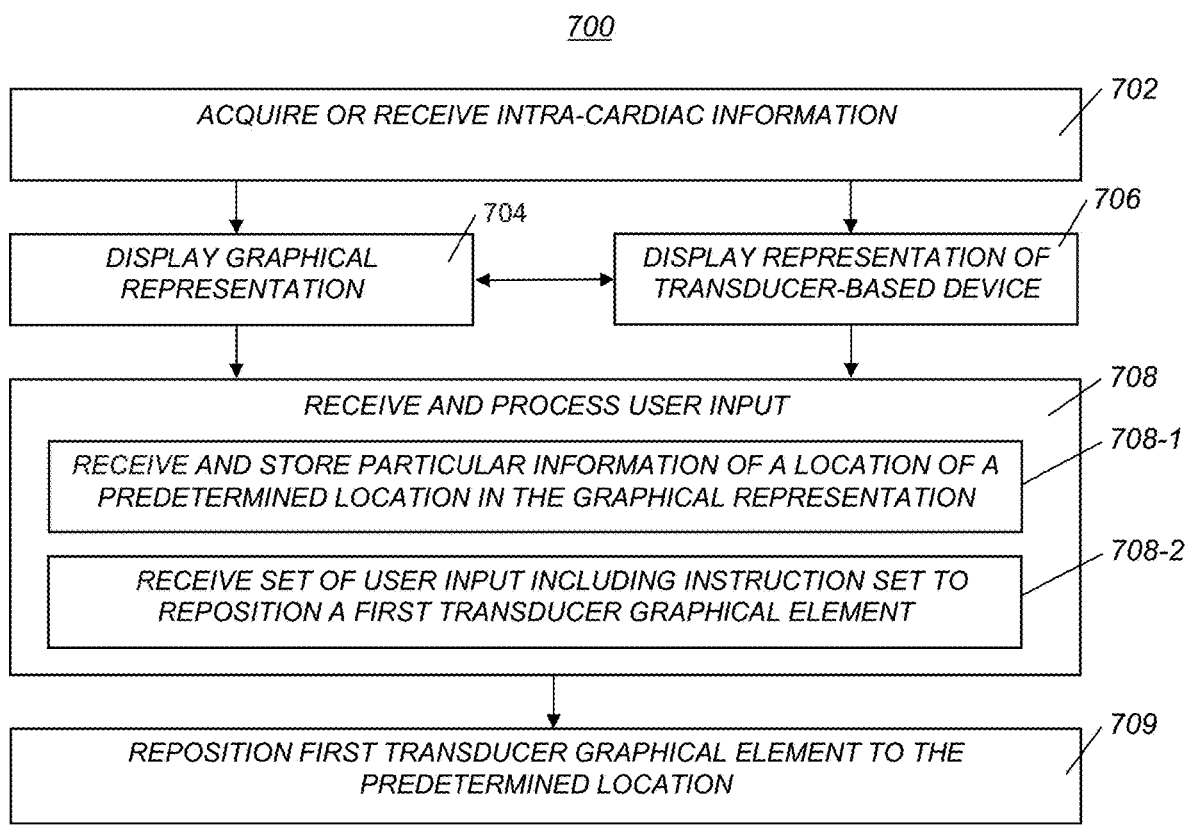
FIG. 7 includes a block diagram of a method for graphical element repositioning according to some example embodiments.

In light of these and other benefits, FIG. 7 includes a respective data generation and flow diagram, which may implement various embodiments of method 700 by way of associated computer-executable instructions according to some example embodiments. In various example embodiments, a memory device system (e.g., memory device systems 130, 330) is communicatively connected to a data processing device system (e.g., data processing device systems 110 or 310, otherwise stated herein as "e.g., 110, 310") and stores a program executable by the data processing device system to cause the data processing device system to execute various embodiments of method 700 via interaction with at least, for example, a transducer-based device (e.g., transducer-based devices 200, 300, or 400). In these various embodiments, the program may include instructions configured to perform, or cause to be performed, various ones of the instructions associated with execution of various embodiments of method 700. In some embodiments, method 700 may include a subset of the associated blocks or additional blocks than those shown in FIG. 7. In some embodiments, method 700 may include a different sequence indicated between various ones of the associated blocks shown in FIG. 7. In this regard, in some embodiments, blocks 702, 704, 706, and 708 correspond to blocks 602, 604, 606, and 608 described above with respect to FIG. 6 (although some embodiments of block 708 do not utilize some or all of sub-blocks 608-1, 608a, 608b, 608c, 608d, and 608e and may, e.g., utilize sub-blocks 708-1 and 708-2, discussed below, instead). Accordingly, at least some duplicative descriptions will be omitted.

In some embodiments, block 702 is associated with computer-executable instructions (e.g., input, acquisition, sampling, or generation instructions and provided by a program) configured to cause the data processing device system (e.g., data processing device systems 110 or 310) to acquire or receive and, e.g., generate, intra-cardiac information from each of one or more transducers of the plurality of transducers (e.g., 220, 306) of the transducer-based device (e.g., 200, 300), as described above with respect to at least block 602 in FIG. 6A, block 602-1 in FIG. 6B, and block 602-2 in FIG. 6C.

Figure 8A:
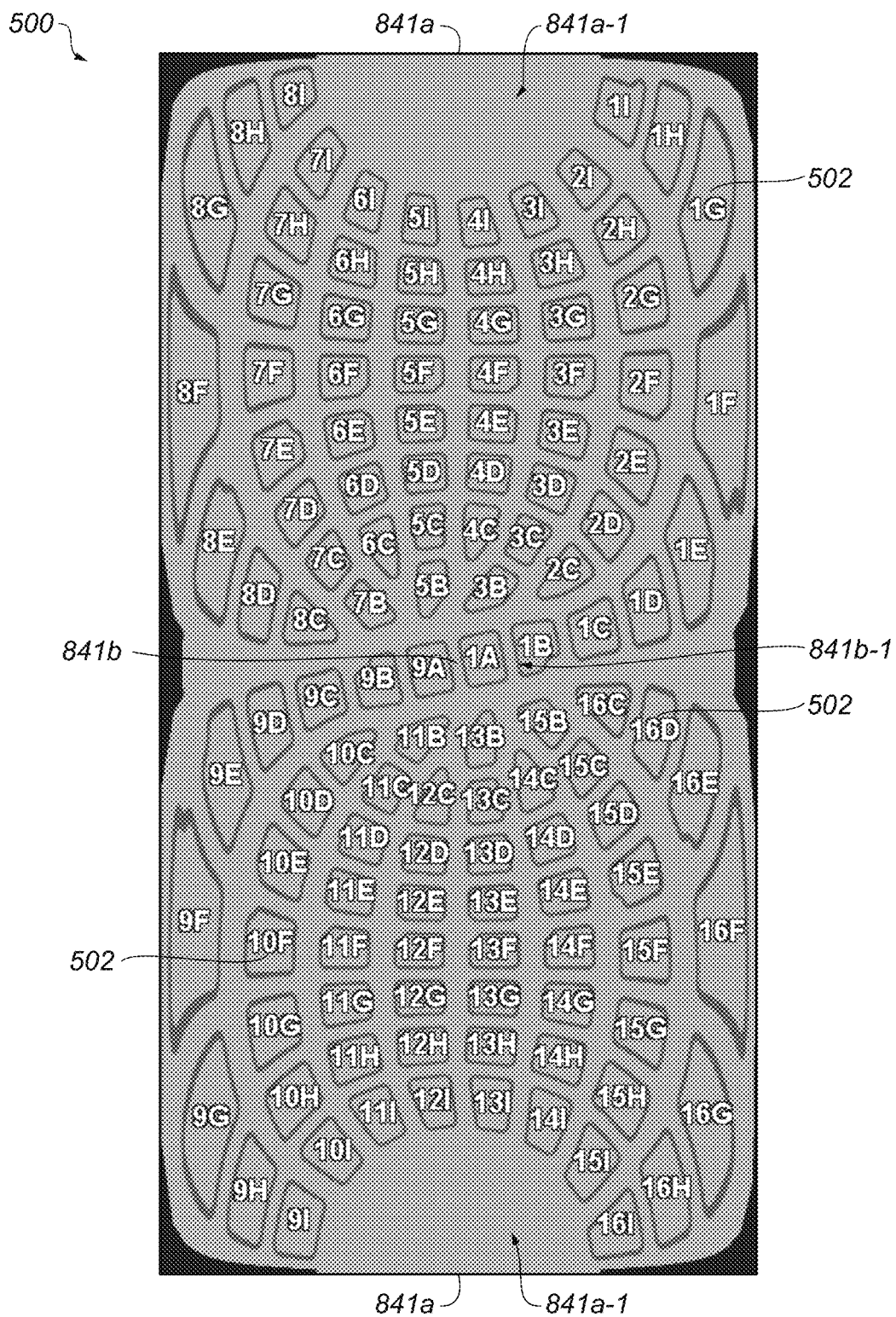
FIGS. 8A-8C illustrate a graphical representation according to various example embodiments illustrating at least some aspects of the method of FIG. 7, a depiction of at least a portion of a transducer-based device including a plurality of transducer graphical elements depicted among the graphical representation of FIGS. 8A-8C.
Figure 8B:
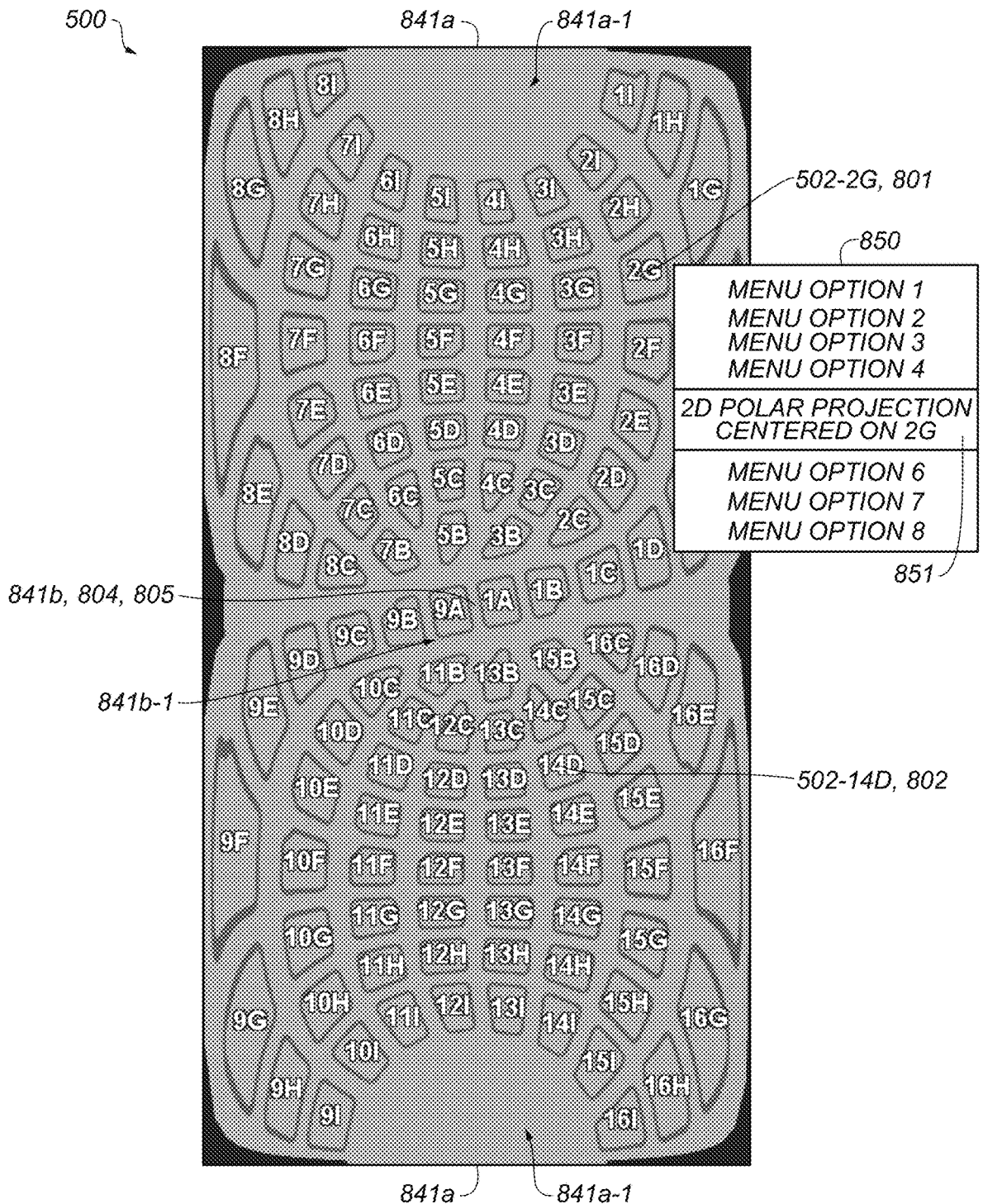
Figure 8C:
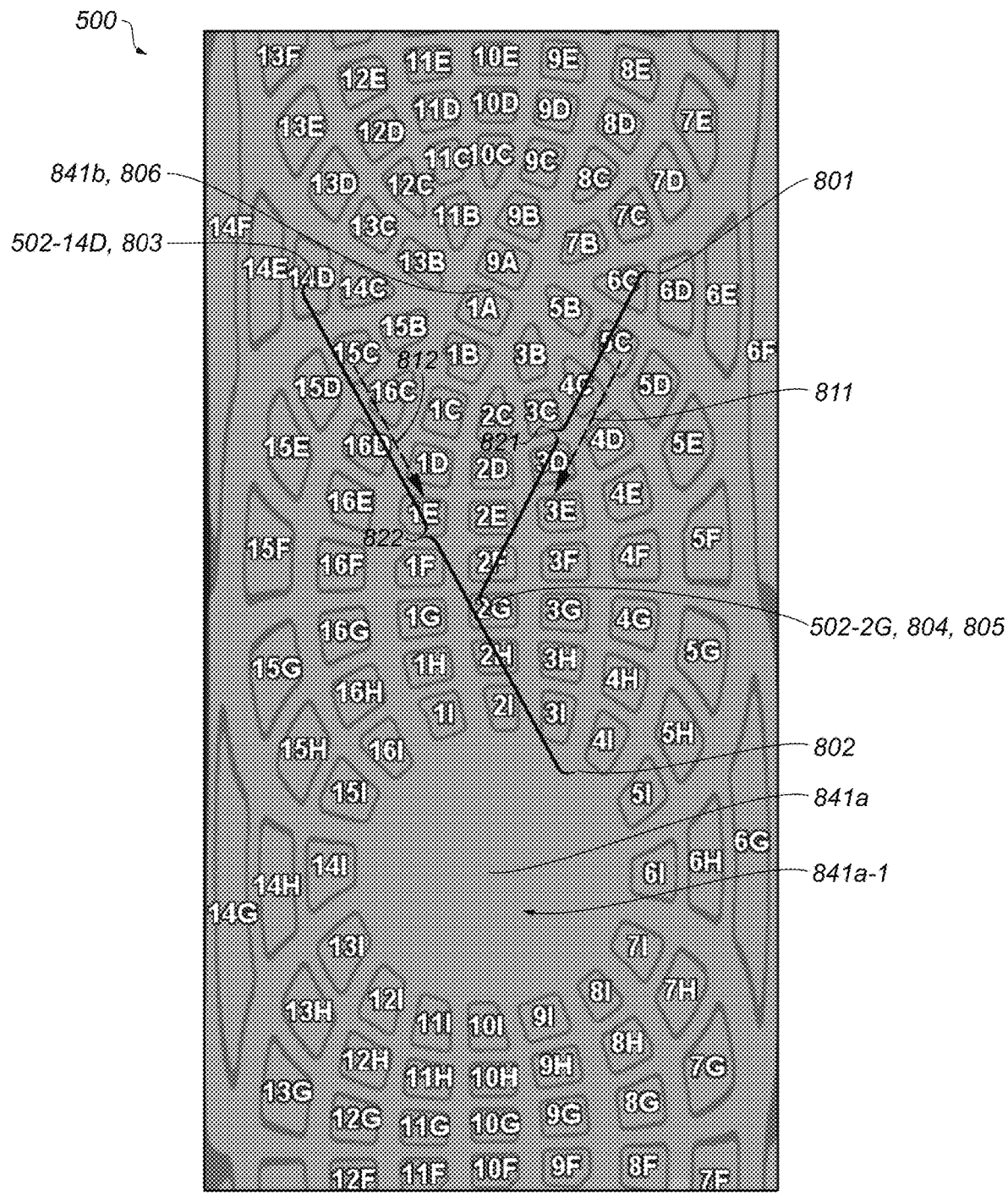

In some embodiments, block 704 is associated with computer-executable instructions (e.g., graphical representation instructions or graphical interface instructions or display instructions provided by a program) configured to cause an input-output device system (e.g., input-output device system 120 or 320) to display a graphical representation, such as at least the various examples of the graphical representation 500 described and illustrated above with respect to at least FIGS. 5A-5R and 5X and block 604 in FIG. 6A. FIGS. 8A-8C illustrate other examples of such graphical representation 500, according to various embodiments. Also, the instructions associated with block 706 may be configured to include in the graphical representation 500 a two-dimensional or three-dimensional graphical representation of at least a portion of a transducer-based device (e.g., structure 308 in FIG. 3) as described above with respect to block 606 in FIG. 6A. It is noted that the graphical representation of the portion of the transducer-based device shown in the graphical representation 500 in each of FIGS. 8A-8C is of a transducer-based device like the transducer-based device 300, but which has fewer elongate members than elongate members 304 of the transducer-based device 300 and fewer transducers than transducers 306 of the transducer-based device 300.

With respect to at least FIG. 8A, only three graphical elements 502 are called out among the plurality for purposes of clarity. In addition, the graphical representation 500 includes a graphical location 841a corresponding to a location of a first pole of the structure (e.g., a pole corresponding to pole 341a of structure 308 shown in FIG. 3C), and a graphical location 841b corresponding to a location of a second pole of the structure opposing the first pole (e.g., a pole corresponding to pole 341b of structure 308 shown in FIG. 3D), according to some embodiments. In the embodiments illustrated in FIGS. 8A-8C, such graphical locations 841a and 841b corresponding to the locations of the poles of the structure of the transducer-based device do not include any particular distinguishing visible markers for the pole locations, but they may be included according to various embodiments. Also note that in FIG. 8A, the graphical location 841a is shown twice at the top and bottom of the graphical representation 500, since the representative location of the first pole is at the edge of the map in this view.

Also with respect to FIG. 8A, the graphical representation 500 may include a graphical region 841a-1 (split across the top and bottom of the graphical representation 500) corresponding to a first polar region surrounding the first pole of the structure (e.g., the pole corresponding to pole 341a of structure 308 shown in FIG. 3C), and a graphical region 841b-1 corresponding to a second polar region surrounding the second pole of the structure (e.g., the pole corresponding to pole 341b of structure 308 shown in FIG. 3D), according to some embodiments. Such polar regions may be defined to be at latitudes greater than or equal to 70 degrees, 75 degrees, 80 degrees, and 85 degrees, according to various embodiments. In some embodiments such as those illustrated in FIGS. 8A-8C, such graphical regions 841a-1 and 841b-1 corresponding to the polar regions of the structure of the transducer-based device do not include any particular distinguishing visible markers for the polar regions, but they may be included according to various embodiments.

In some embodiments, block 708, like block 608, is associated with input-processing instructions indicating reception or reception and processing of various user inputs. In some embodiments, the instructions associated with block 708 may include instructions (e.g., storage instructions associated with block 708-1) configured to cause reception and storage in a memory device system (e.g., memory device system 130 or 330) of particular information indicative of a predetermined location in the graphical representation 500, e.g., to where it may be desired to automatically reposition a location-of-interest in the graphical representation, such as a transducer graphical element 502, for improved viewing by the user. The predetermined location may be a region of the graphical representation 500 that exhibits less mapping distortion so that, for example, a desired transducer graphical element 502 and its associated intra-cardiac information can be repositioned away from a region in the map exhibiting relatively greater distortion for improved viewing, such as away from large edge-based-distortion in a Mercator map or transverse Mercator map. Also, according to some embodiments, the predetermined location may be away from an edge of the graphical representation 500, because such an edge may not only have increased mapping distortion in some embodiments, but such an edge may also or alternatively cause a splitting across the map or a partial disappearance of the associated transducer graphical element 502, its associated intra-cardiac information, or both the associated transducer graphical element 502 and its associated intra-cardiac information. In this regard, depending on a display device or display configuration that a user has implemented, it may be preferable for the user to set the predetermined location to be a center of the graphical representation 500, so that a transducer graphical element 502 of interest to the user can automatically be centered in the graphical representation 500 for improved viewing, e.g., with its improved positioning and reduced mapping distortion, according to some embodiments. However, such a predetermined location need not be the center of the graphical representation 500, and may be any other preferable location within the graphical representation 500. Further, such a predetermined location may have a default location (e.g., that is factory set or otherwise predefined), while allowing a user to redefine the predetermined location to another location within the graphical representation 500 according to the instructions associated with block 708-1. In some embodiments, block 708-1 is omitted from the method 700, so that a default assignment of the predetermined location is not changeable by a user or a particular class of users (e.g., non-administrators, with an administrator being, for instance, a super-user that has special access rights to the computer system needed to administer such system).

In some embodiments, the instructions associated with block 708 may include instructions (e.g., associated with block 708-2) configured to cause reception of a set of user input via the input-output device system (e.g., input-output device system 120 or 320). The set of user input may include an instruction set to reposition a first transducer graphical element (e.g., first transducer graphical element 502-2G in FIG. 8B) of the plurality of transducer graphical elements 502 in a state in which the first transducer graphical element is located at a first location (e.g., first location 801 in FIG. 8B) in the graphical representation 500 and a second transducer graphical element (e.g., second transducer graphical element 502-14D in FIG. 8B) of the plurality of transducer graphical elements 502 is located at a second location (e.g., second location 802 in FIG. 8B) in the graphical representation 500.

The second transducer graphical element 502-14D may be considered a reference transducer graphical element that is not user or machine selected, but merely chosen for this description for purposes of the examples of FIGS. 8B and 8C to help illustrate the dynamics of the movement of the map of transducers 306 via the transducer graphical elements 502 in the graphical representation 500 to reposition the user-selected first transducer graphical element 502-2G to the predetermined location (e.g., predetermined location 804 in the examples of FIGS. 8B and 8C). Accordingly, it should be understood that the present invention is not limited to the user selection of any particular transducer graphical element (i.e., a transducer graphical element other than transducer graphical element 502-2G may be user-selected for placement at the predetermined location) or the use of any particular transducer graphical element as the reference second transducer graphical element (i.e., a transducer graphical element other than transducer graphical element 502-14D may be utilized as a reference to illustrate changes in positioning of the map of transducers 306 via the transducer graphical elements 502 in the graphical representation 500). According to some embodiments, as shown, for example, in FIG. 8B, the second location 802 is closer to a predetermined location 804 in the graphical representation 500 than the first location 801. According to some embodiments, as shown for example in FIG. 8B, the second location 802 and the predetermined location 804 are different locations.

According to some embodiments associated with at least FIGS. 7 and 8A-8C, the word "closer", "distance" (see, e.g., the discussions regarding first distance 821 and second distance 822, below), and the like as used in this and similar contexts pertaining to distances within the graphical representation 500 refers to relative distances or distances across the graphical representation 500 independent of an orientation of the underlying map of transducers (e.g., transducers 306) represented by transducer graphical elements 502. For example, first location 801 is in the same relative location in the graphical representation 500 in both FIGS. 8B and 8C, even though the orientation or configuration of the underlying map of transducers changes between FIGS. 8B and 8C. This definition of "closer", "distance", and the like in these contexts, according to some embodiments, is the same for both two-dimensional mappings of the transducers (e.g., such as those shown in FIGS. 8A-8C) and three-dimensional representations of transducers (e.g., such as those shown in FIGS. 5A-5D and 5R). However, in some embodiments, a three-dimensional representation (e.g., such as those shown in FIGS. 5A-5D and 5R) of transducers (e.g., transducers 306) on a structure (e.g., structure 308) may permit viewing through a representation of a gap in the structure (e.g., through a representation of a gap 344 in FIG. 3D in structure 308 between elongate members 304). In some of such embodiments, it may be possible to view a representation of a transducer (e.g., transducer 306) on a side of the structure (e.g., structure 308) opposite the side represented as closest to the viewer. In these embodiments, it may appear that a representation of a first particular transducer (e.g., via a transducer graphical element 502) on the opposite side of the structure is closer in the graphical representation 500 to a representation of a second particular transducer on the side of the structure represented as closest to the viewer, than a third particular transducer located on the side of the structure represented as closest to the viewer is located with respect to the second particular transducer, even though the third particular transducer physically is located closer to the second particular transducer than the first particular transducer is located with respect to the second particular transducer. In some of these embodiments, the term "closer", "distance", and the like excludes the representations of the transducers on the side of the structure represented as facing away from the viewer, as if the representations of the transducers on the opposing side of the structure were not viewable.

Continuing with respect to the example of FIG. 8B, the set of user input received according to the instructions associated with block 708-2 may include a user-selection of the first transducer graphical element 502-2G, such as by a right-mouse click with a mouse cursor located over the transducer graphical element 502-2G or within some other region of the graphical representation 500 corresponding to transducer graphical element 502-2G, such as, for example, a display region akin to display region 502aa-1 in FIG. 5S). However, any other manner of selecting a transducer graphical element may be implemented, although selection at the transducer graphical element itself or within its corresponding display region (e.g., like display region 502aa-1) may be particularly intuitive and useful to a user in various contexts. The user-selection of the first transducer graphical element 502-2G or any other transducer graphical element 502 may be motivated by various reasons, such as a desire to have such transducer graphical element automatically repositioned to the predetermined location 804 (which may have been defined according to the instructions associated with block 708-1) for better viewing.

In some embodiments, as shown for example in FIG. 8B, the user-selection of the first transducer graphical element 502-2G causes, according to the instructions associated with block 708-2, the display of a menu 850. The menu 850 may include various menu options labeled generically in FIG. 8B as Menu Options 1-4 and 6-8, with the fifth menu option 851 being a request to automatically reposition the selected transducer graphical element 502-2G to the predetermined location. In the example of FIG. 8B, the predetermined location 804 is the center of the two-dimensional projection of the graphical representation 500. However, the predetermined location 804 may be in other predetermined locations within the graphical representation 500 in other embodiments. Also in the example of FIG. 8B, the predetermined location 804 coincides with a first particular location 805 corresponding to the second pole of the structure (e.g., like pole 341*b* of structure 308 shown in FIG. 3D). In this regard, in some embodiments, the first particular location 805 in the graphical representation 500 is closer to the predetermined location 804 than to the first location 801 at least in a state in which the first transducer graphical element 502-2G is located at the first location 801. In some embodiments, such as those encompassed by the example of FIG. 8B, the first particular location 805 is located centrally in the graphical representation 500 at least in the state in which the first transducer graphical element 502-2G is located at the first location 801.

Upon display of the menu 850, according to some embodiments, the user may select menu option 851, e.g., by way of a mouse click or any other selection technique, to initiate the automatic repositioning of the selected first transducer graphical element 502-2G, which occurs according to the instructions associated with block 709. The set of user input received according to the instructions associated with block 708-2 with respect to the example of FIG. 8B may include or be the initial user selection that causes display of the menu 850 as well as the user's subsequent selection of menu option 851, according to some embodiments. However, any number (one or more) and sequence (if more than one) of user inputs needed to produce an instruction set to reposition a transducer graphical element or other graphical element may be implemented, according to various embodiments.

In some embodiments, the instructions associated with block 709 are associated with computer-executable instructions (e.g., graphical representation modification instructions provided by a program) configured to cause, in response to conclusion of receipt of the set of user input including the instruction set to reposition the first transducer graphical element (e.g., first transducer graphical element 502-2G) according to the instructions associated with block 708-2, an input-output device system (e.g., input-output device system 120 or 320) to reposition the first transducer graphical element (e.g., first transducer graphical element 502-2G) from the first location (e.g., first location 801) in the graphical representation 500 to the predetermined location (e.g., predetermined location 804) in the graphical representation 500.

For example, as shown in FIG. 8C, upon conclusion of receipt of the user's selection of the first transducer graphical element 502-2G that brings up the menu 850 and the user's selection of menu option 851, the map of transducers 306 via the transducer graphical elements 502 is automatically shifted from the state of FIG. 8B to the state of FIG. 8C to place the selected first transducer graphical element 502-2G at the predetermined location 804, which, in this example, is centrally located in the graphical representation 500, for improved viewing, according to the instructions associated with block 709. The shifting of the map of transducers 306 via the transducer graphical elements 502 may be implemented, for example, by a re-calculation of the mapping (e.g., via a transverse Mercator projection according to the examples of FIGS. 8B and 8C or other projection) of the structure of the transducer-based device (e.g., like structure 308 of transducer-based device 300), with the selected first transducer graphical element 502-2G located at the predetermined location 804, according to some embodiments. In this regard, it can be seen that the predetermined location 804 is more centrally located in the graphical representation 500 in the example of FIGS. 8B and 8C than the first location 801, and the repositioning of the first transducer graphical element 502-2G according to the instructions associated with block 709 centralizes (e.g., to draw or bring to or toward a center point or to gather into or about a center) the first transducer graphical element 502-2G in the graphical representation 500, according to some embodiments.

According to some embodiments, the repositioning of the first transducer graphical element 502-2G to the predetermined location 804, according to the instructions associated with block 709, causes the second transducer graphical element 502-14D to be repositioned from the second location 802 in FIG. 8B to a third location 803 in FIG. 8C, due to the shifting of the map of transducers 306 via the transducer graphical elements 502 in the graphical representation 500 between FIGS. 8B and 8C. In some embodiments, such as those shown in FIG. 8C, the predetermined location 804 is more centrally located in the graphical representation 500 than the third location 803. According to some embodiments, such as those shown in FIG. 8C, the first location 801 is spaced in the graphical representation 500 from the predetermined location 804 by a first distance 821 and the third location 803 is spaced from the second location 802 by a second distance 822, the first distance 821 and the second distance 822 being different distances. According to some embodiments, this difference in distances may be due at least in part to distortion present in the map of transducers 306 via the transducer graphical elements 502 in the graphical representation 500. According to some embodiments, this difference in distances may be due at least in part to distortion cause by the conformal mapping of transducers 306 via the transducer graphical elements 502 in the graphical representation 500. According to some embodiments, this difference in distances may be due at least in part to distortion caused by a mapping of transducers 306 via the transducer graphical elements 502 in the graphical representation 500 according to a transverse Mercator projection. In the example of FIG. 8C, the illustrated map of transducers 306 via transducer graphical elements 502 includes distortion that increases with distance from the depicted locations of the poles 841*a*, 841*b* in the graphical representation 500, when mapping the three-dimensional structure (e.g., like structure 308) into the two-dimensional planar view according to the transverse Mercator projection. Similarly, according to some embodiments, such as those shown in FIG. 8C, the predetermined location 804 is in a first direction 811 extending from the first location 801 and in a second direction 812 extending from the third location 803 in the graphical representation 500, with the first direction 811 and the second direction 812 being non-parallel directions.

According to some embodiments, and as shown in FIG. 8C, the repositioning of the first transducer graphical element 502-2G to the predetermined location 804, according to the instructions associated with block 709, causes the graphical representation 500 to be reconfigured to cause a second particular location 806 in the graphical representation 500 to correspond to the second pole of the structure (e.g., like pole 341*b* of structure 308 shown in FIG. 3D) instead of the first particular location 805, which corresponded to the second pole of the structure in the state of FIG. 8B. In some embodiments, such as those shown in FIG. 8C, the second particular location 806 is located farther from the predetermined location 804 than the first particular location 805.

According to some embodiments, and as shown by a comparison of FIGS. 8B and 8C, the repositioning of the first transducer graphical element 502-2G to the predetermined location 804, according to the instructions associated with block 709, causes at least the second transducer graphical element 502-14D to appear rotated in the graphical representation 500 about a graphical region corresponding to a pole location (e.g., the graphical region being located at the first particular location 805 in FIG. 8B and at the second particular location 806 in FIG. 8C) of a pole (e.g., pole 841b) of the structure (e.g., structure 308) between a transition from a state in which the first transducer graphical element 502-2G is located at the first location 801 in FIG. 8B and a state in which the first transducer graphical element 502-2G is located at the predetermined location 804 in FIG. 8C upon conclusion of the repositioning of the first transducer graphical element 502-2G from the first location 801 in the graphical representation 500 to the predetermined location 804 in the graphical representation 500.

Although not shown in FIGS. 8A-8C, intra-cardiac information acquired according to the instructions associated with blocks 702 and 602 and illustrated, for example, in FIGS. 5G-5R, may be included in the graphical representation 500 in FIGS. 8A-8C. For instance, according to some embodiments, the graphical representation in FIGS. 8A-8C may represent such intra-cardiac information among the plurality of transducer graphical elements 502. Upon repositioning of the first transducer graphical element 502-2G from the first location 801 to the predetermined location 804 between FIGS. 8B and 8C, any intra-cardiac information included in the graphical representation 500 of FIGS. 8B and 8C would be correspondingly repositioned and updated, according to some embodiments. For instance, the graphical representation modification instructions associated with block 709 may be configured to cause, in response to conclusion of receipt of the set of user input including the instruction set to reposition the first transducer graphical element 502-2G according to the instructions associated with block 708-2, the input-output device system (e.g., input-output device system 120 or 320) to reposition the representation of the intra-cardiac information among the plurality of transducer graphical elements 502 in accordance with the repositioning of the first transducer graphical element 502-2G from the first location 801 in the graphical representation 500 to the predetermined location 804 in the graphical representation 500.

Although the method 700 may appear to terminate with block 709 in FIG. 7, additional blocks, such as, but not limited to, one or more or all of blocks 608, 608-1 (including sub-blocks 608a-608e), 610, 610-1 (including sub-blocks 610-1a to 610-1c), 610-2 (including sub-blocks 610-2a to 610-2d), 612, 612-2 (including sub-blocks 612-2a and 612-2b), and 614 in FIGS. 6A, 6D, 6E, and 6F may follow block 709. For instance, upon repositioning first transducer graphical element 502-2G to the predetermined location 804, the user may proceed with defining a graphical path, activating transducers, or both, as earlier described, according to some embodiments. Also for example, in addition or in the alternative, the defining a graphical path, activating transducers, or both may occur before the repositioning or be interrupted by the repositioning, according to various embodiments.

In this regard in some embodiments, the input-output device system (e.g., input-output device system 120 or 320) is communicatively connected to the transducer-based device (e.g., transducer-based device 300), and the program implementing method 600 or method 700 includes selection instructions (e.g., which may be the instructions associated with block 608 in some embodiments) configured to cause reception of a set of user input (e.g., a second set of user input which may be distinguished from the ('first') set of user input associated with block 708-2) via the input-output device system. This second set of user input may include a second instruction set (e.g., which may be distinguished from the ('first') instruction set associated with block 708-2) to select, in a state (e.g., upon conclusion of execution of the instructions associated with block 709) in which the input-output device system has repositioned the first transducer graphical element from the first location in the graphical representation to the predetermined location in the graphical representation, a set of transducer graphical elements (e.g., such as those transducer graphical elements 502 selected in FIG. 5Q) of the plurality of transducer graphical elements 502. In some embodiments, the set of transducer graphical elements may include the first transducer graphical element (e.g., 502-2G), the second transducer graphical element (e.g., 502-14D), or both the first transducer graphical element (e.g., 502-2G) and the second transducer graphical element (e.g., 502-14D). In some embodiments, the program implementing method 600 or method 700 also includes activation instructions (e.g., which may be the instructions associated with block 614 in some embodiments) configured to cause activation, via the input-output device system, of a set of transducers (e.g., such as those transducers 306 corresponding to the selected transducer graphical elements 502 in FIG. 5Q) of the plurality of transducers 306 of the transducer-based device 300 in response to reception of the second set of user input including the second instruction set to select the set of transducer graphical elements, the set of transducers to be activated corresponding to the selected set of transducer graphical elements. In some embodiments, the activation of the set of transducers may include activating the set of transducers to transmit energy sufficient for tissue ablation.

While some of the embodiments disclosed above are described with examples of cardiac mapping, the same or similar embodiments may be used for mapping other bodily organs, for example, gastric mapping, bladder mapping, arterial mapping and mapping of any lumen or cavity into which the devices of the present invention may be introduced.

While some of the embodiments disclosed above are described with examples of cardiac ablation, the same or similar embodiments may be used for ablating other bodily organs or any lumen or cavity into which the devices of the present invention may be introduced.

Subsets or combinations of various embodiments described above can provide further embodiments.

These and other changes can be made to the invention in light of the above-detailed description. In general, in the following claims, the terms used should not be construed to limit the invention to the specific embodiments disclosed in the specification and the claims, but should be construed to include other transducer-based device systems including all medical treatment device systems and all medical diagnostic device systems in accordance with the claims. Accordingly, the invention is not limited by the disclosure, but instead its scope is to be determined entirely by the following claims.

What is claimed is:

1. A transducer activation system comprising:
   a data processing device system;
   an input-output device system communicatively connected to the data processing device system; and
   a memory device system communicatively connected to the data processing device system and storing a program executable by the data processing device system, the program comprising:
   first display instructions configured to cause display, via the input-output device system, of a plurality of transducer graphical elements, each transducer graphical element of the plurality of transducer graphical elements corresponding to at least part of a respective transducer of a plurality of transducers of a transducer-based device, each respective transducer graphical element of the plurality of transducer graphical elements displayed within a respective display region of a plurality of display regions that encompasses the respective transducer graphical element, and a first transducer graphical element of the plurality of transducer graphical elements located within a first display region of the plurality of display regions, the first transducer graphical element corresponding to a first transducer of the plurality of transducers;
   first input-processing instructions configured to cause reception of user input via the input-output device system, the user input associated with a first display-screen-location;
   determination instructions configured to cause a determination that the first display-screen-location associated with the user input is within the first display region, at least in a state in which the first display-screen-location is not within the first transducer graphical element; and
   activation instructions configured to cause, at least in response to the determination, activation of the first transducer.

2. The transducer activation system of claim 1, wherein each respective display region of the plurality of display regions is mutually exclusive with every other display region of the plurality of display regions.

3. The transducer activation system of claim 1, wherein the program comprises second display instructions configured to cause, at least in response to the determination, a change of a visual characteristic of the first transducer graphical element.

4. The transducer activation system of claim 1, wherein the first display instructions are configured to cause display, via the input-output device system, of the plurality of transducer graphical elements according to a first spatial relationship that is consistent with a second spatial relationship between the respective transducers of the plurality of transducers.

5. The transducer activation system of claim 1,
   wherein each respective transducer of the plurality of transducers is configured to sample data,
   wherein the program comprises:
      sampling instructions configured to cause sampling of data by each respective transducer of the plurality of transducers, and
      generation instructions configured to cause generation, for each respective transducer of the transducer-based device, of corresponding information based at least in part on the data sampled by the respective transducer of the plurality of transducers, and
   wherein the first display instructions are configured to cause display, via the input-output device system, of the corresponding information generated for the respective transducers of the plurality of transducers according to a first spatial relationship that is consistent with a second spatial relationship between a plurality of locations at which the data was sampled by the respective transducers of the plurality of transducers.

6. The transducer activation system of claim 5, wherein the first display instructions are configured to cause display, via the input-output device system, of the plurality of transducer graphical elements in an overlapping relationship with the corresponding information generated for the respective transducers of the plurality of transducers.

7. The transducer activation system of claim 5, wherein the first display instructions are configured to cause display, via the input-output device system, of a representation of interpolated information derived from the corresponding information generated for the respective transducers of at least some of the plurality of transducers in at least part of at least one particular display region of the plurality of display regions.

8. The transducer activation system of claim 5, wherein the first display instructions are configured to cause display, via the input-output device system and at least at the first display-screen-location within the first display region, of a representation of interpolated information derived from the corresponding information generated for the first transducer.

9. The transducer activation system of claim 5, wherein the corresponding information generated for each respective transducer of the plurality of transducers is intra-cardiac information.

10. The transducer activation system of claim 1, wherein the program comprises:
    path definition instructions configured to cause definition of a graphical path at least in part in response to the user input; and
    second display instructions configured to cause display, via the input-output device system, of the graphical path concurrently with the plurality of transducer graphical elements, the graphical path displayed in an overlapping relationship with at least some of the display regions of the plurality of display regions.

11. The transducer activation system of claim 10, wherein the graphical path is displayed as including an interrupted form.

12. The transducer activation system of claim 10, wherein the graphical path is displayed as including a circumferential form.

13. The transducer activation system of claim 10, wherein the second display instructions are configured to cause display, via the input-output device system, of the graphical path concurrently with the plurality of transducer graphical elements, the graphical path displayed in an overlapping relationship with at least some of the plurality of transducer graphical elements.

14. The transducer activation system of claim 1, wherein the user input is part of a user-traced path extending across at least some of the plurality of display regions, the user-traced path extending through the first display-screen-location.

15. The transducer activation system of claim 1, wherein the user input comprises first user input, wherein the input-processing instructions are configured to, in response to receiving the first user input, cause a first user input element to be placed in an activated state, and wherein the first display-screen location is defined according to a parameter set associated with the first user input.

16. The transducer activation system of claim 1, wherein the user input comprises first user input and second user input, and wherein the input-processing instructions are configured to, in response to receiving the first user input, cause a first user input element to be placed in an activated state, and in response to receiving the second user input, cause the first user input element to be placed in a deactivated state, and wherein the first display-screen location is defined according to a parameter set associated with the second user input.

17. The transducer activation system of claim 16, wherein a second display-screen location is defined according to a parameter set associated with the first user input, the second display-screen location other than the first display-screen location.

18. The transducer activation system of claim 1, wherein the user input comprises motion-based user input, wherein the program comprises path definition instructions configured to cause, in response to receiving the motion-based user input, definition of an elongated path according to a path traced by the motion-based user input, and wherein the first display-screen location is defined as a location on the path traced by the motion-based user input.

19. The transducer activation system of claim 1, wherein the activation instructions are configured to cause, at least in response to the determination, activation of the first transducer to transmit energy sufficient for tissue ablation.

20. The transducer activation system of claim 1, wherein the plurality of transducers is located at a distal end of a catheter device, the distal end of the catheter device configured to be insertable into a bodily cavity.

21. The transducer activation system of claim 1, wherein the first display instructions are configured to cause display, via the input-output device system, of a graphical representation of intra-cardiac information in an overlapping relationship with at least some of the plurality of display regions and the respective plurality of transducer graphical elements displayed within the at least some of the plurality of display regions.

22. The transducer activation system of claim 21, wherein the first display instructions are configured to cause the input-output device system to graphically display changes in the displayed intra-cardiac information at least during reception of the user input.

23. The transducer activation system of claim 1, wherein the first display instructions are configured to cause display, via the input-output device system, of a graphical representation of intra-cardiac information in an overlapping relationship with at least part of the first display region, the first display-screen-location within the at least part of the first display region.

24. The transducer activation system of claim 1, wherein the first display instructions are configured to cause display, via the input-output device system, of a plurality of unique identifiers correlating each transducer graphical element of the plurality of transducer graphical elements with the respective transducer of the plurality of transducers.

25. The transducer activation system of claim 1, wherein the first display instructions are configured to cause display, via the input-output device system, of at least one transducer graphical element of the plurality of transducer graphical elements with a shape that is consistent with a shape of the at least the part of the respective transducer of the plurality of transducers.

26. The transducer activation system of claim 1, wherein at least one transducer of the plurality of transducers comprises an electrode, and wherein the first display instructions are configured to cause display, via the input-output device system, of at least the respective transducer graphical element of the plurality of transducer graphical elements corresponding to the at least part of the one transducer of the plurality of transducers with a shape that is consistent with a shape of the electrode of the one transducer of the plurality of transducers.

* * * * *

UNITED STATES PATENT AND TRADEMARK OFFICE
CERTIFICATE OF CORRECTION

PATENT NO. : 11,026,637 B2  
APPLICATION NO. : 16/388063  
DATED : June 8, 2021  
INVENTOR(S) : Brewster et al.

Page 1 of 1

It is certified that error appears in the above-identified patent and that said Letters Patent is hereby corrected as shown below:

On the Title Page

Item (12) delete "Moisa et al." and insert --Brewster et al.--.

Item (72) Inventors:

The following inventor should be deleted:
"Saar Moisa, Vancouver (CA)"

The following inventors should be added as first and second inventors:
--Jeffery Charles Brewster, Burnaby (CA)
Daniel Robert Weinkam, Coquitlam (CA)--.

Signed and Sealed this  
Twenty-third Day of December, 2025

John A. Squires  
*Director of the United States Patent and Trademark Office*